(12) United States Patent
Owczarek et al.

(10) Patent No.: US 11,840,573 B2
(45) Date of Patent: *Dec. 12, 2023

(54) CD131 BINDING PROTEINS AND USES THEREOF

(71) Applicant: CSL LIMITED, Melbourne (AU)

(72) Inventors: Catherine Owczarek, Melbourne (AU); Con Panousis, Melbourne (AU); Nicholas Wilson, Melbourne (AU); Matthew Hardy, Melbourne (AU); Kirsten Edwards, Melbourne (AU); Veronika Rayzman, Melbourne (AU)

(73) Assignee: CSL LIMITED, Melbourne (AU)

( * ) Notice: Subject to any disclaimer, the term of this patent is extended or adjusted under 35 U.S.C. 154(b) by 359 days.

This patent is subject to a terminal disclaimer.

(21) Appl. No.: 16/953,499

(22) Filed: Nov. 20, 2020

(65) Prior Publication Data

US 2021/0324091 A1 Oct. 21, 2021

Related U.S. Application Data

(63) Continuation of application No. 15/779,252, filed as application No. PCT/AU2016/051158 on Nov. 25, 2016, now Pat. No. 10,894,834.

(30) Foreign Application Priority Data

Nov. 27, 2015 (AU) ................................ 2015904924

(51) Int. Cl.
*C07K 16/28* (2006.01)
*A61P 37/06* (2006.01)
*G01N 33/68* (2006.01)
*A61K 39/00* (2006.01)

(52) U.S. Cl.
CPC .......... *C07K 16/2866* (2013.01); *A61P 37/06* (2018.01); *G01N 33/68* (2013.01); *A61K 2039/505* (2013.01); *A61K 2039/54* (2013.01); *A61K 2039/543* (2013.01); *C07K 2317/21* (2013.01); *C07K 2317/55* (2013.01); *C07K 2317/56* (2013.01); *C07K 2317/73* (2013.01); *C07K 2317/76* (2013.01); *C07K 2317/92* (2013.01); *G01N 2333/70596* (2013.01)

(58) Field of Classification Search
CPC ..... C07K 16/2866; C12N 15/00; C12N 15/09
See application file for complete search history.

(56) References Cited

U.S. PATENT DOCUMENTS

| 10,894,834 B2 * | 1/2021 | Owczarek .......... C07K 16/2866 |
| 2004/0018198 A1 | 1/2004 | Gudas et al. |
| 2006/0024295 A1 | 2/2006 | Brunetta |
| 2006/0246077 A1 | 11/2006 | Bar-Eli et al. |
| 2008/0213251 A1 | 9/2008 | Sexton et al. |

FOREIGN PATENT DOCUMENTS

| WO | WO 2000/009561 A1 | 2/2000 |
| WO | WO 2000/047620 A1 | 8/2000 |
| WO | WO 2007/147019 A2 | 12/2007 |
| WO | WO 2013/090989 | 6/2013 |

OTHER PUBLICATIONS

European Search Report PCT/AU2016051158 dated Apr. 26, 2019.
Extended European Search Report issued in Application No. 16867461.2, dated Apr. 26, 2019, 5 pages.
Sun, Q. et al., "Simultaneous Antagonism of Interleukin-5, Granulocyte-Macrophage Colony-Stimulating Factor, and Interleukin-3 Stimulation of Human Eosinophils by Targeting the Common Cytokine Binding Site of Their Receptors," Blood, 94:1943-1951 (1999).
Ramshaw et al., "New approaches in the treatment of asthma," Immunology and Cell Biology, 2001. vol. 79, pp. 154-159.
International Search Report in corresponding International Patent Application No. PCT/AU20/16/051158, dated Feb. 1, 2017, 7 pages.
Written Opinion of International Search Report in corresponding International Patent Application No. PCT/AU20/16/051158, dated Feb. 1, 2017, 5 pages.
Colman (1994), "Effects of amino acid sequence changes on antibody-antigen interactions," 55th Forum in Immunology, 145:1, 33-36.
Kontermann and Brinkmann (2015), "Bispecific antibodies," Drug Discovery Today, 7:20, 838-847.
Desai et al. (2010), "Production of heterologous proteins in plants: Strategies for optimal expression," Biotechnology Advances, 28:4, 427-435.
CD131 Antibody, anti-mouse, Biotin, REAfinity Data Sheet (Aug. 2020).
PE Rat Anti-Mouse CD131 Bd Pharmingen Data Sheet (2016).
Rauch et al. (2012), "Innate Response Activator B Cells Protect Against Microbial Sepsis," Science, 335: 597-601.
Hansen et al. (2008), "The Structure of the GM-CSF Receptor Complex Reveals a Distinct Mode of Cytokine Receptor Activation," Cell, 134, 496-507.
Hercus et al. (2012), "The GM-CSF receptor family: Mechanism of activation and implications for disease," Growth Factors, 30(2): 63-75.
Broughton et al. (2016), "Conformational Changes in the GM-CSF Receptor Suggest a Molecular Mechanism for Affinity Conversion and Receptor Signaling," Structure, 24, 1271-1281.
Broughton et al. (2012), "The GM-CSF/IL-3/IL-5 cytokine receptor family: from ligand recognition to initiation of signaling," Immunological Reviews, 250: 277-302.
Lopez et al. (2010), "Molecular Basis of Cytokine Receptor Activation," IUBMB Life, 62(7): 509-518.

* cited by examiner

*Primary Examiner* — Prema M Mertz
(74) *Attorney, Agent, or Firm* — Finnegan, Henderson, Farabow, Garrett & Dunner, LLP

(57) ABSTRACT

The present disclosure provides a CD131-binding protein comprising an antigen binding domain of an antibody, wherein the antigen binding domain binds to or specifically binds to CD131 and neutralizes signaling by interleukin (IL) 3, IL-5 and granulocyte-macrophage colony stimulating factor (GM-CSF), and uses thereof.

20 Claims, 31 Drawing Sheets

Specification includes a Sequence Listing.

|  | | CDR1 | | CDR2 | | CDR3 | |
|---|---|---|---|---|---|---|---|
| 9A2 | DIQMTQSPSSVSASVGDRVTITC | RASQGISSWLA | WYQQKPGKAPKLLIY | AASSLQS | GVPSRFSGSGSGTDFTLTISSLQPEDFATYYC | QQANSFPIT | |
| 9A2-VR1 | DIQMTQSPSSVSASVGDRVTITC | RASQGTRPFMA | WYQQKPGKAPKLLIY | AASSLQS | GVPSRFSGSGSGTDFTLTISSLQPEDFATYYC | QQANSFPIT | |
| 9A2-VR2 | DIQMTQSPSSVSASVGDRVTITC | RASQGQRPFVS | WYQQKPGKAPKLLIY | AASSLQS | GVPSRFSGSGSGTDFTLTISSLQPEDFATYYC | QQANSFPIT | |
| 9A2-VR3 | DIQMTQSPSSVSASVGDRVTITC | RASQGLRPFVN | WYQQKPGKAPKLLIY | AASSLQS | GVPSRFSGSGSGTDFTLTISSLQPEDFATYYC | QQANSFPIT | |
| 9A2-VR4 | DIQMTQSPSSVSASVGDRVTITC | RASQGIRPFVD | WYQQKPGKAPKLLIY | AASSLQS | GVPSRFSGSGSGTDFTLTISSLQPEDFATYYC | QQANSFPIT | |
| 9A2-VR5 | DIQMTQSPSSVSASVGDRVTITC | RASQGIRPFVA | WYQQKPGKAPKLLIY | AASSLQS | GVPSRFSGSGSGTDFTLTISSLQPEDFATYYC | QQANSFPIT | |
| 9A2-VR6 | DIQMTQSPSSVSASVGDRVTITC | RASQGVRPFVN | WYQQKPGKAPKLLIY | AASSLQS | GVPSRFSGSGSGTDFTLTISSLQPEDFATYYC | QQANSFPIT | |
| 9A2-VR8 | DIQMTQSPSSVSASVGDRVTITC | RASQGVRPFVA | WYQQKPGKAPKLLIY | AASSLQS | GVPSRFSGSGSGTDFTLTISSLQPEDFATYYC | QQANSFPIT | |
| 9A2-VR9 | DIQMTQSPSSVSASVGDRVTITC | RASQGVRPFIS | WYQQKPGKAPKLLIY | AASSLQS | GVPSRFSGSGSGTDFTLTISSLQPEDFATYYC | QQANSFPIT | |
| 9A2-VR11 | DIQMTQSPSSVSASVGDRVTITC | RASQGVRPFID | WYQQKPGKAPKLLIY | AASSLQS | GVPSRFSGSGSGTDFTLTISSLQPEDFATYYC | QQANSFPIT | |
| 9A2-VR12 | DIQMTQSPSSVSASVGDRVTITC | RASQGTRPFVS | WYQQKPGKAPKLLIY | AASSLQS | GVPSRFSGSGSGTDFTLTISSLQPEDFATYYC | QQANSFPIT | |
| 9A2-VR13 | DIQMTQSPSSVSASVGDRVTITC | RASQGTSSWLA | WYQQKPGKAPKLLIY | AASSLQS | GVPSRFSGSGSGTDFTLTISSLQPEDFATYYC | QQANSFPIT | |
| 9A2-VR14 | DIQMTQSPSSVSASVGDRVTITC | RASQGTSSWLA | WYQQKPGKAPKLLIY | AASSLQS | GVPSRFSGSGSGTDFTLTISSLQPEDFATYYC | GKPVLDPIT | |
| 9A2-VR16 | DIQMTQSPSSVSASVGDRVTITC | RASQGTSSWLA | WYQQKPGKAPKLLIY | AASSLQS | GVPSRFSGSGSGTDFTLTISSLQPEDFATYYC | GKPVFDPIT | |
| 9A2-VR19 | DIQMTQSPSSVSASVGDRVTITC | RASQGTSSWLA | WYQQKPGKAPKLLIY | AASSLQS | GVPSRFSGSGSGTDFTLTISSLQPEDFATYYC | GIPVLGPIT | |
| Consensus | DIQMTQSPSSVSASVGDRVTITC | RASQGXXXXXX<br>ISSWLA<br>QRPFMS<br>L VN<br>V ID | WYQQKPGKAPKLLIY | AASSLQS | GVPSRFSGSGSGTDFTLTISSLQPEDFATYYC | XXXXXPIT<br>QQANSF<br>GKPVLD<br>I IFG | |

|  |  |  |
|---|---|---|
| 9A2 | FGQGTRLEIKRTVAA | SEQ ID NO: 5 |
| 9A2-VR1 | FGQGTRLEIKRTVAA | SEQ ID NO: 6 |
| 9A2-VR2 | FGQGTRLEIKRTVAA | SEQ ID NO: 7 |
| 9A2-VR3 | FGQGTRLEIKRTVAA | SEQ ID NO: 8 |
| 9A2-VR4 | FGQGTRLEIKRTVAA | SEQ ID NO: 9 |
| 9A2-VR5 | FGQGTRLEIKRTVAA | SEQ ID NO: 10 |
| 9A2-VR6 | FGQGTRLEIKRTVAA | SEQ ID NO: 11 |
| 9A2-VR8 | FGQGTRLEIKRTVAA | SEQ ID NO: 12 |
| 9A2-VR9 | FGQGTRLEIKRTVAA | SEQ ID NO: 13 |
| 9A2-VR11 | FGQGTRLEIKRTVAA | SEQ ID NO: 14 |
| 9A2-VR12 | FGQGTRLEIKRTVAA | SEQ ID NO: 15 |
| 9A2-VR13 | FGQGTRLEIKRTVAA | SEQ ID NO: 16 |
| 9A2-VR14 | FGQGTRLEIKRTVAA | SEQ ID NO: 17 |
| 9A2-VR16 | FGQGTRLEIKRTVAA | SEQ ID NO: 18 |
| 9A2-VR19 | FGQGTRLEIKRTVAA | SEQ ID NO: 19 |
| Consensus | FGQGTRLEIKRTVAA | |

| | CDR3 | | |
|---|---|---|---|
| 9A2 | FYDSFFDI | WGQGTMVTVSS | SEQ ID NO: 20 |
| 9A2-VR20 | FYDSFFDI | WGQGTMVTVSS | SEQ ID NO: 21 |
| 9A2-VR21 | FYDSFFDI | WGQGTMVTVSS | SEQ ID NO: 22 |
| 9A2-VR22 | FYDSFFDI | WGQGTMVTVSS | SEQ ID NO: 23 |
| 9A2-VR23 | FYDSFFDI | WGQGTMVTVSS | SEQ ID NO: 24 |
| 9A2-VR24 | FYDSFFDI | WGQGTMVTVSS | SEQ ID NO: 25 |
| 9A2-VR26 | FYDSFFDI | WGQGTMVTVSS | SEQ ID NO: 26 |
| 9A2-VR27 | FYDSFFDI | WGQGTMVTVSS | SEQ ID NO: 27 |
| 9A2-VR28 | FYDSFFDI | WGQGTMVTVSS | SEQ ID NO: 28 |
| 9A2-VR31 | FYDSFFDI | WGQGTMVTVSS | SEQ ID NO: 29 |
| 9A2-VR32 | FYDSFFDI | WGQGTMVTVSS | SEQ ID NO: 30 |
| 9A2-VR33 | FYDSFFDI | WGQGTMVTVSS | SEQ ID NO: 31 |
| 9A2-VR34 | FYDSFFDI | WGQGTMVTVSS | SEQ ID NO: 32 |
| 9A2-VR35 | FYDSFFDI | WGQGTMVTVSS | SEQ ID NO: 33 |
| 9A2-VR36 | FYDSFFDI | WGQGTMVTVSS | SEQ ID NO: 34 |
| 9A2-VR37 | FYDSFFDI | WGQGTMVTVSS | SEQ ID NO: 35 |
| 9A2-VR38 | FYDSFFDI | WGQGTMVTVSS | SEQ ID NO: 36 |
| 9A2-VR39 | FYDSFFDI | WGQGTMVTVSS | SEQ ID NO: 37 |
| 9A2-VR40 | FYDSFFDI | WGQGTMVTVSS | SEQ ID NO: 38 |
| 9A2-VR41 | FYDSFFDI | WGQGTMVTVSS | SEQ ID NO: 39 |
| 9A2-VR42 | FYDSFFDI | WGQGTMVTVSS | SEQ ID NO: 40 |
| 9A2-VR43 | FYDSFFDI | WGQGTMVTVSS | SEQ ID NO: 41 |
| 9A2-VR44 | FYSDHFRE | WGQGTMVTVSS | SEQ ID NO: 42 |
| 9A2-VR45 | FYSDHFSP | WGQGTMVTVSS | SEQ ID NO: 43 |
| 9A2-VR46 | FYSDHFKP | WGQGTMVTVSS | SEQ ID NO: 44 |
| 9A2-VR47 | FYSDHFNE | WGQGTMVTVSS | SEQ ID NO: 45 |
| 9A2-VR48 | FYSDHFNP | WGQGTMVTVSS | SEQ ID NO: 46 |
| 9A2-VR49 | FYSDHFAP | WGQGTMVTVSS | SEQ ID NO: 47 |
| 9A2-VR50 | FYSDHFAP | WGQGTMVTVSS | SEQ ID NO: 48 |
| Consensus | FYXXFXX | WGQGTMVTVSS | |
| | DSF DI | | |
| | SDH RE | | |
| | N SP | | |
| | K N | | |
| | A | | |

FIG. 2B

|  | | CDR1 | | CDR2 | | |
|---|---|---|---|---|---|---|
| 9A2-VR24 | EVQLLESGGGLVQPGGSLRLSCAAS | GFTFPWYRVH | WVRQAPGKGLEWVS | SIRSSGGFTYYADSVKG | RFTISRDNSKNTLYLQMNSLRAEDTAVYYCAR |
| 9A2-VR24.04 | EVQLLESGGGLVQPGGSLRLSCAAS | GFTFFPWYRVH | WVRQAFGKGLEWVS | SIHTRHITYYADSVKG | RFTISRDNSKNTLYLQMNSLRAEDTAVYYCAR |
| 9A2-VR24.07 | EVQLLESGGGLVQPGGSLRLSCAAS | GFTFPWYRVH | WVRQAPGKGLEWVS | SIHTHRNSTYYADSVKG | RFTISRDNSKNTLYLQMNSLRAEDTAVYYCAR |
| 9A2-VR24.10 | EVQLLESGGGLVQPGGSLRLSCAAS | GFTFPWYRVH | WVRQAPGKGLEWVS | SIRTGSQWTYYADSVKG | RFTISRDNSKNTLYLQMNSLRAEDTAVYYCAR |
| 9A2-VR24.12 | EVQLLESGGGLVQPGGSLRLSCAAS | GFTFFPWYRVH | WVRQAPGKGLEWVS | SIHTRHYQVTYYADSVKG | RFTISRDNSKNTLYLQMNSLRAEDTAVYYCAR |
| 9A2-VR24.19 | EVQLLESGGGLVQPGGSLRLSCAAS | GFTFPWYRVH | WVRQAPGKGLEWVS | SIHTQSKWTYYADSVKG | RFTISRDNSKNTLYLQMNSLRAEDTAVYYCAR |
| 9A2-VR24.24 | EVQLLESGGGLVQPGGSLRLSCAAS | GFTFPWYRVH | WVRQAPGKGLEWVS | SIRTDGTWTYYADSVKG | RFTISRDNSKNTLYLQMNSLRAEDTAVYYCAR |
| 9A2-VR24.76 | EVQLLESGGGLVQPGGSLRLSCAAS | GFTFPWYRVH | WVRQAPGKGLEWVS | SIQTHGVMTYYADSVKG | RFTISRDNSKNTLYLQMNSLRAEDTAVYYCAR |
| 9A2-VR24.81 | EVQLLESGGGLVQPGGSLRLSCAAS | GFTFPWYRVH | WVRQAPGKGLEWVS | SIKHGGRYTYYADSVKG | RFTISRDNSKNTLYLQMNSLRAEDTAVYYCAR |
| 9A2-VR24.82 | EVQLLESGGGLVQPGGSLRLSCAAS | GFTFPWYRVH | WVRQAPGKGLEWVS | SIHTRPWTYYAESVKG | RFTISRDNSKNTLYLQMNSLRAEDTAVYYCAR |
| 9A2-VR24.84 | EVQLLESGGGLVQPGGSLRLSCAAS | GFTFPWYRVH | WVRQAFGKGLEWVS | SIHTHSDWTYYADSVKG | RFTISRDNSKNTLYLQMNSLRAEDTAVYYCAR |
| 9A2-VR24.87 | EVQLLESGGGLVQPGGSLRLSCAAS | GFTFPWYRVH | WVRQAPGKGLEWVS | SIHTRKQVTYYADSVKG | RFTISRDNSKNTLYLQMNSLRAEDTAVYYCAR |
| 9A2-VR24.91 | EVQLLESGGGLVQPGGSLRLSCAAS | GFTFPWYRVH | WVRQAPGKGLEWVS | SIRNENGWTYYADSVKG | RFTISRDNSKNTLYLQMNSLRAEDTAVYYCAR |
| 9A2-VR24.93 | EVQLLESGGGLVQPGGSLRLSCAAS | GFTFPWYRVH | WVRQAPGKGLEWVS | SIRSSGGFPYYHQKVKG | RFTISRDNSKNTLYLQMNSLRAEDTAVYYCAR |
| 9A2-VR24.27 | EVQLLESGGGLVQPGGSLRLSCAAS | GFTFPWYRVH | WVRQAPGKGLEWVS | SIRSSGGFPYYNRRVKG | RFTISRDNSKNTLYLQMNSLRAEDTAVYYCAR |
| 9A2-VR24.29 | EVQLLESGGGLVQPGGSLRLSCAAS | GFTFPWYRVH | WVRQAPGKGLEWVS | SIRSSGGFPYYNHKVKG | RFTISRDNSKNTLYLQMNSLRAEDTAVYYCAR |
| 9A2-VR24.30 | EVQLLESGGGLVQPGGSLRLSCAAS | GFTFPWYRVH | WVRQAPGKGLEWVS | SIRSSGGFPYYHPSVKG | RFTISRDNSKNTLYLQMNSLRAEDTAVYYCAR |
| 9A2-VR24.33 | EVQLLESGGGLVQPGGSLRLSCAAS | GFTFPWYRVH | WVRQAPGKGLEWVS | SIKSSGGFPYYNSSVKG | RFTISRDNSKNTLYLQMNSLRAEDTAVYYCAR |
| 9A2-VR24.44 | EVQLLESGGGLVQPGGSLRLSCAAS | GFTFPWYRVH | WVRQAFGKGLEWVS | SIRSSGGFPYYNSLVKG | RFTISRDNSKNTLYLQMNSLRAEDTAVYYCAR |
| 9A2-VR24.97 | EVQLLESGGGLVQPGGSLRLSCAAS | GFTFPWYRVH | WVRQAPGKGLEWVS | SIRSSGGFPHYNSVKG | RFTISRDNSKNTLYLQMNSLRAEDTAVYYCAR |
| 9A2-VR24.98 | EVQLLESGGGLVQPGGSLRLSCAAS | GFTFPWYRVH | WVRQAPGKGLEWVS | SIRSSGGFPYYNPFVKG | RFTISRDNSKNTLYLQMNSLRAEDTAVYYCAR |
| 9A2-VR24.102 | EVQLLESGGGLVQPGGSLRLSCAAS | GFTFPWYRVH | WVRQAPGKGLEWVS | SIRSSGGFPYYNNHVKG | RFTISRDNSKNTLYLQMNSLRAEDTAVYYCAR |
| 9A2-VR24.107 | EVQLLESGGGLVQPGGSLRLSCAAS | GFTFPWYRVH | WVRQAPGKGLEWVS | SIRSSGGFPMYNPHVKG | RFTISRDNSKNTLYLQMNSLRAEDTAVYYCAR |
| 9A2-VR24.110 | EVQLLESGGGLVQPGGSLRLSCAAS | GFTFFPWYRVH | WVRQAPGKGLEWVS | SIRSSGGFPYYMINPHKG | RFTISRDNSKNTLYLQMNSLRAEDTAVYYCAR |
| 9A2-VR24.111 | EVQLLESGGGLVQPGGSLRLSCAAS | GFTFPWYRVH | WVRQAPGKGLEWVS | SIRSSGGFPYYYNSVHN | RFTISRDNSKNTLYLQMNSLRAEDTAVYYCAR |
| 9A2-VR24.55 | EVQLLESGGGLVQPGGSLRLSCAAS | GFTFPWYRVH | WVRQAFGKGLEWVS | SIRSSGGFTYYNPAVRG | RFTISRDNSKNTLYLQMNSLRAEDTAVYYCAR |
| 9A2-VR24.56 | EVQLLESGGGLVQPGGSLRLSCAAS | GFTFPWYRVH | WVRQAPGKGLEWVS | SIRSSGGFTYYNSEVKG | RFTISRDNSKNTLYLQMNSLRAEDTAVYYCAR |
| 9A2-VR24.57 | EVQLLESGGGLVQPGGSLRLSCAAS | GFTFPWYRVH | WVRQAPGKGLEWVS | SIRSSGGFTYYNPFVKH | RFTISRDNSKNTLYLQMNSLRAEDTAVYYCAR |
| 9A2-VR24.122 | EVQLLESGGGLVQPGGSLRLSCAAS | GFTFPWYRVH | WVRQAFGKGLEWVS | SIRSSGGFTYYTPSVKG | RFTISRDNSKNTLYLQMNSLRAEDTAVYYCAR |
| 9A2-VR24.124 | EVQLLESGGGLVQPGGSLRLSCAAS | GFTFPWYRVH | WVRQAPGKGLEWVS | SIRSSGGFTYYNPSVNG | RFTISRDNSKNTLYLQMNSLRAEDTAVYYCAR |
| 9A2-VR24.131 | EVQLLESGGGLVQPGGSLRLSCAAS | GFTFPWYRVH | WVRQAPGKGLEWVS | SIRSSGGFTYYNPSVNG | RFTISRDNSKNTLYLQMNSLRAEDTAVYYCAR |
| Consensus | EVQLLESGGGLVQPGGSLRLSCAAS | GFTFPWYRVH | WVRQAPGKGLEWVS | SIXXXXXXXXXXXXXX | RFTISRDNSKNTLYLQMNSLRAEDTAVYYCAR |

```
                                    RSSGGFTY ADS KG
                                    HTHRHIPH HQK FN
                                    QHGSNS  F NYR MH
                                    KNQYQW  M SKV
                                     DNKV   THF
                                     E TY    PH
                                       V     LA
                                       R     SE
                                       F     N
                                       D
```

FIG. 3A

| | CDR3 | | |
|---|---|---|---|
| 9A2-VR24 | FYDSFFDI | WGQGTMVTVSS | SEQ ID NO: 25 |
| 9A2-VR24.04 | FYDSFFDI | WGQGTMVTVSS | SEQ ID NO: 49 |
| 9A2-VR24.07 | FYDSFFDI | WGQGTMVTVSS | SEQ ID NO: 50 |
| 9A2-VR24.10 | FYDSFFDI | WGQGTMVTVSS | SEQ ID NO: 51 |
| 9A2-VR24.12 | FYDSFFDI | WGQGTMVTVSS | SEQ ID NO: 52 |
| 9A2-VR24.19 | FYDSFFDI | WGQGTMVTVSS | SEQ ID NO: 53 |
| 9A2-VR24.24 | FYDSFFDI | WGQGTMVTVSS | SEQ ID NO: 54 |
| 9A2-VR24.76 | FYDSFFDI | WGQGTMVTVSS | SEQ ID NO: 55 |
| 9A2-VR24.81 | FYDSFFDI | WGQGTMVTVSS | SEQ ID NO: 57 |
| 9A2-VR24.82 | FYDSFFDI | WGQGTMVTVSS | SEQ ID NO: 58 |
| 9A2-VR24.84 | FYDSFFDI | WGQGTMVTVSS | SEQ ID NO: 59 |
| 9A2-VR24.87 | FYDSFFDI | WGQGTMVTVSS | SEQ ID NO: 60 |
| 9A2-VR24.91 | FYDSFFDI | WGQGTMVTVSS | SEQ ID NO: 61 |
| 9A2-VR24.93 | FYDSFFDI | WGQGTMVTVSS | SEQ ID NO: 62 |
| 9A2-VR24.27 | FYDSFFDI | WGQGTMVTVSS | SEQ ID NO: 63 |
| 9A2-VR24.29 | FYDSFFDI | WGQGTMVTVSS | SEQ ID NO: 64 |
| 9A2-VR24.30 | FYDSFFDI | WGQGTMVTVSS | SEQ ID NO: 65 |
| 9A2-VR24.33 | FYDSFFDI | WGQGTMVTVSS | SEQ ID NO: 66 |
| 9A2-VR24.44 | FYDSFFDI | WGQGTMVTVSS | SEQ ID NO: 67 |
| 9A2-VR24.97 | FYDSFFDI | WGQGTMVTVSS | SEQ ID NO: 68 |
| 9A2-VR24.98 | FYDSFFDI | WGQGTMVTVSS | SEQ ID NO: 69 |
| 9A2-VR24.102 | FYDSFFDI | WGQGTMVTVSS | SEQ ID NO: 70 |
| 9A2-VR24.107 | FYDSFFDI | WGQGTMVTVSS | SEQ ID NO: 71 |
| 9A2-VR24.110 | FYDSFFDI | WGQGTMVTVSS | SEQ ID NO: 72 |
| 9A2-VR24.111 | FYDSFFDI | WGQGTMVTVSS | SEQ ID NO: 73 |
| 9A2-VR24.55 | FYDSFFDI | WGQGTMVTVSS | SEQ ID NO: 74 |
| 9A2-VR24.56 | FYDSFFDI | WGQGTMVTVSS | SEQ ID NO: 75 |
| 9A2-VR24.57 | FYDSFFDI | WGQGTMVTVSS | SEQ ID NO: 76 |
| 9A2-VR24.122 | FYDSFFDI | WGQGTMVTVSS | SEQ ID NO: 77 |
| 9A2-VR24.124 | FYDSFFDI | WGQGTMVTVSS | SEQ ID NO: 78 |
| 9A2-VR24.131 | FYDSFFDI | WGQGTMVTVSS | SEQ ID NO: 79 |
| Consensus | FYDSFFDI | WGQGTMVTVSS | |

| | CDR3 | | |
|---|---|---|---|
| 9A2-VR39 | FYDSFFDI | WGQGTMVTVSS | SEQ ID NO: 37 |
| 9A2-VR39.01 | FYDSFFDI | WGQGTMVTVSS | SEQ ID NO: 80 |
| 9A2-VR39.02 | FYDSFFDI | WGQGTMVTVSS | SEQ ID NO: 81 |
| 9A2-VR39.04 | FYDSFFDI | WGQGTMVTVSS | SEQ ID NO: 82 |
| 9A2-VR39.05 | FYDSFFDI | WGQGTMVTVSS | SEQ ID NO: 83 |
| 9A2-VR39.06 | FYDSFFDI | WGQGTMVTVSS | SEQ ID NO: 84 |
| 9A2-VR39.11 | FYDSFFDI | WGQGTMVTVSS | SEQ ID NO: 85 |
| 9A2-VR39.12 | FYDSFFDI | WGQGTMVTVSS | SEQ ID NO: 86 |
| 9A2-VR39.15 | FYDSFFDI | WGQGTMVTVSS | SEQ ID NO: 87 |
| 9A2-VR39.17 | FYDSFFDI | WGQGTMVTVSS | SEQ ID NO: 88 |
| 9A2-VR39.18 | FYDSFFDI | WGQGTMVTVSS | SEQ ID NO: 89 |
| 9A2-VR39.19 | FYDSFFDI | WGQGTMVTVSS | SEQ ID NO: 90 |
| 9A2-VR39.21 | FYDSFFDI | WGQGTMVTVSS | SEQ ID NO: 91 |
| 9A2-VR39.22 | FYDSFFDI | WGQGTMVTVSS | SEQ ID NO: 92 |
| 9A2-VR39.23 | FYDSFFDI | WGQGTMVTVSS | SEQ ID NO: 93 |
| 9A2-VR39.24 | FYDSFFDI | WGQGTMVTVSS | SEQ ID NO: 94 |
| 9A2-VR39.97 | FYDSFFDI | WGQGTMVTVSS | SEQ ID NO: 95 |
| 9A2-VR39.98 | FYDSFFDI | WGQGTMVTVSS | SEQ ID NO: 96 |
| 9A2-VR39.102 | FYDSFFDI | WGQGTMVTVSS | SEQ ID NO: 97 |
| 9A2-VR39.105 | FYDSFFDI | WGQGTMVTVSS | SEQ ID NO: 98 |
| 9A2-VR39.109 | FYDSFFDI | WGQGTMVTVSS | SEQ ID NO: 99 |
| 9A2-VR39.110 | FYDSFFDI | WGQGTMVTVSS | SEQ ID NO: 100 |
| 9A2-VR39.111 | FYDSFFDI | WGQGTMVTVSS | SEQ ID NO: 101 |
| 9A2-VR39.112 | FYDSFFDI | WGQGTMVTVSS | SEQ ID NO: 102 |
| 9A2-VR39.116 | FYDSFFDI | WGQGTMVTVSS | SEQ ID NO: 103 |
| 9A2-VR39.27 | FYDSFFDI | WGQGTMVTVSS | SEQ ID NO: 104 |
| 9A2-VR39.28 | FYDSFFDI | WGQGTMVTVSS | SEQ ID NO: 105 |
| 9A2-VR39.46 | FYDSFFDI | WGQGTMVTVSS | SEQ ID NO: 106 |
| 9A2-VR39.122 | FYDSFFDI | WGQGTMVTVSS | SEQ ID NO: 107 |
| 9A2-VR39.139 | FYDSFFDI | WGQGTMVTVSS | SEQ ID NO: 108 |
| 9A2-VR39.140 | FYDSFFDI | WGQGTMVTVSS | SEQ ID NO: 109 |
| 9A2-VR39.148 | FYDSFFDI | WGQGTMVTVSS | SEQ ID NO: 110 |
| 9A2-VR39.152 | FYDSFFDI | WGQGTMVTVSS | SEQ ID NO: 111 |
| 9A2-VR39.77 | FYDSFFDI | WGQGTMVTVSS | SEQ ID NO: 112 |
| 9A2-VR39.93 | FYDSFFDI | WGQGTMVTVSS | SEQ ID NO: 113 |
| 9A2-VR39.174 | FYDSFFDI | WGQGTMVTVSS | SEQ ID NO: 114 |
| 9A2-VR39.177 | FYDSFFDI | WGQGTMVTVSS | SEQ ID NO: 115 |
| | | | SEQ ID NO: 116 |
| Consensus | FYDSFFDI | WGQGTMVTVSS | |

DIQMTQSPSSVSASVGDRVTITCRASQGISSWLAWYQQKPGKAPKLLIYAASSLQS
                                 L1.1

GVPSRFSGSGSGTDFTLTISSLQPEDFATYYCQQANSFPITFGQGTRLEIKRTVAA
                                        L3.1 L3.2

FIG. 5B

EVQLLESGGGLVQPGGSLRLSCAASGFTFSHYHMLWVRQAPGKGLEWVSSIRSSGGF
                              H1.1                    H2.1

TYYADSVKGRFTISRDNSKNTLYLQMNSLRAEDTAVYYCARFYDSFFDIWGQGTMVTVSS
                                          H3.1 H3.2

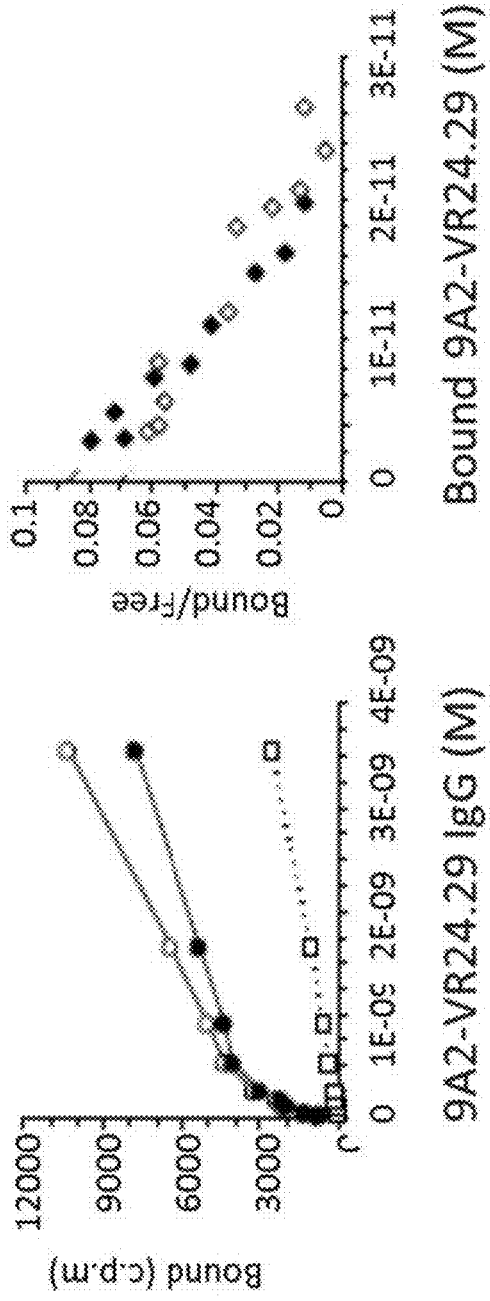
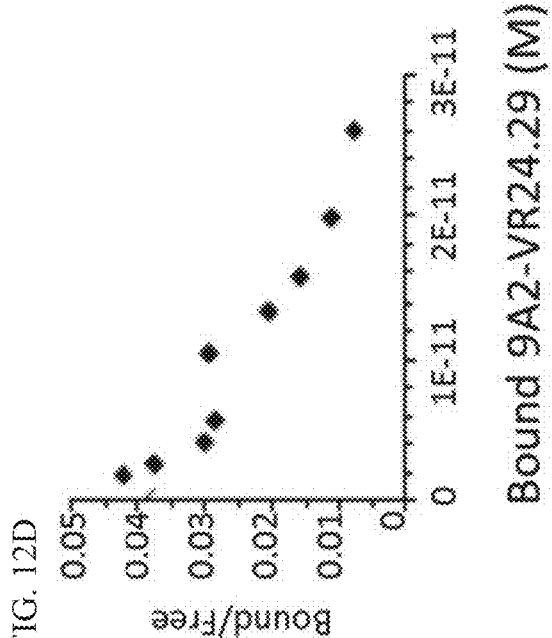
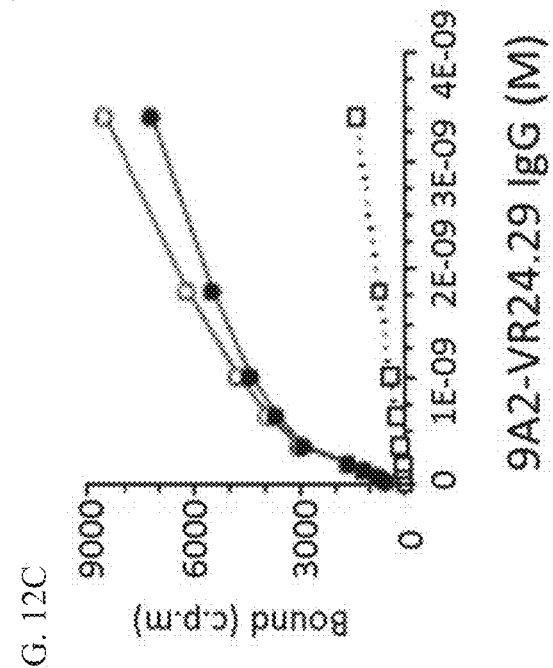
FIG. 12A
FIG. 12B
FIG. 12C
FIG. 12D

| Cells | 9A2-VR24.29 IgG ($K_D$ pM) | 9A2-VR24.29 Fab ($K_D$ pM) |
|---|---|---|
| Neutrophils | 246 ±17 | 384 ±29 |
| Eosinophils | 730 ±83 | |
| | 528 ±78 | |
| TF1 cells | 361 ±24 | 656 ±41 |
| | 303 ±32 | 668 ±25 |
| | 393 ±32 | 522 ±24 |
| Average for all cells (±SEM) | 426 ±79 | 569 ±93 |

FIG. 13

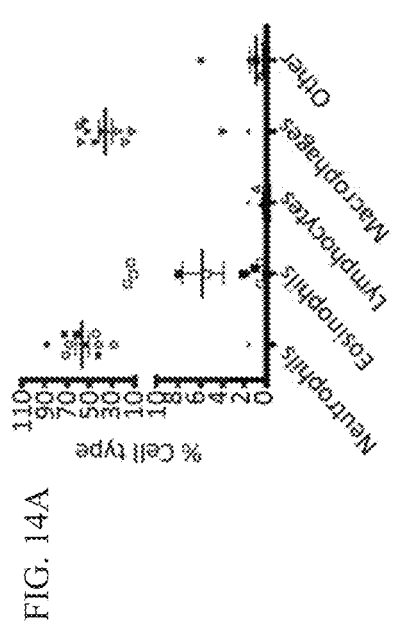
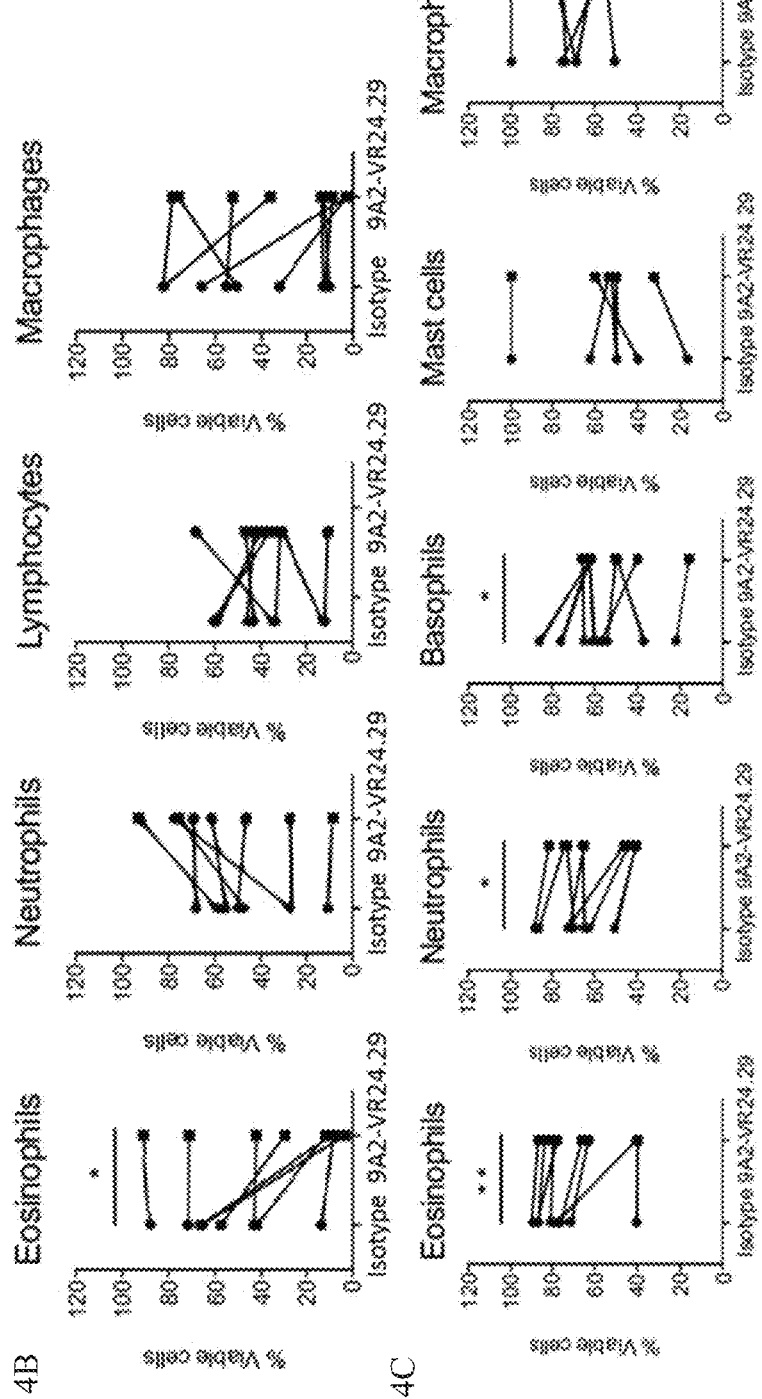
FIG. 14A
FIG. 14B
FIG. 14C

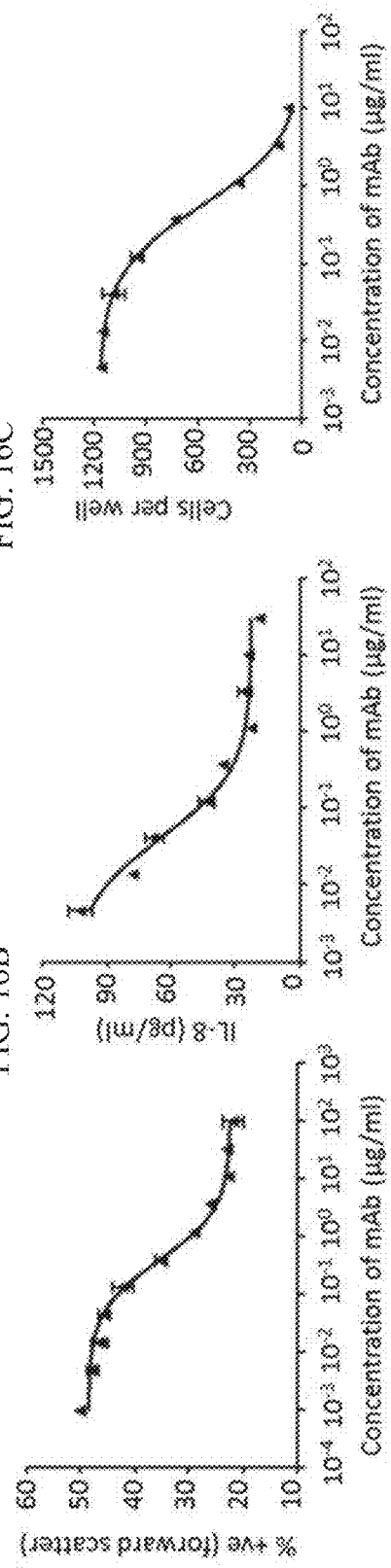
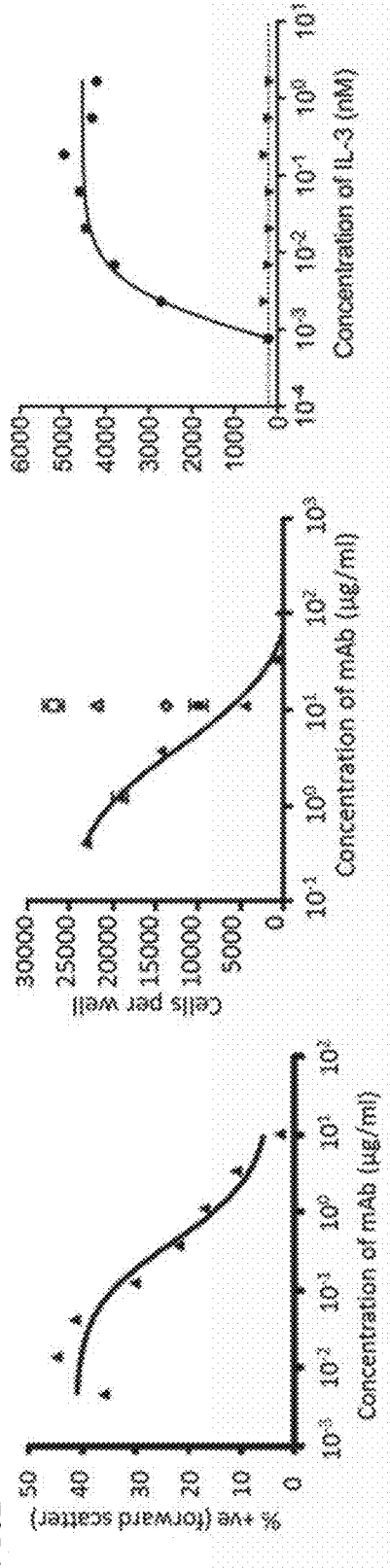
FIG. 16A FIG. 16B FIG. 16C FIG. 16D FIG. 16E FIG. 16F

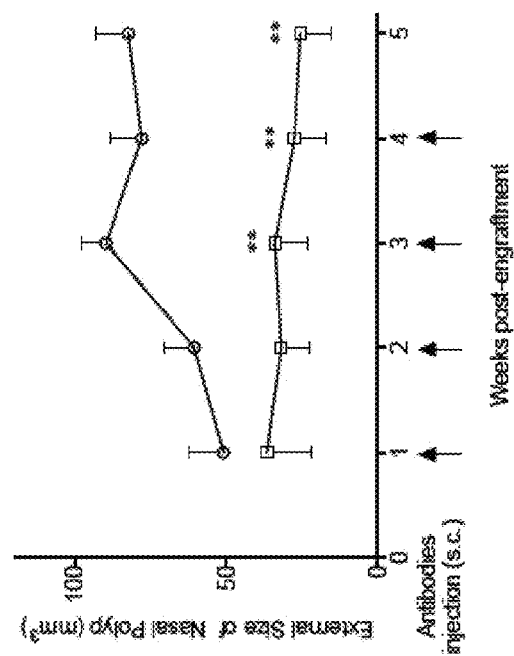
FIG. 17A
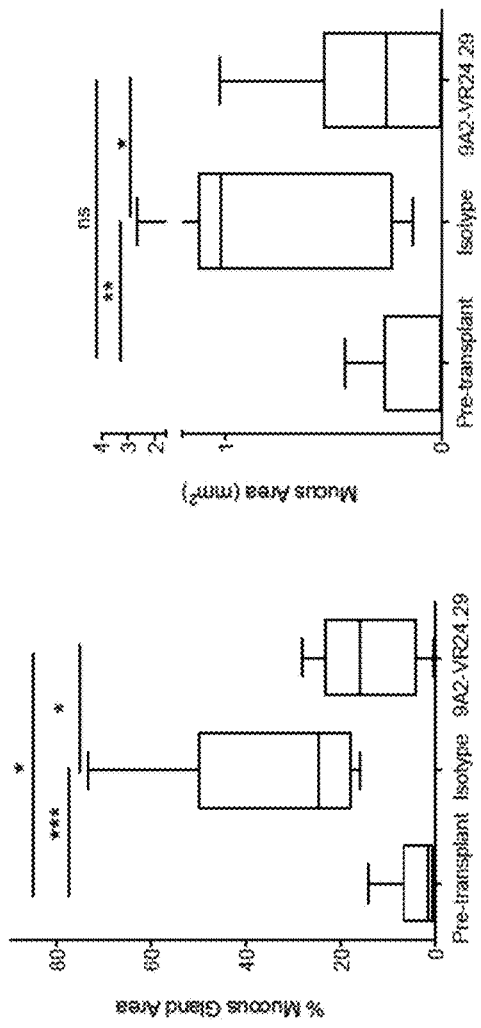
FIG. 17B
FIG. 17C

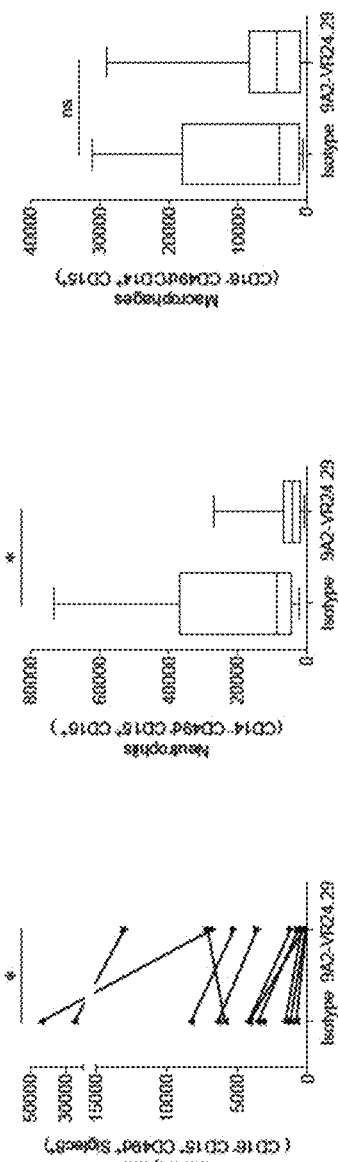
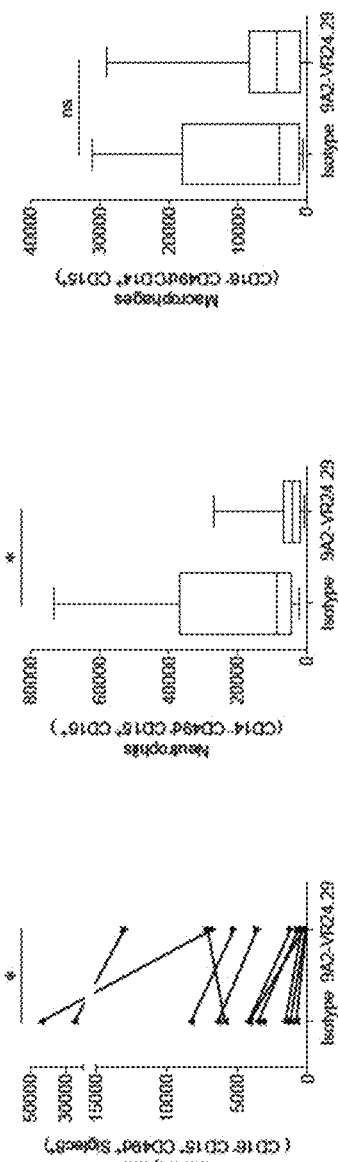
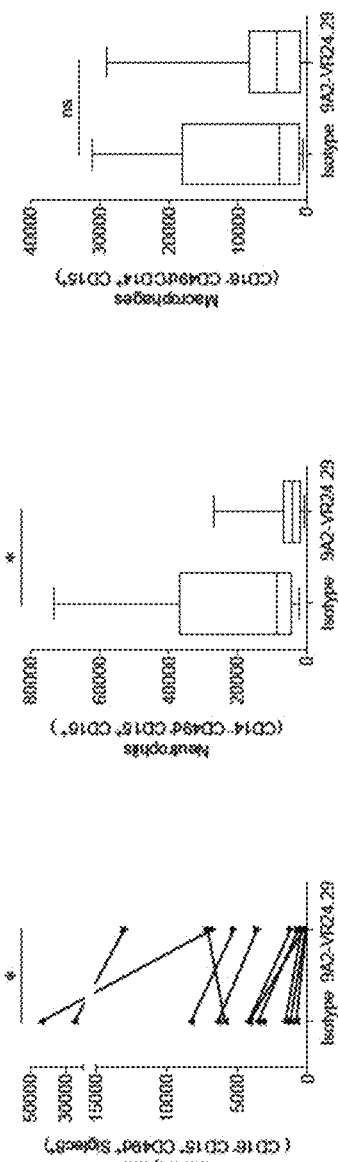
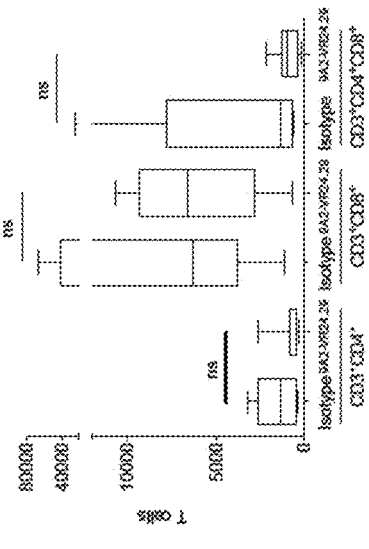
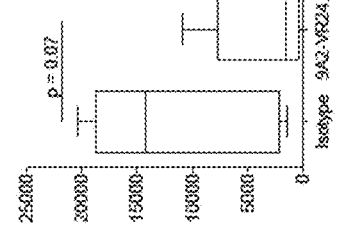
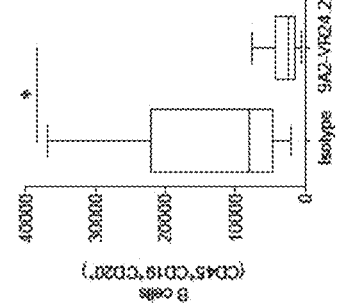
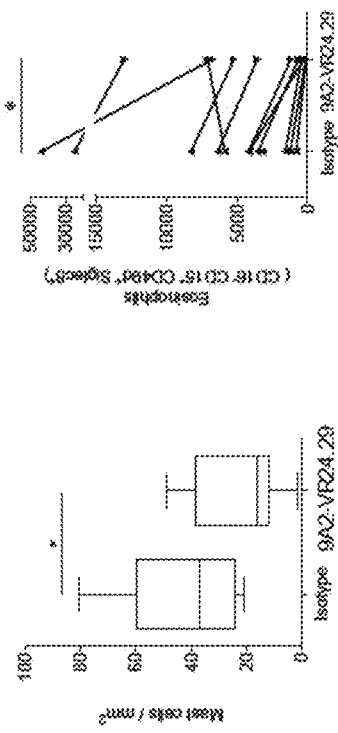

SEQUENCE LISTING

```
<160> NUMBER OF SEQ ID NOS: 197

<210> SEQ ID NO 1
<211> LENGTH: 897
<212> TYPE: PRT
<213> ORGANISM: Homo sapiens

<400> SEQUENCE: 1

Met Val Leu Ala Gln Gly Leu Leu Ser Met Ala Leu Leu Ala Leu Cys
1               5                   10                  15

Trp Glu Arg Ser Leu Ala Gly Ala Glu Glu Thr Ile Pro Leu Gln Thr
            20                  25                  30

Leu Arg Cys Tyr Asn Asp Tyr Thr Ser His Ile Thr Cys Arg Trp Ala
        35                  40                  45

Asp Thr Gln Asp Ala Gln Arg Leu Val Asn Val Thr Leu Ile Arg Arg
    50                  55                  60

Val Asn Glu Asp Leu Leu Glu Pro Val Ser Cys Asp Leu Ser Asp Asp
65                  70                  75                  80

Met Pro Trp Ser Ala Cys Pro His Pro Arg Cys Val Pro Arg Arg Cys
                85                  90                  95

Val Ile Pro Cys Gln Ser Phe Val Val Thr Asp Val Asp Tyr Phe Ser
            100                 105                 110

Phe Gln Pro Asp Arg Pro Leu Gly Thr Arg Leu Thr Val Thr Leu Thr
        115                 120                 125

Gln His Val Gln Pro Pro Glu Pro Arg Asp Leu Gln Ile Ser Thr Asp
    130                 135                 140

Gln Asp His Phe Leu Leu Thr Trp Ser Val Ala Leu Gly Ser Pro Gln
145                 150                 155                 160

Ser His Trp Leu Ser Pro Gly Asp Leu Glu Phe Glu Val Val Tyr Lys
                165                 170                 175

Arg Leu Gln Asp Ser Trp Glu Asp Ala Ala Ile Leu Leu Ser Asn Thr
            180                 185                 190
```

-continued

```
Ser Gln Ala Thr Leu Gly Pro Glu His Leu Met Pro Ser Ser Thr Tyr
    195                 200                 205
Val Ala Arg Val Arg Thr Arg Leu Ala Pro Gly Ser Arg Leu Ser Gly
210                 215                 220
Arg Pro Ser Lys Trp Ser Pro Glu Val Cys Trp Asp Ser Gln Pro Gly
225                 230                 235                 240
Asp Glu Ala Gln Pro Gln Asn Leu Glu Cys Phe Phe Asp Gly Ala Ala
                245                 250                 255
Val Leu Ser Cys Ser Trp Glu Val Arg Lys Glu Val Ala Ser Ser Val
            260                 265                 270
Ser Phe Gly Leu Phe Tyr Lys Pro Ser Pro Asp Ala Gly Glu Glu
        275                 280                 285
Cys Ser Pro Val Leu Arg Glu Gly Leu Gly Ser Leu His Thr Arg His
    290                 295                 300
His Cys Gln Ile Pro Val Pro Asp Pro Ala Thr His Gly Gln Tyr Ile
305                 310                 315                 320
Val Ser Val Gln Pro Arg Arg Ala Glu Lys His Ile Lys Ser Ser Val
                325                 330                 335
Asn Ile Gln Met Ala Pro Pro Ser Leu Asn Val Thr Lys Asp Gly Asp
            340                 345                 350
Ser Tyr Ser Leu Arg Trp Glu Thr Met Lys Met Arg Tyr Glu His Ile
        355                 360                 365
Asp His Thr Phe Glu Ile Gln Tyr Arg Lys Asp Thr Ala Thr Trp Lys
    370                 375                 380
Asp Ser Lys Thr Glu Thr Leu Gln Asn Ala His Ser Met Ala Leu Pro
385                 390                 395                 400
Ala Leu Glu Pro Ser Thr Arg Tyr Trp Ala Arg Val Arg Val Arg Thr
                405                 410                 415
Ser Arg Thr Gly Tyr Asn Gly Ile Trp Ser Glu Trp Ser Glu Ala Arg
            420                 425                 430
Ser Trp Asp Thr Glu Ser Val Leu Pro Met Trp Val Leu Ala Leu Ile
        435                 440                 445
Val Ile Phe Leu Thr Ile Ala Val Leu Leu Ala Leu Arg Phe Cys Gly
    450                 455                 460
Ile Tyr Gly Tyr Arg Leu Arg Arg Lys Trp Glu Glu Lys Ile Pro Asn
465                 470                 475                 480
Pro Ser Lys Ser His Leu Phe Gln Asn Gly Ser Ala Glu Leu Trp Pro
                485                 490                 495
Pro Gly Ser Met Ser Ala Phe Thr Ser Gly Ser Pro Pro His Gln Gly
            500                 505                 510
Pro Trp Gly Ser Arg Phe Pro Glu Leu Glu Gly Val Phe Pro Val Gly
        515                 520                 525
Phe Gly Asp Ser Glu Val Ser Pro Leu Thr Ile Glu Asp Pro Lys His
    530                 535                 540
Val Cys Asp Pro Pro Ser Gly Pro Asp Thr Thr Pro Ala Ala Ser Asp
545                 550                 555                 560
Leu Pro Thr Glu Gln Pro Pro Ser Pro Gln Pro Gly Pro Pro Ala Ala
                565                 570                 575
Ser His Thr Pro Glu Lys Gln Ala Ser Ser Phe Asp Phe Asn Gly Pro
            580                 585                 590
Tyr Leu Gly Pro Pro His Ser Arg Ser Leu Pro Asp Ile Leu Gly Gln
        595                 600                 605
```

```
Pro Glu Pro Pro Gln Glu Gly Gly Ser Gln Lys Ser Pro Pro Gly
    610                 615                 620
Ser Leu Glu Tyr Leu Cys Leu Pro Ala Gly Gln Val Gln Leu Val
625                 630                 635                 640
Pro Leu Ala Gln Ala Met Gly Pro Gly Gln Ala Val Glu Val Glu Arg
            645                 650                 655
Arg Pro Ser Gln Gly Ala Ala Gly Ser Pro Ser Leu Glu Ser Gly Gly
            660                 665                 670
Gly Pro Ala Pro Ala Leu Gly Pro Arg Val Gly Gln Asp Gln
            675                 680                 685
Lys Asp Ser Pro Val Ala Ile Pro Met Ser Ser Gly Asp Thr Glu Asp
690                 695                 700
Pro Gly Val Ala Ser Gly Tyr Val Ser Ser Ala Asp Leu Val Phe Thr
705                 710                 715                 720
Pro Asn Ser Gly Ala Ser Ser Val Ser Leu Val Pro Ser Leu Gly Leu
            725                 730                 735
Pro Ser Asp Gln Thr Pro Ser Leu Cys Pro Gly Leu Ala Ser Gly Pro
            740                 745                 750
Pro Gly Ala Pro Gly Pro Val Lys Ser Gly Phe Glu Gly Tyr Val Glu
            755                 760                 765
Leu Pro Pro Ile Glu Gly Arg Ser Pro Arg Ser Pro Arg Asn Asn Pro
770                 775                 780
Val Pro Pro Glu Ala Lys Ser Pro Val Leu Asn Pro Gly Glu Arg Pro
785                 790                 795                 800
Ala Asp Val Ser Pro Thr Ser Pro Gln Pro Glu Gly Leu Leu Val Leu
            805                 810                 815
Gln Gln Val Gly Asp Tyr Cys Phe Leu Pro Gly Leu Gly Pro Gly Pro
            820                 825                 830
Leu Ser Leu Arg Ser Lys Pro Ser Ser Pro Gly Pro Gly Pro Glu Ile
            835                 840                 845
Lys Asn Leu Asp Gln Ala Phe Gln Val Lys Lys Pro Pro Gly Gln Ala
850                 855                 860
Val Pro Gln Val Pro Val Ile Gln Leu Phe Lys Ala Leu Lys Gln Gln
865                 870                 875                 880
Asp Tyr Leu Ser Leu Pro Pro Trp Glu Val Asn Lys Pro Gly Glu Val
            885                 890                 895
Cys
```

<210> SEQ ID NO 2
<211> LENGTH: 378
<212> TYPE: PRT
<213> ORGANISM: Homo sapiens
<400> SEQUENCE: 2

```
Met Val Leu Leu Trp Leu Thr Leu Leu Leu Ile Ala Leu Pro Cys Leu
1                   5                   10                  15
Leu Gln Thr Lys Glu Asp Pro Asn Pro Ile Thr Asn Leu Arg Met
                20                  25                  30
Lys Ala Lys Ala Gln Gln Leu Thr Trp Asp Leu Asn Arg Asn Val Thr
            35                  40                  45
Asp Ile Glu Cys Val Lys Asp Ala Asp Tyr Ser Met Pro Ala Val Asn
        50                  55                  60
Asn Ser Tyr Cys Gln Phe Gly Ala Ile Ser Leu Cys Glu Val Thr Asn
65                  70                  75                  80
```

```
Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
    130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Phe Ser Gln Ile Glu Ile Leu
        195                 200                 205

Thr Pro Pro Asn Met Thr Ala Lys Cys Asn Lys Thr His Ser Phe Met
    210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Glu Gly Ala Asn Thr Arg Ala Trp
    290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
    370                 375

<210> SEQ ID NO 3
<211> LENGTH: 836
<212> TYPE: PRT
<213> ORGANISM: Homo sapiens

<400> SEQUENCE: 3

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
        35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80
```

```
Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
    130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
    370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415

Ser Arg Pro Thr Pro Val Val Phe Ser Glu Ser Arg Gly Pro Ala Leu
            420                 425                 430

Thr Arg Leu His Ala Met Ala Arg Asp Pro His Ser Leu Trp Val Gly
        435                 440                 445

Trp Glu Pro Pro Asn Pro Trp Pro Gln Gly Tyr Val Ile Glu Trp Gly
    450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495
```

```
Phe Gln Leu Tyr Glu Ile Ile Val Thr Pro Leu Tyr Gln Asp Thr Met
            500                 505                 510

Gly Pro Ser Gln His Val Tyr Ala Tyr Ser Gln Glu Met Ala Pro Ser
        515                 520                 525

His Ala Pro Glu Leu His Leu Lys His Ile Gly Lys Thr Trp Ala Gln
    530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                565                 570                 575

Ile Leu Asn Ala Ser Ser Arg Gly Phe Val Leu His Gly Leu Glu Pro
            580                 585                 590

Ala Ser Leu Tyr His Ile His Leu Met Ala Ala Ser Gln Ala Gly Ala
        595                 600                 605

Thr Asn Ser Thr Val Leu Thr Leu Met Thr Leu Thr Pro Glu Gly Ser
    610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
            660                 665                 670

Trp Val Pro Thr Ile Met Glu Glu Asp Ala Phe Gln Leu Pro Gly Leu
        675                 680                 685

Gly Thr Pro Pro Ile Thr Lys Leu Thr Val Leu Glu Glu Asp Glu Lys
    690                 695                 700

Lys Pro Val Pro Trp Glu Ser His Asn Ser Ser Glu Thr Cys Gly Leu
705                 710                 715                 720

Pro Thr Leu Val Gln Thr Tyr Val Leu Gln Gly Asp Pro Arg Ala Val
                725                 730                 735

Ser Thr Gln Pro Gln Ser Gln Ser Gly Thr Ser Asp Gln Val Leu Tyr
            740                 745                 750

Gly Gln Leu Leu Gly Ser Pro Thr Ser Pro Gly Pro Gly His Tyr Leu
        755                 760                 765

Arg Cys Asp Ser Thr Gln Pro Leu Leu Ala Gly Leu Thr Pro Ser Pro
    770                 775                 780

Lys Ser Tyr Glu Asn Leu Trp Phe Gln Ala Ser Pro Leu Gly Thr Leu
785                 790                 795                 800

Val Thr Pro Ala Pro Ser Gln Glu Asp Asp Cys Val Phe Gly Pro Leu
                805                 810                 815

Leu Asn Phe Pro Leu Leu Gln Gly Ile Arg Val His Gly Met Glu Ala
            820                 825                 830

Leu Gly Ser Phe
        835

<210> SEQ ID NO 4
<211> LENGTH: 420
<212> TYPE: PRT
<213> ORGANISM: Homo sapiens

<400> SEQUENCE: 4

Met Ile Ile Val Ala His Val Leu Leu Ile Leu Leu Gly Ala Thr Glu
1               5                   10                  15

Ile Leu Gln Ala Asp Leu Leu Pro Asp Glu Lys Ile Ser Leu Leu Pro
            20                  25                  30
```

Pro Val Asn Phe Thr Ile Lys Val Thr Gly Leu Ala Gln Val Leu Leu
            35                  40                  45

Gln Trp Lys Pro Asn Pro Asp Gln Glu Gln Arg Asn Val Asn Leu Glu
 50                  55                  60

Tyr Gln Val Lys Ile Asn Ala Pro Lys Glu Asp Asp Tyr Glu Thr Arg
 65                  70                  75                  80

Ile Thr Glu Ser Lys Cys Val Thr Ile Leu His Lys Gly Phe Ser Ala
                 85                  90                  95

Ser Val Arg Thr Ile Leu Gln Asn Asp His Ser Leu Leu Ala Ser Ser
            100                 105                 110

Trp Ala Ser Ala Glu Leu His Ala Pro Pro Gly Ser Pro Gly Thr Ser
            115                 120                 125

Ile Val Asn Leu Thr Cys Thr Thr Asn Thr Thr Glu Asp Asn Tyr Ser
            130                 135                 140

Arg Leu Arg Ser Tyr Gln Val Ser Leu His Cys Thr Trp Leu Val Gly
145                 150                 155                 160

Thr Asp Ala Pro Glu Asp Thr Gln Tyr Phe Leu Tyr Tyr Arg Tyr Gly
                165                 170                 175

Ser Trp Thr Glu Glu Cys Gln Glu Tyr Ser Lys Asp Thr Leu Gly Arg
            180                 185                 190

Asn Ile Ala Cys Trp Phe Pro Arg Thr Phe Ile Leu Ser Lys Gly Arg
            195                 200                 205

Asp Trp Leu Ala Val Leu Val Asn Gly Ser Ser Lys His Ser Ala Ile
            210                 215                 220

Arg Pro Phe Asp Gln Leu Phe Ala Leu His Ala Ile Asp Gln Ile Asn
225                 230                 235                 240

Pro Pro Leu Asn Val Thr Ala Glu Ile Glu Gly Thr Arg Leu Ser Ile
                245                 250                 255

Gln Trp Glu Lys Pro Val Ser Ala Phe Pro Ile His Cys Phe Asp Tyr
            260                 265                 270

Glu Val Lys Ile His Asn Thr Arg Asn Gly Tyr Leu Gln Ile Glu Lys
            275                 280                 285

Leu Met Thr Asn Ala Phe Ile Ser Ile Ile Asp Asp Leu Ser Lys Tyr
            290                 295                 300

Asp Val Gln Val Arg Ala Ala Val Ser Ser Met Cys Arg Glu Ala Gly
305                 310                 315                 320

Leu Trp Ser Glu Trp Ser Gln Pro Ile Tyr Val Gly Asn Asp Glu His
                325                 330                 335

Lys Pro Leu Arg Glu Trp Phe Val Ile Val Met Ala Thr Ile Cys
            340                 345                 350

Phe Ile Leu Leu Ile Leu Ser Leu Ile Cys Lys Ile Cys His Leu Trp
            355                 360                 365

Ile Lys Leu Phe Pro Pro Ile Pro Ala Pro Lys Ser Asn Ile Lys Asp
            370                 375                 380

Leu Phe Val Thr Thr Asn Tyr Glu Lys Ala Gly Ser Ser Glu Thr Glu
385                 390                 395                 400

Ile Glu Val Ile Cys Tyr Ile Glu Lys Pro Gly Val Glu Thr Leu Glu
                405                 410                 415

Asp Ser Val Phe
            420

<210> SEQ ID NO 5
<211> LENGTH: 112

```
<212> TYPE: PRT
<213> ORGANISM: Artificial Sequence
<220> FEATURE:
<223> OTHER INFORMATION: VL chain of antibody 9A2

<400> SEQUENCE: 5

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

<210> SEQ ID NO 6
<211> LENGTH: 112
<212> TYPE: PRT
<213> ORGANISM: Artificial Sequence
<220> FEATURE:
<223> OTHER INFORMATION: VL chain of antibody 9A2-VR1

<400> SEQUENCE: 6

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Pro Phe
            20                  25                  30

Met Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: VL chain of antibody 9A2-VR2

<400> SEQUENCE: 7

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Gln Arg Pro Phe
            20                  25                  30

Val Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
               100                 105                 110

<210> SEQ ID NO 8
<211> LENGTH: 112
<212> TYPE: PRT
<213> ORGANISM: Artificial Sequence
<220> FEATURE:
<223> OTHER INFORMATION: VL chain of antibody 9A2-VR3

<400> SEQUENCE: 8

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Leu Arg Pro Phe
                20                  25                  30

Val Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
               100                 105                 110

<210> SEQ ID NO 9
<211> LENGTH: 112
<212> TYPE: PRT
<213> ORGANISM: Artificial Sequence
<220> FEATURE:
<223> OTHER INFORMATION: VL chain of antibody 9A2-VR4

<400> SEQUENCE: 9

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Arg Pro Phe
                20                  25                  30

Val Asp Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
               100                 105                 110

<210> SEQ ID NO 10
<211> LENGTH: 112
<212> TYPE: PRT
<213> ORGANISM: Artificial Sequence
<220> FEATURE:
```

<223> OTHER INFORMATION: VL chain of antibody 9A2-VR5

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Pro Phe
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: VL chain of antibody 9A2-VR6

<400> SEQUENCE: 11

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Arg Pro Phe
            20                  25                  30

Val Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: VL chain of antibody 9A2-VR8

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Arg Pro Phe
            20                  25                  30

Ile Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ala Asn Ser Phe Pro Ile
                    85                  90                  95

Thr Phe Gly Gln Gly Thr Arg Leu Glu Ile Lys Arg Thr Val Ala Ala
                100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: VL chain of antibody 9A2-VR9

<400> SEQUENCE: 13

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Pro Phe
                20                  25                  30

Ile Asp Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                    85                  90                  95

Thr Phe Gly Gln Gly Thr Arg Leu Glu Ile Lys Arg Thr Val Ala Ala
                100                 105                 110
```

<210> SEQ ID NO 14
<211> LENGTH: 112
<212> TYPE: PRT
<213> ORGANISM: Artificial Sequence
<220> FEATURE:
<223> OTHER INFORMATION: VL chain of antibody 9A2-VR11

<400> SEQUENCE: 14

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Arg Pro Phe
                20                  25                  30

Val Ser Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                    85                  90                  95

Thr Phe Gly Gln Gly Thr Arg Leu Glu Ile Lys Arg Thr Val Ala Ala
                100                 105                 110
```

<210> SEQ ID NO 15
<211> LENGTH: 112
<212> TYPE: PRT
<213> ORGANISM: Artificial Sequence
<220> FEATURE:
<223> OTHER INFORMATION: VL chain of antibody 9A2-VR12

<400> SEQUENCE: 15

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Pro Phe
            20                  25                  30

Val Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: VL chain of antibody 9A2-VR13

<400> SEQUENCE: 16

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Lys Pro Val Leu Asp Pro Ile
                85                  90                  95

Thr Phe Gly Gln Gly Thr Arg Leu Glu Ile Lys Arg Thr Val Ala Ala
            100                 105                 110
```

<210> SEQ ID NO 17
<211> LENGTH: 112
<212> TYPE: PRT
<213> ORGANISM: Artificial Sequence
<220> FEATURE:
<223> OTHER INFORMATION: VL chain of antibody 9A2-VR14

<400> SEQUENCE: 17

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Lys Pro Val Phe Asp Pro Ile
```

```
                    85                  90                  95

Thr Phe Gly Gln Gly Thr Arg Leu Glu Ile Lys Arg Thr Val Ala Ala
                100                 105                 110

<210> SEQ ID NO 18
<211> LENGTH: 112
<212> TYPE: PRT
<213> ORGANISM: Artificial Sequence
<220> FEATURE:
<223> OTHER INFORMATION: VL chain of antibody 9A2-VR16

<400> SEQUENCE: 18

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Ile Pro Val Leu Gly Pro Ile
                85                  90                  95

Thr Phe Gly Gln Gly Thr Arg Leu Glu Ile Lys Arg Thr Val Ala Ala
                100                 105                 110

<210> SEQ ID NO 19
<211> LENGTH: 112
<212> TYPE: PRT
<213> ORGANISM: Artificial Sequence
<220> FEATURE:
<223> OTHER INFORMATION: VL chain of antibody 9A2-VR19

<400> SEQUENCE: 19

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Ile Pro Ile Leu Gly Pro Ile
                85                  90                  95

Thr Phe Gly Gln Gly Thr Arg Leu Glu Ile Lys Arg Thr Val Ala Ala
                100                 105                 110

<210> SEQ ID NO 20
<211> LENGTH: 117
<212> TYPE: PRT
<213> ORGANISM: Artificial Sequence
<220> FEATURE:
<223> OTHER INFORMATION: VH chain of antibody 9A2

<400> SEQUENCE: 20

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser His Tyr
        20                  25                  30

His Met Leu Trp Val Arg Gln Ala Pro Gly Lys Gly Leu Glu Trp Val
            35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 21
<211> LENGTH: 117
<212> TYPE: PRT
<213> ORGANISM: Artificial Sequence
<220> FEATURE:
<223> OTHER INFORMATION: VH chain of antibody 9A2-VR20

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn His Tyr
        20                  25                  30

Arg Val His Trp Val Arg Gln Ala Pro Gly Lys Gly Leu Glu Trp Val
            35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 22
<211> LENGTH: 117
<212> TYPE: PRT
<213> ORGANISM: Artificial Sequence
<220> FEATURE:
<223> OTHER INFORMATION: VH chain of antibody 9A2-VR21

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met His Tyr
        20                  25                  30

Arg Val His Trp Val Arg Gln Ala Pro Gly Lys Gly Leu Glu Trp Val
            35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
```

```
              65                  70                  75                  80
Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 23
<211> LENGTH: 117
<212> TYPE: PRT
<213> ORGANISM: Artificial Sequence
<220> FEATURE:
<223> OTHER INFORMATION: VH chain of antibody 9A2-VR22

<400> SEQUENCE: 23

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Gln Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 24
<211> LENGTH: 117
<212> TYPE: PRT
<213> ORGANISM: Artificial Sequence
<220> FEATURE:
<223> OTHER INFORMATION: VH chain of antibody 9A2-VR23

<400> SEQUENCE: 24

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Glu Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
            115
```

```
<210> SEQ ID NO 25
<211> LENGTH: 117
<212> TYPE: PRT
<213> ORGANISM: Artificial Sequence
<220> FEATURE:
<223> OTHER INFORMATION: VH chain of antibody 9A2-VR24

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 26
<211> LENGTH: 117
<212> TYPE: PRT
<213> ORGANISM: Artificial Sequence
<220> FEATURE:
<223> OTHER INFORMATION: VH chain of antibody 9A2-VR26

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile His Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 27
<211> LENGTH: 117
<212> TYPE: PRT
<213> ORGANISM: Artificial Sequence
<220> FEATURE:
<223> OTHER INFORMATION: VH chain of antibody 9A2-VR27

<400> SEQUENCE: 27

Glu Val Gln Leu Leu Glu Ser Gly Gly Gly Leu Val Gln Pro Gly Gly
```

```
1               5                  10                  15
Ser Leu Arg Leu Ser Cys Ala Ala Ser Gly Phe Thr Phe Thr His Tyr
            20                  25                  30

Arg Val His Trp Val Arg Gln Ala Pro Gly Lys Gly Leu Glu Trp Val
            35                  40                  45

Ser Ser Ile Arg Ser Ser Gly Gly Phe Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 28
<211> LENGTH: 117
<212> TYPE: PRT
<213> ORGANISM: Artificial Sequence
<220> FEATURE:
<223> OTHER INFORMATION: VH chain of antibody 9A2-VR28

<400> SEQUENCE: 28

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Val His Tyr
            20                  25                  30

Arg Val His Trp Val Arg Gln Ala Pro Gly Lys Gly Leu Glu Trp Val
            35                  40                  45

Ser Ser Ile Arg Ser Ser Gly Gly Phe Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 29
<211> LENGTH: 117
<212> TYPE: PRT
<213> ORGANISM: Artificial Sequence
<220> FEATURE:
<223> OTHER INFORMATION: VH chain of antibody 9A2-VR31

<400> SEQUENCE: 29

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
            35                  40                  45

Ser Ser Ile Ser Gly Ala Gln Trp Ser Thr Tyr Tyr Ala Asp Ser Val
        50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 30
<211> LENGTH: 117
<212> TYPE: PRT
<213> ORGANISM: Artificial Sequence
<220> FEATURE:
<223> OTHER INFORMATION: VH chain of antibody 9A2-VR32

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Ser Gly Ser Val Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: VH chain of antibody 9A2-VR33

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Ser Gly Trp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 32
<211> LENGTH: 117
<212> TYPE: PRT
<213> ORGANISM: Artificial Sequence
<220> FEATURE:
<223> OTHER INFORMATION: VH chain of antibody 9A2-VR34

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Ser Gly Ser His Phe Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 33
<211> LENGTH: 117
<212> TYPE: PRT
<213> ORGANISM: Artificial Sequence
<220> FEATURE:
<223> OTHER INFORMATION: VH chain of antibody 9A2-VR35

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Phe Gly Arg Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 34
<211> LENGTH: 117
<212> TYPE: PRT
<213> ORGANISM: Artificial Sequence
<220> FEATURE:
<223> OTHER INFORMATION: VH chain of antibody 9A2-VR36

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Gly Gly Asp Lys Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 35
<211> LENGTH: 117
<212> TYPE: PRT
<213> ORGANISM: Artificial Sequence
<220> FEATURE:
<223> OTHER INFORMATION: VH chain of antibody 9A2-VR37

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Ser Gly Ser Met Trp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: VH chain of antibody 9A2-VR38

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Met Gly Ala Thr Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 37
<211> LENGTH: 117
<212> TYPE: PRT
<213> ORGANISM: Artificial Sequence
<220> FEATURE:
<223> OTHER INFORMATION: VH chain of antibody 9A2-VR39

<400> SEQUENCE: 37

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser His Tyr
                20                  25                  30

His Met Leu Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 38
<211> LENGTH: 117
<212> TYPE: PRT
<213> ORGANISM: Artificial Sequence
<220> FEATURE:
<223> OTHER INFORMATION: VH chain of antibody 9A2-VR40

<400> SEQUENCE: 38

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser His Tyr
                20                  25                  30

His Met Leu Trp Val Arg Gln Ala Pro Gly Lys Gly Leu Glu Trp Val
            35                  40                  45

Ser Ser Ile Asn Gly Tyr Gly Ile Gln Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
```

<210> SEQ ID NO 39
<211> LENGTH: 117
<212> TYPE: PRT
<213> ORGANISM: Artificial Sequence
<220> FEATURE:
<223> OTHER INFORMATION: VH chain of antibody 9A2-VR41

<400> SEQUENCE: 39

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Lys Gly Trp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 40
<211> LENGTH: 117
<212> TYPE: PRT
<213> ORGANISM: Artificial Sequence
<220> FEATURE:
<223> OTHER INFORMATION: VH chain of antibody 9A2-VR42

<400> SEQUENCE: 40

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Gly Gly Asp Ile Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 41
<211> LENGTH: 117
<212> TYPE: PRT
<213> ORGANISM: Artificial Sequence
<220> FEATURE:
<223> OTHER INFORMATION: VH chain of antibody 9A2-VR43

<400> SEQUENCE: 41

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Ser Asp His Phe Asp Ile Trp Gly Gln Gly Thr Met
            100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: VH chain of antibody 9A2-VR44

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser His Phe Asp Ile Trp Gly Gln Gly Thr Met
            100                 105                 110

Val Thr Val Ser Ser
        115

<210> SEQ ID NO 43
<211> LENGTH: 117
<212> TYPE: PRT
<213> ORGANISM: Artificial Sequence
<220> FEATURE:
<223> OTHER INFORMATION: VH chain of antibody 9A2-VR45

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
```

```
                50             55             60
Lys Gly Arg Phe Thr Ile Ser Arg Asp Asn Ser Lys Asn Thr Leu Tyr
 65                 70                 75                 80

Leu Gln Met Asn Ser Leu Arg Ala Glu Asp Thr Ala Val Tyr Tyr Cys
                 85                 90                 95

Ala Arg Phe Tyr Ser Asp Asn Phe Asp Ile Trp Gly Gln Gly Thr Met
                100                105                110

Val Thr Val Ser Ser
            115

<210> SEQ ID NO 44
<211> LENGTH: 117
<212> TYPE: PRT
<213> ORGANISM: Artificial Sequence
<220> FEATURE:
<223> OTHER INFORMATION: VH chain of antibody 9A2-VR46

<400> SEQUENCE: 44

Glu Val Gln Leu Leu Glu Ser Gly Gly Gly Leu Val Gln Pro Gly Gly
  1               5                  10                 15

Ser Leu Arg Leu Ser Cys Ala Ala Ser Gly Phe Thr Phe Ser His Tyr
                 20                 25                 30

His Met Leu Trp Val Arg Gln Ala Pro Gly Lys Gly Leu Glu Trp Val
             35                 40                 45

Ser Ser Ile Arg Ser Ser Gly Gly Phe Thr Tyr Tyr Ala Asp Ser Val
         50                 55                 60

Lys Gly Arg Phe Thr Ile Ser Arg Asp Asn Ser Lys Asn Thr Leu Tyr
 65                 70                 75                 80

Leu Gln Met Asn Ser Leu Arg Ala Glu Asp Thr Ala Val Tyr Tyr Cys
                 85                 90                 95

Ala Arg Phe Tyr Ser Asp His Phe Arg Glu Trp Gly Gln Gly Thr Met
                100                105                110

Val Thr Val Ser Ser
            115

<210> SEQ ID NO 45
<211> LENGTH: 117
<212> TYPE: PRT
<213> ORGANISM: Artificial Sequence
<220> FEATURE:
<223> OTHER INFORMATION: VH chain of antibody 9A2-VR47

<400> SEQUENCE: 45

Glu Val Gln Leu Leu Glu Ser Gly Gly Gly Leu Val Gln Pro Gly Gly
  1               5                  10                 15

Ser Leu Arg Leu Ser Cys Ala Ala Ser Gly Phe Thr Phe Ser His Tyr
                 20                 25                 30

His Met Leu Trp Val Arg Gln Ala Pro Gly Lys Gly Leu Glu Trp Val
             35                 40                 45

Ser Ser Ile Arg Ser Ser Gly Gly Phe Thr Tyr Tyr Ala Asp Ser Val
         50                 55                 60

Lys Gly Arg Phe Thr Ile Ser Arg Asp Asn Ser Lys Asn Thr Leu Tyr
 65                 70                 75                 80

Leu Gln Met Asn Ser Leu Arg Ala Glu Asp Thr Ala Val Tyr Tyr Cys
                 85                 90                 95

Ala Arg Phe Tyr Ser Asp His Phe Ser Pro Trp Gly Gln Gly Thr Met
                100                105                110
```

```
Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: VH chain of antibody 9A2-VR48

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Ser Asp His Phe Lys Pro Trp Gly Gln Gly Thr Met
            100                 105                 110

Val Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: VH chain of antibody 9A2-VR49

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Ser Asp His Phe Asn Pro Trp Gly Gln Gly Thr Met
            100                 105                 110

Val Thr Val Ser Ser
        115

<210> SEQ ID NO 48
<211> LENGTH: 117
<212> TYPE: PRT
<213> ORGANISM: Artificial Sequence
<220> FEATURE:
<223> OTHER INFORMATION: VH chain of antibody 9A2-VR50
```

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Ser Asp His Phe Ala Pro Trp Gly Gln Gly Thr Met
            100                 105                 110

Val Thr Val Ser Ser
        115

<210> SEQ ID NO 49
<211> LENGTH: 117
<212> TYPE: PRT
<213> ORGANISM: Artificial Sequence
<220> FEATURE:
<223> OTHER INFORMATION: VH chain of antibody 9A2-VR24.04

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile His Thr His Arg His Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 50
<211> LENGTH: 117
<212> TYPE: PRT
<213> ORGANISM: Artificial Sequence
<220> FEATURE:
<223> OTHER INFORMATION: VH chain of antibody 9A2-VR24.07

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile His Thr His Arg Asn Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 51
<211> LENGTH: 117
<212> TYPE: PRT
<213> ORGANISM: Artificial Sequence
<220> FEATURE:
<223> OTHER INFORMATION: VH chain of antibody 9A2-VR24.10

<400> SEQUENCE: 51

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
            35                  40                  45

Ser Ser Ile His Thr Gly Ser Gln Trp Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 52
<211> LENGTH: 117
<212> TYPE: PRT
<213> ORGANISM: Artificial Sequence
<220> FEATURE:
<223> OTHER INFORMATION: VH chain of antibody 9A2-VR24.12

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
            35                  40                  45

Ser Ser Ile His Thr His Tyr Gln Tyr Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

```
Val Thr Val Ser Ser
        115

<210> SEQ ID NO 53
<211> LENGTH: 117
<212> TYPE: PRT
<213> ORGANISM: Artificial Sequence
<220> FEATURE:
<223> OTHER INFORMATION: VH chain of antibody 9A2-VR24.19

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile His Thr Gln Ser Lys Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 54
<211> LENGTH: 117
<212> TYPE: PRT
<213> ORGANISM: Artificial Sequence
<220> FEATURE:
<223> OTHER INFORMATION: VH chain of antibody 9A2-VR24.24

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Thr Asp Gly Thr Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 55
<211> LENGTH: 117
<212> TYPE: PRT
<213> ORGANISM: Artificial Sequence
<220> FEATURE:
<223> OTHER INFORMATION: VH chain of antibody 9A2-VR24.76
```

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Gln Thr His Gly Val Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: VH chain of antibody 9A2-VR24.78

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile His Thr His Arg Asn Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 57
<211> LENGTH: 117
<212> TYPE: PRT
<213> ORGANISM: Artificial Sequence
<220> FEATURE:
<223> OTHER INFORMATION: VH chain of antibody 9A2-VR24.81

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

```
Ser Ser Ile His Thr His Arg Asn Tyr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
                100                 105                 110

Val Thr Val Ser Ser
        115

<210> SEQ ID NO 58
<211> LENGTH: 117
<212> TYPE: PRT
<213> ORGANISM: Artificial Sequence
<220> FEATURE:
<223> OTHER INFORMATION: VH chain of antibody 9A2-VR24.82

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
                20                  25                  30

Arg Val His Trp Val Arg Gln Ala Pro Gly Lys Gly Leu Glu Trp Val
            35                  40                  45

Ser Ser Ile Lys His Gly Gly Arg Tyr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
                100                 105                 110

Val Thr Val Ser Ser
        115

<210> SEQ ID NO 59
<211> LENGTH: 117
<212> TYPE: PRT
<213> ORGANISM: Artificial Sequence
<220> FEATURE:
<223> OTHER INFORMATION: VH chain of antibody 9A2-VR24.84

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
                20                  25                  30

Arg Val His Trp Val Arg Gln Ala Pro Gly Lys Gly Leu Glu Trp Val
            35                  40                  45

Ser Ser Ile His Thr His Arg Pro Trp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
```

Val Thr Val Ser Ser
        115

<210> SEQ ID NO 60
<211> LENGTH: 117
<212> TYPE: PRT
<213> ORGANISM: Artificial Sequence
<220> FEATURE:
<223> OTHER INFORMATION: VH chain of antibody 9A2-VR24.87

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile His Thr His Ser Asp Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 61
<211> LENGTH: 117
<212> TYPE: PRT
<213> ORGANISM: Artificial Sequence
<220> FEATURE:
<223> OTHER INFORMATION: VH chain of antibody 9A2-VR24.91

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile His Thr His Arg Gln Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 62
<211> LENGTH: 117
<212> TYPE: PRT
<213> ORGANISM: Artificial Sequence
<220> FEATURE:

<223> OTHER INFORMATION: VH chain of antibody 9A2-VR24.93

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Asn Glu Asn Gly Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 63
<211> LENGTH: 117
<212> TYPE: PRT
<213> ORGANISM: Artificial Sequence
<220> FEATURE:
<223> OTHER INFORMATION: VH chain of antibody 9A2-VR24.27

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Pro Tyr Tyr His Gln Lys Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 64
<211> LENGTH: 117
<212> TYPE: PRT
<213> ORGANISM: Artificial Sequence
<220> FEATURE:
<223> OTHER INFORMATION: VH chain of antibody 9A2-VR24.29

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val

```
                35                  40                  45
Ser Ser Ile Arg Ser Ser Gly Gly Phe Pro Tyr Tyr Asn Tyr Lys Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 65
<211> LENGTH: 117
<212> TYPE: PRT
<213> ORGANISM: Artificial Sequence
<220> FEATURE:
<223> OTHER INFORMATION: VH chain of antibody 9A2-VR24.30

<400> SEQUENCE: 65

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Trp Tyr
             20                  25                  30

Arg Val His Trp Val Arg Gln Ala Pro Gly Lys Gly Leu Glu Trp Val
         35                  40                  45

Ser Ser Ile Arg Ser Ser Gly Gly Phe Pro Tyr Tyr Asn Arg Arg Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 66
<211> LENGTH: 117
<212> TYPE: PRT
<213> ORGANISM: Artificial Sequence
<220> FEATURE:
<223> OTHER INFORMATION: VH chain of antibody 9A2-VR24.33

<400> SEQUENCE: 66

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Trp Tyr
             20                  25                  30

Arg Val His Trp Val Arg Gln Ala Pro Gly Lys Gly Leu Glu Trp Val
         35                  40                  45

Ser Ser Ile Arg Ser Ser Gly Gly Phe Pro Tyr Tyr Asn His Lys Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Phe Tyr Asp Ser Phe Phe Asp Ile Trp Gly Gln Gly Thr Met
            100                 105                 110

Val Thr Val Ser Ser
        115

<210> SEQ ID NO 67
<211> LENGTH: 117
<212> TYPE: PRT
<213> ORGANISM: Artificial Sequence
<220> FEATURE:
<223> OTHER INFORMATION: VH chain of antibody 9A2-VR24.44

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Pro Tyr Tyr His Pro Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 68
<211> LENGTH: 117
<212> TYPE: PRT
<213> ORGANISM: Artificial Sequence
<220> FEATURE:
<223> OTHER INFORMATION: VH chain of antibody 9A2-VR24.97

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Pro Tyr Tyr Ser Leu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 69
<211> LENGTH: 117
<212> TYPE: PRT
<213> ORGANISM: Artificial Sequence
```

```
<220> FEATURE:
<223> OTHER INFORMATION: VH chain of antibody 9A2-VR24.98

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Pro His Tyr Asn Ser Val Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 70
<211> LENGTH: 117
<212> TYPE: PRT
<213> ORGANISM: Artificial Sequence
<220> FEATURE:
<223> OTHER INFORMATION: VH chain of antibody 9A2-VR24.102

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Pro Tyr Tyr Asn Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 71
<211> LENGTH: 117
<212> TYPE: PRT
<213> ORGANISM: Artificial Sequence
<220> FEATURE:
<223> OTHER INFORMATION: VH chain of antibody 9A2-VR24.107

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30
```

```
Arg Val His Trp Val Arg Gln Ala Pro Gly Lys Gly Leu Glu Trp Val
            35                  40                  45

Ser Ser Ile Arg Ser Ser Gly Gly Phe Pro Tyr Tyr Asn Pro Phe Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 72
<211> LENGTH: 117
<212> TYPE: PRT
<213> ORGANISM: Artificial Sequence
<220> FEATURE:
<223> OTHER INFORMATION: VH chain of antibody 9A2-VR24.110

<400> SEQUENCE: 72

Glu Val Gln Leu Leu Glu Ser Gly Gly Gly Leu Val Gln Pro Gly Gly
1                5                  10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
            35                  40                  45

Ser Ser Ile Arg Ser Ser Gly Gly Phe Pro Tyr Tyr Asn Asn His Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 73
<211> LENGTH: 117
<212> TYPE: PRT
<213> ORGANISM: Artificial Sequence
<220> FEATURE:
<223> OTHER INFORMATION: VH chain of antibody 9A2-VR24.111

<400> SEQUENCE: 73

Glu Val Gln Leu Leu Glu Ser Gly Gly Gly Leu Val Gln Pro Gly Gly
1                5                  10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
            35                  40                  45

Ser Ser Ile Arg Ser Ser Gly Phe Pro Met Tyr Asn Pro His Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Arg Phe Tyr Asp Ser Phe Phe Asp Ile Trp Gly Gln Gly Thr Met
            100                 105                 110

Val Thr Val Ser Ser
        115

<210> SEQ ID NO 74
<211> LENGTH: 117
<212> TYPE: PRT
<213> ORGANISM: Artificial Sequence
<220> FEATURE:
<223> OTHER INFORMATION: VH chain of antibody 9A2-VR24.55

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Asn Pro Ser Val
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 75
<211> LENGTH: 117
<212> TYPE: PRT
<213> ORGANISM: Artificial Sequence
<220> FEATURE:
<223> OTHER INFORMATION: VH chain of antibody 9A2-VR24.56

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Asn Pro Ala Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 76
<211> LENGTH: 117
<212> TYPE: PRT

<213> ORGANISM: Artificial Sequence
<220> FEATURE:
<223> OTHER INFORMATION: VH chain of antibody 9A2-VR24.57

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Asn Pro Lys Val
    50                  55                  60

Lys His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 77
<211> LENGTH: 117
<212> TYPE: PRT
<213> ORGANISM: Artificial Sequence
<220> FEATURE:
<223> OTHER INFORMATION: VH chain of antibody 9A2-VR24.122

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Asn Ser Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 78
<211> LENGTH: 117
<212> TYPE: PRT
<213> ORGANISM: Artificial Sequence
<220> FEATURE:
<223> OTHER INFORMATION: VH chain of antibody 9A2-VR24.124

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

```
Arg Val His Trp Val Arg Gln Ala Pro Gly Lys Gly Leu Glu Trp Val
            35                  40                  45

Ser Ser Ile Arg Ser Ser Gly Gly Phe Thr Tyr Tyr Thr Pro Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 79
<211> LENGTH: 117
<212> TYPE: PRT
<213> ORGANISM: Artificial Sequence
<220> FEATURE:
<223> OTHER INFORMATION: VH chain of antibody 9A2-VR24.131

<400> SEQUENCE: 79

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
            35                  40                  45

Ser Ser Ile Arg Ser Ser Gly Gly Phe Thr Tyr Tyr Asn Pro Ser Val
     50                  55                  60

Met Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 80
<211> LENGTH: 117
<212> TYPE: PRT
<213> ORGANISM: Artificial Sequence
<220> FEATURE:
<223> OTHER INFORMATION: VH chain of antibody 9A2-VR39.01

<400> SEQUENCE: 80

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Trp Phe
            20                  25                  30

His His Val Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

85                  90                  95
Ala Arg Phe Tyr Asp Ser Phe Phe Asp Ile Trp Gly Gln Gly Thr Met
            100                 105                 110

Val Thr Val Ser Ser
        115

<210> SEQ ID NO 81
<211> LENGTH: 117
<212> TYPE: PRT
<213> ORGANISM: Artificial Sequence
<220> FEATURE:
<223> OTHER INFORMATION: VH chain of antibody 9A2-VR39.02

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Trp Tyr
            20                  25                  30

His Met Ile Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 82
<211> LENGTH: 117
<212> TYPE: PRT
<213> ORGANISM: Artificial Sequence
<220> FEATURE:
<223> OTHER INFORMATION: VH chain of antibody 9A2-VR39.04

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Trp Phe
            20                  25                  30

Gln His Ile Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 83
<211> LENGTH: 117

```
<212> TYPE: PRT
<213> ORGANISM: Artificial Sequence
<220> FEATURE:
<223> OTHER INFORMATION: VH chain of antibody 9A2-VR39.05

<400> SEQUENCE: 83
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Phe
            20                  25                  30

His Thr Val Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

```
<210> SEQ ID NO 84
<211> LENGTH: 117
<212> TYPE: PRT
<213> ORGANISM: Artificial Sequence
<220> FEATURE:
<223> OTHER INFORMATION: VH chain of antibody 9A2-VR39.06

<400> SEQUENCE: 84
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Tyr
            20                  25                  30

His Tyr Ile Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

```
<210> SEQ ID NO 85
<211> LENGTH: 117
<212> TYPE: PRT
<213> ORGANISM: Artificial Sequence
<220> FEATURE:
<223> OTHER INFORMATION: VH chain of antibody 9A2-VR39.11

<400> SEQUENCE: 85
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Glu Phe

```
                    20                  25                  30
His Thr Ile Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
                100                 105                 110

Val Thr Val Ser Ser
        115

<210> SEQ ID NO 86
<211> LENGTH: 117
<212> TYPE: PRT
<213> ORGANISM: Artificial Sequence
<220> FEATURE:
<223> OTHER INFORMATION: VH chain of antibody 9A2-VR39.12

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Trp Phe
            20                  25                  30

Asn Thr Val Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
                100                 105                 110

Val Thr Val Ser Ser
        115

<210> SEQ ID NO 87
<211> LENGTH: 117
<212> TYPE: PRT
<213> ORGANISM: Artificial Sequence
<220> FEATURE:
<223> OTHER INFORMATION: VH chain of antibody 9A2-VR39.16

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Phe
            20                  25                  30

Asn Ile Val Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 88
<211> LENGTH: 117
<212> TYPE: PRT
<213> ORGANISM: Artificial Sequence
<220> FEATURE:
<223> OTHER INFORMATION: VH chain of antibody 9A2-VR39.17

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Phe Tyr
            20                  25                  30

His Lys Val Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 89
<211> LENGTH: 117
<212> TYPE: PRT
<213> ORGANISM: Artificial Sequence
<220> FEATURE:
<223> OTHER INFORMATION: VH chain of antibody 9A2-VR39.18

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Gly Tyr
            20                  25                  30

Val Trp Ile Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 90
```

```
<211> LENGTH: 117
<212> TYPE: PRT
<213> ORGANISM: Artificial Sequence
<220> FEATURE:
<223> OTHER INFORMATION: VH chain of antibody 9A2-VR39.19

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Tyr Phe
            20                  25                  30

Asn Val Ile Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: VH chain of antibody 9A2-VR39.21

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln His Tyr
            20                  25                  30

His Thr Val Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: VH chain of antibody 9A2-VR39.22

<400> SEQUENCE: 92

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Gln Trp Tyr
            20                  25                  30

His Val Ile Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: VH chain of antibody 9A2-VR39.23

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His His Tyr
            20                  25                  30

His Thr Val Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: VH chain of antibody 9A2-VR39.24

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His His Phe
            20                  25                  30

His Val Ile Trp Val Arg Gln Ala Pro Gly Lys Gly Leu Glu Trp Val
            35                  40                  45

Ser Ser Ile Asn Gly Arg Gly Arg Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 95
<211> LENGTH: 117
<212> TYPE: PRT
<213> ORGANISM: Artificial Sequence
<220> FEATURE:
<223> OTHER INFORMATION: VH chain of antibody 9A2-VR39.97

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Phe
            20                  25                  30

His Phe Val Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 96
<211> LENGTH: 117
<212> TYPE: PRT
<213> ORGANISM: Artificial Sequence
<220> FEATURE:
<223> OTHER INFORMATION: VH chain of antibody 9A2-VR39.98

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu His Tyr
            20                  25                  30

His Thr Ile Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 97
<211> LENGTH: 117
<212> TYPE: PRT
<213> ORGANISM: Artificial Sequence
<220> FEATURE:
<223> OTHER INFORMATION: VH chain of antibody 9A2-VR39.102

<400> SEQUENCE: 97

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Trp Phe
            20                  25                  30

His Tyr Ile Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 98
<211> LENGTH: 117
<212> TYPE: PRT
<213> ORGANISM: Artificial Sequence
<220> FEATURE:
<223> OTHER INFORMATION: VH chain of antibody 9A2-VR39.103

<400> SEQUENCE: 98

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln His Phe
            20                  25                  30

His Trp Val Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 99
<211> LENGTH: 117
<212> TYPE: PRT
<213> ORGANISM: Artificial Sequence
<220> FEATURE:
<223> OTHER INFORMATION: VH chain of antibody 9A2-VR39.105

<400> SEQUENCE: 99

```
Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Pro Tyr Tyr
            20                  25                  30

His Met Ile Trp Val Arg Gln Ala Pro Gly Lys Gly Leu Glu Trp Val
                35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 100
<211> LENGTH: 117
<212> TYPE: PRT
<213> ORGANISM: Artificial Sequence
<220> FEATURE:
<223> OTHER INFORMATION: VH chain of antibody 9A2-VR39.109

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Trp Tyr
            20                  25                  30

His His Ile Trp Val Arg Gln Ala Pro Gly Lys Gly Leu Glu Trp Val
                35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 101
<211> LENGTH: 117
<212> TYPE: PRT
<213> ORGANISM: Artificial Sequence
<220> FEATURE:
<223> OTHER INFORMATION: VH chain of antibody 9A2-VR39.110

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Trp Tyr
            20                  25                  30

His His Ile Trp Val Arg Gln Ala Pro Gly Lys Gly Leu Glu Trp Val
                35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr

```
                65                   70                  75                  80
Leu Gln Met Asn Ser Leu Arg Ala Glu Asp Thr Ala Val Tyr Tyr Cys
                    85                  90                  95

Ala Arg Phe Tyr Asp Ser Phe Phe Asp Ile Trp Gly Gln Gly Thr Met
                    100                 105                 110

Val Thr Val Ser Ser
                115

<210> SEQ ID NO 102
<211> LENGTH: 117
<212> TYPE: PRT
<213> ORGANISM: Artificial Sequence
<220> FEATURE:
<223> OTHER INFORMATION: VH chain of antibody 9A2-VR39.111

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Phe
                20                  25                  30

His Phe Val Trp Val Arg Gln Ala Pro Gly Lys Gly Leu Glu Trp Val
                35                  40                  45

Ser Ser Ile Asn Gly Arg Gly Arg Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Phe Tyr Asp Ser Phe Phe Asp Ile Trp Gly Gln Gly Thr Met
                    100                 105                 110

Val Thr Val Ser Ser
                115

<210> SEQ ID NO 103
<211> LENGTH: 117
<212> TYPE: PRT
<213> ORGANISM: Artificial Sequence
<220> FEATURE:
<223> OTHER INFORMATION: VH chain of antibody 9A2-VR39.112

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Tyr Tyr
                20                  25                  30

His Gln Val Trp Val Arg Gln Ala Pro Gly Lys Gly Leu Glu Trp Val
                35                  40                  45

Ser Ser Ile Asn Gly Arg Gly Arg Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Phe Tyr Asp Ser Phe Phe Asp Ile Trp Gly Gln Gly Thr Met
                    100                 105                 110

Val Thr Val Ser Ser
                115
```

```
<210> SEQ ID NO 104
<211> LENGTH: 117
<212> TYPE: PRT
<213> ORGANISM: Artificial Sequence
<220> FEATURE:
<223> OTHER INFORMATION: VH chain of antibody 9A2-VR39.116

<400> SEQUENCE: 104

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Trp Phe
            20                  25                  30

Val Met Val Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 105
<211> LENGTH: 117
<212> TYPE: PRT
<213> ORGANISM: Artificial Sequence
<220> FEATURE:
<223> OTHER INFORMATION: VH chain of antibody 9A2-VR39.27

<400> SEQUENCE: 105

Glu Val Gln Leu Leu Glu Ser Gly Gly Gly Leu Val Gln Pro Gly Gly
 1               5                  10                  15

Ser Leu Arg Leu Ser Cys Ala Ala Ser Arg Thr Ser Phe Met Trp Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 106
<211> LENGTH: 117
<212> TYPE: PRT
<213> ORGANISM: Artificial Sequence
<220> FEATURE:
<223> OTHER INFORMATION: VH chain of antibody 9A2-VR39.28

<400> SEQUENCE: 106

Glu Val Gln Leu Leu Glu Ser Gly Gly Gly Leu Val Gln Pro Gly Gly
```

```
                1               5                  10                 15
Ser Leu Arg Leu Ser Cys Ala Ala Ser Arg Gly Ala Pro Met Trp Tyr
            20                  25                 30

His Met Leu Trp Val Arg Gln Ala Pro Gly Lys Gly Leu Glu Trp Val
            35                  40                 45

Ser Ser Ile Asn Gly Arg Gly Arg Val Thr Tyr Tyr Ala Asp Ser Val
            50                  55                 60

Lys Gly Arg Phe Thr Ile Ser Arg Asp Asn Ser Lys Asn Thr Leu Tyr
65                              70                 75              80

Leu Gln Met Asn Ser Leu Arg Ala Glu Asp Thr Ala Val Tyr Tyr Cys
            85                  90                 95

Ala Arg Phe Tyr Asp Ser Phe Phe Asp Ile Trp Gly Gln Gly Thr Met
            100                 105                110

Val Thr Val Ser Ser
            115
```

<210> SEQ ID NO 107
<211> LENGTH: 117
<212> TYPE: PRT
<213> ORGANISM: Artificial Sequence
<220> FEATURE:
<223> OTHER INFORMATION: VH chain of antibody 9A2-VR39.46

<400> SEQUENCE: 107

```
Glu Val Gln Leu Leu Glu Ser Gly Gly Gly Leu Val Gln Pro Gly Gly
1               5                  10                 15

Ser Leu Arg Leu Ser Cys Ala Ala Ser Asp Val Asp Phe Gly Trp Tyr
            20                  25                 30

His Met Leu Trp Val Arg Gln Ala Pro Gly Lys Gly Leu Glu Trp Val
            35                  40                 45

Ser Ser Ile Asn Gly Arg Gly Arg Val Thr Tyr Tyr Ala Asp Ser Val
            50                  55                 60

Lys Gly Arg Phe Thr Ile Ser Arg Asp Asn Ser Lys Asn Thr Leu Tyr
65                              70                 75              80

Leu Gln Met Asn Ser Leu Arg Ala Glu Asp Thr Ala Val Tyr Tyr Cys
            85                  90                 95

Ala Arg Phe Tyr Asp Ser Phe Phe Asp Ile Trp Gly Gln Gly Thr Met
            100                 105                110

Val Thr Val Ser Ser
            115
```

<210> SEQ ID NO 108
<211> LENGTH: 117
<212> TYPE: PRT
<213> ORGANISM: Artificial Sequence
<220> FEATURE:
<223> OTHER INFORMATION: VH chain of antibody 9A2-VR39.122

<400> SEQUENCE: 108

```
Glu Val Gln Leu Leu Glu Ser Gly Gly Gly Leu Val Gln Pro Gly Gly
1               5                  10                 15

Ser Leu Arg Leu Ser Cys Ala Ala Ser Ala Gly Phe Phe Glu Tyr Tyr
            20                  25                 30

His Met Leu Trp Val Arg Gln Ala Pro Gly Lys Gly Leu Glu Trp Val
            35                  40                 45

Ser Ser Ile Asn Gly Arg Gly Arg Val Thr Tyr Tyr Ala Asp Ser Val
            50                  55                 60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 109
<211> LENGTH: 117
<212> TYPE: PRT
<213> ORGANISM: Artificial Sequence
<220> FEATURE:
<223> OTHER INFORMATION: VH chain of antibody 9A2-VR39.139

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Pro Arg Trp Glu Trp Asn Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 110
<211> LENGTH: 117
<212> TYPE: PRT
<213> ORGANISM: Artificial Sequence
<220> FEATURE:
<223> OTHER INFORMATION: VH chain of antibody 9A2-VR39.140

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Ala Tyr Ser Glu Met Trp Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115
```

<210> SEQ ID NO 111
<211> LENGTH: 117
<212> TYPE: PRT
<213> ORGANISM: Artificial Sequence
<220> FEATURE:
<223> OTHER INFORMATION: VH chain of antibody 9A2-VR39.148

<400> SEQUENCE: 111

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr His Val Ala Gln Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 112
<211> LENGTH: 117
<212> TYPE: PRT
<213> ORGANISM: Artificial Sequence
<220> FEATURE:
<223> OTHER INFORMATION: VH chain of antibody 9A2-VR39.162

<400> SEQUENCE: 112

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Pro Gln Met Ala Gln Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 113
<211> LENGTH: 117
<212> TYPE: PRT
<213> ORGANISM: Artificial Sequence
<220> FEATURE:
<223> OTHER INFORMATION: VH chain of antibody 9A2-VR39.77

<400> SEQUENCE: 113

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Gln Trp Pro Met
50                  55                  60

Asn Lys Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Tyr Asp Ser Phe Phe Asp Ile Trp Gly Gln Gly Thr Met
                100                 105                 110

Val Thr Val Ser Ser
            115

<210> SEQ ID NO 114
<211> LENGTH: 117
<212> TYPE: PRT
<213> ORGANISM: Artificial Sequence
<220> FEATURE:
<223> OTHER INFORMATION: VH chain of antibody 9A2-VR39.93

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Asn Pro Ala Trp
50                  55                  60

Lys Lys Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Tyr Asp Ser Phe Phe Asp Ile Trp Gly Gln Gly Thr Met
                100                 105                 110

Val Thr Val Ser Ser
            115

<210> SEQ ID NO 115
<211> LENGTH: 117
<212> TYPE: PRT
<213> ORGANISM: Artificial Sequence
<220> FEATURE:
<223> OTHER INFORMATION: VH chain of antibody 9A2-VR39.174

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Ala Arg Asp His
50                  55                  60
```

Lys Lys Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 116
<211> LENGTH: 117
<212> TYPE: PRT
<213> ORGANISM: Artificial Sequence
<220> FEATURE:
<223> OTHER INFORMATION: VH chain of antibody 9A2-VR39.177

<400> SEQUENCE: 116

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
                20                  25                  30

His Met Leu Trp Val Arg Gln Ala Pro Gly Lys Gly Leu Glu Trp Val
             35                  40                  45

Ser Ser Ile Asn Gly Arg Gly Arg Val Thr Tyr Tyr Ala Leu Glu Tyr
 50                  55                  60

Lys Lys Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
            100                 105                 110

Val Thr Val Ser Ser
            115

<210> SEQ ID NO 117
<211> LENGTH: 428
<212> TYPE: PRT
<213> ORGANISM: Homo sapiens

<400> SEQUENCE: 117

Trp Glu Arg Ser Leu Ala Gly Ala Glu Glu Thr Ile Pro Leu Gln Thr
 1               5                  10                  15

Leu Arg Cys Tyr Ala Asp Tyr Thr Ser His Ile Thr Cys Arg Trp Ala
                20                  25                  30

Asp Thr Gln Asp Ala Gln Arg Leu Val Asn Val Thr Leu Ile Arg Arg
             35                  40                  45

Val Asn Glu Asp Leu Leu Glu Pro Val Ser Cys Asp Leu Ser Asp Asp
 50                  55                  60

Met Pro Trp Ser Ala Cys Pro His Pro Arg Cys Val Pro Arg Arg Cys
 65                  70                  75                  80

Val Ile Pro Cys Gln Ser Phe Val Val Thr Asp Val Asp Tyr Phe Ser
                 85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
        130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His His
            420                 425

<210> SEQ ID NO 118
<211> LENGTH: 428
<212> TYPE: PRT
<213> ORGANISM: Homo sapiens

<400> SEQUENCE: 118

Trp Glu Arg Ser Leu Ala Gly Ala Glu Glu Thr Ile Pro Leu Gln Thr
1               5                   10                  15

Leu Arg Cys Tyr Asn Ala Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
        50                  55                  60

Met Pro Trp Ser Ala Cys Pro His Pro Arg Cys Val Pro Arg Arg Cys
65                  70                  75                  80

Val Ile Pro Cys Gln Ser Phe Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 119
<211> LENGTH: 428
<212> TYPE: PRT
<213> ORGANISM: Homo sapiens

<400> SEQUENCE: 119

Trp Glu Arg Ser Leu Ala Gly Ala Glu Glu Thr Ile Pro Leu Gln Thr
1               5                   10                  15

Leu Arg Cys Tyr Asn Asp Ala Thr Ser His Ile Thr Cys Arg Trp Ala

```
            20                  25                  30
Asp Thr Gln Asp Ala Gln Arg Leu Val Asn Val Thr Leu Ile Arg Arg
            35                  40                  45
Val Asn Glu Asp Leu Leu Glu Pro Val Ser Cys Asp Leu Ser Asp Asp
        50                  55                  60
Met Pro Trp Ser Ala Cys Pro His Pro Arg Cys Val Pro Arg Arg Cys
65                  70                  75                  80
Val Ile Pro Cys Gln Ser Phe Val Val Thr Asp Val Asp Tyr Phe Ser
                85                  90                  95
Phe Gln Pro Asp Arg Pro Leu Gly Thr Arg Leu Thr Val Thr Leu Thr
            100                 105                 110
Gln His Val Gln Pro Pro Glu Pro Arg Asp Leu Gln Ile Ser Thr Asp
            115                 120                 125
Gln Asp His Phe Leu Leu Thr Trp Ser Val Ala Leu Gly Ser Pro Gln
        130                 135                 140
Ser His Trp Leu Ser Pro Gly Asp Leu Glu Phe Glu Val Val Tyr Lys
145                 150                 155                 160
Arg Leu Gln Asp Ser Trp Glu Asp Ala Ala Ile Leu Leu Ser Asn Thr
                165                 170                 175
Ser Gln Ala Thr Leu Gly Pro Glu His Leu Met Pro Ser Ser Thr Tyr
            180                 185                 190
Val Ala Arg Val Arg Thr Arg Leu Ala Pro Gly Ser Arg Leu Ser Gly
            195                 200                 205
Arg Pro Ser Lys Trp Ser Pro Glu Val Cys Trp Asp Ser Gln Pro Gly
        210                 215                 220
Asp Glu Ala Gln Pro Gln Asn Leu Glu Cys Phe Phe Asp Gly Ala Ala
225                 230                 235                 240
Val Leu Ser Cys Ser Trp Glu Val Arg Lys Glu Val Ala Ser Ser Val
                245                 250                 255
Ser Phe Gly Leu Phe Tyr Lys Pro Ser Pro Asp Ala Gly Glu Glu
            260                 265                 270
Cys Ser Pro Val Leu Arg Glu Gly Leu Gly Ser Leu His Thr Arg His
            275                 280                 285
His Cys Gln Ile Pro Val Pro Asp Pro Ala Thr His Gly Gln Tyr Ile
        290                 295                 300
Val Ser Val Gln Pro Arg Arg Ala Glu Lys His Ile Lys Ser Ser Val
305                 310                 315                 320
Asn Ile Gln Met Ala Pro Pro Ser Leu Asn Val Thr Lys Asp Gly Asp
                325                 330                 335
Ser Tyr Ser Leu Arg Trp Glu Thr Met Lys Met Arg Tyr Glu His Ile
            340                 345                 350
Asp His Thr Phe Glu Ile Gln Tyr Arg Lys Asp Thr Ala Thr Trp Lys
            355                 360                 365
Asp Ser Lys Thr Glu Thr Leu Gln Asn Ala His Ser Met Ala Leu Pro
        370                 375                 380
Ala Leu Glu Pro Ser Thr Arg Tyr Trp Ala Arg Val Arg Val Arg Thr
385                 390                 395                 400
Ser Arg Thr Gly Tyr Asn Gly Ile Trp Ser Glu Trp Ser Glu Ala Arg
                405                 410                 415
Ser Trp Asp Thr Glu Ser His His His His His
            420                 425

<210> SEQ ID NO 120
```

```
<211> LENGTH: 428
<212> TYPE: PRT
<213> ORGANISM: Homo sapiens

<400> SEQUENCE: 120

Trp Glu Arg Ser Leu Ala Gly Ala Glu Thr Ile Pro Leu Gln Thr
1               5                   10                  15

Leu Arg Cys Tyr Asn Asp Tyr Ala Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
```

```
385                 390                 395                 400
Ser Arg Thr Gly Tyr Asn Gly Ile Trp Ser Glu Trp Ser Glu Ala Arg
                405                 410                 415

Ser Trp Asp Thr Glu Ser His His His His His
            420             425

<210> SEQ ID NO 121
<211> LENGTH: 428
<212> TYPE: PRT
<213> ORGANISM: Homo sapiens

<400> SEQUENCE: 121

Trp Glu Arg Ser Leu Ala Gly Ala Glu Glu Thr Ile Pro Leu Gln Thr
1               5                   10                  15

Leu Arg Cys Tyr Asn Asp Tyr Thr Ala His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335
```

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
            370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 122
<211> LENGTH: 428
<212> TYPE: PRT
<213> ORGANISM: Homo sapiens

<400> SEQUENCE: 122

Trp Glu Arg Ser Leu Ala Gly Ala Glu Glu Thr Ile Pro Leu Gln Thr
1               5                   10                  15

Leu Arg Cys Tyr Asn Asp Tyr Thr Ser Ala Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
        290                 295                 300

Val Ser Val Gln Pro Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
                340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
                420                 425

<210> SEQ ID NO 123
<211> LENGTH: 428
<212> TYPE: PRT
<213> ORGANISM: Homo sapiens

<400> SEQUENCE: 123

Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ala Phe Val Val Thr Asp Val Asp Tyr Phe Ser
                85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala

-continued

```
                225                 230                 235                 240
    Val Leu Ser Cys Ser Trp Glu Val Arg Lys Glu Val Ala Ser Ser Val
                    245                 250                 255

Ser Phe Gly Leu Phe Tyr Lys Pro Ser Pro Asp Ala Gly Glu Glu Glu
                    260                 265                 270

Cys Ser Pro Val Leu Arg Glu Gly Leu Gly Ser Leu His Thr Arg His
                    275                 280                 285

His Cys Gln Ile Pro Val Pro Asp Pro Ala Thr His Gly Gln Tyr Ile
                    290                 295                 300

Val Ser Val Gln Pro Arg Arg Ala Glu Lys His Ile Lys Ser Ser Val
    305                 310                 315                 320

Asn Ile Gln Met Ala Pro Pro Ser Leu Asn Val Thr Lys Asp Gly Asp
                    325                 330                 335

Ser Tyr Ser Leu Arg Trp Glu Thr Met Lys Met Arg Tyr Glu His Ile
                    340                 345                 350

Asp His Thr Phe Glu Ile Gln Tyr Arg Lys Asp Thr Ala Thr Trp Lys
                    355                 360                 365

Asp Ser Lys Thr Glu Thr Leu Gln Asn Ala His Ser Met Ala Leu Pro
                    370                 375                 380

Ala Leu Glu Pro Ser Thr Arg Tyr Trp Ala Arg Val Arg Val Arg Thr
    385                 390                 395                 400

Ser Arg Thr Gly Tyr Asn Gly Ile Trp Ser Glu Trp Ser Glu Ala Arg
                    405                 410                 415

Ser Trp Asp Thr Glu Ser His His His His His His
                    420                 425

<210> SEQ ID NO 124
<211> LENGTH: 428
<212> TYPE: PRT
<213> ORGANISM: Homo sapiens

<400> SEQUENCE: 124

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
        50                  55                  60

Met Pro Trp Ser Ala Cys Pro His Pro Arg Cys Val Pro Arg Arg Cys
65                  70                  75                  80

Val Ile Pro Cys Gln Ser Ala Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
    130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175
```

```
Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
    370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 125
<211> LENGTH: 428
<212> TYPE: PRT
<213> ORGANISM: Homo sapiens

<400> SEQUENCE: 125

Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
        50                  55                  60

Met Pro Trp Ser Ala Cys Pro His Pro Arg Cys Val Pro Arg Arg Cys
65                  70                  75                  80

Val Ile Pro Cys Gln Ser Phe Ala Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125
```

Gln Asp His Phe Leu Leu Thr Trp Ser Val Ala Leu Gly Ser Pro Gln
            130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 126
<211> LENGTH: 428
<212> TYPE: PRT
<213> ORGANISM: Homo sapiens

<400> SEQUENCE: 126

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys

```
              65                  70                  75                  80
Val Ile Pro Cys Gln Ser Phe Val Ala Thr Asp Val Asp Tyr Phe Ser
                         85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
        130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
                180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
        210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
                260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
        290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
                340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
        370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
                420                 425

<210> SEQ ID NO 127
<211> LENGTH: 428
<212> TYPE: PRT
<213> ORGANISM: Homo sapiens

<400> SEQUENCE: 127

Trp Glu Arg Ser Leu Ala Gly Ala Glu Glu Thr Ile Pro Leu Gln Thr
1               5                   10                  15
```

-continued

```
Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Ala Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425
```

<210> SEQ ID NO 128
<211> LENGTH: 428
<212> TYPE: PRT
<213> ORGANISM: Homo sapiens

<400> SEQUENCE: 128

```
Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Ala Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
    370                 375                 380
```

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
            405                 410                 415

Ser Trp Asp Thr Glu Ser His His His His His His
            420                 425

<210> SEQ ID NO 129
<211> LENGTH: 428
<212> TYPE: PRT
<213> ORGANISM: Homo sapiens

<400> SEQUENCE: 129

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Ala Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

```
Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
            405                 410                 415

Ser Trp Asp Thr Glu Ser His His His His His His
            420                 425
```

<210> SEQ ID NO 130
<211> LENGTH: 428
<212> TYPE: PRT
<213> ORGANISM: Homo sapiens

<400> SEQUENCE: 130

```
Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
```

|  |  |  | 275 |  |  |  | 280 |  |  |  | 285 |  |
|---|---|---|---|---|---|---|---|---|---|---|---|---|

His Cys Gln Ile Pro Val Pro Asp Pro Ala Thr His Gly Gln Tyr Ile
    290                  295                  300

Val Ser Val Gln Pro Arg Arg Ala Glu Lys His Ile Lys Ser Ser Val
305                  310                  315                320

Ala Ile Gln Met Ala Pro Pro Ser Leu Asn Val Thr Lys Asp Gly Asp
                325                  330                335

Ser Tyr Ser Leu Arg Trp Glu Thr Met Lys Met Arg Tyr Glu His Ile
            340                  345                350

Asp His Thr Phe Glu Ile Gln Tyr Arg Lys Asp Thr Ala Thr Trp Lys
        355                  360                365

Asp Ser Lys Thr Glu Thr Leu Gln Asn Ala His Ser Met Ala Leu Pro
    370                  375                  380

Ala Leu Glu Pro Ser Thr Arg Tyr Trp Ala Arg Val Arg Val Arg Thr
385                  390                  395                400

Ser Arg Thr Gly Tyr Asn Gly Ile Trp Ser Glu Trp Ser Glu Ala Arg
            405                  410                415

Ser Trp Asp Thr Glu Ser His His His His His His
        420                  425

<210> SEQ ID NO 131
<211> LENGTH: 444
<212> TYPE: PRT
<213> ORGANISM: Homo sapiens

<400> SEQUENCE: 131

Met Val Leu Ala Gln Gly Leu Leu Ser Met Ala Leu Ala Leu Cys
1                5                  10                15

Trp Glu Arg Ser Leu Ala Gly Ala Glu Glu Thr Ile Pro Leu Gln Thr
        20                  25                30

Leu Arg Cys Tyr Asn Asp Tyr Thr Ser His Ile Thr Cys Arg Trp Ala
            35                  40                45

Asp Thr Gln Asp Ala Gln Arg Leu Val Asn Val Thr Leu Ile Arg Arg
    50                  55                  60

Val Asn Glu Asp Leu Leu Glu Pro Val Ser Cys Asp Leu Ser Asp Asp
65                  70                  75                80

Met Pro Trp Ser Ala Cys Pro His Pro Arg Cys Val Pro Arg Arg Cys
                85                  90                95

Val Ile Pro Cys Gln Ser Phe Val Val Thr Asp Val Asp Tyr Phe Ser
            100                  105                110

Phe Gln Pro Asp Arg Pro Leu Gly Thr Arg Leu Thr Val Thr Leu Thr
        115                  120                125

Gln His Val Gln Pro Pro Glu Pro Arg Asp Leu Gln Ile Ser Thr Asp
    130                  135                140

Gln Asp His Phe Leu Leu Thr Trp Ser Val Ala Leu Gly Ser Pro Gln
145                  150                  155                160

Ser His Trp Leu Ser Pro Gly Asp Leu Glu Phe Glu Val Val Tyr Lys
            165                  170                175

Arg Leu Gln Asp Ser Trp Glu Asp Ala Ala Ile Leu Leu Ser Asn Thr
              180                  185                190

Ser Gln Ala Thr Leu Gly Pro Glu His Leu Met Pro Ser Ser Thr Tyr
        195                  200                205

Val Ala Arg Val Arg Thr Arg Leu Ala Pro Gly Ser Arg Leu Ser Gly
    210                  215                220

Arg Pro Ser Lys Trp Ser Pro Glu Val Cys Trp Asp Ser Gln Pro Gly
225                 230                 235                 240

Asp Glu Ala Gln Pro Gln Asn Leu Glu Cys Phe Phe Asp Gly Ala Ala
            245                 250                 255

Val Leu Ser Cys Ser Trp Glu Val Arg Lys Glu Val Ala Ser Ser Val
        260                 265                 270

Ser Phe Gly Leu Phe Tyr Lys Pro Ser Pro Asp Ala Gly Glu Glu Glu
    275                 280                 285

Cys Ser Pro Val Leu Arg Glu Gly Leu Gly Ser Leu His Thr Arg His
290                 295                 300

His Cys Gln Ile Pro Val Pro Asp Pro Ala Thr His Gly Gln Tyr Ile
305                 310                 315                 320

Val Ser Val Gln Pro Arg Arg Ala Glu Lys His Ile Lys Ser Ser Val
            325                 330                 335

Asn Ala Gln Met Ala Pro Pro Ser Leu Asn Val Thr Lys Asp Gly Asp
        340                 345                 350

Ser Tyr Ser Leu Arg Trp Glu Thr Met Lys Met Arg Tyr Glu His Ile
    355                 360                 365

Asp His Thr Phe Glu Ile Gln Tyr Arg Lys Asp Thr Ala Thr Trp Lys
370                 375                 380

Asp Ser Lys Thr Glu Thr Leu Gln Asn Ala His Ser Met Ala Leu Pro
385                 390                 395                 400

Ala Leu Glu Pro Ser Thr Arg Tyr Trp Ala Arg Val Arg Val Arg Thr
            405                 410                 415

Ser Arg Thr Gly Tyr Asn Gly Ile Trp Ser Glu Trp Ser Glu Ala Arg
        420                 425                 430

Ser Trp Asp Thr Glu Ser His His His His His His
    435                 440

<210> SEQ ID NO 132
<211> LENGTH: 428
<212> TYPE: PRT
<213> ORGANISM: Homo sapiens

<400> SEQUENCE: 132

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
            85                  90                  95

Phe Gln Pro Asp Arg Pro Leu Gly Thr Arg Leu Thr Val Thr Leu Thr
        100                 105                 110

Gln His Val Gln Pro Pro Glu Pro Arg Asp Leu Gln Ile Ser Thr Asp
    115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

```
Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Ala Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
    370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 133
<211> LENGTH: 428
<212> TYPE: PRT
<213> ORGANISM: Homo sapiens

<400> SEQUENCE: 133

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
        50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
```

```
            100                 105                 110
Gln His Val Gln Pro Glu Pro Arg Asp Leu Gln Ile Ser Thr Asp
            115                 120                 125
Gln Asp His Phe Leu Leu Thr Trp Ser Val Ala Leu Gly Ser Pro Gln
130                 135                 140
Ser His Trp Leu Ser Pro Gly Asp Leu Glu Phe Glu Val Val Tyr Lys
145                 150                 155                 160
Arg Leu Gln Asp Ser Trp Glu Asp Ala Ala Ile Leu Leu Ser Asn Thr
                165                 170                 175
Ser Gln Ala Thr Leu Gly Pro Glu His Leu Met Pro Ser Ser Thr Tyr
            180                 185                 190
Val Ala Arg Val Arg Thr Arg Leu Ala Pro Gly Ser Arg Leu Ser Gly
        195                 200                 205
Arg Pro Ser Lys Trp Ser Pro Glu Val Cys Trp Asp Ser Gln Pro Gly
    210                 215                 220
Asp Glu Ala Gln Pro Gln Asn Leu Glu Cys Phe Phe Asp Gly Ala Ala
225                 230                 235                 240
Val Leu Ser Cys Ser Trp Glu Val Arg Lys Glu Val Ala Ser Ser Val
                245                 250                 255
Ser Phe Gly Leu Phe Tyr Lys Pro Ser Pro Asp Ala Gly Glu Glu
            260                 265                 270
Cys Ser Pro Val Leu Arg Glu Gly Leu Gly Ser Leu His Thr Arg His
        275                 280                 285
His Cys Gln Ile Pro Val Pro Asp Pro Ala Thr His Gly Gln Tyr Ile
    290                 295                 300
Val Ser Val Gln Pro Arg Arg Ala Glu Lys His Ile Lys Ser Ser Val
305                 310                 315                 320
Asn Ile Gln Ala Ala Pro Pro Ser Leu Asn Val Thr Lys Asp Gly Asp
                325                 330                 335
Ser Tyr Ser Leu Arg Trp Glu Thr Met Lys Met Arg Tyr Glu His Ile
            340                 345                 350
Asp His Thr Phe Glu Ile Gln Tyr Arg Lys Asp Thr Ala Thr Trp Lys
        355                 360                 365
Asp Ser Lys Thr Glu Thr Leu Gln Asn Ala His Ser Met Ala Leu Pro
    370                 375                 380
Ala Leu Glu Pro Ser Thr Arg Tyr Trp Ala Arg Val Arg Val Arg Thr
385                 390                 395                 400
Ser Arg Thr Gly Tyr Asn Gly Ile Trp Ser Glu Trp Ser Glu Ala Arg
                405                 410                 415
Ser Trp Asp Thr Glu Ser His His His His His
            420                 425

<210> SEQ ID NO 134
<211> LENGTH: 428
<212> TYPE: PRT
<213> ORGANISM: Homo sapiens

<400> SEQUENCE: 134

Trp Glu Arg Ser Leu Ala Gly Ala Glu Glu Thr Ile Pro Leu Gln Thr
1               5                   10                  15
Leu Arg Cys Tyr Asn Asp Tyr Thr Ser His Ile Thr Cys Arg Trp Ala
                20                  25                  30
Asp Thr Gln Asp Ala Gln Arg Leu Val Asn Val Thr Leu Ile Arg Arg
            35                  40                  45
```

```
Val Asn Glu Asp Leu Leu Glu Pro Val Ser Cys Asp Leu Ser Asp Asp
 50                  55                  60
Met Pro Trp Ser Ala Cys Pro His Pro Arg Cys Val Pro Arg Arg Cys
 65                  70                  75                  80
Val Ile Pro Cys Gln Ser Phe Val Val Thr Asp Val Asp Tyr Phe Ser
                 85                  90                  95
Phe Gln Pro Asp Arg Pro Leu Gly Thr Arg Leu Thr Val Thr Leu Thr
                100                 105                 110
Gln His Val Gln Pro Pro Glu Arg Asp Leu Gln Ile Ser Thr Asp
                115                 120                 125
Gln Asp His Phe Leu Leu Thr Trp Ser Val Ala Leu Gly Ser Pro Gln
            130                 135                 140
Ser His Trp Leu Ser Pro Gly Asp Leu Glu Phe Glu Val Val Tyr Lys
145                 150                 155                 160
Arg Leu Gln Asp Ser Trp Glu Asp Ala Ala Ile Leu Leu Ser Asn Thr
                165                 170                 175
Ser Gln Ala Thr Leu Gly Pro Glu His Leu Met Pro Ser Ser Thr Tyr
                180                 185                 190
Val Ala Arg Val Arg Thr Arg Leu Ala Pro Gly Ser Arg Leu Ser Gly
            195                 200                 205
Arg Pro Ser Lys Trp Ser Pro Glu Val Cys Trp Asp Ser Gln Pro Gly
210                 215                 220
Asp Glu Ala Gln Pro Gln Asn Leu Glu Cys Phe Phe Asp Gly Ala Ala
225                 230                 235                 240
Val Leu Ser Cys Ser Trp Glu Val Arg Lys Glu Val Ala Ser Ser Val
                245                 250                 255
Ser Phe Gly Leu Phe Tyr Lys Pro Ser Pro Asp Ala Gly Glu Glu Glu
                260                 265                 270
Cys Ser Pro Val Leu Arg Glu Gly Leu Gly Ser Leu His Thr Arg His
            275                 280                 285
His Cys Gln Ile Pro Val Pro Asp Pro Ala Thr His Gly Gln Tyr Ile
290                 295                 300
Val Ser Val Gln Pro Arg Arg Ala Glu Lys His Ile Lys Ser Ser Val
305                 310                 315                 320
Asn Ile Gln Met Ala Pro Pro Ser Leu Asn Val Thr Lys Asp Gly Asp
                325                 330                 335
Ser Tyr Ser Leu Arg Trp Glu Thr Met Ala Met Arg Tyr Glu His Ile
                340                 345                 350
Asp His Thr Phe Glu Ile Gln Tyr Arg Lys Asp Thr Ala Thr Trp Lys
            355                 360                 365
Asp Ser Lys Thr Glu Thr Leu Gln Asn Ala His Ser Met Ala Leu Pro
370                 375                 380
Ala Leu Glu Pro Ser Thr Arg Tyr Trp Ala Arg Val Arg Val Arg Thr
385                 390                 395                 400
Ser Arg Thr Gly Tyr Asn Gly Ile Trp Ser Glu Trp Ser Glu Ala Arg
                405                 410                 415
Ser Trp Asp Thr Glu Ser His His His His His
            420                 425

<210> SEQ ID NO 135
<211> LENGTH: 428
<212> TYPE: PRT
<213> ORGANISM: Homo sapiens

<400> SEQUENCE: 135
```

```
Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
        50                  55                  60

Met Pro Trp Ser Ala Cys Pro His Pro Arg Cys Val Pro Arg Arg Cys
65                      70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu
                260                 265                 270

Cys Ser Pro Val Leu Arg Glu Gly Leu Gly Ser Leu His Thr Arg His
                275                 280                 285

His Cys Gln Ile Pro Val Pro Asp Pro Ala Thr His Gly Gln Tyr Ile
        290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Ala Arg Tyr Glu His Ile
                340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415
```

-continued

```
Ser Trp Asp Thr Glu Ser His His His His His
            420                 425
```

<210> SEQ ID NO 136
<211> LENGTH: 428
<212> TYPE: PRT
<213> ORGANISM: Homo sapiens

<400> SEQUENCE: 136

```
Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
        290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Ala Tyr Glu His Ile
            340                 345                 350

Asp His Thr Phe Glu Ile Gln Tyr Arg Lys Asp Thr Ala Thr Trp Lys
            355                 360                 365
```

```
Asp Ser Lys Thr Glu Thr Leu Gln Asn Ala His Ser Met Ala Leu Pro
            370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 137
<211> LENGTH: 428
<212> TYPE: PRT
<213> ORGANISM: Homo sapiens

<400> SEQUENCE: 137

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
            85                  90                  95

Phe Gln Pro Asp Arg Pro Leu Gly Thr Arg Leu Thr Val Thr Leu Thr
        100                 105                 110

Gln His Val Gln Pro Pro Glu Pro Arg Asp Leu Gln Ile Ser Thr Asp
    115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
            165                 170                 175

Ser Gln Ala Thr Leu Gly Pro Glu His Leu Met Pro Ser Ser Thr Tyr
        180                 185                 190

Val Ala Arg Val Arg Thr Arg Leu Ala Pro Gly Ser Arg Leu Ser Gly
    195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
            245                 250                 255

Ser Phe Gly Leu Phe Tyr Lys Pro Ser Pro Asp Ala Gly Glu Glu Glu
        260                 265                 270

Cys Ser Pro Val Leu Arg Glu Gly Leu Gly Ser Leu His Thr Arg His
    275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
```

```
305                 310                 315                 320
Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Ala Glu His Ile
                340                 345                 350

Asp His Thr Phe Glu Ile Gln Tyr Arg Lys Asp Thr Ala Thr Trp Lys
                355                 360                 365

Asp Ser Lys Thr Glu Thr Leu Gln Asn Ala His Ser Met Ala Leu Pro
            370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His His
                420                 425
```

<210> SEQ ID NO 138
<211> LENGTH: 428
<212> TYPE: PRT
<213> ORGANISM: Homo sapiens

<400> SEQUENCE: 138

```
Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
        210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255
```

```
Ser Phe Gly Leu Phe Tyr Lys Pro Ser Pro Asp Ala Gly Glu Glu
                260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Ala His Ile
            340                 345                 350

Asp His Thr Phe Glu Ile Gln Tyr Arg Lys Asp Thr Ala Thr Trp Lys
    355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His His
            420                 425

<210> SEQ ID NO 139
<211> LENGTH: 428
<212> TYPE: PRT
<213> ORGANISM: Homo sapiens

<400> SEQUENCE: 139

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205
```

Arg Pro Ser Lys Trp Ser Pro Glu Val Cys Trp Asp Ser Gln Pro Gly
            210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
            245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
            290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
            325                 330                 335

Ser Tyr Ser Leu Arg Trp Glu Thr Met Lys Met Arg Tyr Glu Ala Ile
            340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
            370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Trp Ser Glu Ala Arg
            405                 410                 415

Ser Trp Asp Thr Glu Ser His His His His His His
            420                 425

<210> SEQ ID NO 140
<211> LENGTH: 428
<212> TYPE: PRT
<213> ORGANISM: Homo sapiens

<400> SEQUENCE: 140

Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys

```
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ala
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
    370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 141
<211> LENGTH: 428
<212> TYPE: PRT
<213> ORGANISM: Homo sapiens

<400> SEQUENCE: 141

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
        50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95
```

```
Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
        130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser His His His His His His
            420                 425

<210> SEQ ID NO 142
<211> LENGTH: 428
<212> TYPE: PRT
<213> ORGANISM: Homo sapiens

<400> SEQUENCE: 142

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45
```

```
Val Asn Glu Asp Leu Leu Glu Pro Val Ser Cys Asp Leu Ser Asp Asp
 50                  55                  60

Met Pro Trp Ser Ala Cys Pro His Pro Arg Cys Val Pro Arg Arg Cys
 65                  70                  75                  80

Val Ile Pro Cys Gln Ser Phe Val Thr Asp Val Asp Tyr Phe Ser
                 85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
                115                 120                 125

Gln Asp His Phe Leu Leu Thr Trp Ser Val Ala Leu Gly Ser Pro Gln
            130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
                180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
            290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
                340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Ala Thr Gly Tyr Asn Gly Ile Trp Ser Glu Trp Ser Glu Ala Arg
                405                 410                 415

Ser Trp Asp Thr Glu Ser His His His His His
            420                 425

<210> SEQ ID NO 143
<211> LENGTH: 428
<212> TYPE: PRT
<213> ORGANISM: Homo sapiens
```

<400> SEQUENCE: 143

```
Trp Glu Arg Ser Leu Ala Gly Ala Glu Thr Ile Pro Leu Gln Thr
  1               5                  10                  15

Leu Arg Cys Tyr Asn Asp Tyr Thr Ser His Ile Thr Cys Arg Trp Ala
                 20                  25                  30

Asp Thr Gln Asp Ala Gln Arg Leu Val Asn Val Thr Leu Ile Arg Arg
             35                  40                  45

Val Asn Glu Asp Leu Leu Glu Pro Val Ser Cys Asp Leu Ser Asp Asp
 50                  55                  60

Met Pro Trp Ser Ala Cys Pro His Pro Arg Cys Val Pro Arg Arg Cys
 65                  70                  75                  80

Val Ile Pro Cys Gln Ser Phe Val Val Thr Asp Val Asp Tyr Phe Ser
                 85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Ala Thr Gly Tyr Asn Gly Ile Trp Ser Glu Trp Ser Glu Ala Arg
                405                 410                 415
```

```
Ser Trp Asp Thr Glu Ser His His His His His
            420             425

<210> SEQ ID NO 144
<211> LENGTH: 444
<212> TYPE: PRT
<213> ORGANISM: Homo sapiens

<400> SEQUENCE: 144

Met Val Leu Ala Gln Gly Leu Leu Ser Met Ala Leu Ala Leu Cys
1               5                   10                  15

Trp Glu Arg Ser Leu Ala Gly Ala Glu Glu Thr Ile Pro Leu Gln Thr
                20                  25                  30

Leu Arg Cys Tyr Asn Asp Tyr Thr Ser His Ile Thr Cys Arg Trp Ala
            35                  40                  45

Asp Thr Gln Asp Ala Gln Arg Leu Val Asn Val Thr Leu Ile Arg Arg
        50                  55                  60

Val Asn Glu Asp Leu Leu Glu Pro Val Ser Cys Asp Leu Ser Asp Asp
65                  70                  75                  80

Met Pro Trp Ser Ala Cys Pro His Pro Arg Cys Val Pro Arg Arg Cys
                85                  90                  95

Val Ile Pro Cys Gln Ser Phe Val Val Thr Asp Val Asp Tyr Phe Ser
                100                 105                 110

Phe Gln Pro Asp Arg Pro Leu Gly Thr Arg Leu Thr Val Thr Leu Thr
            115                 120                 125

Gln His Val Gln Pro Pro Glu Pro Arg Asp Leu Gln Ile Ser Thr Asp
        130                 135                 140

Gln Asp His Phe Leu Leu Thr Trp Ser Val Ala Leu Gly Ser Pro Gln
145                 150                 155                 160

Ser His Trp Leu Ser Pro Gly Asp Leu Glu Phe Glu Val Val Tyr Lys
                165                 170                 175

Arg Leu Gln Asp Ser Trp Glu Asp Ala Ala Ile Leu Leu Ser Asn Thr
            180                 185                 190

Ser Gln Ala Thr Leu Gly Pro Glu His Leu Met Pro Ser Ser Thr Tyr
        195                 200                 205

Val Ala Arg Val Arg Thr Arg Leu Ala Pro Gly Ser Arg Leu Ser Gly
    210                 215                 220

Arg Pro Ser Lys Trp Ser Pro Glu Val Cys Trp Asp Ser Gln Pro Gly
225                 230                 235                 240

Asp Glu Ala Gln Pro Gln Asn Leu Glu Cys Phe Phe Asp Gly Ala Ala
                245                 250                 255

Val Leu Ser Cys Ser Trp Glu Val Arg Lys Glu Val Ala Ser Ser Val
            260                 265                 270

Ser Phe Gly Leu Phe Tyr Lys Pro Ser Pro Asp Ala Gly Glu Glu Glu
        275                 280                 285

Cys Ser Pro Val Leu Arg Glu Gly Leu Gly Ser Leu His Thr Arg His
    290                 295                 300

His Cys Gln Ile Pro Val Pro Asp Pro Ala Thr His Gly Gln Tyr Ile
305                 310                 315                 320

Val Ser Val Gln Pro Arg Arg Ala Glu Lys His Ile Lys Ser Ser Val
                325                 330                 335

Asn Ile Gln Met Ala Pro Pro Ser Leu Asn Val Thr Lys Asp Gly Asp
            340                 345                 350

Ser Tyr Ser Leu Arg Trp Glu Thr Met Lys Met Arg Tyr Glu His Ile
```

-continued

```
                355                 360                 365

Asp His Thr Phe Glu Ile Gln Tyr Arg Lys Asp Thr Ala Thr Trp Lys
    370                 375                 380

Asp Ser Lys Thr Glu Thr Leu Gln Asn Ala His Ser Met Ala Leu Pro
385                 390                 395                 400

Ala Leu Glu Pro Ser Thr Arg Tyr Trp Ala Arg Val Arg Val Arg Thr
                405                 410                 415

Ser Arg Thr Ala Tyr Asn Gly Ile Trp Ser Glu Trp Ser Glu Ala Arg
            420                 425                 430

Ser Trp Asp Thr Glu Ser His His His His His His
            435                 440

<210> SEQ ID NO 145
<211> LENGTH: 428
<212> TYPE: PRT
<213> ORGANISM: Homo sapiens

<400> SEQUENCE: 145

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
    130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285
```

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Ala Asn Gly Ile Trp Ser Glu Trp Ser Glu Ala Arg
                405                 410                 415

Ser Trp Asp Thr Glu Ser His His His His His His
            420                 425

<210> SEQ ID NO 146
<211> LENGTH: 428
<212> TYPE: PRT
<213> ORGANISM: Homo sapiens

<400> SEQUENCE: 146

Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

```
Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
    370                 375                 380

Ala Leu Glu Pro Ser Thr Arg Tyr Trp Ala Arg Val Arg Val Arg Thr
385                 390                 395                 400

Ser Arg Thr Gly Tyr Ala Gly Ile Trp Ser Glu Trp Ser Glu Ala Arg
                405                 410                 415

Ser Trp Asp Thr Glu Ser His His His His His His
                420                 425

<210> SEQ ID NO 147
<211> LENGTH: 428
<212> TYPE: PRT
<213> ORGANISM: Homo sapiens

<400> SEQUENCE: 147

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
    130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
```

```
            180                 185                 190
Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
            210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
            245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
            290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
                340                 345                 350

Asp His Thr Phe Glu Ile Gln Tyr Arg Lys Asp Thr Ala Thr Trp Lys
                355                 360                 365

Asp Ser Lys Thr Glu Thr Leu Gln Asn Ala His Ser Met Ala Leu Pro
            370                 375                 380

Ala Leu Glu Pro Ser Thr Arg Tyr Trp Ala Arg Val Arg Val Arg Thr
385                 390                 395                 400

Ser Arg Thr Gly Tyr Asn Ala Ile Trp Ser Trp Ser Glu Ala Arg
                405                 410                 415

Ser Trp Asp Thr Glu Ser His His His His His
            420                 425

<210> SEQ ID NO 148
<211> LENGTH: 428
<212> TYPE: PRT
<213> ORGANISM: Homo sapiens

<400> SEQUENCE: 148

Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
            115                 120                 125
```

```
Gln Asp His Phe Leu Leu Thr Trp Ser Val Ala Leu Gly Ser Pro Gln
            130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
                180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
            290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
                340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ala Trp Ser Glu Trp Ser Glu Ala Arg
                405                 410                 415

Ser Trp Asp Thr Glu Ser His His His His His
            420                 425
```

<210> SEQ ID NO 149
<211> LENGTH: 41
<212> TYPE: DNA
<213> ORGANISM: Artificial Sequence
<220> FEATURE:
<223> OTHER INFORMATION: nucleotide acid sequence encoding trimer oligonucleotide 9A2 L1.1
<220> FEATURE:
<221> NAME/KEY: n
<222> LOCATION: (18)..(23)
<223> OTHER INFORMATION: n is any nucleotide provided that a codon comprising the n encoding an amino acid other than cysteine
<220> FEATURE:
<221> NAME/KEY: misc_feature
<222> LOCATION: (18)..(23)
<223> OTHER INFORMATION: n is a, c, g, or t

<400> SEQUENCE: 149
gtcgtgcaag ccagggtnnn nnntggtatc agcagaaacc g          41

<210> SEQ ID NO 150
<211> LENGTH: 45
<212> TYPE: DNA
<213> ORGANISM: Artificial Sequence
<220> FEATURE:
<223> OTHER INFORMATION: nucleotide acid sequence encoding trimer
      oligonucleotide 9A2 L3.1
<220> FEATURE:
<221> NAME/KEY: n
<222> LOCATION: (22)..(27)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (22)..(27)
<223> OTHER INFORMATION: n is a, c, g, or t
<220> FEATURE:
<221> NAME/KEY: n
<222> LOCATION: (32)..(37)
<223> OTHER INFORMATION: "N" is any nucleotide provided that a codon
      comprising the n encoding an amino acid other than cysteine

<400> SEQUENCE: 150
gattttgcaa cctattattg cnnnnnnccg attacctttg gtcag                45

<210> SEQ ID NO 151
<211> LENGTH: 42
<212> TYPE: DNA
<213> ORGANISM: Artificial Sequence
<220> FEATURE:
<223> OTHER INFORMATION: nucleotide acid sequence encoding trimer
      oligonucleotide 9A2 L3.2
<220> FEATURE:
<221> NAME/KEY: n
<222> LOCATION: (20)..(25)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (20)..(25)
<223> OTHER INFORMATION: n is a, c, g, or t
<220> FEATURE:
<221> NAME/KEY: n
<222> LOCATION: (21)..(26)
<223> OTHER INFORMATION: "N" is any nucleotide provided that a codon
      comprising the n encoding an amino acid other than cysteine

<400> SEQUENCE: 151
ctattattgc cagcaggcan nnnnntttgg tcagggcacc cg                   42

<210> SEQ ID NO 152
<211> LENGTH: 42
<212> TYPE: DNA
<213> ORGANISM: Artificial Sequence
<220> FEATURE:
<223> OTHER INFORMATION: nucleotide acid sequence encoding trimer
      oligonucleotide 9A2 H1.1
<220> FEATURE:
<221> NAME/KEY: n
<222> LOCATION: (20)..(25)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (20)..(25)
<223> OTHER INFORMATION: n is a, c, g, or t

<400> SEQUENCE: 152
agcaagcggt tttacctttn nnnnntgggt tcgtcaggca cc                   42

<210> SEQ ID NO 153
<211> LENGTH: 44

```
<212> TYPE: DNA
<213> ORGANISM: Artificial Sequence
<220> FEATURE:
<223> OTHER INFORMATION: nucleotide acid sequence encoding trimer
      oligonucleotide 9A2 H2.1
<220> FEATURE:
<221> NAME/KEY: n
<222> LOCATION: (20)..(25)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (20)..(25)
<223> OTHER INFORMATION: n is a, c, g, or t

<400> SEQUENCE: 153
ggaatgggtt agcagcattn nnnnnaccta ttatgccgat agcg                44

<210> SEQ ID NO 154
<211> LENGTH: 43
<212> TYPE: DNA
<213> ORGANISM: Artificial Sequence
<220> FEATURE:
<223> OTHER INFORMATION: nucleotide acid sequence encoding trimer
      oligonucleotide 9A2 H3.1
<220> FEATURE:
<221> NAME/KEY: n
<222> LOCATION: (20)..(25)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (20)..(25)
<223> OTHER INFORMATION: n is a, c, g, or t

<400> SEQUENCE: 154
agtttattat tgcgcacgcn nnnngatat ttggggtcag ggt                  43

<210> SEQ ID NO 155
<211> LENGTH: 44
<212> TYPE: DNA
<213> ORGANISM: Artificial Sequence
<220> FEATURE:
<223> OTHER INFORMATION: nucleotide acid sequence encoding trimer
      oligonucleotide 9A2 H3.2
<220> FEATURE:
<221> NAME/KEY: n
<222> LOCATION: (21)..(26)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (21)..(26)
<223> OTHER INFORMATION: n is a, c, g, or t

<400> SEQUENCE: 155
attattgcgc acgctttat nnnnnntggg gtcagggtac aatg                 44

<210> SEQ ID NO 156
<211> LENGTH: 44
<212> TYPE: DNA
<213> ORGANISM: Artificial Sequence
<220> FEATURE:
<223> OTHER INFORMATION: nucleotide acid sequence encoding trimer
      oligonucleotide 9A2-VR24-H2.1
<220> FEATURE:
<221> NAME/KEY: n
<222> LOCATION: (20)..(25)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (20)..(25)
```

```
<223> OTHER INFORMATION: n is a, c, g, or t

<400> SEQUENCE: 156
ggaatgggtt agcagcattn nnnnnaccta ttatgccgat agcg                    44

<210> SEQ ID NO 157
<211> LENGTH: 44
<212> TYPE: DNA
<213> ORGANISM: Artificial Sequence
<220> FEATURE:
<223> OTHER INFORMATION: nucleotide acid sequence encoding trimer
      oligonucleotide 9A2-VR24-H2.2
<220> FEATURE:
<221> NAME/KEY: n
<222> LOCATION: (19)..(24)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (19)..(24)
<223> OTHER INFORMATION: n is a, c, g, or t

<400> SEQUENCE: 157
cgtagcagcg gtggttttnn nnnngtgaaa ggtcgtttta ccat                    44

<210> SEQ ID NO 158
<211> LENGTH: 45
<212> TYPE: DNA
<213> ORGANISM: Artificial Sequence
<220> FEATURE:
<223> OTHER INFORMATION: nucleotide acid sequence encoding trimer
      oligonucleotide 9A2-VR24-H2.3
<220> FEATURE:
<221> NAME/KEY: n
<222> LOCATION: (21)..(26)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (21)..(26)
<223> OTHER INFORMATION: n is a, c, g, or t

<400> SEQUENCE: 158
gcggtggttt tacctattat nnnnnncgtt ttaccattag ccgtg                   45

<210> SEQ ID NO 159
<211> LENGTH: 42
<212> TYPE: DNA
<213> ORGANISM: Artificial Sequence
<220> FEATURE:
<223> OTHER INFORMATION: nucleotide acid sequence encoding trimer
      oligonucleotide 9A2-VR39-H1.1
<220> FEATURE:
<221> NAME/KEY: n
<222> LOCATION: (20)..(25)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (20)..(25)
<223> OTHER INFORMATION: n is a, c, g, or t

<400> SEQUENCE: 159
agcaagcggt tttaccttttn nnnntgggt tcgtcaggca cc                      42

<210> SEQ ID NO 160
<211> LENGTH: 42
<212> TYPE: DNA
<213> ORGANISM: Artificial Sequence
<220> FEATURE:
<223> OTHER INFORMATION: nucleotide acid sequence encoding trimer
``` oligonucleotide 9A2-VR39-H1.2
<220> FEATURE:
<221> NAME/KEY: n
<222> LOCATION: (18)..(23)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (18)..(23)
<223> OTHER INFORMATION: n is a, c, g, or t

<400> SEQUENCE: 160
tgagctgtgc agcaagcnnn nnntatcata tgctgtgggt tc                         42

<210> SEQ ID NO 161
<211> LENGTH: 43
<212> TYPE: DNA
<213> ORGANISM: Artificial Sequence
<220> FEATURE:
<223> OTHER INFORMATION: nucleotide acid sequence encoding trimer
      oligonucleotide 9A2-VR39-H2.2
<220> FEATURE:
<221> NAME/KEY: n
<222> LOCATION: (19)..(24)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (19)..(24)
<223> OTHER INFORMATION: n is a, c, g, or t

<400> SEQUENCE: 161
aatggtcgtg gtcgtgttnn nnnngtgaaa ggtcgtttta cca                        43

<210> SEQ ID NO 162
<211> LENGTH: 45
<212> TYPE: DNA
<213> ORGANISM: Artificial Sequence
<220> FEATURE:
<223> OTHER INFORMATION: nucleotide acid sequence encoding trimer
      oligonucleotide 9A2-VR39-H2.3
<220> FEATURE:
<221> NAME/KEY: n
<222> LOCATION: (21)..(26)
<223> OTHER INFORMATION: "N" is any nucleotide provided that a codon
      comprising the n encoding an amino acid other than cysteine
<220> FEATURE:
<221> NAME/KEY: misc_feature
<222> LOCATION: (21)..(26)
<223> OTHER INFORMATION: n is a, c, g, or t

<400> SEQUENCE: 162
gtggtcgtgt tacctattat nnnnnncgtt ttaccattag ccgtg                      45

<210> SEQ ID NO 163
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 H1.1
<220> FEATURE:
<221> NAME/KEY: misc_feature
<222> LOCATION: (30)..(35)
<223> OTHER INFORMATION: Xaa can be any naturally occurring amino acid

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

```
Xaa Xaa Xaa Trp Val Arg Gln Ala Pro Gly Lys Gly Leu Glu Trp Val
        35                  40                  45

Ser Ser Ile Arg Ser Ser Gly Gly Phe Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
                100                 105                 110

Val Thr Val Ser Ser
            115

<210> SEQ ID NO 164
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 H2.1
<220> FEATURE:
<221> NAME/KEY: misc_feature
<222> LOCATION: (52)..(57)
<223> OTHER INFORMATION: Xaa can be any naturally occurring amino acid

<400> SEQUENCE: 164

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
                20                  25                  30

His Met Leu Trp Val Arg Gln Ala Pro Gly Lys Gly Leu Glu Trp Val
        35                  40                  45

Ser Ser Ile Xaa Xaa Xaa Xaa Xaa Xaa Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Asp Ser Phe Phe Asp Ile Trp Gly Gln Gly Thr Met
                100                 105                 110

Val Thr Val Ser Ser
            115

<210> SEQ ID NO 165
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 H3.1
<220> FEATURE:
<221> NAME/KEY: misc_feature
<222> LOCATION: (99)..(104)
<223> OTHER INFORMATION: Xaa can be any naturally occurring amino acid

<400> SEQUENCE: 165

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
                20                  25                  30
```

His Met Leu Trp Val Arg Gln Ala Pro Gly Lys Gly Leu Glu Trp Val
            35                  40                  45

Ser Ser Ile Arg Ser Ser Gly Gly Phe Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Xaa Xaa Xaa Xaa Xaa Xaa Asp Ile Trp Gly Gln Gly Thr Met
            100                 105                 110

Val Thr Val Ser Ser
        115

<210> SEQ ID NO 166
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 H3.2
<220> FEATURE:
<221> NAME/KEY: misc_feature
<222> LOCATION: (101)..(106)
<223> OTHER INFORMATION: Xaa can be any naturally occurring amino acid

<400> SEQUENCE: 166

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
             20                  25                  30

His Met Leu Trp Val Arg Gln Ala Pro Gly Lys Gly Leu Glu Trp Val
            35                  40                  45

Ser Ser Ile Arg Ser Ser Gly Gly Phe Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Xaa Xaa Xaa Xaa Xaa Xaa Trp Gly Gln Gly Thr Met
            100                 105                 110

Val Thr Val Ser Ser
        115

<210> SEQ ID NO 167
<211> LENGTH: 112
<212> TYPE: PRT
<213> ORGANISM: Artificial Sequence
<220> FEATURE:
<223> OTHER INFORMATION: amino acid sequence of VL chain of stop
      template of 9A2 L1.1
<220> FEATURE:
<221> NAME/KEY: misc_feature
<222> LOCATION: (29)..(34)
<223> OTHER INFORMATION: Xaa can be any naturally occurring amino acid

<400> SEQUENCE: 167

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Xaa Xaa Xaa Xaa
             20                  25                  30

Xaa Xaa Trp Tyr Gln Gln Lys Pro Gly Lys Ala Pro Lys Leu Leu Ile

```
                35                  40                  45
Tyr Ala Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Asn Ser Phe Pro Ile
                 85                  90                  95
Thr Phe Gly Gln Gly Thr Arg Leu Glu Ile Lys Arg Thr Val Ala Ala
            100                 105                 110

<210> SEQ ID NO 168
<211> LENGTH: 112
<212> TYPE: PRT
<213> ORGANISM: Artificial Sequence
<220> FEATURE:
<223> OTHER INFORMATION: amino acid sequence of VL chain of stop
      template of 9A2 L3.1
<220> FEATURE:
<221> NAME/KEY: misc_feature
<222> LOCATION: (89)..(94)
<223> OTHER INFORMATION: Xaa can be any naturally occurring amino acid

<400> SEQUENCE: 168

Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Ser Trp
             20                  25                  30
Leu Ala Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Xaa Xaa Xaa Xaa Xaa Xaa Pro Ile
                 85                  90                  95
Thr Phe Gly Gln Gly Thr Arg Leu Glu Ile Lys Arg Thr Val Ala Ala
            100                 105                 110

<210> SEQ ID NO 169
<211> LENGTH: 112
<212> TYPE: PRT
<213> ORGANISM: Artificial Sequence
<220> FEATURE:
<223> OTHER INFORMATION: amino acid sequence of VL chain of stop
      template of 9A2 L3.2
<220> FEATURE:
<221> NAME/KEY: misc_feature
<222> LOCATION: (92)..(97)
<223> OTHER INFORMATION: Xaa can be any naturally occurring amino acid

<400> SEQUENCE: 169

Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Ser Trp
             20                  25                  30
Leu Ala Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
```

```
Glu Asp Phe Ala Thr Tyr Tyr Cys Gln Gln Ala Xaa Xaa Xaa Xaa
                85                  90                  95

Xaa Phe Gly Gln Gly Thr Arg Leu Glu Ile Lys Arg Thr Val Ala Ala
            100                 105                 110
```

<210> SEQ ID NO 170
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 VR24-H2.1
<220> FEATURE:
<221> NAME/KEY: misc_feature
<222> LOCATION: (52)..(57)
<223> OTHER INFORMATION: Xaa can be any naturally occurring amino acid

<400> SEQUENCE: 170

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Xaa Xaa Xaa Xaa Xaa Xaa Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115
```

<210> SEQ ID NO 171
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 VR24-H2.2
<220> FEATURE:
<221> NAME/KEY: misc_feature
<222> LOCATION: (58)..(63)
<223> OTHER INFORMATION: Xaa can be any naturally occurring amino acid

<400> SEQUENCE: 171

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Xaa Xaa Xaa Xaa Xaa Xaa Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Phe Tyr Asp Ser Phe Phe Asp Ile Trp Gly Gln Gly Thr Met
                100                 105                 110

Val Thr Val Ser Ser
        115

<210> SEQ ID NO 172
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 VR24-H2.3
<220> FEATURE:
<221> NAME/KEY: misc_feature
<222> LOCATION: (61)..(66)
<223> OTHER INFORMATION: Xaa can be any naturally occurring amino acid

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Thr Tyr Tyr Xaa Xaa Xaa Xaa
    50                  55                  60

Xaa Xaa Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
                100                 105                 110

Val Thr Val Ser Ser
        115

<210> SEQ ID NO 173
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 VR39-H1.1
<220> FEATURE:
<221> NAME/KEY: misc_feature
<222> LOCATION: (30)..(35)
<223> OTHER INFORMATION: Xaa can be any naturally occurring amino acid

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Xaa Xaa Xaa Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met

Val Thr Val Ser Ser
        115

<210> SEQ ID NO 174
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 VR39-H1.2
<220> FEATURE:
<221> NAME/KEY: misc_feature
<222> LOCATION: (26)..(31)
<223> OTHER INFORMATION: Xaa can be any naturally occurring amino acid

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Tyr Asp Ser Phe Phe Asp Ile Trp Gly Gln Gly Thr Met
        100                 105                 110

Val Thr Val Ser Ser
        115

<210> SEQ ID NO 175
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 VR39-H2.2
<220> FEATURE:
<221> NAME/KEY: misc_feature
<222> LOCATION: (58)..(63)
<223> OTHER INFORMATION: Xaa can be any naturally occurring amino acid

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Xaa Xaa Xaa Xaa Xaa Xaa Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Tyr Asp Ser Phe Phe Asp Ile Trp Gly Gln Gly Thr Met
        100                 105                 110

Val Thr Val Ser Ser
        115

<210> SEQ ID NO 176
<211> LENGTH: 117
<212> TYPE: PRT
<213> ORGANISM: Artificial Sequence
<220> FEATURE:
<223> OTHER INFORMATION: amino acid sequence of VH chain of stop
      template of 9A2 VR39-H2.3
<220> FEATURE:
<221> NAME/KEY: misc_feature
<222> LOCATION: (61)..(66)
<223> OTHER INFORMATION: Xaa can be any naturally occurring amino acid

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

His Met Leu Trp Val Arg Gln Ala Pro Gly Lys Gly Leu Glu Trp Val
        35                  40                  45

Ser Ser Ile Asn Gly Arg Gly Arg Val Thr Tyr Tyr Xaa Xaa Xaa Xaa
    50                  55                  60

Xaa Xaa Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 177
<211> LENGTH: 112
<212> TYPE: PRT
<213> ORGANISM: Artificial Sequence
<220> FEATURE:
<223> OTHER INFORMATION: amino acid sequence of consensus of VL chain
      of 9A2 and derivatives
<220> FEATURE:
<221> NAME/KEY: X
<222> LOCATION: (29)..(29)
<223> OTHER INFORMATION: I, Q, L or V
<220> FEATURE:
<221> NAME/KEY: X
<222> LOCATION: (30)..(30)
<223> OTHER INFORMATION: S or R
<220> FEATURE:
<221> NAME/KEY: X
<222> LOCATION: (31)..(31)
<223> OTHER INFORMATION: S or P
<220> FEATURE:
<221> NAME/KEY: X
<222> LOCATION: (32)..(32)
<223> OTHER INFORMATION: W or F
<220> FEATURE:
<221> NAME/KEY: X
<222> LOCATION: (33)..(33)
<223> OTHER INFORMATION: L, M, V or I
<220> FEATURE:
<221> NAME/KEY: X
<222> LOCATION: (34)..(34)
<223> OTHER INFORMATION: A, S, N or D
<220> FEATURE:
<221> NAME/KEY: X
<222> LOCATION: (89)..(89)
<223> OTHER INFORMATION: Q or G

```
<220> FEATURE:
<221> NAME/KEY: X
<222> LOCATION: (90)..(90)
<223> OTHER INFORMATION: Q, K or I
<220> FEATURE:
<221> NAME/KEY: X
<222> LOCATION: (91)..(91)
<223> OTHER INFORMATION: A or P
<220> FEATURE:
<221> NAME/KEY: X
<222> LOCATION: (92)..(92)
<223> OTHER INFORMATION: N, V or I
<220> FEATURE:
<221> NAME/KEY: X
<222> LOCATION: (93)..(93)
<223> OTHER INFORMATION: S, L or F
<220> FEATURE:
<221> NAME/KEY: X
<222> LOCATION: (94)..(94)
<223> OTHER INFORMATION: F, D or G

<400> SEQUENCE: 177

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Xaa Xaa Xaa Xaa
            20                  25                  30

Xaa Xaa Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Xaa Xaa Xaa Xaa Xaa Xaa Pro Ile
                85                  90                  95

Thr Phe Gly Gln Gly Thr Arg Leu Glu Ile Lys Arg Thr Val Ala Ala
            100                 105                 110

<210> SEQ ID NO 178
<211> LENGTH: 11
<212> TYPE: PRT
<213> ORGANISM: Artificial Sequence
<220> FEATURE:
<223> OTHER INFORMATION: amino acid sequence of consensus of CDR1 of VL
      chain of 9A2 and derivatives
<220> FEATURE:
<221> NAME/KEY: X
<222> LOCATION: (6)..(6)
<223> OTHER INFORMATION: I, Q, L or V
<220> FEATURE:
<221> NAME/KEY: X
<222> LOCATION: (7)..(7)
<223> OTHER INFORMATION: S or R
<220> FEATURE:
<221> NAME/KEY: X
<222> LOCATION: (8)..(8)
<223> OTHER INFORMATION: S or P
<220> FEATURE:
<221> NAME/KEY: X
<222> LOCATION: (9)..(9)
<223> OTHER INFORMATION: W or F
<220> FEATURE:
<221> NAME/KEY: X
<222> LOCATION: (10)..(10)
<223> OTHER INFORMATION: L, M, V or I
<220> FEATURE:
<221> NAME/KEY: X
<222> LOCATION: (11)..(11)
<223> OTHER INFORMATION: A, S, N or D

<400> SEQUENCE: 178
```

Arg Ala Ser Gln Gly Xaa Xaa Xaa Xaa Xaa Xaa
1               5                   10

<210> SEQ ID NO 179
<211> LENGTH: 9
<212> TYPE: PRT
<213> ORGANISM: Artificial Sequence
<220> FEATURE:
<223> OTHER INFORMATION: amino acid sequence of consensus of CDR3 of VL
      chain of 9A2 and derivatives
<220> FEATURE:
<221> NAME/KEY: X
<222> LOCATION: (1)..(1)
<223> OTHER INFORMATION: Q or G
<220> FEATURE:
<221> NAME/KEY: X
<222> LOCATION: (2)..(2)
<223> OTHER INFORMATION: Q,K or I
<220> FEATURE:
<221> NAME/KEY: X
<222> LOCATION: (3)..(3)
<223> OTHER INFORMATION: A or P
<220> FEATURE:
<221> NAME/KEY: X
<222> LOCATION: (4)..(4)
<223> OTHER INFORMATION: N,V or I
<220> FEATURE:
<221> NAME/KEY: X
<222> LOCATION: (5)..(5)
<223> OTHER INFORMATION: S,L or F
<220> FEATURE:
<221> NAME/KEY: X
<222> LOCATION: (6)..(6)
<223> OTHER INFORMATION: F, D or G

<400> SEQUENCE: 179

Xaa Xaa Xaa Xaa Xaa Xaa Pro Ile Thr
1               5

<210> SEQ ID NO 180
<211> LENGTH: 117
<212> TYPE: PRT
<213> ORGANISM: Artificial Sequence
<220> FEATURE:
<223> OTHER INFORMATION: amino acid sequence of consensus of VH chain
      of 9A2 and derivatives
<220> FEATURE:
<221> NAME/KEY: X
<222> LOCATION: (30)..(30)
<223> OTHER INFORMATION: S,N,M,Q,E,P,I,T or V
<220> FEATURE:
<221> NAME/KEY: X
<222> LOCATION: (31)..(31)
<223> OTHER INFORMATION: H or W
<220> FEATURE:
<221> NAME/KEY: X
<222> LOCATION: (33)..(33)
<223> OTHER INFORMATION: H or R
<220> FEATURE:
<221> NAME/KEY: X
<222> LOCATION: (34)..(34)
<223> OTHER INFORMATION: M or V
<220> FEATURE:
<221> NAME/KEY: X
<222> LOCATION: (35)..(35)
<223> OTHER INFORMATION: L or H
<220> FEATURE:
<221> NAME/KEY: X
<222> LOCATION: (52)..(52)
<223> OTHER INFORMATION: R,S,N or G
<220> FEATURE:
<221> NAME/KEY: X
<222> LOCATION: (53)..(53)
<223> OTHER INFORMATION: S or G
<220> FEATURE:
<221> NAME/KEY: X

```
<222> LOCATION: (54)..(54)
<223> OTHER INFORMATION: S,A,F,D,M,R,Y or K
<220> FEATURE:
<221> NAME/KEY: X
<222> LOCATION: (55)..(55)
<223> OTHER INFORMATION: G,Q,V,H,K,M or I
<220> FEATURE:
<221> NAME/KEY: X
<222> LOCATION: (56)..(56)
<223> OTHER INFORMATION: G,W,R,F,W,A or I
<220> FEATURE:
<221> NAME/KEY: X
<222> LOCATION: (57)..(57)
<223> OTHER INFORMATION: F,S,T,P,N,Q or V
<220> FEATURE:
<221> NAME/KEY: X
<222> LOCATION: (101)..(101)
<223> OTHER INFORMATION: D or S
<220> FEATURE:
<221> NAME/KEY: X
<222> LOCATION: (102)..(102)
<223> OTHER INFORMATION: S or D
<220> FEATURE:
<221> NAME/KEY: X
<222> LOCATION: (103)..(103)
<223> OTHER INFORMATION: F,H or N
<220> FEATURE:
<221> NAME/KEY: X
<222> LOCATION: (105)..(105)
<223> OTHER INFORMATION: D,R,S,K,N or A
<220> FEATURE:
<221> NAME/KEY: X
<222> LOCATION: (106)..(106)
<223> OTHER INFORMATION: I,E or P

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Tyr
            20                  25                  30

Xaa Xaa Xaa Trp Val Arg Gln Ala Pro Gly Lys Gly Leu Glu Trp Val
        35                  40                  45

Ser Ser Ile Xaa Xaa Xaa Xaa Xaa Xaa Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Xaa Xaa Xaa Phe Xaa Xaa Trp Gly Gln Gly Thr Met
            100                 105                 110

Val Thr Val Ser Ser
        115

<210> SEQ ID NO 181
<211> LENGTH: 10
<212> TYPE: PRT
<213> ORGANISM: Artificial Sequence
<220> FEATURE:
<223> OTHER INFORMATION: amino acid sequence of consensus of CDR1 of VH
      chain of 9A2 and derivatives
<220> FEATURE:
<221> NAME/KEY: X
<222> LOCATION: (5)..(5)
<223> OTHER INFORMATION: S,N,M,Q,E,P,I,T or V
<220> FEATURE:
<221> NAME/KEY: X
<222> LOCATION: (6)..(6)
<223> OTHER INFORMATION: H or W
<220> FEATURE:
<221> NAME/KEY: X
```

```
<222> LOCATION: (8)..(8)
<223> OTHER INFORMATION: H or R
<220> FEATURE:
<221> NAME/KEY: X
<222> LOCATION: (9)..(9)
<223> OTHER INFORMATION: M or V
<220> FEATURE:
<221> NAME/KEY: X
<222> LOCATION: (10)..(10)
<223> OTHER INFORMATION: L or H

<400> SEQUENCE: 181

Gly Phe Thr Phe Xaa Xaa Tyr Xaa Xaa Xaa
1               5                   10

<210> SEQ ID NO 182
<211> LENGTH: 17
<212> TYPE: PRT
<213> ORGANISM: Artificial Sequence
<220> FEATURE:
<223> OTHER INFORMATION: amino acid sequence of consensus of CDR2 of VH
      chain of 9A2 and derivatives
<220> FEATURE:
<221> NAME/KEY: X
<222> LOCATION: (3)..(3)
<223> OTHER INFORMATION: R,S,N or G
<220> FEATURE:
<221> NAME/KEY: X
<222> LOCATION: (4)..(4)
<223> OTHER INFORMATION: S or G
<220> FEATURE:
<221> NAME/KEY: X
<222> LOCATION: (5)..(5)
<223> OTHER INFORMATION: S,A,F,D,M,R,Y or K
<220> FEATURE:
<221> NAME/KEY: X
<222> LOCATION: (6)..(6)
<223> OTHER INFORMATION: G,Q,V,H,K,M or I
<220> FEATURE:
<221> NAME/KEY: X
<222> LOCATION: (7)..(7)
<223> OTHER INFORMATION: G,W,R,F,W,A or I
<220> FEATURE:
<221> NAME/KEY: X
<222> LOCATION: (8)..(8)
<223> OTHER INFORMATION: F,S,T,P,N,Q or V

<400> SEQUENCE: 182

Ser Ile Xaa Xaa Xaa Xaa Xaa Xaa Thr Tyr Tyr Ala Asp Ser Val Lys
1               5                   10                  15
Gly

<210> SEQ ID NO 183
<211> LENGTH: 8
<212> TYPE: PRT
<213> ORGANISM: Artificial Sequence
<220> FEATURE:
<223> OTHER INFORMATION: amino acid sequence of consensus of CDR3 of VH
      chain of 9A2 and derivatives
<220> FEATURE:
<221> NAME/KEY: X
<222> LOCATION: (3)..(3)
<223> OTHER INFORMATION: D or S
<220> FEATURE:
<221> NAME/KEY: X
<222> LOCATION: (4)..(4)
<223> OTHER INFORMATION: S or D
<220> FEATURE:
<221> NAME/KEY: X
<222> LOCATION: (5)..(5)
<223> OTHER INFORMATION: F,H or N
<220> FEATURE:
<221> NAME/KEY: X
<222> LOCATION: (7)..(7)
```

```
<223> OTHER INFORMATION: D,R,S,K,N or A
<220> FEATURE:
<221> NAME/KEY: X
<222> LOCATION: (8)..(8)
<223> OTHER INFORMATION: I, E or P

<400> SEQUENCE: 183

Phe Tyr Xaa Xaa Xaa Phe Xaa Xaa
1               5

<210> SEQ ID NO 184
<211> LENGTH: 117
<212> TYPE: PRT
<213> ORGANISM: Artificial Sequence
<220> FEATURE:
<223> OTHER INFORMATION: amino acid sequence of consensus of VH chain
      of 9A2-VR24 and derivatives
<220> FEATURE:
<221> NAME/KEY: X
<222> LOCATION: (52)..(52)
<223> OTHER INFORMATION: R,H,Q or K
<220> FEATURE:
<221> NAME/KEY: X
<222> LOCATION: (53)..(53)
<223> OTHER INFORMATION: S,T,H or N
<220> FEATURE:
<221> NAME/KEY: X
<222> LOCATION: (54)..(54)
<223> OTHER INFORMATION: S,H,G,Q,D or E
<220> FEATURE:
<221> NAME/KEY: X
<222> LOCATION: (55)..(55)
<223> OTHER INFORMATION: G,R,S,Y or N
<220> FEATURE:
<221> NAME/KEY: X
<222> LOCATION: (56)..(56)
<223> OTHER INFORMATION: G,H,N,Q,K,T,V,R,P or D
<220> FEATURE:
<221> NAME/KEY: X
<222> LOCATION: (57)..(57)
<223> OTHER INFORMATION: F,I,S,W,V or Y
<220> FEATURE:
<221> NAME/KEY: X
<222> LOCATION: (58)..(58)
<223> OTHER INFORMATION: T or P
<220> FEATURE:
<221> NAME/KEY: X
<222> LOCATION: (59)..(59)
<223> OTHER INFORMATION: Y,H,F or M
<220> FEATURE:
<221> NAME/KEY: X
<222> LOCATION: (61)..(61)
<223> OTHER INFORMATION: A,H,N,S or T
<220> FEATURE:
<221> NAME/KEY: X
<222> LOCATION: (62)..(62)
<223> OTHER INFORMATION: D,Q,Y,R,H,P,L,S or N
<220> FEATURE:
<221> NAME/KEY: X
<222> LOCATION: (63)..(63)
<223> OTHER INFORMATION: S,K,R,V,F,H,A or E
<220> FEATURE:
<221> NAME/KEY: X
<222> LOCATION: (65)..(65)
<223> OTHER INFORMATION: K,R or M
<220> FEATURE:
<221> NAME/KEY: X
<222> LOCATION: (66)..(66)
<223> OTHER INFORMATION: G,N or H

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30
```

```
Arg Val His Trp Val Arg Gln Ala Pro Gly Lys Gly Leu Glu Trp Val
        35                  40                  45

Ser Ser Ile Xaa Xaa Xaa Xaa Xaa Xaa Xaa Tyr Xaa Xaa Xaa Val
    50                  55                  60

Xaa Xaa Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
                100                 105                 110

Val Thr Val Ser Ser
        115

<210> SEQ ID NO 185
<211> LENGTH: 10
<212> TYPE: PRT
<213> ORGANISM: Artificial Sequence
<220> FEATURE:
<223> OTHER INFORMATION: amino acid sequence of consensus of CDR1 of VH
      chain of 9A2-VR24 and derivatives

<400> SEQUENCE: 185

Gly Phe Thr Phe Pro Trp Tyr Arg Val His
1               5                   10

<210> SEQ ID NO 186
<211> LENGTH: 17
<212> TYPE: PRT
<213> ORGANISM: Artificial Sequence
<220> FEATURE:
<223> OTHER INFORMATION: amino acid sequence of consensus of CDR2 of VH
      chain of 9A2-VR24 and derivatives
<220> FEATURE:
<221> NAME/KEY: X
<222> LOCATION: (3)..(3)
<223> OTHER INFORMATION: R, H, Q or K
<220> FEATURE:
<221> NAME/KEY: X
<222> LOCATION: (4)..(4)
<223> OTHER INFORMATION: S, T, H or N
<220> FEATURE:
<221> NAME/KEY: X
<222> LOCATION: (5)..(5)
<223> OTHER INFORMATION: S, H, G, Q, D or E
<220> FEATURE:
<221> NAME/KEY: X
<222> LOCATION: (6)..(6)
<223> OTHER INFORMATION: G, R, S, Y or N
<220> FEATURE:
<221> NAME/KEY: X
<222> LOCATION: (7)..(7)
<223> OTHER INFORMATION: G, H, N, Q, K, T, V, R, P or D
<220> FEATURE:
<221> NAME/KEY: X
<222> LOCATION: (8)..(8)
<223> OTHER INFORMATION: F, I, S, W, V or Y
<220> FEATURE:
<221> NAME/KEY: X
<222> LOCATION: (9)..(9)
<223> OTHER INFORMATION: T or P
<220> FEATURE:
<221> NAME/KEY: X
<222> LOCATION: (10)..(10)
<223> OTHER INFORMATION: Y, H , F or M
<220> FEATURE:
<221> NAME/KEY: X
<222> LOCATION: (12)..(12)
<223> OTHER INFORMATION: A, H, N, S or T
<220> FEATURE:
<221> NAME/KEY: X
```

```
<222> LOCATION: (13)..(13)
<223> OTHER INFORMATION: D, Q, Y, R, H, P, L, S or N
<220> FEATURE:
<221> NAME/KEY: X
<222> LOCATION: (14)..(14)
<223> OTHER INFORMATION: S, K, R, V, F, H, A or E
<220> FEATURE:
<221> NAME/KEY: X
<222> LOCATION: (16)..(16)
<223> OTHER INFORMATION: K, R or M
<220> FEATURE:
<221> NAME/KEY: X
<222> LOCATION: (17)..(17)
<223> OTHER INFORMATION: G, N or H

<400> SEQUENCE: 186

Ser Ile Xaa Xaa Xaa Xaa Xaa Xaa Xaa Xaa Tyr Xaa Xaa Xaa Val Xaa
1               5                   10                  15

Xaa

<210> SEQ ID NO 187
<211> LENGTH: 8
<212> TYPE: PRT
<213> ORGANISM: Artificial Sequence
<220> FEATURE:
<223> OTHER INFORMATION: amino acid sequence of consensus of CDR3 of VH
      chain of 9A2-VR24 and derivatives

<400> SEQUENCE: 187

Phe Tyr Asp Ser Phe Phe Asp Ile
1               5

<210> SEQ ID NO 188
<211> LENGTH: 117
<212> TYPE: PRT
<213> ORGANISM: Artificial Sequence
<220> FEATURE:
<223> OTHER INFORMATION: amino acid sequence of consensus of VH chain
      of 9A2-VR39 and derivatives
<220> FEATURE:
<221> NAME/KEY: X
<222> LOCATION: (26)..(26)
<223> OTHER INFORMATION: G, R, D, A or P
<220> FEATURE:
<221> NAME/KEY: X
<222> LOCATION: (27)..(27)
<223> OTHER INFORMATION: F, G, V, R or Y
<220> FEATURE:
<221> NAME/KEY: X
<222> LOCATION: (28)..(28)
<223> OTHER INFORMATION: T, S, A, P, F or W
<220> FEATURE:
<221> NAME/KEY: X
<222> LOCATION: (29)..(29)
<223> OTHER INFORMATION: F, P or E
<220> FEATURE:
<221> NAME/KEY: X
<222> LOCATION: (30)..(30)
<223> OTHER INFORMATION: S, F, Y, N, P, Q, H, E, M, V, G, W or M
<220> FEATURE:
<221> NAME/KEY: X
<222> LOCATION: (31)..(31)
<223> OTHER INFORMATION: H, W, E, F, G, Y or N
<220> FEATURE:
<221> NAME/KEY: X
<222> LOCATION: (32)..(32)
<223> OTHER INFORMATION: Y or F
<220> FEATURE:
<221> NAME/KEY: X
<222> LOCATION: (33)..(33)
<223> OTHER INFORMATION: H, M, Q, N or V
<220> FEATURE:
<221> NAME/KEY: X
<222> LOCATION: (34)..(34)
```

```
<223> OTHER INFORMATION: M, H, T, Y, I, K, W, V, F or Q
<220> FEATURE:
<221> NAME/KEY: X
<222> LOCATION: (35)..(35)
<223> OTHER INFORMATION: L, V or I
<220> FEATURE:
<221> NAME/KEY: X
<222> LOCATION: (59)..(59)
<223> OTHER INFORMATION: Y, H or Q
<220> FEATURE:
<221> NAME/KEY: X
<222> LOCATION: (60)..(60)
<223> OTHER INFORMATION: Y, V or M
<220> FEATURE:
<221> NAME/KEY: X
<222> LOCATION: (61)..(61)
<223> OTHER INFORMATION: A, Q or N
<220> FEATURE:
<221> NAME/KEY: X
<222> LOCATION: (62)..(62)
<223> OTHER INFORMATION: D, Q, W, P, R or L
<220> FEATURE:
<221> NAME/KEY: X
<222> LOCATION: (63)..(63)
<223> OTHER INFORMATION: S, E, P, A or D
<220> FEATURE:
<221> NAME/KEY: X
<222> LOCATION: (64)..(64)
<223> OTHER INFORMATION: V, M, W, H or Y
<220> FEATURE:
<221> NAME/KEY: X
<222> LOCATION: (65)..(65)
<223> OTHER INFORMATION: K or N
<220> FEATURE:
<221> NAME/KEY: X
<222> LOCATION: (66)..(66)
<223> OTHER INFORMATION: G or K

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa Xaa
            20                  25                  30

Xaa Xaa Xaa Trp Val Arg Gln Ala Pro Gly Lys Gly Leu Glu Trp Val
            35                  40                  45

Ser Ser Ile Asn Gly Arg Gly Arg Val Thr Xaa Xaa Xaa Xaa Xaa Xaa
    50                  55                  60

Xaa Xaa Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser
        115

<210> SEQ ID NO 189
<211> LENGTH: 10
<212> TYPE: PRT
<213> ORGANISM: Artificial Sequence
<220> FEATURE:
<223> OTHER INFORMATION: amino acid sequence of consensus of CDR1 of VH
      chain of 9A2-VR39 and derivatives
<220> FEATURE:
<221> NAME/KEY: X
<222> LOCATION: (1)..(1)
<223> OTHER INFORMATION: G, R, D, A or P
<220> FEATURE:
<221> NAME/KEY: X
<222> LOCATION: (2)..(2)
```

```
<223> OTHER INFORMATION: F, G, V, R or Y
<220> FEATURE:
<221> NAME/KEY: X
<222> LOCATION: (3)..(3)
<223> OTHER INFORMATION: T, S, A, P, F or W
<220> FEATURE:
<221> NAME/KEY: X
<222> LOCATION: (4)..(4)
<223> OTHER INFORMATION: F, P or E
<220> FEATURE:
<221> NAME/KEY: X
<222> LOCATION: (5)..(5)
<223> OTHER INFORMATION: S, F, Y, N, P, Q, H, E, M, V, G, W or M
<220> FEATURE:
<221> NAME/KEY: X
<222> LOCATION: (6)..(6)
<223> OTHER INFORMATION: H, W, E, F, G, Y or N
<220> FEATURE:
<221> NAME/KEY: X
<222> LOCATION: (7)..(7)
<223> OTHER INFORMATION: Y or F
<220> FEATURE:
<221> NAME/KEY: X
<222> LOCATION: (8)..(8)
<223> OTHER INFORMATION: H, M, Q, N or V
<220> FEATURE:
<221> NAME/KEY: X
<222> LOCATION: (9)..(9)
<223> OTHER INFORMATION: M, H, T, Y, I, K, W, V, F or Q
<220> FEATURE:
<221> NAME/KEY: X
<222> LOCATION: (10)..(10)
<223> OTHER INFORMATION: L, V or I

<400> SEQUENCE: 189

Xaa Xaa Xaa Xaa Xaa Xaa Xaa Xaa Xaa Xaa
1               5                   10

<210> SEQ ID NO 190
<211> LENGTH: 17
<212> TYPE: PRT
<213> ORGANISM: Artificial Sequence
<220> FEATURE:
<223> OTHER INFORMATION: amino acid sequence of consensus of CDR2 of VH
      chain of 9A2-VR39 and derivatives
<220> FEATURE:
<221> NAME/KEY: X
<222> LOCATION: (10)..(10)
<223> OTHER INFORMATION: Y, H or Q
<220> FEATURE:
<221> NAME/KEY: X
<222> LOCATION: (11)..(11)
<223> OTHER INFORMATION: Y, V or M
<220> FEATURE:
<221> NAME/KEY: X
<222> LOCATION: (12)..(12)
<223> OTHER INFORMATION: A, Q or N
<220> FEATURE:
<221> NAME/KEY: X
<222> LOCATION: (13)..(13)
<223> OTHER INFORMATION: D, Q, W, P, R or L
<220> FEATURE:
<221> NAME/KEY: X
<222> LOCATION: (14)..(14)
<223> OTHER INFORMATION: S, E, P, A or D
<220> FEATURE:
<221> NAME/KEY: X
<222> LOCATION: (15)..(15)
<223> OTHER INFORMATION: V, M, W, H or Y
<220> FEATURE:
<221> NAME/KEY: X
<222> LOCATION: (16)..(16)
<223> OTHER INFORMATION: K or N
<220> FEATURE:
<221> NAME/KEY: X
<222> LOCATION: (17)..(17)
<223> OTHER INFORMATION: G or K
```

-continued

<400> SEQUENCE: 190

Ser Ile Asn Gly Arg Gly Arg Val Thr Xaa Xaa Xaa Xaa Xaa Xaa
1               5                   10                  15

Xaa

<210> SEQ ID NO 191
<211> LENGTH: 8
<212> TYPE: PRT
<213> ORGANISM: Artificial Sequence
<220> FEATURE:
<223> OTHER INFORMATION: amino acid sequence of consensus of CDR3 of VH
      chain of 9A2-VR39 and derivatives

<400> SEQUENCE: 191

Phe Tyr Asp Ser Phe Phe Asp Ile
1               5

<210> SEQ ID NO 192
<211> LENGTH: 428
<212> TYPE: PRT
<213> ORGANISM: Homo sapiens

<400> SEQUENCE: 192

Trp Glu Arg Ser Leu Ala Gly Ala Glu Thr Ile Pro Leu Gln Thr
1               5                   10                  15

Leu Arg Cys Tyr Asn Asp Tyr Thr Ser His Ile Thr Cys Arg Trp Ala
            20                  25                  30

Asp Thr Gln Asp Ala Gln Arg Leu Val Asn Val Thr Leu Ile Arg Arg
        35                  40                  45

Val Asn Glu Asp Leu Leu Glu Pro Val Ser Cys Asp Leu Ser Asp Asp
    50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
            100                 105                 110

Gln His Val Gln Pro Pro Glu Pro Arg Asp Leu Gln Ile Ser Thr Asp
        115                 120                 125

Gln Asp His Phe Leu Leu Thr Trp Ser Val Ala Leu Gly Ser Pro Gln
    130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu

```
                    260                 265                 270
Cys Ser Pro Val Leu Arg Glu Gly Leu Gly Ser Leu His Thr Arg His
            275                 280                 285

His Cys Gln Ile Pro Val Pro Asp Pro Ala Thr His Gly Gln Tyr Ile
            290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
            325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
            355                 360                 365

Asp Ser Lys Thr Glu Thr Leu Gln Asn Ala His Ser Met Ala Leu Pro
            370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
            405                 410                 415

Ser Trp Asp Thr Glu Ser His His His His His His
            420                 425

<210> SEQ ID NO 193
<211> LENGTH: 117
<212> TYPE: PRT
<213> ORGANISM: Artificial Sequence
<220> FEATURE:
<223> OTHER INFORMATION: amino acid sequence of VH chain of 9A2-VR24
      HCDR2 mutants
<220> FEATURE:
<221> NAME/KEY: misc_feature
<222> LOCATION: (52)..(59)
<223> OTHER INFORMATION: Xaa can be any naturally occurring amino acid
<220> FEATURE:
<221> NAME/KEY: misc_feature
<222> LOCATION: (61)..(63)
<223> OTHER INFORMATION: Xaa can be any naturally occurring amino acid
<220> FEATURE:
<221> NAME/KEY: misc_feature
<222> LOCATION: (65)..(66)
<223> OTHER INFORMATION: Xaa can be any naturally occurring amino acid

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
            35                  40                  45

Ser Ser Ile Xaa Xaa Xaa Xaa Xaa Xaa Xaa Tyr Xaa Xaa Xaa Xaa Val
50                  55                  60

Xaa Xaa Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Tyr Asp Ser Phe Phe Asp Ile Trp Gly Gln Gly Thr Met
            100                 105                 110

Val Thr Val Ser Ser
            115
```

<210> SEQ ID NO 194
<211> LENGTH: 444
<212> TYPE: PRT
<213> ORGANISM: Artificial Sequence
<220> FEATURE:
<223> OTHER INFORMATION: amino acid sequence of antibody 9A2 heavy chain

<400> SEQUENCE: 194

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Trp Tyr
            20                  25                  30

Arg Val His Trp Val Arg Gln Ala Pro Gly Lys Gly Leu Glu Trp Val
        35                  40                  45

Ser Ser Ile Arg Ser Ser Gly Gly Phe Pro Tyr Tyr Asn Tyr Lys Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Asp Ser Phe Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365
```

```
Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 195
<211> LENGTH: 214
<212> TYPE: PRT
<213> ORGANISM: Artificial Sequence
<220> FEATURE:
<223> OTHER INFORMATION: amino acid sequence of antibody 9A2 light chain

<400> SEQUENCE: 195

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Leu Arg Pro Phe
            20                  25                  30

Val Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 196
<211> LENGTH: 327
<212> TYPE: PRT
<213> ORGANISM: Artificial Sequence
<220> FEATURE:
<223> OTHER INFORMATION: amino acid sequence of stabilized IgG4 heavy
      chain constant region

<400> SEQUENCE: 196

Ala Ser Thr Lys Gly Pro Ser Val Phe Pro Leu Ala Pro Cys Ser Arg
```

```
                1               5              10              15
            Ser Thr Ser Glu Ser Thr Ala Ala Leu Gly Cys Leu Val Lys Asp Tyr
                        20              25              30

Phe Pro Glu Pro Val Thr Val Ser Trp Asn Ser Gly Ala Leu Thr Ser
                        35              40              45

Gly Val His Thr Phe Pro Ala Val Leu Gln Ser Ser Gly Leu Tyr Ser
                        50              55              60

Leu Ser Ser Val Val Thr Val Pro Ser Ser Leu Gly Thr Lys Thr
             65              70              75              80

Tyr Thr Cys Asn Val Asp His Lys Pro Ser Asn Thr Lys Val Asp Lys
                            85              90              95

Arg Val Glu Ser Lys Tyr Gly Pro Pro Cys Pro Pro Cys Pro Ala Pro
                        100             105             110

Glu Phe Leu Gly Gly Pro Ser Val Phe Leu Phe Pro Pro Lys Pro Lys
                        115             120             125

Asp Thr Leu Met Ile Ser Arg Thr Pro Glu Val Thr Cys Val Val Val
                        130             135             140

Asp Val Ser Gln Glu Asp Pro Glu Val Gln Phe Asn Trp Tyr Val Asp
            145             150             155             160

Gly Val Glu Val His Asn Ala Lys Thr Lys Pro Arg Glu Glu Gln Phe
                            165             170             175

Asn Ser Thr Tyr Arg Val Val Ser Val Leu Thr Val Leu His Gln Asp
                        180             185             190

Trp Leu Asn Gly Lys Glu Tyr Lys Cys Lys Val Ser Asn Lys Gly Leu
                        195             200             205

Pro Ser Ser Ile Glu Lys Thr Ile Ser Lys Ala Lys Gly Gln Pro Arg
                        210             215             220

Glu Pro Gln Val Tyr Thr Leu Pro Pro Ser Gln Glu Glu Met Thr Lys
            225             230             235             240

Asn Gln Val Ser Leu Thr Cys Leu Val Lys Gly Phe Tyr Pro Ser Asp
                        245             250             255

Ile Ala Val Glu Trp Glu Ser Asn Gly Gln Pro Glu Asn Asn Tyr Lys
                        260             265             270

Thr Thr Pro Pro Val Leu Asp Ser Asp Gly Ser Phe Phe Leu Tyr Ser
                        275             280             285

Arg Leu Thr Val Asp Lys Ser Arg Trp Gln Glu Gly Asn Val Phe Ser
                        290             295             300

Cys Ser Val Met His Glu Ala Leu His Asn His Tyr Thr Gln Lys Ser
            305             310             315             320

Leu Ser Leu Ser Leu Gly Lys
                        325

<210> SEQ ID NO 197
<211> LENGTH: 104
<212> TYPE: PRT
<213> ORGANISM: Artificial Sequence
<220> FEATURE:
<223> OTHER INFORMATION: amino acid sequence of kappa light chain
      constant region

<400> SEQUENCE: 197

Ala Ala Pro Ser Val Phe Ile Phe Pro Pro Ser Asp Glu Gln Leu Lys
 1               5              10              15

Ser Gly Thr Ala Ser Val Val Cys Leu Leu Asn Asn Phe Tyr Pro Arg
            20              25              30
```

-continued

```
Glu Ala Lys Val Gln Trp Lys Val Asp Asn Ala Leu Gln Ser Gly Asn
        35                  40                  45

Ser Gln Glu Ser Val Thr Glu Gln Asp Ser Lys Asp Ser Thr Tyr Ser
    50                  55                  60

Leu Ser Ser Thr Leu Thr Leu Ser Lys Ala Asp Tyr Glu Lys His Lys
65                  70                  75                  80

Val Tyr Ala Cys Glu Val Thr His Gln Gly Leu Ser Ser Pro Val Thr
                85                  90                  95

Lys Ser Phe Asn Arg Gly Glu Cys
            100
```

CD131 BINDING PROTEINS AND USES THEREOF

RELATED APPLICATION DATA

The present application is a continuation of U.S. patent application Ser. No. 15/779,252, filed Nov. 5, 2018 and issued as U.S. Pat. No. 10,894,834, which is the U.S. national stage entry under 35 U.S.C. § 371 of International Application No. PCT/AU2016/051158, filed on Nov. 25, 2016, which claims priority to Australian Patent Application No. 2015904924, filed on Nov. 27, 2015. The contents of these applications are each incorporated herein by reference in their entirety.

SEQUENCE LISTING

The present application is filed with a Sequence Listing in electronic form. The entire contents of the Sequence Listing are hereby incorporated by reference.

FIELD

The present disclosure relates to CD131-binding proteins and compounds and uses thereof.

BACKGROUND

The pleiotropic cytokines interleukin (IL)-3 (IL-3), IL-5 and granulocyte-macrophage colony stimulating factor (GM-CSF) play critical and overlapping roles in the differentiation and function of myeloid cells. They are important mediators of host defense and innate immunity, but can also contribute significantly to the development and progression of inflammatory pathologies including inflammatory airway diseases such as asthma, chronic rhinosinusitis with and without nasal polyposis (CRSwNP, CRSsNP), chronic obstructive pulmonary disease (COPD) and asthma-COPD overlap syndrome (ACOS). GM-CSF has also been implicated in autoimmune conditions, such as rheumatoid arthritis and IL-3 has been implicated in conditions, such as leukemia. In asthma and COPD, GM-CSF expression is elevated in sputum, bronchoalveolar lavage fluid (BALF) and bronchial biopsies. IL-3 acts at the early stages of hematopoiesis and synergizes with other growth factors for hemopoietic development. It also modulates the activity of mature cell types such as monocytes, dendritic cells, megakaryocytes, mast cells and can activate eosinophils and prime basophils to release histamine. A growth factor for basophils, increased levels of IL-3 in BALF are typically present after allergen challenge. IL-5 is more cell type-specific, regulating the production and release of mature eosinophils from the bone marrow into the circulation. Elevated levels of IL-5 have been found in the serum and airway fluid of patients with asthma. In asthmatic subjects, IL-5 inhalation increased AHR as well as the recruitment of activated eosinophils to the airways.

Each of IL-3, IL-5 and GM-CSF all signal through a multimeric receptor made up of a common β chain ($β_c$ chain or CD131) and a cytokine specific α chain.

As a consequence of the evidence supporting a key role for cells of the myeloid lineage and IL-3, IL-5 and GM-CSF in the development and progression of inflammatory airway disease, a number of therapeutic antibodies targeting individual cytokines or receptor α-chains are in clinical development. While these agents may prove useful in selected subsets of patients it is likely that their broader application will be limited by both the redundant and overlapping function of the molecules that they target and by the variable nature of the inflammatory cell infiltrate that can underpin asthma. For example, studies of the anti-IL-5 antibody mepolizumab have shown that targeting only IL-5 has no effects on airway obstruction or airway hyperresponsiveness in patients with asthma.

It will be clear to the skilled artisan based on the foregoing that there is a need in the art for compounds (e.g., antibodies and antibody-derived proteins) that can treat conditions mediated by IL-3, IL-5 and/or GM-CSF.

SUMMARY

In producing the present invention, the inventors sought to produce reagents (e.g., antibodies and proteins comprising antigen binding domains thereof) that bind to CD131 and neutralize signaling by IL-3, IL-5 and GM-CSF. The inventors produced a series of antibodies having such activity, some of which potently neutralize signaling by IL-3, IL-5 and GM-CSF, e.g., prevent proliferation of TF-1 cell in response to each of those cytokines amongst numerous other assays. The inventors also performed epitope mapping and found that the antibodies bound to CD131 within a region designated "Site 2" and also found that certain residues within Site 2 which are important for binding of IL-3, IL-5 and GM-CSF are also important for binding of the antibodies.

The inventors additionally showed that an antibody they had produced was capable of reducing survival of inflammatory cells from human subjects suffering from airway disease (e.g., asthma and/or nasal polyposis). This suppression in survival of inflammatory cells was greater than that observed using the current standard of care for inflammatory airway diseases, such as asthma (i.e., prednisolone). Using a xenograft model of nasal polyposis, the inventors showed that an antibody they produced reduced the size and weight of polyps and the number of B cells infiltrating polyps compared to a control antibody The inventors also showed that neutralizing signaling of IL-3, IL-5 and GM-CSF is an effective manner of reducing survival of eosinophils, e.g., to treat eosinophilia. This was shown using an antibody of the disclosure that binds to CD131 or using a combination of antibodies against each of IL-3Rα, IL-5R and GM-CSF-R. While the combination of antibodies was effective in reducing survival of eosinophils, the antibody of the disclosure was more effective.

Based on the foregoing, it will be apparent to the skilled artisan that the inventors have produced a protein comprising an antigen binding domain of an antibody, the antigen binding domain capable of binding to or specifically binding to CD131 and neutralizing IL-3, IL-5 and GM-CSF signaling. The inventors have also produced methods for treating various conditions and/or reducing survival of eosinophils by neutralizing IL-3, IL-5 and GM-CSF signaling, e.g., using a protein of the disclosure.

In one example, the present disclosure provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein inhibits GM-CSF-induced proliferation of TF-1 erythroleukemic cells with an $IC_{50}$ of at least 700 nM.

In one example, the CD131-binding protein inhibits GM-CSF-induced proliferation of TF-1 cells with an $IC_{50}$ of at least 600 nM or 500 nM. For example, the $IC_{50}$ is at least about 460 nM. For example, the $IC_{50}$ is at least about 300 nM or 200 nM or 100 nM. For example, the $IC_{50}$ is at least about 460 nM. For example, the $IC_{50}$ is at least about 10 nM or 5 nM or 1 nM. In one example, the $IC_{50}$ is at least about 1 nM. For example, the $IC_{50}$ is at least about 0.9 nM or 0.8 nM or 0.6 nM. In one example, the $IC_{50}$ is at least about 0.5 nM. In one example, the $IC_{50}$ is at least about 0.4 nM. In one example, the $IC_{50}$ is at least about 0.3 nM.

In one example, the CD131-binding protein inhibits IL-3-induced proliferation of TF-1 cells with an $IC_{50}$ of at least 600 nM or 500 nM. For example, the $IC_{50}$ is at least about 460 nM. For example, the $IC_{50}$ is at least about 300 nM or 200 nM or 100 nM. For example, the $IC_{50}$ is at least about 10 nM or 5 nM or 1 nM. In one example, the $IC_{50}$ is at least about 1 nM. For example, the $IC_{50}$ is at least about 0.9 nM or 0.8 nM or 0.6 nM. In one example, the $IC_{50}$ is at least about 0.5 nM. In one example, the $IC_{50}$ is at least about 0.2 nM or at least about 0.1 nM. In one example, the $IC_{50}$ is at least about 0.15 nM. In one example, the CD131-binding protein inhibits IL-5-induced proliferation of TF-1 cells with an $IC_{50}$ of at least 600 nM or 500 nM. For example, the $IC_{50}$ is at least about 460 nM. For example, the $IC_{50}$ is at least about 300 nM or 200 nM or 100 nM. For example, the $IC_{50}$ is at least about 10 nM or 5 nM or 1 nM. In one example, the $IC_{50}$ is at least about 5 nM. For example, the $IC_{50}$ is at least about 4 nM. In one example, the $IC_{50}$ is at least about 4.5 nM or at least about 4.6 or at least about 4.7 nM. In one example, the $IC_{50}$ is at least about 4.6 nM.

Methods for determining the $IC_{50}$ include culturing TF-1 cells (e.g., about $1\times10^4$ TF-1 cells) in the presence of the CD131-binding protein (e.g., for at least about 3 minutes or 1 hour, such as about 30 minutes) prior to adding the relevant growth factor (GM-CSF, IL-3 and/or IL-5) and culturing the cells further (e.g., for at least about 48 hours or at least about 72 hours or at least about 96 hours, e.g., for about 72 hours) and then determining cell proliferation. Cell proliferation can be determined by growing the cells in the presence of $^3$[H]-thymidine for about 6 hours and determining $^3$[H]-thymidine incorporation, e.g., by liquid-scintillation counting. By determining proliferation in a variety of concentrations of the CD131-binding protein an $IC_{50}$ can be determined.

In one example, the present disclosure provides a CD131-binding protein comprising an antigen binding domain of an antibody, wherein the antigen binding domain binds to or specifically binds to CD131 and neutralizes signaling by IL-3, IL-5 and GM-CSF to a degree greater than antibody BION-1 (as disclosed in Sun et al., *Blood.* 94: 1943-1951, 1999).

The present disclosure additionally provides a CD131-binding protein comprising an antigen binding domain of an antibody, wherein the antigen binding domain binds to or specifically binds to an epitope within Site 2 of CD131 and neutralizes signaling by IL-3, IL-5 and GM-CSF. In this regard, the skilled artisan will be aware that Site 2 of CD131 is made up of residues from two CD131 polypeptides that form a dimer, e.g., Site 2 comprises residues within loops A-B and E-F of domain 1 of one CD131 polypeptide and residues within loops B-C and F-G of another CD131 polypeptide.

In one example, the antigen binding domain binds to an epitope formed upon dimerization of two CD131 polypeptides. For example, the antigen binding domain binds to residues within domain 1 of a CD131 polypeptide and residues within domain 4 of another CD131 polypeptide.

In one example, the antigen binding domain binds to an epitope comprising one or more of amino acids corresponding to residues 39 and/or 103 of SEQ ID NO: 1. In another example, the antigen binding domain binds to an epitope comprising one or more of amino acids corresponding to residues 338, 365, 367 and 368 of SEQ ID NO: 1.

In a further example, the antigen binding domain binds to an epitope formed upon dimerization of two CD131 polypeptides, wherein the epitope comprises one or more (or all) of amino acids corresponding to residues 39 and 103 of one CD131 polypeptide and residues 338, 365, 367 and 368 of the other CD131 polypeptide.

In another example, present disclosure provides a CD131-binding protein comprising an antigen binding domain of an antibody, wherein the antigen binding domain binds to or specifically binds to an epitope within Site 2 of CD131 and neutralizes signaling by IL-3, IL-5 and GM-CSF, wherein the antigen binding domain binds to an epitope comprising amino acids involved in binding of IL-3, IL-5 and/or GM-CSF to CD131. For example, the amino acids correspond to residues 39, 103, 338, 365, 367 and 368 of SEQ ID NO: 1. For example, the amino acid corresponds to residue 39 of SEQ ID NO: 1. For example, the residues correspond to residues 39 and 103 of one CD131 polypeptide and residues 338, 365, 367 and 368 of another CD131 polypeptide. For example, the residues correspond to residue 39 of one CD131 polypeptide and residue 365 and/or residue 367 of another CD131 polypeptide.

The present disclosure additionally provides a compound that binds to or specifically binds to an epitope within Site 2 of CD131 and neutralizes signaling by IL-3, IL-5 and GM-CSF. For example, the compound binds to an epitope formed upon dimerization of two CD131 polypeptides. For example, the compound binds to residues within domain 1 of a CD131 polypeptide and residues within domain 4 of another CD131 polypeptide.

In one example, the compound binds to an epitope comprising one or more of amino acids corresponding to residues 39 and/or 103 of SEQ ID NO: 1.

In another example, the compound binds to an epitope comprising one or more of amino acids corresponding to residues 365 and 367 of SEQ ID NO: 1.

In another example, the compound binds to an epitope comprising one or more of amino acids corresponding to residues 338, 365, 367 and 368 of SEQ ID NO: 1.

In a further example, the compound binds to an epitope formed upon dimerization of two CD131 polypeptides, wherein the epitope comprises one or more (or all) of amino acids corresponding to residues 39 and 103 of one CD131 polypeptide and residues 338, 365, 367 and 368 of the other CD131 polypeptide.

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein binds to one or more (or all) of the following mutant polypeptide(s):

(i) a mutant polypeptide comprising a sequence set forth in SEQ ID NO: 119;
(ii) a mutant polypeptide comprising a sequence set forth in SEQ ID NO: 123;
(iii) a mutant polypeptide comprising a sequence set forth in SEQ ID NO: 124;
(iv) a mutant polypeptide comprising a sequence set forth in SEQ ID NO: 135;
(v) a mutant polypeptide comprising a sequence set forth in SEQ ID NO: 131;
(vi) a mutant polypeptide comprising a sequence set forth in SEQ ID NO: 136;

(vii) a mutant polypeptide comprising a sequence set forth in SEQ ID NO: 137;
(viii) a mutant polypeptide comprising a sequence set forth in SEQ ID NO: 139;
(ix) a mutant polypeptide comprising a sequence set forth in SEQ ID NO: 145,
at a level that is reduced compared to the level of binding of the CD131-binding protein to a polypeptide comprising a sequence set forth in SEQ ID NO: 192.

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein binds to a mutant polypeptide comprising a sequence set forth in SEQ ID NO: 137 at a level that is reduced compared to the level of binding of the CD131-binding protein to a polypeptide comprising a sequence set forth in SEQ ID NO: 192.

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein binds to a mutant polypeptide comprising a sequence set forth in SEQ ID NO: 139 at a level that is reduced compared to the level of binding of the CD131-binding protein to a polypeptide comprising a sequence set forth in SEQ ID NO: 192.

In one example, the level of binding (e.g., as determined by $K_D$) of the CD131-binding protein to the mutant polypeptide is reduced by at least about 3 fold or 4 fold or 5 fold or 10 fold. For example, the level of binding to the mutant polypeptide is reduced by at least about 20 fold or 50 fold or 100 fold.

In one example, the affinity ($K_D$) of the CD131-binding protein for the mutant polypeptide is about $4\times10^{-6}$ or greater, e.g., $4.5\times10^{-6}$ or $1\times10^{-5}$.

In one example, the disclosure provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein preferentially binds to binds to polypeptide comprising a sequence set forth in SEQ ID NO: 192 compared to one or more (or all) of the following mutant polypeptide(s):
(i) a mutant polypeptide comprising a sequence set forth in SEQ ID NO: 119;
(ii) a mutant polypeptide comprising a sequence set forth in SEQ ID NO: 124;
(iii) a mutant polypeptide comprising a sequence set forth in SEQ ID NO: 131;
(iv) a mutant polypeptide comprising a sequence set forth in SEQ ID NO: 137;
(v) a mutant polypeptide comprising a sequence set forth in SEQ ID NO: 139; or
(vi) a mutant polypeptide comprising a sequence set forth in SEQ ID NO: 140.

In one example, the CD131-binding protein does not detectably bind or does not significantly bind to the mutant polypeptide. For example, the CD131-binding protein does not detectably bind to does not significantly bind to one or more of the following mutant polypeptide(s):
(i) a mutant polypeptide comprising a sequence set forth in SEQ ID NO: 119;
(ii) a mutant polypeptide comprising a sequence set forth in SEQ ID NO: 124;
(iii) a mutant polypeptide comprising a sequence set forth in SEQ ID NO: 131; or
(iv) a mutant polypeptide comprising a sequence set forth in SEQ ID NO: 137.

In one example, a CD131-binding protein of the disclosure binds to or cross-reacts with a polypeptide comprising a sequence set forth in any one of SEQ ID NOs: 117, 118, 120-123, 125-130, 132-136, 138 or 140-148.

In one example, a CD131-binding protein of the disclosure binds to a polypeptide comprising a sequence set forth in SEQ ID NO: 127 with a higher affinity than it does to a polypeptide comprising a sequence set forth in SEQ ID NO: 192.

In one example, a CD131-binding protein of the disclosure binds to or cross-reacts with one or more of the following mutant polypeptide(s):
(i) a mutant polypeptide comprising a sequence set forth in SEQ ID NO: 135;
(ii) a mutant polypeptide comprising a sequence set forth in SEQ ID NO: 136; and/or
(iii) a mutant polypeptide comprising a sequence set forth in SEQ ID NO: 138.

The present disclosure also provides a compound that binds to or specifically binds to CD131 and neutralizes signaling by IL-3, IL-5 and GM-CSF, and wherein the compound binds to one or more (or all) of the following mutant polypeptide(s):
(i) a mutant polypeptide comprising a sequence set forth in SEQ ID NO: 119;
(ii) a mutant polypeptide comprising a sequence set forth in SEQ ID NO: 124;
(iii) a mutant polypeptide comprising a sequence set forth in SEQ ID NO: 131;
(iv) a mutant polypeptide comprising a sequence set forth in SEQ ID NO: 137;
(v) a mutant polypeptide comprising a sequence set forth in SEQ ID NO: 139;
(vi) a mutant polypeptide comprising a sequence set forth in SEQ ID NO: 140,
at a level that is reduced compared to the level of binding of the compound to a polypeptide comprising a sequence set forth in SEQ ID NO: 192.

Methods for determining binding of a CD131-binding protein to a polypeptide will be apparent to the skilled artisan. For example, the polypeptide is immobilized on a solid or semi-solid surface and the CD131-binding protein is contacted to the immobilized polypeptide. Binding is then determined, e.g., by surface plasmon resonance.

The present disclosure additionally provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein competitively inhibits binding of antibody 9A2 (comprising a $V_L$ comprising a sequence set forth in SEQ ID NO: 5 and a $V_H$ comprising a sequence set forth in SEQ ID NO: 20) to CD131 and/or a polypeptide comprising a sequence set forth in SEQ ID NO: 192.

In one example, the present disclosure provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein competitively inhibits binding of antibody 9A2 (comprising a $V_L$ comprising a sequence set forth in SEQ ID NO: 5 and a human kappa light chain constant region and a $V_H$ comprising a sequence set forth in SEQ ID NO: 20 and a human IgG4 constant region) to CD131 and/or a polypeptide comprising a sequence set forth in SEQ ID NO: 192.

The present disclosure additionally provides a CD131-binding protein comprising an antigen binding domain of an antibody, wherein the antigen binding domain binds to or specifically binds to CD131 and neutralizes signaling by IL-3, IL-5 and GM-CSF, and wherein the CD131-binding protein competitively inhibits binding of antibody 9A2 (comprising a light chain comprising a sequence set forth in SEQ ID NO: 5 and a heavy chain comprising a sequence set forth in SEQ ID NO: 20) to CD131 and/or a polypeptide comprising a sequence set forth in SEQ ID NO: 192.

The present disclosure additionally provides a compound that binds to or specifically binds to CD131 and neutralizes signaling by IL-3, IL-5 and GM-CSF and competitively inhibits binding of one or more of the following antibodies to CD131 and/or a polypeptide comprising a sequence set forth in SEQ ID NO: 192:

(i) an antibody comprising a $V_L$ comprising a sequence set forth in SEQ ID NO: 5 and a $V_H$ comprising a sequence set forth in SEQ ID NO: 20;
(ii) an antibody comprising a $V_L$ comprising a sequence set forth in SEQ ID NO: 5 and a human kappa light chain constant region and a $V_H$ comprising a sequence set forth in SEQ ID NO: 20 and a human IgG4 constant region; and/or
(iii) an antibody comprising a light chain comprising a sequence set forth in SEQ ID NO: 5 and a heavy chain comprising a sequence set forth in SEQ ID NO: 20.

The present disclosure additionally or alternatively provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises at least one of:

(i) a $V_H$ comprising a complementarity determining region (CDR) 1 comprising a sequence at least about 40% identical to a sequence set forth between amino acids 26-35 of SEQ ID NO: 20, a CDR2 comprising a sequence at least about 65% identical to a sequence set forth between amino acids 50-66 of SEQ ID NO: 20 and a CDR3 comprising a sequence at least about 44% identical to a sequence set forth between amino acids 99-106 of SEQ ID NO: 20;
(ii) a $V_H$ comprising a sequence at least about 89% or 90% or 91% or 92% or 93% or 94% or 95% or 96% or 97% or 98% or 99% identical to a sequence set forth in any one of SEQ ID NOs: 20, 25, 37, 59, 63, 64, 65, 68, 69, 72 or 101;
(iii) a $V_L$ comprising a CDR1 comprising a sequence at least about 45% identical to a sequence set forth between amino acids 24-34 of SEQ ID NO: 5, a CDR2 comprising a sequence set forth between amino acids 44-51 of SEQ ID NO: 5 and a CDR3 comprising a sequence at least about 44% identical to a sequence set forth between amino acids 89-97 of SEQ ID NO: 5;
(iv) a $V_L$ comprising a sequence at least about 94% or 95% or 96% or 97% or 98% or 99% identical to a sequence set forth in SEQ ID NO: 5;
(v) a $V_H$ comprising a CDR1 comprising a sequence set forth between amino acids 26-35 of SEQ ID NO: 180, a CDR2 comprising a sequence set forth between amino acids 50-66 of SEQ ID NO: 180 and a CDR3 comprising a sequence set forth between amino acids 99-106 of SEQ ID NO: 180;
(vi) a $V_H$ comprising a sequence set forth in SEQ ID NO: 180;
(vii) a $V_L$ comprising a CDR1 comprising a sequence set forth between amino acids 24-34 of SEQ ID NO: 177, a CDR2 comprising a sequence set forth between amino acids 44-51 of SEQ ID NO: 177 and a CDR3 comprising a sequence set forth between amino acids 89-97 of SEQ ID NO: 177;
(viii) a $V_L$ comprising a sequence set forth in SEQ ID NO: 177;
(ix) a $V_L$ comprising an amino acid sequence set forth in SEQ ID NO: 5;
(x) a $V_H$ as set forth in (i) and a $V_L$ as set forth in (iii);
(xi) a $V_H$ as set forth in (i) and a $V_L$ as set forth in (iv);
(xii) a $V_H$ as set forth in (i) and a $V_L$ as set forth in (ix);
(xiii) a $V_H$ as set forth in (ii) and a $V_L$ as set forth in (iii);
(xiv) a $V_H$ as set forth in (ii) and a $V_L$ as set forth in (iv);
(xv) a $V_H$ as set forth in (ii) and a $V_L$ as set forth in (ix);
(xvi) a $V_H$ as set forth in (v) and a $V_L$ as set forth in (vii);
(xvii) a $V_H$ as set forth in (v) and a $V_L$ as set forth in (viii);
(xviii) a $V_H$ as set forth in (v) and a $V_L$ as set forth in (ix);
(xix) a $V_H$ as set forth in (vi) and a $V_L$ as set forth in (vii);
(xx) a $V_H$ as set forth in (vi) and a $V_L$ as set forth in (viii); or
(xxi) a $V_H$ as set forth in (vi) and a $V_L$ as set forth in (ix).

In one example, reference in the foregoing paragraph(s) to CDRs within a defined sequence (i.e., SEQ ID NO) will be understood as follows:

For a $V_H$, CDR1 is between amino acids 26-35; CDR2 is between amino acids 50-66; and CDR3 is between amino acids 99-106; and For a $V_L$, CDR1 is between amino acids 24-34; CDR2 is between amino acids 44-51; and CDR3 is between amino acids 89-97.

In one example, the antigen binding domain comprises a $V_H$ comprising a sequence set forth in SEQ ID NO: 193 and a $V_L$ comprising a sequence set forth in SEQ ID NO: 5.

The present disclosure additionally or alternatively provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_L$ comprising a sequence set forth in SEQ ID NO: 5.

The present disclosure additionally or alternatively provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_L$ comprising a sequence set forth in SEQ ID NO: 5 (or comprising the CDRs of a $V_L$ comprising a sequence set forth in SEQ ID NO: 5) and wherein the antigen binding domain comprises a $V_H$ comprising a CDR2 as set forth in any one of SEQ ID Nos: 49, 52, 53, 56, 57, 59, 61, 62, 63, 64, 65, 66, 67, 68, 69, 70, 71, 72, 73, 74, 75, 76, 77, 78, 80, 81, 83, 88, 91, 92, 93, 94, 95, 99, 100, 101, 102, 103, 114, 115, 116, 182, 186 or 195. In one example, the antigen binding domain comprises a $V_H$ comprising a CDR2 as set forth in any one of SEQ ID Nos: 59, 63, 64, 65, 68, 69, 72 or 100.

The present disclosure additionally or alternatively provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_L$ comprising a sequence set forth in SEQ ID NO: 5 (or comprising the CDRs of a $V_L$ comprising a sequence set forth in SEQ ID NO: 5) and wherein the antigen binding domain comprises a $V_H$ comprising a CDR2 and CDR3 as set forth in any one of SEQ ID Nos: 49, 52, 53, 56, 57, 59, 61, 62, 63, 64, 65, 66, 67, 68, 69, 70, 71, 72, 73, 74, 75, 76, 77, 78, 80, 81, 83, 88, 91, 92, 93, 94, 95, 99, 100, 101, 102, 103, 114, 115, 116, 182, 186 or 195. In one example, the antigen binding domain comprises a $V_H$ comprising a CDR2 and CDR3 as set forth in any one of SEQ ID Nos: 59, 63, 64, 65, 68, 69, 72 or 100.

The present disclosure additionally or alternatively provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_L$ comprising a sequence set forth in SEQ ID NO: 5 (or comprising the CDRs of a $V_L$ comprising a sequence set forth in SEQ ID NO: 5) and wherein the antigen binding domain comprises a $V_H$ comprising a CDR1 and CDR3 as set forth in any one of SEQ ID Nos: 49, 52, 53, 56, 57, 59, 61, 62, 63, 64, 65, 66, 67, 68, 69, 70, 71, 72, 73, 74, 75, 76, 77, 78, 80, 81, 83, 88, 91, 92, 93, 94, 95, 99, 100, 101, 102, 103, 114, 115, 116, 182, 186 or 195. In one example, the antigen binding domain comprises a $V_H$ comprising a CDR1 and CDR3 as set forth in any one of SEQ ID Nos: 59, 63, 64, 65, 68, 69, 72 or 100. In one example, the antigen binding domain comprises a $V_H$ comprising a CDR1 and CDR3 as set forth in SEQ ID NO: 25.

In one example, reference in the foregoing paragraph(s) to CDRs within a defined sequence (i.e., SEQ ID NO) will be understood as follows:

For a $V_H$, CDR1 is between amino acids 26-35; CDR2 is between amino acids 50-66; and CDR3 is between amino acids 99-106; and For a $V_L$, CDR1 is between amino acids 24-34; CDR2 is between amino acids 44-51; and CDR3 is between amino acids 89-97.

The present disclosure additionally or alternatively provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises:

(i) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 5;
(ii) a $V_H$ comprising a sequence set forth in SEQ ID NO: 20 and a $V_L$ comprising a sequence set forth in SEQ ID NO: 5;
(iii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 6;
(iv) a $V_H$ comprising a sequence set forth in SEQ ID NO: 20 and a $V_L$ comprising a sequence set forth in SEQ ID NO: 6;
(v) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 7;
(vi) a $V_H$ comprising a sequence set forth in SEQ ID NO: 20 and a $V_L$ comprising a sequence set forth in SEQ ID NO: 7;
(vii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 8;
(viii) a $V_H$ comprising a sequence set forth in SEQ ID NO: 20 and a $V_L$ comprising a sequence set forth in SEQ ID NO: 8;
(ix) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 9;

(x) a $V_H$ comprising a sequence set forth in SEQ ID NO: 20 and a $V_L$ comprising a sequence set forth in SEQ ID NO: 9;
(xi) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 10;
(xii) a $V_H$ comprising a sequence set forth in SEQ ID NO: 20 and a $V_L$ comprising a sequence set forth in SEQ ID NO: 10;
(xiii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 11;
(xiv) a $V_H$ comprising a sequence set forth in SEQ ID NO: 20 and a $V_L$ comprising a sequence set forth in SEQ ID NO: 11;
(xv) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 12;
(xvi) a $V_H$ comprising a sequence set forth in SEQ ID NO: 20 and a $V_L$ comprising a sequence set forth in SEQ ID NO: 12;
(xvii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 13;
(xviii) a $V_H$ comprising a sequence set forth in SEQ ID NO: 20 and a $V_L$ comprising a sequence set forth in SEQ ID NO: 13;
(xix) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 14;
(xx) a $V_H$ comprising a sequence set forth in SEQ ID NO: 20 and a $V_L$ comprising a sequence set forth in SEQ ID NO: 14;
(xxi) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 15;
(xxii) a $V_H$ comprising a sequence set forth in SEQ ID NO: 20 and a $V_L$ comprising a sequence set forth in SEQ ID NO: 15;
(xxiii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 16;
(xxiv) a $V_H$ comprising a sequence set forth in SEQ ID NO: 20 and a $V_L$ comprising a sequence set forth in SEQ ID NO: 16;
(xxv) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 17;
(xxvi) a $V_H$ comprising a sequence set forth in SEQ ID NO: 20 and a $V_L$ comprising a sequence set forth in SEQ ID NO: 17;
(xxvii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 18;
(xxviii) a $V_H$ comprising a sequence set forth in SEQ ID NO: 20 and a $V_L$ comprising a sequence set forth in SEQ ID NO: 18;
(xxix) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 19;
(xxx) a $V_H$ comprising a sequence set forth in SEQ ID NO: 20 and a $V_L$ comprising a sequence set forth in SEQ ID NO: 19;
(xxxi) a $V_H$ comprising CDRs 1, 2 and 3 of a sequence set forth in SEQ ID NO: 21 and a $V_L$ comprising CDRs 1, 2 and 3 of a sequence set forth in SEQ ID NO: 5;

(xxxii) a $V_H$ comprising a sequence set forth in SEQ ID NO: 21 and a $V_L$ comprising a sequence set forth in SEQ ID NO: 5;

(xxxiii) a $V_H$ comprising CDRs 1, 2 and 3 of a sequence set forth in SEQ ID NO: 22 and a $V_L$ comprising CDRs 1, 2 and 3 of a sequence set forth in SEQ ID NO: 5;

(xxxiv) a $V_H$ comprising a sequence set forth in SEQ ID NO: 22 and a $V_L$ comprising a sequence set forth in SEQ ID NO: 5;

(xxxv) a $V_H$ comprising CDRs 1, 2 and 3 of a sequence set forth in SEQ ID NO: 23 and a $V_L$ comprising CDRs 1, 2 and 3 of a sequence set forth in SEQ ID NO: 5;

(xxxvi) a $V_H$ comprising a sequence set forth in SEQ ID NO: 23 and a $V_L$ comprising a sequence set forth in SEQ ID NO: 5;

(xxxvii) a $V_H$ comprising CDRs 1, 2 and 3 of a sequence set forth in SEQ ID NO: 24 and a $V_L$ comprising CDRs 1, 2 and 3 of a sequence set forth in SEQ ID NO: 5;

(xxxviii) a $V_H$ comprising a sequence set forth in SEQ ID NO: 24 and a $V_L$ comprising a sequence set forth in SEQ ID NO: 5;

(xxxix) a $V_H$ comprising CDRs 1, 2 and 3 of a sequence set forth in SEQ ID NO: 25 and a $V_L$ comprising CDRs 1, 2 and 3 of a sequence set forth in SEQ ID NO: 5;

(x) a $V_H$ comprising a sequence set forth in SEQ ID NO: 25 and a $V_L$ Comprising a sequence set forth in SEQ ID NO: 5;

(xli) a $V_H$ comprising CDRs 1, 2 and 3 of a sequence set forth in SEQ ID NO: 26 and a $V_L$ comprising CDRs 1, 2 and 3 of a sequence set forth in SEQ ID NO: 5;

(xlii) a $V_H$ comprising a sequence set forth in SEQ ID NO: 26 and a $V_L$ comprising a sequence set forth in SEQ ID NO: 5;

(xliii) a $V_H$ comprising CDRs 1, 2 and 3 of a sequence set forth in SEQ ID NO: 27 and a $V_L$ comprising CDRs 1, 2 and 3 of a sequence set forth in SEQ ID NO: 5;

(xliv) a $V_H$ comprising a sequence set forth in SEQ ID NO: 27 and a $V_L$ comprising a (xlv) a $V_H$ comprising CDRs 1, 2 and 3 of a sequence set forth in SEQ ID NO: 28 and a $V_L$ comprising CDRs 1, 2 and 3 of a sequence set forth in SEQ ID NO: 5;

(xlvi) a $V_H$ comprising a sequence set forth in SEQ ID NO: 28 and a $V_L$ comprising a sequence set forth in SEQ ID NO: 5;

(xlvii) a $V_H$ comprising CDRs 1, 2 and 3 of a sequence set forth in SEQ ID NO: 29 and a $V_L$ comprising CDRs 1, 2 and 3 of a sequence set forth in SEQ ID NO: 5;

(xlviii) a $V_H$ comprising a sequence set forth in SEQ ID NO: 29 and a $V_L$ comprising a sequence set forth in SEQ ID NO: 5;

(xlix) a $V_H$ comprising CDRs 1, 2 and 3 of a sequence set forth in SEQ ID NO: 30 and a $V_L$ comprising CDRs 1, 2 and 3 of a sequence set forth in SEQ ID NO: 5;

(l) a $V_H$ comprising a sequence set forth in SEQ ID NO: 30 and a $V_L$ comprising a sequence set forth in SEQ ID NO: 5;

(li) a $V_H$ comprising CDRs 1, 2 and 3 of a sequence set forth in SEQ ID NO: 31 and a $V_L$ comprising CDRs 1, 2 and 3 of a sequence set forth in SEQ ID NO: 5;

(lii) a $V_H$ comprising a sequence set forth in SEQ ID NO: 31 and a $V_L$ comprising a sequence set forth in SEQ ID NO: 5;

(liii) a $V_H$ comprising CDRs 1, 2 and 3 of a sequence set forth in SEQ ID NO: 32 and a $V_L$ comprising CDRs 1, 2 and 3 of a sequence set forth in SEQ ID NO: 5;

(liv) a $V_H$ comprising a sequence set forth in SEQ ID NO: 32 and a $V_L$ comprising a sequence set forth in SEQ ID NO: 5;

(lv) a $V_H$ comprising CDRs 1, 2 and 3 of a sequence set forth in SEQ ID NO: 33 and a $V_L$ comprising CDRs 1, 2 and 3 of a sequence set forth in SEQ ID NO: 5;

(lvi) a $V_H$ comprising a sequence set forth in SEQ ID NO: 33 and a $V_L$ comprising a sequence set forth in SEQ ID NO: 5;

(lvii) a $V_H$ comprising CDRs 1, 2 and 3 of a sequence set forth in SEQ ID NO: 34 and a $V_L$ comprising CDRs 1, 2 and 3 of a sequence set forth in SEQ ID NO: 5;

(lviii) a $V_H$ comprising a sequence set forth in SEQ ID NO: 34 and a $V_L$ comprising a sequence set forth in SEQ ID NO: 5;

(lix) a $V_H$ comprising CDRs 1, 2 and 3 of a sequence set forth in SEQ ID NO: 35 and a $V_L$ comprising CDRs 1, 2 and 3 of a sequence set forth in SEQ ID NO: 5;

(lx) a $V_H$ comprising a sequence set forth in SEQ ID NO: 35 and a $V_L$ comprising a sequence set forth in SEQ ID NO: 5;

(lxi) a $V_H$ comprising CDRs 1, 2 and 3 of a sequence set forth in SEQ ID NO: 36 and a $V_L$ comprising CDRs 1, 2 and 3 of a sequence set forth in SEQ ID NO: 5;

(lxii) a $V_H$ comprising a sequence set forth in SEQ ID NO: 36 and a $V_L$ comprising a (lxiii) a $V_H$ comprising CDRs 1, 2 and 3 of a sequence set forth in SEQ ID NO: 37 and a $V_L$ comprising CDRs 1, 2 and 3 of a sequence set forth in SEQ ID NO: 5;

(lxiv) a $V_H$ comprising a sequence set forth in SEQ ID NO: 37 and a $V_L$ comprising a sequence set forth in SEQ ID NO: 5;

(lxv) a $V_H$ comprising CDRs 1, 2 and 3 of a sequence set forth in SEQ ID NO: 38 and a $V_L$ comprising CDRs 1, 2 and 3 of a sequence set forth in SEQ ID NO: 5;

(lxvi) a $V_H$ comprising a sequence set forth in SEQ ID NO: 38 and a $V_L$ comprising a sequence set forth in SEQ ID NO: 5;

(lxvii) a $V_H$ comprising CDRs 1, 2 and 3 of a sequence set forth in SEQ ID NO: 39 and a $V_L$ comprising CDRs 1, 2 and 3 of a sequence set forth in SEQ ID NO: 5;

(lxviii) a $V_H$ comprising a sequence set forth in SEQ ID NO: 39 and a $V_L$ comprising a sequence set forth in SEQ ID NO: 5;

(lxix) a $V_H$ comprising CDRs 1, 2 and 3 of a sequence set forth in SEQ ID NO: 40 and a $V_L$ comprising CDRs 1, 2 and 3 of a sequence set forth in SEQ ID NO: 5;

(lxx) a $V_H$ comprising a sequence set forth in SEQ ID NO: 40 and a $V_L$ comprising a sequence set forth in SEQ ID NO: 5;

(lxxi) a $V_H$ comprising CDRs 1, 2 and 3 of a sequence set forth in SEQ ID NO: 41 and a $V_L$ comprising CDRs 1, 2 and 3 of a sequence set forth in SEQ ID NO: 5;

(lxxii) a $V_H$ comprising a sequence set forth in SEQ ID NO: 41 and a $V_L$ comprising a sequence set forth in SEQ ID NO: 5;

(lxxiii) a $V_H$ comprising CDRs 1, 2 and 3 of a sequence set forth in SEQ ID NO: 42 and a $V_L$ comprising CDRs 1, 2 and 3 of a sequence set forth in SEQ ID NO: 5;

(lxxiv) a $V_H$ comprising a sequence set forth in SEQ ID NO: 42 and a $V_L$ comprising a sequence set forth in SEQ ID NO: 5;

(lxxv) a $V_H$ comprising CDRs 1, 2 and 3 of a sequence set forth in SEQ ID NO: 43 and a $V_L$ comprising CDRs 1, 2 and 3 of a sequence set forth in SEQ ID NO: 5;

(lxxvi) a $V_H$ comprising a sequence set forth in SEQ ID NO: 43 and a $V_L$ comprising a sequence set forth in SEQ ID NO: 5;
(lxxvii) a $V_H$ comprising CDRs 1, 2 and 3 of a sequence set forth in SEQ ID NO: 44 and a $V_L$ comprising CDRs 1, 2 and 3 of a sequence set forth in SEQ ID NO: 5;
(lxxviii) a $V_H$ comprising a sequence set forth in SEQ ID NO: 44 and a $V_L$ comprising a sequence set forth in SEQ ID NO: 5;
(lxxix) a $V_H$ comprising CDRs 1, 2 and 3 of a sequence set forth in SEQ ID NO: 45 and a $V_L$ comprising CDRs 1, 2 and 3 of a sequence set forth in SEQ ID NO: 5;
(lxxx) a $V_H$ comprising a sequence set forth in SEQ ID NO: 45 and a $V_L$ comprising a sequence set forth in SEQ ID NO: 5;
(lxxxi) a $V_H$ comprising CDRs 1, 2 and 3 of a sequence set forth in SEQ ID NO: 46 and a $V_L$ comprising CDRs 1, 2 and 3 of a sequence set forth in SEQ ID NO: 5;
(lxxxii) a $V_H$ comprising a sequence set forth in SEQ ID NO: 46 and a $V_L$ comprising a sequence set forth in SEQ ID NO: 5;
(lxxxiii) a $V_H$ comprising CDRs 1, 2 and 3 of a sequence set forth in SEQ ID NO: 47 and a $V_L$ comprising CDRs 1, 2 and 3 of a sequence set forth in SEQ ID NO: 5;
(lxxxiv) a $V_H$ comprising a sequence set forth in SEQ ID NO: 47 and a $V_L$ comprising a sequence set forth in SEQ ID NO: 5;
(lxxxv) a $V_H$ comprising CDRs 1, 2 and 3 of a sequence set forth in SEQ ID NO: 48 and a $V_L$ comprising CDRs 1, 2 and 3 of a sequence set forth in SEQ ID NO: 5;
(lxxxvi) a $V_H$ comprising a sequence set forth in SEQ ID NO: 48 and a $V_L$ comprising a sequence set forth in SEQ ID NO: 5;
(lxxxvii) a $V_H$ comprising CDRs 1, 2 and 3 of a sequence set forth in SEQ ID NO: 49 and a $V_L$ comprising CDRs 1, 2 and 3 of a sequence set forth in SEQ ID NO: 5;
(lxxxviii) a $V_H$ comprising a sequence set forth in SEQ ID NO: 49 and a $V_L$ comprising a sequence set forth in SEQ ID NO: 5;
(lxxxix) a $V_H$ comprising CDRs 1, 2 and 3 of a sequence set forth in SEQ ID NO: 50 and a $V_L$ comprising CDRs 1, 2 and 3 of a sequence set forth in SEQ ID NO: 5;
(xc) a $V_H$ comprising a sequence set forth in SEQ ID NO: 50 and a $V_L$ comprising a sequence set forth in SEQ ID NO: 5;
(xci) a $V_H$ comprising CDRs 1, 2 and 3 of a sequence set forth in SEQ ID NO: 51 and a $V_L$ comprising CDRs 1, 2 and 3 of a sequence set forth in SEQ ID NO: 5;
(xcii) a $V_H$ comprising a sequence set forth in SEQ ID NO: 51 and a $V_L$ comprising a sequence set forth in SEQ ID NO: 5;
(xciii) a $V_H$ comprising CDRs 1, 2 and 3 of a sequence set forth in SEQ ID NO: 52 and a $V_L$ comprising CDRs 1, 2 and 3 of a sequence set forth in SEQ ID NO: 5;
(xciv) a $V_H$ comprising a sequence set forth in SEQ ID NO: 52 and a $V_L$ comprising a sequence set forth in SEQ ID NO: 5;
(xcv) a $V_H$ comprising CDRs 1, 2 and 3 of a sequence set forth in SEQ ID NO: 53 and a $V_L$ comprising CDRs 1, 2 and 3 of a sequence set forth in SEQ ID NO: 5;
(xcvi) a $V_H$ comprising a sequence set forth in SEQ ID NO: 53 and a $V_L$ comprising a sequence set forth in SEQ ID NO: 5;
(xcvii) a $V_H$ comprising CDRs 1, 2 and 3 of a sequence set forth in SEQ ID NO: 54 and a $V_L$ comprising CDRs 1, 2 and 3 of a sequence set forth in SEQ ID NO: 5;
(xcviii) a $V_H$ comprising a sequence set forth in SEQ ID NO: 54 and a $V_L$ comprising a sequence set forth in SEQ ID NO: 5;
(xcix) a $V_H$ comprising CDRs 1, 2 and 3 of a sequence set forth in SEQ ID NO: 55 and a $V_L$ comprising CDRs 1, 2 and 3 of a sequence set forth in SEQ ID NO: 5;
(c) a $V_H$ comprising a sequence set forth in SEQ ID NO: 55 and a $V_L$ comprising a sequence set forth in SEQ ID NO: 5;
(ci) a $V_H$ comprising CDRs 1, 2 and 3 of a sequence set forth in SEQ ID NO: 56 and a $V_L$ comprising CDRs 1, 2 and 3 of a sequence set forth in SEQ ID NO: 5;
(cii) a $V_H$ comprising a sequence set forth in SEQ ID NO: 56 and a $V_L$ comprising a sequence set forth in SEQ ID NO: 5;
(ciii) a $V_H$ comprising CDRs 1, 2 and 3 of a sequence set forth in SEQ ID NO: 57 and a $V_L$ comprising CDRs 1, 2 and 3 of a sequence set forth in SEQ ID NO: 5;
(civ) a $V_H$ comprising a sequence set forth in SEQ ID NO: 57 and a $V_L$ comprising a sequence set forth in SEQ ID NO: 5;
(cv) a $V_H$ comprising CDRs 1, 2 and 3 of a sequence set forth in SEQ ID NO: 58 and a $V_L$ comprising CDRs 1, 2 and 3 of a sequence set forth in SEQ ID NO: 5;
(cvi) a $V_H$ comprising a sequence set forth in SEQ ID NO: 58 and a $V_L$ comprising a sequence set forth in SEQ ID NO: 5;
(cvii) a $V_H$ comprising CDRs 1, 2 and 3 of a sequence set forth in SEQ ID NO: 59 and a $V_L$ comprising CDRs 1, 2 and 3 of a sequence set forth in SEQ ID NO: 5;
(cviii) a $V_H$ comprising a sequence set forth in SEQ ID NO: 59 and a $V_L$ comprising a sequence set forth in SEQ ID NO: 5;
(cix) a $V_H$ comprising CDRs 1, 2 and 3 of a sequence set forth in SEQ ID NO: 60 and a $V_L$ comprising CDRs 1, 2 and 3 of a sequence set forth in SEQ ID NO: 5;
(cx) a $V_H$ comprising a sequence set forth in SEQ ID NO: 60 and a $V_L$ comprising a sequence set forth in SEQ ID NO: 5;
(cxi) a $V_H$ comprising CDRs 1, 2 and 3 of a sequence set forth in SEQ ID NO: 61 and a $V_L$ comprising CDRs 1, 2 and 3 of a sequence set forth in SEQ ID NO: 5;
(cxii) a $V_H$ comprising a sequence set forth in SEQ ID NO: 61 and a $V_L$ comprising a sequence set forth in SEQ ID NO: 5;
(cxiii) a $V_H$ comprising CDRs 1, 2 and 3 of a sequence set forth in SEQ ID NO: 62 and a $V_L$ comprising CDRs 1, 2 and 3 of a sequence set forth in SEQ ID NO: 5;
(cxiv) a $V_H$ comprising a sequence set forth in SEQ ID NO: 62 and a $V_L$ comprising a sequence set forth in SEQ ID NO: 5;
(cxv) a $V_H$ comprising CDRs 1, 2 and 3 of a sequence set forth in SEQ ID NO: 63 and a $V_L$ comprising CDRs 1, 2 and 3 of a sequence set forth in SEQ ID NO: 5;
(cxvi) a $V_H$ comprising a sequence set forth in SEQ ID NO: 63 and a $V_L$ comprising a sequence set forth in SEQ ID NO: 5;
(cxvii) a $V_H$ comprising CDRs 1, 2 and 3 of a sequence set forth in SEQ ID NO: 64 and a $V_L$ comprising CDRs 1, 2 and 3 of a sequence set forth in SEQ ID NO: 5;
(cxviii) a $V_H$ comprising a sequence set forth in SEQ ID NO: 64 and a $V_L$ comprising a sequence set forth in SEQ ID NO: 5;
(cxix) a $V_H$ comprising CDRs 1, 2 and 3 of a sequence set forth in SEQ ID NO: 65 and a $V_L$ comprising CDRs 1, 2 and 3 of a sequence set forth in SEQ ID NO: 5;

(cxx) a $V_H$ comprising a sequence set forth in SEQ ID NO: 65 and a $V_L$ comprising a sequence set forth in SEQ ID NO: 5;
(cxxi) a $V_H$ comprising CDRs 1, 2 and 3 of a sequence set forth in SEQ ID NO: 66 and a $V_L$ comprising CDRs 1, 2 and 3 of a sequence set forth in SEQ ID NO: 5;
(cxxii) a $V_H$ comprising a sequence set forth in SEQ ID NO: 66 and a $V_L$ comprising a sequence set forth in SEQ ID NO: 5;
(cxxiii) a $V_H$ comprising CDRs 1, 2 and 3 of a sequence set forth in SEQ ID NO: 67 and a $V_L$ comprising CDRs 1, 2 and 3 of a sequence set forth in SEQ ID NO: 5;
(cxxiv) a $V_H$ comprising a sequence set forth in SEQ ID NO: 67 and a $V_L$ comprising a sequence set forth in SEQ ID NO: 5;
(cxxv) a $V_H$ comprising CDRs 1, 2 and 3 of a sequence set forth in SEQ ID NO: 68 and a $V_L$ comprising CDRs 1, 2 and 3 of a sequence set forth in SEQ ID NO: 5;
(cxxvi) a $V_H$ comprising a sequence set forth in SEQ ID NO: 68 and a $V_L$ comprising a sequence set forth in SEQ ID NO: 5;
(cxxvii) a $V_H$ comprising CDRs 1, 2 and 3 of a sequence set forth in SEQ ID NO: 69 and a $V_L$ comprising CDRs 1, 2 and 3 of a sequence set forth in SEQ ID NO: 5;
(cxxviii) a $V_H$ comprising a sequence set forth in SEQ ID NO: 69 and a $V_L$ comprising a sequence set forth in SEQ ID NO: 5;
(cxxix) a $V_H$ comprising CDRs 1, 2 and 3 of a sequence set forth in SEQ ID NO: 70 and a $V_L$ comprising CDRs 1, 2 and 3 of a sequence set forth in SEQ ID NO: 5;
(cxxx) a $V_H$ comprising a sequence set forth in SEQ ID NO: 70 and a $V_L$ comprising a sequence set forth in SEQ ID NO: 5;
(cxxxi) a $V_H$ comprising CDRs 1, 2 and 3 of a sequence set forth in SEQ ID NO: 71 and a $V_L$ comprising CDRs 1, 2 and 3 of a sequence set forth in SEQ ID NO: 5;
(cxxxii) a $V_H$ comprising a sequence set forth in SEQ ID NO: 71 and a $V_L$ comprising a sequence set forth in SEQ ID NO: 5;
(cxxxiii) a $V_H$ comprising CDRs 1, 2 and 3 of a sequence set forth in SEQ ID NO: 72 and a $V_L$ comprising CDRs 1, 2 and 3 of a sequence set forth in SEQ ID NO: 5;
(cxxxiv) a $V_H$ comprising a sequence set forth in SEQ ID NO: 72 and a $V_L$ comprising a sequence set forth in SEQ ID NO: 5;
(cxxxv) a $V_H$ comprising CDRs 1, 2 and 3 of a sequence set forth in SEQ ID NO: 73 and a $V_L$ comprising CDRs 1, 2 and 3 of a sequence set forth in SEQ ID NO: 5;
(cxxxvi) a $V_H$ comprising a sequence set forth in SEQ ID NO: 73 and a $V_L$ comprising a sequence set forth in SEQ ID NO: 5;
(cxxxvii) a $V_H$ comprising CDRs 1, 2 and 3 of a sequence set forth in SEQ ID NO: 75 and a $V_L$ comprising CDRs 1, 2 and 3 of a sequence set forth in SEQ ID NO: 5;
(cxxxviii) a $V_H$ comprising a sequence set forth in SEQ ID NO: 75 and a $V_L$ comprising a sequence set forth in SEQ ID NO: 5;
(cxxxix) a $V_H$ comprising CDRs 1, 2 and 3 of a sequence set forth in SEQ ID NO: 76 and a $V_L$ comprising CDRs 1, 2 and 3 of a sequence set forth in SEQ ID NO: 5;
(cxl) a $V_H$ comprising a sequence set forth in SEQ ID NO: 76 and a $V_L$ comprising a sequence set forth in SEQ ID NO: 5;
(cxli) a $V_H$ comprising CDRs 1, 2 and 3 of a sequence set forth in SEQ ID NO: 77 and a $V_L$ comprising CDRs 1, 2 and 3 of a sequence set forth in SEQ ID NO: 5;
(cxlii) a $V_H$ comprising a sequence set forth in SEQ ID NO: 77 and a $V_L$ comprising a sequence set forth in SEQ ID NO: 5;
(cxliii) a $V_H$ comprising CDRs 1, 2 and 3 of a sequence set forth in SEQ ID NO: 78 and a $V_L$ comprising CDRs 1, 2 and 3 of a sequence set forth in SEQ ID NO: 5;
(cxliv) a $V_H$ comprising a sequence set forth in SEQ ID NO: 78 and a $V_L$ comprising a (cxlv) a $V_H$ comprising CDRs 1, 2 and 3 of a sequence set forth in SEQ ID NO: 79 and a $V_L$ comprising CDRs 1, 2 and 3 of a sequence set forth in SEQ ID NO: 5;
(cxlvi) a $V_H$ comprising a sequence set forth in SEQ ID NO: 79 and a $V_L$ comprising a sequence set forth in SEQ ID NO: 5;
(cxlvii) a $V_H$ comprising CDRs 1, 2 and 3 of a sequence set forth in SEQ ID NO: 80 and a $V_L$ comprising CDRs 1, 2 and 3 of a sequence set forth in SEQ ID NO: 5;
(cxlviii) a $V_H$ comprising a sequence set forth in SEQ ID NO: 80 and a $V_L$ comprising a sequence set forth in SEQ ID NO: 5;
(cxlix) a $V_H$ comprising CDRs 1, 2 and 3 of a sequence set forth in SEQ ID NO: 81 and a $V_L$ comprising CDRs 1, 2 and 3 of a sequence set forth in SEQ ID NO: 5;
(cl) a $V_H$ comprising a sequence set forth in SEQ ID NO: 81 and a $V_L$ Comprising a sequence set forth in SEQ ID NO: 5;
(cli) a $V_H$ comprising CDRs 1, 2 and 3 of a sequence set forth in SEQ ID NO: 82 and a $V_L$ comprising CDRs 1, 2 and 3 of a sequence set forth in SEQ ID NO: 5;
(clii) a $V_H$ comprising a sequence set forth in SEQ ID NO: 82 and a $V_L$ comprising a sequence set forth in SEQ ID NO: 5;
(cliii) a $V_H$ comprising CDRs 1, 2 and 3 of a sequence set forth in SEQ ID NO: 83 and a $V_L$ comprising CDRs 1, 2 and 3 of a sequence set forth in SEQ ID NO: 5;
(cliv) a $V_H$ comprising a sequence set forth in SEQ ID NO: 83 and a $V_L$ comprising a sequence set forth in SEQ ID NO: 5;
(clv) a $V_H$ comprising CDRs 1, 2 and 3 of a sequence set forth in SEQ ID NO: 84 and a $V_L$ comprising CDRs 1, 2 and 3 of a sequence set forth in SEQ ID NO: 5;
(clvi) a $V_H$ comprising a sequence set forth in SEQ ID NO: 84 and a $V_L$ comprising a sequence set forth in SEQ ID NO: 5;
(clvii) a $V_H$ comprising CDRs 1, 2 and 3 of a sequence set forth in SEQ ID NO: 85 and a $V_L$ comprising CDRs 1, 2 and 3 of a sequence set forth in SEQ ID NO: 5;
(clviii) a $V_H$ comprising a sequence set forth in SEQ ID NO: 85 and a $V_L$ comprising a sequence set forth in SEQ ID NO: 5;
(clix) a $V_H$ comprising CDRs 1, 2 and 3 of a sequence set forth in SEQ ID NO: 86 and a $V_L$ comprising CDRs 1, 2 and 3 of a sequence set forth in SEQ ID NO: 5;
(clx) a $V_H$ comprising a sequence set forth in SEQ ID NO: 86 and a $V_L$ comprising a sequence set forth in SEQ ID NO: 5;
(clxi) a $V_H$ comprising CDRs 1, 2 and 3 of a sequence set forth in SEQ ID NO: 87 and a $V_L$ comprising CDRs 1, 2 and 3 of a sequence set forth in SEQ ID NO: 5;
(clxii) a $V_H$ comprising a sequence set forth in SEQ ID NO: 87 and a $V_L$ comprising a sequence set forth in SEQ ID NO: 5;
(clxiii) a $V_H$ comprising CDRs 1, 2 and 3 of a sequence set forth in SEQ ID NO: 88 and a $V_L$ comprising CDRs 1, 2 and 3 of a sequence set forth in SEQ ID NO: 5;

(clxiv) a $V_H$ comprising a sequence set forth in SEQ ID NO: 88 and a $V_L$ comprising a sequence set forth in SEQ ID NO: 5;
(clxv) a $V_H$ comprising CDRs 1, 2 and 3 of a sequence set forth in SEQ ID NO: 89 and a $V_L$ comprising CDRs 1, 2 and 3 of a sequence set forth in SEQ ID NO: 5;
(clxvi) a $V_H$ comprising a sequence set forth in SEQ ID NO: 89 and a $V_L$ comprising a sequence set forth in SEQ ID NO: 5;
(clxvii) a $V_H$ comprising CDRs 1, 2 and 3 of a sequence set forth in SEQ ID NO: 90 and a $V_L$ comprising CDRs 1, 2 and 3 of a sequence set forth in SEQ ID NO: 5;
(clxviii) a $V_H$ comprising a sequence set forth in SEQ ID NO: 90 and a $V_L$ comprising a sequence set forth in SEQ ID NO: 5;
(clxix) a $V_H$ comprising CDRs 1, 2 and 3 of a sequence set forth in SEQ ID NO: 91 and a $V_L$ comprising CDRs 1, 2 and 3 of a sequence set forth in SEQ ID NO: 5;
(clxx) a $V_H$ comprising a sequence set forth in SEQ ID NO: 91 and a $V_L$ comprising a sequence set forth in SEQ ID NO: 5;
(clxxi) a $V_H$ comprising CDRs 1, 2 and 3 of a sequence set forth in SEQ ID NO: 92 and a $V_L$ comprising CDRs 1, 2 and 3 of a sequence set forth in SEQ ID NO: 5;
(clxxii) a $V_H$ comprising a sequence set forth in SEQ ID NO: 92 and a $V_L$ comprising a sequence set forth in SEQ ID NO: 5;
(clxxiii) a $V_H$ comprising CDRs 1, 2 and 3 of a sequence set forth in SEQ ID NO: 93 and a $V_L$ comprising CDRs 1, 2 and 3 of a sequence set forth in SEQ ID NO: 5;
(clxxiv) a $V_H$ comprising a sequence set forth in SEQ ID NO: 93 and a $V_L$ comprising a sequence set forth in SEQ ID NO: 5;
(clxxv) a $V_H$ comprising CDRs 1, 2 and 3 of a sequence set forth in SEQ ID NO: 94 and a $V_L$ comprising CDRs 1, 2 and 3 of a sequence set forth in SEQ ID NO: 5;
(clxxvi) a $V_H$ comprising a sequence set forth in SEQ ID NO: 94 and a $V_L$ comprising a sequence set forth in SEQ ID NO: 5;
(clxxvii) a $V_H$ comprising CDRs 1, 2 and 3 of a sequence set forth in SEQ ID NO: 95 and a $V_L$ comprising CDRs 1, 2 and 3 of a sequence set forth in SEQ ID NO: 5;
(clxxviii) a $V_H$ comprising a sequence set forth in SEQ ID NO: 95 and a $V_L$ comprising a sequence set forth in SEQ ID NO: 5;
(clxxix) a $V_H$ comprising CDRs 1, 2 and 3 of a sequence set forth in SEQ ID NO: 96 and a $V_L$ comprising CDRs 1, 2 and 3 of a sequence set forth in SEQ ID NO: 5;
(clxxx) a $V_H$ comprising a sequence set forth in SEQ ID NO: 96 and a $V_L$ comprising a sequence set forth in SEQ ID NO: 5;
(clxxxi) a $V_H$ comprising CDRs 1, 2 and 3 of a sequence set forth in SEQ ID NO: 97 and a $V_L$ comprising CDRs 1, 2 and 3 of a sequence set forth in SEQ ID NO: 5;
(clxxxii) a $V_H$ comprising a sequence set forth in SEQ ID NO: 97 and a $V_L$ comprising a sequence set forth in SEQ ID NO: 5;
(clxxxiii) a $V_H$ comprising CDRs 1, 2 and 3 of a sequence set forth in SEQ ID NO: 98 and a $V_L$ comprising CDRs 1, 2 and 3 of a sequence set forth in SEQ ID NO: 5;
(clxxxiv) a $V_H$ comprising a sequence set forth in SEQ ID NO: 98 and a $V_L$ comprising a sequence set forth in SEQ ID NO: 5;
(clxxxv) a $V_H$ comprising CDRs 1, 2 and 3 of a sequence set forth in SEQ ID NO: 99 and a $V_L$ comprising CDRs 1, 2 and 3 of a sequence set forth in SEQ ID NO: 5;
(clxxxvi) a $V_H$ comprising a sequence set forth in SEQ ID NO: 99 and a $V_L$ comprising a sequence set forth in SEQ ID NO: 5;
(clxxxvii) a $V_H$ comprising CDRs 1, 2 and 3 of a sequence set forth in SEQ ID NO: 100 and a $V_L$ comprising CDRs 1, 2 and 3 of a sequence set forth in SEQ ID NO: 5;
(clxxxviii) a $V_H$ comprising a sequence set forth in SEQ ID NO: 100 and a $V_L$ comprising a sequence set forth in SEQ ID NO: 5;
(clxxxix) a $V_H$ comprising CDRs 1, 2 and 3 of a sequence set forth in SEQ ID NO: 101 and a $V_L$ comprising CDRs 1, 2 and 3 of a sequence set forth in SEQ ID NO: 5;
(cxc) a $V_H$ comprising a sequence set forth in SEQ ID NO: 101 and a $V_L$ comprising a sequence set forth in SEQ ID NO: 5;
(cxci) a $V_H$ comprising CDRs 1, 2 and 3 of a sequence set forth in SEQ ID NO: 102 and a $V_L$ comprising CDRs 1, 2 and 3 of a sequence set forth in SEQ ID NO: 5;
(cxcii) a $V_H$ comprising a sequence set forth in SEQ ID NO: 102 and a $V_L$ comprising a
(cxciii) a $V_H$ comprising CDRs 1, 2 and 3 of a sequence set forth in SEQ ID NO: 103 and a $V_L$ comprising CDRs 1, 2 and 3 of a sequence set forth in SEQ ID NO: 5;
(cxciv) a $V_H$ comprising a sequence set forth in SEQ ID NO: 103 and a $V_L$ comprising a sequence set forth in SEQ ID NO: 5;
(cxcv) a $V_H$ comprising CDRs 1, 2 and 3 of a sequence set forth in SEQ ID NO: 104 and a $V_L$ comprising CDRs 1, 2 and 3 of a sequence set forth in SEQ ID NO: 5;
(cxcvi) a $V_H$ comprising a sequence set forth in SEQ ID NO: 104 and a $V_L$ comprising a sequence set forth in SEQ ID NO: 5;
(cxcvii) a $V_H$ comprising CDRs 1, 2 and 3 of a sequence set forth in SEQ ID NO: 105 and a $V_L$ comprising CDRs 1, 2 and 3 of a sequence set forth in SEQ ID NO: 5;
(cxcviii) a $V_H$ comprising a sequence set forth in SEQ ID NO: 105 and a $V_L$ comprising a sequence set forth in SEQ ID NO: 5;
(cxcix) a $V_H$ comprising CDRs 1, 2 and 3 of a sequence set forth in SEQ ID NO: 106 and a $V_L$ comprising CDRs 1, 2 and 3 of a sequence set forth in SEQ ID NO: 5;
(cc) a $V_H$ comprising a sequence set forth in SEQ ID NO: 106 and a $V_L$ comprising a sequence set forth in SEQ ID NO: 5;
(cci) a $V_H$ comprising CDRs 1, 2 and 3 of a sequence set forth in SEQ ID NO: 107 and a $V_L$ comprising CDRs 1, 2 and 3 of a sequence set forth in SEQ ID NO: 5;
(ccii) a $V_H$ comprising a sequence set forth in SEQ ID NO: 107 and a $V_L$ comprising a sequence set forth in SEQ ID NO: 5;
(cciii) a $V_H$ comprising CDRs 1, 2 and 3 of a sequence set forth in SEQ ID NO: 108 and a $V_L$ comprising CDRs 1, 2 and 3 of a sequence set forth in SEQ ID NO: 5;
(cciv) a $V_H$ comprising a sequence set forth in SEQ ID NO: 108 and a $V_L$ comprising a sequence set forth in SEQ ID NO: 5;
(ccv) a $V_H$ comprising CDRs 1, 2 and 3 of a sequence set forth in SEQ ID NO: 109 and a $V_L$ comprising CDRs 1, 2 and 3 of a sequence set forth in SEQ ID NO: 5;
(ccvi) a $V_H$ comprising a sequence set forth in SEQ ID NO: 109 and a $V_L$ comprising a sequence set forth in SEQ ID NO: 5;

(ccvii) a $V_H$ comprising CDRs 1, 2 and 3 of a sequence set forth in SEQ ID NO: 110 and a $V_L$ comprising CDRs 1, 2 and 3 of a sequence set forth in SEQ ID NO: 5;
(ccviii) a $V_H$ comprising a sequence set forth in SEQ ID NO: 110 and a $V_L$ comprising a sequence set forth in SEQ ID NO: 5;
(ccix) a $V_H$ comprising CDRs 1, 2 and 3 of a sequence set forth in SEQ ID NO: 111 and a $V_L$ comprising CDRs 1, 2 and 3 of a sequence set forth in SEQ ID NO: 5;
(ccx) a $V_H$ comprising a sequence set forth in SEQ ID NO: 111 and a $V_L$ comprising a sequence set forth in SEQ ID NO: 5;
(ccxi) a $V_H$ comprising CDRs 1, 2 and 3 of a sequence set forth in SEQ ID NO: 112 and a $V_L$ comprising CDRs 1, 2 and 3 of a sequence set forth in SEQ ID NO: 5;
(ccxii) a $V_H$ comprising a sequence set forth in SEQ ID NO: 112 and a $V_L$ comprising a sequence set forth in SEQ ID NO: 5;
(ccxiii) a $V_H$ comprising CDRs 1, 2 and 3 of a sequence set forth in SEQ ID NO: 113 and a $V_L$ comprising CDRs 1, 2 and 3 of a sequence set forth in SEQ ID NO: 5;
(ccxiv) a $V_H$ comprising a sequence set forth in SEQ ID NO: 113 and a $V_L$ comprising a sequence set forth in SEQ ID NO: 5;
(ccxv) a $V_H$ comprising CDRs 1, 2 and 3 of a sequence set forth in SEQ ID NO: 114 and a $V_L$ comprising CDRs 1, 2 and 3 of a sequence set forth in SEQ ID NO: 5;
(ccxvi) a $V_H$ comprising a sequence set forth in SEQ ID NO: 114 and a $V_L$ comprising a sequence set forth in SEQ ID NO: 5;
(ccxvii) a $V_H$ comprising CDRs 1, 2 and 3 of a sequence set forth in SEQ ID NO: 115 and a $V_L$ comprising CDRs 1, 2 and 3 of a sequence set forth in SEQ ID NO: 5;
(ccxviii) a $V_H$ comprising a sequence set forth in SEQ ID NO: 115 and a $V_L$ comprising a sequence set forth in SEQ ID NO: 5;
(ccxix) a $V_H$ comprising CDRs 1, 2 and 3 of a sequence set forth in SEQ ID NO: 116 and a $V_L$ comprising CDRs 1, 2 and 3 of a sequence set forth in SEQ ID NO: 5; or
(ccxx) a $V_H$ comprising a sequence set forth in SEQ ID NO: 116 and a $V_L$ comprising a sequence set forth in SEQ ID NO: 5.

In one example, reference in the foregoing paragraph(s) to CDRs within a defined sequence (i.e., SEQ ID NO) will be understood as follows:

For a $V_H$, CDR1 is between amino acids 26-35; CDR2 is between amino acids 50-66; and CDR3 is between amino acids 99-106; and For a $V_L$, CDR1 is between amino acids 24-34; CDR2 is between amino acids 44-51; and CDR3 is between amino acids 89-97.

The present disclosure additionally or alternatively provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises:

(i) a $V_H$ comprising CDRs 1, 2 and 3 of a sequence set forth in SEQ ID NO: 49 and a $V_L$ comprising CDRs 1, 2 and 3 of a sequence set forth in SEQ ID NO: 5;
(ii) a $V_H$ comprising a sequence set forth in SEQ ID NO: 49 and a $V_L$ comprising a sequence set forth in SEQ ID NO: 5;
(iii) a $V_H$ comprising CDRs 1, 2 and 3 of a sequence set forth in SEQ ID NO: 52 and a $V_L$ comprising CDRs 1, 2 and 3 of a sequence set forth in SEQ ID NO: 5;
(iv) a $V_H$ comprising a sequence set forth in SEQ ID NO: 52 and a $V_L$ comprising a sequence set forth in SEQ ID NO: 5;
(v) a $V_H$ comprising CDRs 1, 2 and 3 of a sequence set forth in SEQ ID NO: 53 and a $V_L$ comprising CDRs 1, 2 and 3 of a sequence set forth in SEQ ID NO: 5;
(vi) a $V_H$ comprising a sequence set forth in SEQ ID NO: 53 and a $V_L$ comprising a sequence set forth in SEQ ID NO: 5;
(vii) a $V_H$ comprising CDRs 1, 2 and 3 of a sequence set forth in SEQ ID NO: 56 and a $V_L$ comprising CDRs 1, 2 and 3 of a sequence set forth in SEQ ID NO: 5;
(viii) a $V_H$ comprising a sequence set forth in SEQ ID NO: 56 and a $V_L$ comprising a sequence set forth in SEQ ID NO: 5;
(ix) a $V_H$ comprising CDRs 1, 2 and 3 of a sequence set forth in SEQ ID NO: 57 and a $V_L$ comprising CDRs 1, 2 and 3 of a sequence set forth in SEQ ID NO: 5;
(x) a $V_H$ comprising a sequence set forth in SEQ ID NO: 57 and a $V_L$ comprising a sequence set forth in SEQ ID NO: 5;
(xi) a $V_H$ comprising CDRs 1, 2 and 3 of a sequence set forth in SEQ ID NO: 59 and a $V_L$ comprising CDRs 1, 2 and 3 of a sequence set forth in SEQ ID NO: 5;
(xii) a $V_H$ comprising a sequence set forth in SEQ ID NO: 59 and a $V_L$ comprising a sequence set forth in SEQ ID NO: 5;
(xiii) a $V_H$ comprising CDRs 1, 2 and 3 of a sequence set forth in SEQ ID NO: 61 and a $V_L$ comprising CDRs 1, 2 and 3 of a sequence set forth in SEQ ID NO: 5;
(xiv) a $V_H$ comprising a sequence set forth in SEQ ID NO: 61 and a $V_L$ comprising a sequence set forth in SEQ ID NO: 5;
(xv) a $V_H$ comprising CDRs 1, 2 and 3 of a sequence set forth in SEQ ID NO: 62 and a $V_L$ comprising CDRs 1, 2 and 3 of a sequence set forth in SEQ ID NO: 5;
(xvi) a $V_H$ comprising a sequence set forth in SEQ ID NO: 62 and a $V_L$ comprising a sequence set forth in SEQ ID NO: 5;
(xvii) a $V_H$ comprising CDRs 1, 2 and 3 of a sequence set forth in SEQ ID NO: 63 and a $V_L$ comprising CDRs 1, 2 and 3 of a sequence set forth in SEQ ID NO: 5;
(xviii) a $V_H$ comprising a sequence set forth in SEQ ID NO: 63 and a $V_L$ comprising a
(xix) a $V_H$ comprising CDRs 1, 2 and 3 of a sequence set forth in SEQ ID NO: 64 and a $V_L$ comprising CDRs 1, 2 and 3 of a sequence set forth in SEQ ID NO: 5;
(xx) a $V_H$ comprising a sequence set forth in SEQ ID NO: 64 and a $V_L$ comprising a sequence set forth in SEQ ID NO: 5;
(xxi) a $V_H$ comprising CDRs 1, 2 and 3 of a sequence set forth in SEQ ID NO: 65 and a $V_L$ comprising CDRs 1, 2 and 3 of a sequence set forth in SEQ ID NO: 5;
(xxii) a $V_H$ comprising a sequence set forth in SEQ ID NO: 65 and a $V_L$ comprising a sequence set forth in SEQ ID NO: 5;
(xxiii) a $V_H$ comprising CDRs 1, 2 and 3 of a sequence set forth in SEQ ID NO: 66 and a $V_L$ comprising CDRs 1, 2 and 3 of a sequence set forth in SEQ ID NO: 5;
(xxiv) a $V_H$ comprising a sequence set forth in SEQ ID NO: 66 and a $V_L$ comprising a sequence set forth in SEQ ID NO: 5;

(xxv) a $V_H$ comprising CDRs 1, 2 and 3 of a sequence set forth in SEQ ID NO: 67 and a $V_L$ comprising CDRs 1, 2 and 3 of a sequence set forth in SEQ ID NO: 5;
(xxvi) a $V_H$ comprising a sequence set forth in SEQ ID NO: 67 and a $V_L$ comprising a sequence set forth in SEQ ID NO: 5;
(xxvii) a $V_H$ comprising CDRs 1, 2 and 3 of a sequence set forth in SEQ ID NO: 68 and a $V_L$ comprising CDRs 1, 2 and 3 of a sequence set forth in SEQ ID NO: 5;
(xxviii) a $V_H$ comprising a sequence set forth in SEQ ID NO: 68 and a $V_L$ comprising a sequence set forth in SEQ ID NO: 5;
(xxix) a $V_H$ comprising CDRs 1, 2 and 3 of a sequence set forth in SEQ ID NO: 69 and a $V_L$ comprising CDRs 1, 2 and 3 of a sequence set forth in SEQ ID NO: 5;
(xxx) a $V_H$ comprising a sequence set forth in SEQ ID NO: 69 and a $V_L$ comprising a sequence set forth in SEQ ID NO: 5;
(xxxi) a $V_H$ comprising CDRs 1, 2 and 3 of a sequence set forth in SEQ ID NO: 70 and a $V_L$ comprising CDRs 1, 2 and 3 of a sequence set forth in SEQ ID NO: 5;
(xxxii) a $V_H$ comprising a sequence set forth in SEQ ID NO: 70 and a $V_L$ comprising a sequence set forth in SEQ ID NO: 5;
(xxxiii) a $V_H$ comprising CDRs 1, 2 and 3 of a sequence set forth in SEQ ID NO: 71 and a $V_L$ comprising CDRs 1, 2 and 3 of a sequence set forth in SEQ ID NO: 5;
(xxxiv) a $V_H$ comprising a sequence set forth in SEQ ID NO: 71 and a $V_L$ comprising a sequence set forth in SEQ ID NO: 5;
(xxxv) a $V_H$ comprising CDRs 1, 2 and 3 of a sequence set forth in SEQ ID NO: 72 and a $V_L$ comprising CDRs 1, 2 and 3 of a sequence set forth in SEQ ID NO: 5;
(xxxvi) a $V_H$ comprising a sequence set forth in SEQ ID NO: 72 and a $V_L$ comprising a sequence set forth in SEQ ID NO: 5;
(xxxvii) a $V_H$ comprising CDRs 1, 2 and 3 of a sequence set forth in SEQ ID NO: 73 and a $V_L$ comprising CDRs 1, 2 and 3 of a sequence set forth in SEQ ID NO: 5;
(xxxviii) a $V_H$ comprising a sequence set forth in SEQ ID NO: 73 and a $V_L$ comprising a sequence set forth in SEQ ID NO: 5;
(xxxix) a $V_H$ comprising CDRs 1, 2 and 3 of a sequence set forth in SEQ ID NO: 75 and a $V_L$ comprising CDRs 1, 2 and 3 of a sequence set forth in SEQ ID NO: 5;
(x) a $V_H$ comprising a sequence set forth in SEQ ID NO: 75 and a $V_L$ Comprising a sequence set forth in SEQ ID NO: 5;
(xli) a $V_H$ comprising CDRs 1, 2 and 3 of a sequence set forth in SEQ ID NO: 76 and a $V_L$ comprising CDRs 1, 2 and 3 of a sequence set forth in SEQ ID NO: 5;
(xlii) a $V_H$ comprising a sequence set forth in SEQ ID NO: 76 and a $V_L$ comprising a sequence set forth in SEQ ID NO: 5;
(xliii) a $V_H$ comprising CDRs 1, 2 and 3 of a sequence set forth in SEQ ID NO: 77 and a $V_L$ comprising CDRs 1, 2 and 3 of a sequence set forth in SEQ ID NO: 5;
(xliv) a $V_H$ comprising a sequence set forth in SEQ ID NO: 77 and a $V_L$ comprising a sequence set forth in SEQ ID NO: 5;
(xlv) a $V_H$ comprising CDRs 1, 2 and 3 of a sequence set forth in SEQ ID NO: 78 and a $V_L$ comprising CDRs 1, 2 and 3 of a sequence set forth in SEQ ID NO: 5;
(xlvi) a $V_H$ comprising a sequence set forth in SEQ ID NO: 78 and a $V_L$ comprising a sequence set forth in SEQ ID NO: 5;
(xlvii) a $V_H$ comprising CDRs 1, 2 and 3 of a sequence set forth in SEQ ID NO: 80 and a $V_L$ comprising CDRs 1, 2 and 3 of a sequence set forth in SEQ ID NO: 5;
(xlviii) a $V_H$ comprising a sequence set forth in SEQ ID NO: 80 and a $V_L$ comprising a sequence set forth in SEQ ID NO: 5;
(xlix) a $V_H$ comprising CDRs 1, 2 and 3 of a sequence set forth in SEQ ID NO: 81 and a $V_L$ comprising CDRs 1, 2 and 3 of a sequence set forth in SEQ ID NO: 5;
(l) a $V_H$ comprising a sequence set forth in SEQ ID NO: 81 and a $V_L$ comprising a sequence set forth in SEQ ID NO: 5;
(li) a $V_H$ comprising CDRs 1, 2 and 3 of a sequence set forth in SEQ ID NO: 83 and a $V_L$ comprising CDRs 1, 2 and 3 of a sequence set forth in SEQ ID NO: 5;
(lii) a $V_H$ comprising a sequence set forth in SEQ ID NO: 83 and a $V_L$ comprising a (liii) a $V_H$ comprising CDRs 1, 2 and 3 of a sequence set forth in SEQ ID NO: 88 and a $V_L$ comprising CDRs 1, 2 and 3 of a sequence set forth in SEQ ID NO: 5;
(liv) a $V_H$ comprising a sequence set forth in SEQ ID NO: 88 and a $V_L$ comprising a sequence set forth in SEQ ID NO: 5;
(lv) a $V_H$ comprising CDRs 1, 2 and 3 of a sequence set forth in SEQ ID NO: 91 and a $V_L$ comprising CDRs 1, 2 and 3 of a sequence set forth in SEQ ID NO: 5;
(lvi) a $V_H$ comprising a sequence set forth in SEQ ID NO: 91 and a $V_L$ comprising a sequence set forth in SEQ ID NO: 5;
(lvii) a $V_H$ comprising CDRs 1, 2 and 3 of a sequence set forth in SEQ ID NO: 92 and a $V_L$ comprising CDRs 1, 2 and 3 of a sequence set forth in SEQ ID NO: 5;
(lviii) a $V_H$ comprising a sequence set forth in SEQ ID NO: 92 and a $V_L$ comprising a sequence set forth in SEQ ID NO: 5;
(lix) a $V_H$ comprising CDRs 1, 2 and 3 of a sequence set forth in SEQ ID NO: 93 and a $V_L$ comprising CDRs 1, 2 and 3 of a sequence set forth in SEQ ID NO: 5;
(lx) a $V_H$ comprising a sequence set forth in SEQ ID NO: 93 and a $V_L$ comprising a sequence set forth in SEQ ID NO: 5;
(lxi) a $V_H$ comprising CDRs 1, 2 and 3 of a sequence set forth in SEQ ID NO: 94 and a $V_L$ comprising CDRs 1, 2 and 3 of a sequence set forth in SEQ ID NO: 5;
(lxii) a $V_H$ comprising a sequence set forth in SEQ ID NO: 94 and a $V_L$ comprising a sequence set forth in SEQ ID NO: 5;
(lxiii) a $V_H$ comprising CDRs 1, 2 and 3 of a sequence set forth in SEQ ID NO: 95 and a $V_L$ comprising CDRs 1, 2 and 3 of a sequence set forth in SEQ ID NO: 5;
(lxiv) a $V_H$ comprising a sequence set forth in SEQ ID NO: 95 and a $V_L$ comprising a sequence set forth in SEQ ID NO: 5;
(lxv) a $V_H$ comprising CDRs 1, 2 and 3 of a sequence set forth in SEQ ID NO: 99 and a $V_L$ comprising CDRs 1, 2 and 3 of a sequence set forth in SEQ ID NO: 5;
(lxvi) a $V_H$ comprising a sequence set forth in SEQ ID NO: 99 and a $V_L$ comprising a sequence set forth in SEQ ID NO: 5;
(lxvii) a $V_H$ comprising CDRs 1, 2 and 3 of a sequence set forth in SEQ ID NO: 100 and a $V_L$ comprising CDRs 1, 2 and 3 of a sequence set forth in SEQ ID NO: 5;
(lxviii) a $V_H$ comprising a sequence set forth in SEQ ID NO: 100 and a $V_L$ comprising a sequence set forth in SEQ ID NO: 5;

(lxix) a V_H comprising CDRs 1, 2 and 3 of a sequence set forth in SEQ ID NO: 101 and a V_L comprising CDRs 1, 2 and 3 of a sequence set forth in SEQ ID NO: 5;
(lxx) a V_H comprising a sequence set forth in SEQ ID NO: 101 and a V_L comprising a (lxxi) a V_H comprising CDRs 1, 2 and 3 of a sequence set forth in SEQ ID NO: 102 and a V_L comprising CDRs 1, 2 and 3 of a sequence set forth in SEQ ID NO: 5;
(lxxii) a V_H comprising a sequence set forth in SEQ ID NO: 102 and a V_L comprising a sequence set forth in SEQ ID NO: 5;
(lxxiii) a V_H comprising CDRs 1, 2 and 3 of a sequence set forth in SEQ ID NO: 103 and a V_L comprising CDRs 1, 2 and 3 of a sequence set forth in SEQ ID NO: 5;
(lxxiv) a V_H comprising a sequence set forth in SEQ ID NO: 103 and a V_L comprising a sequence set forth in SEQ ID NO: 5;
(lxxv) a V_H comprising CDRs 1, 2 and 3 of a sequence set forth in SEQ ID NO: 114 and a V_L comprising CDRs 1, 2 and 3 of a sequence set forth in SEQ ID NO: 5;
(lxxvi) a V_H comprising a sequence set forth in SEQ ID NO: 114 and a V_L comprising a sequence set forth in SEQ ID NO: 5;
(lxxvii) a V_H comprising CDRs 1, 2 and 3 of a sequence set forth in SEQ ID NO: 115 and a V_L comprising CDRs 1, 2 and 3 of a sequence set forth in SEQ ID NO: 5;
(lxxviii) a V_H comprising a sequence set forth in SEQ ID NO: 115 and a V_L comprising a sequence set forth in SEQ ID NO: 5;
(lxxix) a V_H comprising CDRs 1, 2 and 3 of a sequence set forth in SEQ ID NO: 116 and a V_L comprising CDRs 1, 2 and 3 of a sequence set forth in SEQ ID NO: 5; or
(lxxx) a V_H comprising a sequence set forth in SEQ ID NO: 116 and a V_L comprising a sequence set forth in SEQ ID NO: 5.

In one example, reference in the foregoing paragraph(s) to CDRs within a defined sequence (i.e., SEQ ID NO) will be understood as follows:

For a V_H, CDR1 is between amino acids 26-35; CDR2 is between amino acids 50-66; and CDR3 is between amino acids 99-106; and For a V_L, CDR1 is between amino acids 24-34; CDR2 is between amino acids 44-51; and CDR3 is between amino acids 89-97.

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising CDRs 1, 2 and 3 of a sequence set forth in SEQ ID NO: 59 and a V_L comprising CDRs 1, 2 and 3 of a sequence set forth in SEQ ID NO: 5; or The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising a sequence set forth in SEQ ID NO: 59 and a V_L comprising a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising CDRs 1, 2 and 3 of a sequence set forth in SEQ ID NO: 63 and a V_L comprising CDRs 1, 2 and 3 of a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising a sequence set forth in SEQ ID NO: 63 and a V_L comprising a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising CDRs 1, 2 and 3 of a sequence set forth in SEQ ID NO: 64 and a V_L comprising CDRs 1, 2 and 3 of a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising a sequence set forth in SEQ ID NO: 64 and a V_L comprising a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising CDRs 1, 2 and 3 of a sequence set forth in SEQ ID NO: 65 and a V_L comprising CDRs 1, 2 and 3 of a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising a sequence set forth in SEQ ID NO: 65 and a V_L comprising a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising CDRs 1, 2 and 3 of a sequence set forth in SEQ ID NO: 68 and a V_L comprising CDRs 1, 2 and 3 of a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising a sequence set forth in SEQ ID NO: 68 and a V_L comprising a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a V_H comprising CDRs 1, 2 and 3 of a sequence set forth in SEQ ID NO: 69 and a $V_L$ comprising CDRs 1, 2 and 3 of a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_H$ comprising a sequence set forth in SEQ ID NO: 69 and a $V_L$ comprising a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_H$ comprising CDRs 1, 2 and 3 of a sequence set forth in SEQ ID NO: 72 and a $V_L$ comprising CDRs 1, 2 and 3 of a sequence set forth in SEQ ID NO: 5;

The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_H$ comprising a sequence set forth in SEQ ID NO: 72 and a $V_L$ comprising a sequence set forth in SEQ ID NO: 5; or The present disclosure also provides a CD131-binding protein comprising an antigen binding domain of an antibody, wherein the antigen binding domain binds to or specifically binds to CD131 and neutralizes signaling by IL-3, IL-5 and GM-CSF, and wherein the antigen binding domain comprises a $V_H$ comprising CDRs 1, 2 and 3 of a sequence set forth in SEQ ID NO: 100 and a $V_L$ comprising CDRs 1, 2 and 3 of a sequence set forth in SEQ ID NO: 5.

In one example, reference in the foregoing paragraph(s) to CDRs within a defined sequence (i.e., SEQ ID NO) will be understood as follows:

For a $V_H$, CDR1 is between amino acids 26-35; CDR2 is between amino acids 50-66; and CDR3 is between amino acids 99-106; and For a $V_L$, CDR1 is between amino acids 24-34; CDR2 is between amino acids 44-51; and CDR3 is between amino acids 89-97.

In one example, a CD131-binding protein described herein comprises at least a $V_H$ and a $V_L$, wherein the $V_H$ and $V_L$ bind to form a Fv comprising an antigen binding domain. The skilled artisan will understand that the antigen binding domain comprises the binding site of the antibody.

In one example, the $V_H$ and the $V_L$ are in a single polypeptide chain. For example, the protein is:
(i) a single chain Fv fragment (scFv);
(ii) a dimeric scFv (di-scFv);
(iii) one of (i) or (ii) linked to a constant region of an antibody, Fc or a heavy chain constant domain ($C_H$) 2 and/or $C_H 3$; or
(iv) one of (i) or (ii) linked to a protein that binds to an immune effector cell.

In one example, the $V_L$ and $V_H$ are in separate polypeptide chains.

For example, the protein is:
(i) a diabody;
(ii) a triabody;
(iii) a tetrabody;
(iv) a Fab;
(v) a F(ab')$_2$;
(vi) a Fv;
(vii) one of (i) to (vi) linked to a constant region of an antibody, Fc or a heavy chain constant domain ($C_H$) 2 and/or $C_H 3$;
(viii) one of (i) to (vi) linked to a protein that binds to an immune effector cell.

The foregoing proteins (described in the previous two lists) can also be referred to as antigen binding domains of antibodies.

In one example, the protein is an antibody, for example, a monoclonal antibody.

In one example, the antibody is a naked antibody.

In one example, a protein (or antibody) is chimeric, de-immunized, humanized, human or primatized.

In one example, the protein or antibody is human. For example, the present disclosure provides an antibody which binds to or specifically binds to CD131 and neutralizes signaling by IL-3, IL-5 and GM-CSF, and wherein the antibody comprises an antigen binding domain or a $V_H$ and/or $V_L$ as described herein in any example.

In one example, an antibody of the disclosure comprises a $V_L$ comprising a sequence set forth in any one of SEQ ID NOs: 5 to 19, e.g., in SEQ ID NO: 5.

In one example, an antibody of the disclosure comprises a $V_L$ comprising a sequence set forth in SEQ ID No: 179.

In one example, an antibody of the disclosure comprises a $V_H$ comprising a sequence set forth in any one of SEQ ID NOs: 20 to 116.

In one example, an antibody of the disclosure comprises a $V_H$ comprising a sequence set forth in any one of SEQ ID NOs: 182, 186 or 90.

In one example, the present disclosure provides a CD131-binding antibody which binds to or specifically binds to CD131 and neutralizes signaling by IL-3, IL-5 and GM-CSF, and wherein the antigen binding domain comprises:
(i) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 5;
(ii) a $V_H$ comprising a sequence set forth in SEQ ID NO: 20 and a $V_L$ comprising a sequence set forth in SEQ ID NO: 5;
(iii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 6;
(iv) a $V_H$ comprising a sequence set forth in SEQ ID NO: 20 and a $V_L$ comprising a sequence set forth in SEQ ID NO: 6;
(v) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 7;
(vi) a $V_H$ comprising a sequence set forth in SEQ ID NO: 20 and a $V_L$ comprising a sequence set forth in SEQ ID NO: 7;
(vii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 8;
(viii) a $V_H$ comprising a sequence set forth in SEQ ID NO: 20 and a $V_L$ comprising a sequence set forth in SEQ ID NO: 8;
(ix) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 9;
(x) a $V_H$ comprising a sequence set forth in SEQ ID NO: 20 and a $V_L$ Comprising a sequence set forth in SEQ ID NO: 9;
(xi) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 10;

(xii) a $V_H$ comprising a sequence set forth in SEQ ID NO: 20 and a $V_L$ comprising a sequence set forth in SEQ ID NO: 10;

(xiii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 11;

(xiv) a $V_H$ comprising a sequence set forth in SEQ ID NO: 20 and a $V_L$ comprising a sequence set forth in SEQ ID NO: 11;

(xv) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 12;

(xvi) a $V_H$ comprising a sequence set forth in SEQ ID NO: 20 and a $V_L$ comprising a sequence set forth in SEQ ID NO: 12;

(xvii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 13;

(xviii) a $V_H$ comprising a sequence set forth in SEQ ID NO: 20 and a $V_L$ comprising a sequence set forth in SEQ ID NO: 13;

(xix) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 14;

(xx) a $V_H$ comprising a sequence set forth in SEQ ID NO: 20 and a $V_L$ comprising a sequence set forth in SEQ ID NO: 14;

(xxi) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 15;

(xxii) a $V_H$ comprising a sequence set forth in SEQ ID NO: 20 and a $V_L$ comprising a sequence set forth in SEQ ID NO: 15;

(xxiii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 16;

(xxiv) a $V_H$ comprising a sequence set forth in SEQ ID NO: 20 and a $V_L$ comprising a sequence set forth in SEQ ID NO: 16;

(xxv) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 17;

(xxvi) a $V_H$ comprising a sequence set forth in SEQ ID NO: 20 and a $V_L$ comprising a sequence set forth in SEQ ID NO: 17;

(xxvii) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 18;

(xxviii) a $V_H$ comprising a sequence set forth in SEQ ID NO: 20 and a $V_L$ comprising a sequence set forth in SEQ ID NO: 18;

(xxix) a $V_H$ comprising CDRs 1, 2 and 3 of a sequence set forth in SEQ ID NO: 20 and a $V_L$ comprising CDRs 1, 2 and 3 of a sequence set forth in SEQ ID NO: 19;

(xxx) a $V_H$ comprising a sequence set forth in SEQ ID NO: 20 and a $V_L$ comprising a sequence set forth in SEQ ID NO: 19;

(xxxi) a $V_H$ comprising CDRs 1, 2 and 3 of a sequence set forth in SEQ ID NO: 21 and a $V_L$ comprising CDRs 1, 2 and 3 of a sequence set forth in SEQ ID NO: 5;

(xxxii) a $V_H$ comprising a sequence set forth in SEQ ID NO: 21 and a $V_L$ Comprising a sequence set forth in SEQ ID NO: 5;

(xxxiii) a $V_H$ comprising CDRs 1, 2 and 3 of a sequence set forth in SEQ ID NO: 22 and a $V_L$ comprising CDRs 1, 2 and 3 of a sequence set forth in SEQ ID NO: 5;

(xxxiv) a $V_H$ comprising a sequence set forth in SEQ ID NO: 22 and a $V_L$ comprising a sequence set forth in SEQ ID NO: 5;

(xxxv) a $V_H$ comprising CDRs 1, 2 and 3 of a sequence set forth in SEQ ID NO: 23 and a $V_L$ comprising CDRs 1, 2 and 3 of a sequence set forth in SEQ ID NO: 5;

(xxxvi) a $V_H$ comprising a sequence set forth in SEQ ID NO: 23 and a $V_L$ comprising a sequence set forth in SEQ ID NO: 5;

(xxxvii) a $V_H$ comprising CDRs 1, 2 and 3 of a sequence set forth in SEQ ID NO: 24 and a $V_L$ comprising CDRs 1, 2 and 3 of a sequence set forth in SEQ ID NO: 5;

(xxxviii) a $V_H$ comprising a sequence set forth in SEQ ID NO: 24 and a $V_L$ comprising a sequence set forth in SEQ ID NO: 5;

(xxxix) a $V_H$ comprising CDRs 1, 2 and 3 of a sequence set forth in SEQ ID NO: 25 and a $V_L$ comprising CDRs 1, 2 and 3 of a sequence set forth in SEQ ID NO: 5;

(x) a $V_H$ comprising a sequence set forth in SEQ ID NO: 25 and a $V_L$ Comprising a sequence set forth in SEQ ID NO: 5;

(xli) a $V_H$ comprising CDRs 1, 2 and 3 of a sequence set forth in SEQ ID NO: 26 and a $V_L$ comprising CDRs 1, 2 and 3 of a sequence set forth in SEQ ID NO: 5;

(xlii) a $V_H$ comprising a sequence set forth in SEQ ID NO: 26 and a $V_L$ comprising a sequence set forth in SEQ ID NO: 5;

(xliii) a $V_H$ comprising CDRs 1, 2 and 3 of a sequence set forth in SEQ ID NO: 27 and a $V_L$ comprising CDRs 1, 2 and 3 of a sequence set forth in SEQ ID NO: 5;

(xliv) a $V_H$ comprising a sequence set forth in SEQ ID NO: 27 and a $V_L$ comprising a sequence set forth in SEQ ID NO: 5;

(xlv) a $V_H$ comprising CDRs 1, 2 and 3 of a sequence set forth in SEQ ID NO: 28 and a $V_L$ comprising CDRs 1, 2 and 3 of a sequence set forth in SEQ ID NO: 5;

(xlvi) a $V_H$ comprising a sequence set forth in SEQ ID NO: 28 and a $V_L$ comprising a sequence set forth in SEQ ID NO: 5;

(xlvii) a $V_H$ comprising CDRs 1, 2 and 3 of a sequence set forth in SEQ ID NO: 29 and a $V_L$ comprising CDRs 1, 2 and 3 of a sequence set forth in SEQ ID NO: 5;

(xlviii) a $V_H$ comprising a sequence set forth in SEQ ID NO: 29 and a $V_L$ comprising a sequence set forth in SEQ ID NO: 5;

(xlix) a $V_H$ comprising CDRs 1, 2 and 3 of a sequence set forth in SEQ ID NO: 30 and a $V_L$ comprising CDRs 1, 2 and 3 of a sequence set forth in SEQ ID NO: 5;

(l) a $V_H$ comprising a sequence set forth in SEQ ID NO: 30 and a $V_L$ comprising a sequence set forth in SEQ ID NO: 5;

(li) a $V_H$ comprising CDRs 1, 2 and 3 of a sequence set forth in SEQ ID NO: 31 and a $V_L$ comprising CDRs 1, 2 and 3 of a sequence set forth in SEQ ID NO: 5;

(lii) a $V_H$ comprising a sequence set forth in SEQ ID NO: 31 and a $V_L$ comprising a sequence set forth in SEQ ID NO: 5;

(liii) a $V_H$ comprising CDRs 1, 2 and 3 of a sequence set forth in SEQ ID NO: 32 and a $V_L$ comprising CDRs 1, 2 and 3 of a sequence set forth in SEQ ID NO: 5;

(liv) a $V_H$ comprising a sequence set forth in SEQ ID NO: 32 and a $V_L$ comprising a sequence set forth in SEQ ID NO: 5;

(lv) a $V_H$ comprising CDRs 1, 2 and 3 of a sequence set forth in SEQ ID NO: 33 and a $V_L$ comprising CDRs 1, 2 and 3 of a sequence set forth in SEQ ID NO: 5;

(lvi) a $V_H$ comprising a sequence set forth in SEQ ID NO: 33 and a $V_L$ comprising a sequence set forth in SEQ ID NO: 5;

(lvii) a $V_H$ comprising CDRs 1, 2 and 3 of a sequence set forth in SEQ ID NO: 34 and a $V_L$ comprising CDRs 1, 2 and 3 of a sequence set forth in SEQ ID NO: 5;

(lviii) a $V_H$ comprising a sequence set forth in SEQ ID NO: 34 and a $V_L$ comprising a sequence set forth in SEQ ID NO: 5;

(lix) a $V_H$ comprising CDRs 1, 2 and 3 of a sequence set forth in SEQ ID NO: 35 and a $V_L$ comprising CDRs 1, 2 and 3 of a sequence set forth in SEQ ID NO: 5;

(lx) a $V_H$ comprising a sequence set forth in SEQ ID NO: 35 and a $V_L$ comprising a sequence set forth in SEQ ID NO: 5;

(lxi) a $V_H$ comprising CDRs 1, 2 and 3 of a sequence set forth in SEQ ID NO: 36 and a $V_L$ comprising CDRs 1, 2 and 3 of a sequence set forth in SEQ ID NO: 5;

(lxii) a $V_H$ comprising a sequence set forth in SEQ ID NO: 36 and a $V_L$ comprising a sequence set forth in SEQ ID NO: 5;

(lxiii) a $V_H$ comprising CDRs 1, 2 and 3 of a sequence set forth in SEQ ID NO: 37 and a $V_L$ comprising CDRs 1, 2 and 3 of a sequence set forth in SEQ ID NO: 5;

(lxiv) a $V_H$ comprising a sequence set forth in SEQ ID NO: 37 and a $V_L$ comprising a sequence set forth in SEQ ID NO: 5;

(lxv) a $V_H$ comprising CDRs 1, 2 and 3 of a sequence set forth in SEQ ID NO: 38 and a $V_L$ comprising CDRs 1, 2 and 3 of a sequence set forth in SEQ ID NO: 5;

(lxvi) a $V_H$ comprising a sequence set forth in SEQ ID NO: 38 and a $V_L$ comprising a sequence set forth in SEQ ID NO: 5;

(lxvii) a $V_H$ comprising CDRs 1, 2 and 3 of a sequence set forth in SEQ ID NO: 39 and a $V_L$ comprising CDRs 1, 2 and 3 of a sequence set forth in SEQ ID NO: 5;

(lxviii) a $V_H$ comprising a sequence set forth in SEQ ID NO: 39 and a $V_L$ comprising a sequence set forth in SEQ ID NO: 5;

(lxix) a $V_H$ comprising CDRs 1, 2 and 3 of a sequence set forth in SEQ ID NO: 40 and a $V_L$ comprising CDRs 1, 2 and 3 of a sequence set forth in SEQ ID NO: 5;

(lxx) a $V_H$ comprising a sequence set forth in SEQ ID NO: 40 and a $V_L$ comprising a sequence set forth in SEQ ID NO: 5;

(lxxi) a $V_H$ comprising CDRs 1, 2 and 3 of a sequence set forth in SEQ ID NO: 41 and a $V_L$ comprising CDRs 1, 2 and 3 of a sequence set forth in SEQ ID NO: 5;

(lxxii) a $V_H$ comprising a sequence set forth in SEQ ID NO: 41 and a $V_L$ comprising a sequence set forth in SEQ ID NO: 5;

(lxxiii) a $V_H$ comprising CDRs 1, 2 and 3 of a sequence set forth in SEQ ID NO: 42 and a $V_L$ comprising CDRs 1, 2 and 3 of a sequence set forth in SEQ ID NO: 5;

(lxxiv) a $V_H$ comprising a sequence set forth in SEQ ID NO: 42 and a $V_L$ comprising a sequence set forth in SEQ ID NO: 5;

(lxxv) a $V_H$ comprising CDRs 1, 2 and 3 of a sequence set forth in SEQ ID NO: 43 and a $V_L$ comprising CDRs 1, 2 and 3 of a sequence set forth in SEQ ID NO: 5;

(lxxvi) a $V_H$ comprising a sequence set forth in SEQ ID NO: 43 and a $V_L$ comprising a sequence set forth in SEQ ID NO: 5;

(lxxvii) a $V_H$ comprising CDRs 1, 2 and 3 of a sequence set forth in SEQ ID NO: 44 and a $V_L$ comprising CDRs 1, 2 and 3 of a sequence set forth in SEQ ID NO: 5;

(lxxviii) a $V_H$ comprising a sequence set forth in SEQ ID NO: 44 and a $V_L$ comprising a sequence set forth in SEQ ID NO: 5;

(lxxix) a $V_H$ comprising CDRs 1, 2 and 3 of a sequence set forth in SEQ ID NO: 45 and a $V_L$ comprising CDRs 1, 2 and 3 of a sequence set forth in SEQ ID NO: 5;

(lxxx) a $V_H$ comprising a sequence set forth in SEQ ID NO: 45 and a $V_L$ comprising a sequence set forth in SEQ ID NO: 5;

(lxxxi) a $V_H$ comprising CDRs 1, 2 and 3 of a sequence set forth in SEQ ID NO: 46 and a $V_L$ comprising CDRs 1, 2 and 3 of a sequence set forth in SEQ ID NO: 5;

(lxxxii) a $V_H$ comprising a sequence set forth in SEQ ID NO: 46 and a $V_L$ comprising a sequence set forth in SEQ ID NO: 5;

(lxxxiii) a $V_H$ comprising CDRs 1, 2 and 3 of a sequence set forth in SEQ ID NO: 47 and a $V_L$ comprising CDRs 1, 2 and 3 of a sequence set forth in SEQ ID NO: 5;

(lxxxiv) a $V_H$ comprising a sequence set forth in SEQ ID NO: 47 and a $V_L$ comprising a sequence set forth in SEQ ID NO: 5;

(lxxxv) a $V_H$ comprising CDRs 1, 2 and 3 of a sequence set forth in SEQ ID NO: 48 and a $V_L$ comprising CDRs 1, 2 and 3 of a sequence set forth in SEQ ID NO: 5;

(lxxxvi) a $V_H$ comprising a sequence set forth in SEQ ID NO: 48 and a $V_L$ comprising a sequence set forth in SEQ ID NO: 5;

(lxxxvii) a $V_H$ comprising CDRs 1, 2 and 3 of a sequence set forth in SEQ ID NO: 49 and a $V_L$ comprising CDRs 1, 2 and 3 of a sequence set forth in SEQ ID NO: 5;

(lxxxviii) a $V_H$ comprising a sequence set forth in SEQ ID NO: 49 and a $V_L$ comprising a sequence set forth in SEQ ID NO: 5;

(lxxxix) a $V_H$ comprising CDRs 1, 2 and 3 of a sequence set forth in SEQ ID NO: 50 and a $V_L$ comprising CDRs 1, 2 and 3 of a sequence set forth in SEQ ID NO: 5;

(xc) a $V_H$ comprising a sequence set forth in SEQ ID NO: 50 and a $V_L$ Comprising a sequence set forth in SEQ ID NO: 5;

(xci) a $V_H$ comprising CDRs 1, 2 and 3 of a sequence set forth in SEQ ID NO: 51 and a $V_L$ comprising CDRs 1, 2 and 3 of a sequence set forth in SEQ ID NO: 5;

(xcii) a $V_H$ comprising a sequence set forth in SEQ ID NO: 51 and a $V_L$ comprising a sequence set forth in SEQ ID NO: 5;

(xciii) a $V_H$ comprising CDRs 1, 2 and 3 of a sequence set forth in SEQ ID NO: 52 and a $V_L$ comprising CDRs 1, 2 and 3 of a sequence set forth in SEQ ID NO: 5;

(xciv) a $V_H$ comprising a sequence set forth in SEQ ID NO: 52 and a $V_L$ comprising a sequence set forth in SEQ ID NO: 5;

(xcv) a $V_H$ comprising CDRs 1, 2 and 3 of a sequence set forth in SEQ ID NO: 53 and a $V_L$ comprising CDRs 1, 2 and 3 of a sequence set forth in SEQ ID NO: 5;

(xcvi) a $V_H$ comprising a sequence set forth in SEQ ID NO: 53 and a $V_L$ comprising a sequence set forth in SEQ ID NO: 5;

(xcvii) a $V_H$ comprising CDRs 1, 2 and 3 of a sequence set forth in SEQ ID NO: 54 and a $V_L$ comprising CDRs 1, 2 and 3 of a sequence set forth in SEQ ID NO: 5;

(xcviii) a $V_H$ comprising a sequence set forth in SEQ ID NO: 54 and a $V_L$ comprising a sequence set forth in SEQ ID NO: 5;

(xcix) a $V_H$ comprising CDRs 1, 2 and 3 of a sequence set forth in SEQ ID NO: 55 and a $V_L$ comprising CDRs 1, 2 and 3 of a sequence set forth in SEQ ID NO: 5;

(c) a $V_H$ comprising a sequence set forth in SEQ ID NO: 55 and a $V_L$ comprising a sequence set forth in SEQ ID NO: 5;
(ci) a $V_H$ comprising CDRs 1, 2 and 3 of a sequence set forth in SEQ ID NO: 56 and a $V_L$ comprising CDRs 1, 2 and 3 of a sequence set forth in SEQ ID NO: 5;
(cii) a $V_H$ comprising a sequence set forth in SEQ ID NO: 56 and a $V_L$ comprising a sequence set forth in SEQ ID NO: 5;
(ciii) a $V_H$ comprising CDRs 1, 2 and 3 of a sequence set forth in SEQ ID NO: 57 and a $V_L$ comprising CDRs 1, 2 and 3 of a sequence set forth in SEQ ID NO: 5;
(civ) a $V_H$ comprising a sequence set forth in SEQ ID NO: 57 and a $V_L$ comprising a sequence set forth in SEQ ID NO: 5;
(cv) a $V_H$ comprising CDRs 1, 2 and 3 of a sequence set forth in SEQ ID NO: 58 and a $V_L$ comprising CDRs 1, 2 and 3 of a sequence set forth in SEQ ID NO: 5;
(cvi) a $V_H$ comprising a sequence set forth in SEQ ID NO: 58 and a $V_L$ comprising a sequence set forth in SEQ ID NO: 5;
(cvii) a $V_H$ comprising CDRs 1, 2 and 3 of a sequence set forth in SEQ ID NO: 59 and a $V_L$ comprising CDRs 1, 2 and 3 of a sequence set forth in SEQ ID NO: 5;
(cviii) a $V_H$ comprising a sequence set forth in SEQ ID NO: 59 and a $V_L$ comprising a sequence set forth in SEQ ID NO: 5;
(cix) a $V_H$ comprising CDRs 1, 2 and 3 of a sequence set forth in SEQ ID NO: 60 and a $V_L$ comprising CDRs 1, 2 and 3 of a sequence set forth in SEQ ID NO: 5;
(cx) a $V_H$ comprising a sequence set forth in SEQ ID NO: 60 and a $V_L$ comprising a sequence set forth in SEQ ID NO: 5;
(cxi) a $V_H$ comprising CDRs 1, 2 and 3 of a sequence set forth in SEQ ID NO: 61 and a $V_L$ comprising CDRs 1, 2 and 3 of a sequence set forth in SEQ ID NO: 5;
(cxii) a $V_H$ comprising a sequence set forth in SEQ ID NO: 61 and a $V_L$ comprising a sequence set forth in SEQ ID NO: 5;
(cxiii) a $V_H$ comprising CDRs 1, 2 and 3 of a sequence set forth in SEQ ID NO: 62 and a $V_L$ comprising CDRs 1, 2 and 3 of a sequence set forth in SEQ ID NO: 5;
(cxiv) a $V_H$ comprising a sequence set forth in SEQ ID NO: 62 and a $V_L$ comprising a sequence set forth in SEQ ID NO: 5;
(cxv) a $V_H$ comprising CDRs 1, 2 and 3 of a sequence set forth in SEQ ID NO: 63 and a $V_L$ comprising CDRs 1, 2 and 3 of a sequence set forth in SEQ ID NO: 5;
(cxvi) a $V_H$ comprising a sequence set forth in SEQ ID NO: 63 and a $V_L$ comprising a sequence set forth in SEQ ID NO: 5;
(cxvii) a $V_H$ comprising CDRs 1, 2 and 3 of a sequence set forth in SEQ ID NO: 64 and a $V_L$ comprising CDRs 1, 2 and 3 of a sequence set forth in SEQ ID NO: 5;
(cxviii) a $V_H$ comprising a sequence set forth in SEQ ID NO: 64 and a $V_L$ comprising a sequence set forth in SEQ ID NO: 5;
(cxix) a $V_H$ comprising CDRs 1, 2 and 3 of a sequence set forth in SEQ ID NO: 65 and a $V_L$ comprising CDRs 1, 2 and 3 of a sequence set forth in SEQ ID NO: 5;
(cxx) a $V_H$ comprising a sequence set forth in SEQ ID NO: 65 and a $V_L$ comprising a sequence set forth in SEQ ID NO: 5;
(cxxi) a $V_H$ comprising CDRs 1, 2 and 3 of a sequence set forth in SEQ ID NO: 66 and a $V_L$ comprising CDRs 1, 2 and 3 of a sequence set forth in SEQ ID NO: 5;
(cxxii) a $V_H$ comprising a sequence set forth in SEQ ID NO: 66 and a $V_L$ comprising a
(cxxiii) a $V_H$ comprising CDRs 1, 2 and 3 of a sequence set forth in SEQ ID NO: 67 and a $V_L$ comprising CDRs 1, 2 and 3 of a sequence set forth in SEQ ID NO: 5;
(cxxiv) a $V_H$ comprising a sequence set forth in SEQ ID NO: 67 and a $V_L$ comprising a sequence set forth in SEQ ID NO: 5;
(cxxv) a $V_H$ comprising CDRs 1, 2 and 3 of a sequence set forth in SEQ ID NO: 68 and a $V_L$ comprising CDRs 1, 2 and 3 of a sequence set forth in SEQ ID NO: 5;
(cxxvi) a $V_H$ comprising a sequence set forth in SEQ ID NO: 68 and a $V_L$ comprising a sequence set forth in SEQ ID NO: 5;
(cxxvii) a $V_H$ comprising CDRs 1, 2 and 3 of a sequence set forth in SEQ ID NO: 69 and a $V_L$ comprising CDRs 1, 2 and 3 of a sequence set forth in SEQ ID NO: 5;
(cxxviii) a $V_H$ comprising a sequence set forth in SEQ ID NO: 69 and a $V_L$ comprising a sequence set forth in SEQ ID NO: 5;
(cxxix) a $V_H$ comprising CDRs 1, 2 and 3 of a sequence set forth in SEQ ID NO: 70 and a $V_L$ comprising CDRs 1, 2 and 3 of a sequence set forth in SEQ ID NO: 5;
(cxxx) a $V_H$ comprising a sequence set forth in SEQ ID NO: 70 and a $V_L$ comprising a sequence set forth in SEQ ID NO: 5;
(cxxxi) a $V_H$ comprising CDRs 1, 2 and 3 of a sequence set forth in SEQ ID NO: 71 and a $V_L$ comprising CDRs 1, 2 and 3 of a sequence set forth in SEQ ID NO: 5;
(cxxxii) a $V_H$ comprising a sequence set forth in SEQ ID NO: 71 and a $V_L$ comprising a sequence set forth in SEQ ID NO: 5;
(cxxxiii) a $V_H$ comprising CDRs 1, 2 and 3 of a sequence set forth in SEQ ID NO: 72 and a $V_L$ comprising CDRs 1, 2 and 3 of a sequence set forth in SEQ ID NO: 5;
(cxxxiv) a $V_H$ comprising a sequence set forth in SEQ ID NO: 72 and a $V_L$ comprising a sequence set forth in SEQ ID NO: 5;
(cxxxv) a $V_H$ comprising CDRs 1, 2 and 3 of a sequence set forth in SEQ ID NO: 73 and a $V_L$ comprising CDRs 1, 2 and 3 of a sequence set forth in SEQ ID NO: 5;
(cxxxvi) a $V_H$ comprising a sequence set forth in SEQ ID NO: 73 and a $V_L$ comprising a sequence set forth in SEQ ID NO: 5;
(cxxxvii) a $V_H$ comprising CDRs 1, 2 and 3 of a sequence set forth in SEQ ID NO: 75 and a $V_L$ comprising CDRs 1, 2 and 3 of a sequence set forth in SEQ ID NO: 5;
(cxxxviii) a $V_H$ comprising a sequence set forth in SEQ ID NO: 75 and a $V_L$ comprising a sequence set forth in SEQ ID NO: 5;
(cxxxix) a $V_H$ comprising CDRs 1, 2 and 3 of a sequence set forth in SEQ ID NO: 76 and a $V_L$ comprising CDRs 1, 2 and 3 of a sequence set forth in SEQ ID NO: 5;
(cxl) a $V_H$ comprising a sequence set forth in SEQ ID NO: 76 and a $V_L$ comprising a sequence set forth in SEQ ID NO: 5;
(cxli) a $V_H$ comprising CDRs 1, 2 and 3 of a sequence set forth in SEQ ID NO: 77 and a $V_L$ comprising CDRs 1, 2 and 3 of a sequence set forth in SEQ ID NO: 5;
(cxlii) a $V_H$ comprising a sequence set forth in SEQ ID NO: 77 and a $V_L$ comprising a sequence set forth in SEQ ID NO: 5;
(cxliii) a $V_H$ comprising CDRs 1, 2 and 3 of a sequence set forth in SEQ ID NO: 78 and a $V_L$ comprising CDRs 1, 2 and 3 of a sequence set forth in SEQ ID NO: 5;

(cxliv) a $V_H$ comprising a sequence set forth in SEQ ID NO: 78 and a $V_L$ comprising a sequence set forth in SEQ ID NO: 5;
(cxlv) a $V_H$ comprising CDRs 1, 2 and 3 of a sequence set forth in SEQ ID NO: 79 and a $V_L$ comprising CDRs 1, 2 and 3 of a sequence set forth in SEQ ID NO: 5;
(cxlvi) a $V_H$ comprising a sequence set forth in SEQ ID NO: 79 and a $V_L$ comprising a sequence set forth in SEQ ID NO: 5;
(cxlvii) a $V_H$ comprising CDRs 1, 2 and 3 of a sequence set forth in SEQ ID NO: 80 and a $V_L$ comprising CDRs 1, 2 and 3 of a sequence set forth in SEQ ID NO: 5;
(cxlviii) a $V_H$ comprising a sequence set forth in SEQ ID NO: 80 and a $V_L$ comprising a sequence set forth in SEQ ID NO: 5;
(cxlix) a $V_H$ comprising CDRs 1, 2 and 3 of a sequence set forth in SEQ ID NO: 81 and a $V_L$ comprising CDRs 1, 2 and 3 of a sequence set forth in SEQ ID NO: 5;
(cl) a $V_H$ comprising a sequence set forth in SEQ ID NO: 81 and a $V_L$ comprising a sequence set forth in SEQ ID NO: 5;
(cli) a $V_H$ comprising CDRs 1, 2 and 3 of a sequence set forth in SEQ ID NO: 82 and a $V_L$ comprising CDRs 1, 2 and 3 of a sequence set forth in SEQ ID NO: 5;
(clii) a $V_H$ comprising a sequence set forth in SEQ ID NO: 82 and a $V_L$ comprising a (cliii) a $V_H$ comprising CDRs 1, 2 and 3 of a sequence set forth in SEQ ID NO: 83 and a $V_L$ comprising CDRs 1, 2 and 3 of a sequence set forth in SEQ ID NO: 5;
(cliv) a $V_H$ comprising a sequence set forth in SEQ ID NO: 83 and a $V_L$ comprising a sequence set forth in SEQ ID NO: 5;
(clv) a $V_H$ comprising CDRs 1, 2 and 3 of a sequence set forth in SEQ ID NO: 84 and a $V_L$ comprising CDRs 1, 2 and 3 of a sequence set forth in SEQ ID NO: 5;
(clvi) a $V_H$ comprising a sequence set forth in SEQ ID NO: 84 and a $V_L$ comprising a sequence set forth in SEQ ID NO: 5;
(clvii) a $V_H$ comprising CDRs 1, 2 and 3 of a sequence set forth in SEQ ID NO: 85 and a $V_L$ comprising CDRs 1, 2 and 3 of a sequence set forth in SEQ ID NO: 5;
(clviii) a $V_H$ comprising a sequence set forth in SEQ ID NO: 85 and a $V_L$ comprising a sequence set forth in SEQ ID NO: 5;
(clix) a $V_H$ comprising CDRs 1, 2 and 3 of a sequence set forth in SEQ ID NO: 86 and a $V_L$ comprising CDRs 1, 2 and 3 of a sequence set forth in SEQ ID NO: 5;
(clx) a $V_H$ comprising a sequence set forth in SEQ ID NO: 86 and a $V_L$ comprising a sequence set forth in SEQ ID NO: 5;
(clxi) a $V_H$ comprising CDRs 1, 2 and 3 of a sequence set forth in SEQ ID NO: 87 and a $V_L$ comprising CDRs 1, 2 and 3 of a sequence set forth in SEQ ID NO: 5;
(clxii) a $V_H$ comprising a sequence set forth in SEQ ID NO: 87 and a $V_L$ comprising a sequence set forth in SEQ ID NO: 5;
(clxiii) a $V_H$ comprising CDRs 1, 2 and 3 of a sequence set forth in SEQ ID NO: 88 and a $V_L$ comprising CDRs 1, 2 and 3 of a sequence set forth in SEQ ID NO: 5;
(clxiv) a $V_H$ comprising a sequence set forth in SEQ ID NO: 88 and a $V_L$ comprising a sequence set forth in SEQ ID NO: 5;
(clxv) a $V_H$ comprising CDRs 1, 2 and 3 of a sequence set forth in SEQ ID NO: 89 and a $V_L$ comprising CDRs 1, 2 and 3 of a sequence set forth in SEQ ID NO: 5;
(clxvi) a $V_H$ comprising a sequence set forth in SEQ ID NO: 89 and a $V_L$ comprising a sequence set forth in SEQ ID NO: 5;
(clxvii) a $V_H$ comprising CDRs 1, 2 and 3 of a sequence set forth in SEQ ID NO: 90 and a $V_L$ comprising CDRs 1, 2 and 3 of a sequence set forth in SEQ ID NO: 5;
(clxviii) a $V_H$ comprising a sequence set forth in SEQ ID NO: 90 and a $V_L$ comprising a sequence set forth in SEQ ID NO: 5;
(clxix) a $V_H$ comprising CDRs 1, 2 and 3 of a sequence set forth in SEQ ID NO: 91 and a $V_L$ comprising CDRs 1, 2 and 3 of a sequence set forth in SEQ ID NO: 5;
(clxx) a $V_H$ comprising a sequence set forth in SEQ ID NO: 91 and a $V_L$ comprising a sequence set forth in SEQ ID NO: 5;
(clxxi) a $V_H$ comprising CDRs 1, 2 and 3 of a sequence set forth in SEQ ID NO: 92 and a $V_L$ comprising CDRs 1, 2 and 3 of a sequence set forth in SEQ ID NO: 5;
(clxxii) a $V_H$ comprising a sequence set forth in SEQ ID NO: 92 and a $V_L$ comprising a sequence set forth in SEQ ID NO: 5;
(clxxiii) a $V_H$ comprising CDRs 1, 2 and 3 of a sequence set forth in SEQ ID NO: 93 and a $V_L$ comprising CDRs 1, 2 and 3 of a sequence set forth in SEQ ID NO: 5;
(clxxiv) a $V_H$ comprising a sequence set forth in SEQ ID NO: 93 and a $V_L$ comprising a sequence set forth in SEQ ID NO: 5;
(clxxv) a $V_H$ comprising CDRs 1, 2 and 3 of a sequence set forth in SEQ ID NO: 94 and a $V_L$ comprising CDRs 1, 2 and 3 of a sequence set forth in SEQ ID NO: 5;
(clxxvi) a $V_H$ comprising a sequence set forth in SEQ ID NO: 94 and a $V_L$ comprising a sequence set forth in SEQ ID NO: 5;
(clxxvii) a $V_H$ comprising CDRs 1, 2 and 3 of a sequence set forth in SEQ ID NO: 95 and a $V_L$ comprising CDRs 1, 2 and 3 of a sequence set forth in SEQ ID NO: 5;
(clxxviii) a $V_H$ comprising a sequence set forth in SEQ ID NO: 95 and a $V_L$ comprising a sequence set forth in SEQ ID NO: 5;
(clxxix) a $V_H$ comprising CDRs 1, 2 and 3 of a sequence set forth in SEQ ID NO: 96 and a $V_L$ comprising CDRs 1, 2 and 3 of a sequence set forth in SEQ ID NO: 5;
(clxxx) a $V_H$ comprising a sequence set forth in SEQ ID NO: 96 and a $V_L$ comprising a sequence set forth in SEQ ID NO: 5;
(clxxxi) a $V_H$ comprising CDRs 1, 2 and 3 of a sequence set forth in SEQ ID NO: 97 and a $V_L$ comprising CDRs 1, 2 and 3 of a sequence set forth in SEQ ID NO: 5;
(clxxxii) a $V_H$ comprising a sequence set forth in SEQ ID NO: 97 and a $V_L$ comprising a sequence set forth in SEQ ID NO: 5;
(clxxxiii) a $V_H$ comprising CDRs 1, 2 and 3 of a sequence set forth in SEQ ID NO: 98 and a $V_L$ comprising CDRs 1, 2 and 3 of a sequence set forth in SEQ ID NO: 5;
(clxxxiv) a $V_H$ comprising a sequence set forth in SEQ ID NO: 98 and a $V_L$ comprising a sequence set forth in SEQ ID NO: 5;
(clxxxv) a $V_H$ comprising CDRs 1, 2 and 3 of a sequence set forth in SEQ ID NO: 99 and a $V_L$ comprising CDRs 1, 2 and 3 of a sequence set forth in SEQ ID NO: 5;
(clxxxvi) a $V_H$ comprising a sequence set forth in SEQ ID NO: 99 and a $V_L$ comprising a sequence set forth in SEQ ID NO: 5;
(clxxxvii) a $V_H$ comprising CDRs 1, 2 and 3 of a sequence set forth in SEQ ID NO: 100 and a $V_L$ comprising CDRs 1, 2 and 3 of a sequence set forth in SEQ ID NO: 5;

(clxxxviii) a $V_H$ comprising a sequence set forth in SEQ ID NO: 100 and a $V_L$ comprising a sequence set forth in SEQ ID NO: 5;

(clxxxix) a $V_H$ comprising CDRs 1, 2 and 3 of a sequence set forth in SEQ ID NO: 101 and a $V_L$ comprising CDRs 1, 2 and 3 of a sequence set forth in SEQ ID NO: 5;

(cxc) a $V_H$ comprising a sequence set forth in SEQ ID NO: 101 and a $V_L$ comprising a sequence set forth in SEQ ID NO: 5;

(cxci) a $V_H$ comprising CDRs 1, 2 and 3 of a sequence set forth in SEQ ID NO: 102 and a $V_L$ comprising CDRs 1, 2 and 3 of a sequence set forth in SEQ ID NO: 5;

(cxcii) a $V_H$ comprising a sequence set forth in SEQ ID NO: 102 and a $V_L$ comprising a sequence set forth in SEQ ID NO: 5;

(cxciii) a $V_H$ comprising CDRs 1, 2 and 3 of a sequence set forth in SEQ ID NO: 103 and a $V_L$ comprising CDRs 1, 2 and 3 of a sequence set forth in SEQ ID NO: 5;

(cxciv) a $V_H$ comprising a sequence set forth in SEQ ID NO: 103 and a $V_L$ comprising a sequence set forth in SEQ ID NO: 5;

(cxcv) a $V_H$ comprising CDRs 1, 2 and 3 of a sequence set forth in SEQ ID NO: 104 and a $V_L$ comprising CDRs 1, 2 and 3 of a sequence set forth in SEQ ID NO: 5;

(cxcvi) a $V_H$ comprising a sequence set forth in SEQ ID NO: 104 and a $V_L$ comprising a sequence set forth in SEQ ID NO: 5;

(cxcvii) a $V_H$ comprising CDRs 1, 2 and 3 of a sequence set forth in SEQ ID NO: 105 and a $V_L$ comprising CDRs 1, 2 and 3 of a sequence set forth in SEQ ID NO: 5;

(cxcviii) a $V_H$ comprising a sequence set forth in SEQ ID NO: 105 and a $V_L$ comprising a sequence set forth in SEQ ID NO: 5;

(cxcix) a $V_H$ comprising CDRs 1, 2 and 3 of a sequence set forth in SEQ ID NO: 106 and a $V_L$ comprising CDRs 1, 2 and 3 of a sequence set forth in SEQ ID NO: 5;

(cc) a $V_H$ comprising a sequence set forth in SEQ ID NO: 106 and a $V_L$ comprising a sequence set forth in SEQ ID NO: 5;

(cci) a $V_H$ comprising CDRs 1, 2 and 3 of a sequence set forth in SEQ ID NO: 107 and a $V_L$ comprising CDRs 1, 2 and 3 of a sequence set forth in SEQ ID NO: 5;

(ccii) a $V_H$ comprising a sequence set forth in SEQ ID NO: 107 and a $V_L$ comprising a sequence set forth in SEQ ID NO: 5;

(cciii) a $V_H$ comprising CDRs 1, 2 and 3 of a sequence set forth in SEQ ID NO: 108 and a $V_L$ comprising CDRs 1, 2 and 3 of a sequence set forth in SEQ ID NO: 5;

(cciv) a $V_H$ comprising a sequence set forth in SEQ ID NO: 108 and a $V_L$ comprising a sequence set forth in SEQ ID NO: 5;

(ccv) a $V_H$ comprising CDRs 1, 2 and 3 of a sequence set forth in SEQ ID NO: 109 and a $V_L$ comprising CDRs 1, 2 and 3 of a sequence set forth in SEQ ID NO: 5;

(ccvi) a $V_H$ comprising a sequence set forth in SEQ ID NO: 109 and a $V_L$ comprising a sequence set forth in SEQ ID NO: 5;

(ccvii) a $V_H$ comprising CDRs 1, 2 and 3 of a sequence set forth in SEQ ID NO: 110 and a $V_L$ comprising CDRs 1, 2 and 3 of a sequence set forth in SEQ ID NO: 5;

(ccviii) a $V_H$ comprising a sequence set forth in SEQ ID NO: 110 and a $V_L$ comprising a sequence set forth in SEQ ID NO: 5;

(ccix) a $V_H$ comprising CDRs 1, 2 and 3 of a sequence set forth in SEQ ID NO: 111 and a $V_L$ comprising CDRs 1, 2 and 3 of a sequence set forth in SEQ ID NO: 5;

(ccx) a $V_H$ comprising a sequence set forth in SEQ ID NO: 111 and a $V_L$ comprising a sequence set forth in SEQ ID NO: 5;

(ccxi) a $V_H$ comprising CDRs 1, 2 and 3 of a sequence set forth in SEQ ID NO: 112 and a $V_L$ comprising CDRs 1, 2 and 3 of a sequence set forth in SEQ ID NO: 5;

(ccxii) a $V_H$ comprising a sequence set forth in SEQ ID NO: 112 and a $V_L$ Comprising a sequence set forth in SEQ ID NO: 5;

(ccxiii) a $V_H$ comprising CDRs 1, 2 and 3 of a sequence set forth in SEQ ID NO: 113 and a $V_L$ comprising CDRs 1, 2 and 3 of a sequence set forth in SEQ ID NO: 5;

(ccxiv) a $V_H$ comprising a sequence set forth in SEQ ID NO: 113 and a $V_L$ comprising a sequence set forth in SEQ ID NO: 5;

(ccxv) a $V_H$ comprising CDRs 1, 2 and 3 of a sequence set forth in SEQ ID NO: 114 and a $V_L$ comprising CDRs 1, 2 and 3 of a sequence set forth in SEQ ID NO: 5;

(ccxvi) a $V_H$ comprising a sequence set forth in SEQ ID NO: 114 and a $V_L$ comprising a (ccxvii) a $V_H$ comprising CDRs 1, 2 and 3 of a sequence set forth in SEQ ID NO: 115 and a $V_L$ comprising CDRs 1, 2 and 3 of a sequence set forth in SEQ ID NO: 5;

(ccxviii) a $V_H$ comprising a sequence set forth in SEQ ID NO: 115 and a $V_L$ comprising a sequence set forth in SEQ ID NO: 5;

(ccxix) a $V_H$ comprising CDRs 1, 2 and 3 of a sequence set forth in SEQ ID NO: 116 and a $V_L$ comprising CDRs 1, 2 and 3 of a sequence set forth in SEQ ID NO: 5; or (ccxx) a $V_H$ comprising a sequence set forth in SEQ ID NO: 116 and a $V_L$ comprising a sequence set forth in SEQ ID NO: 5.

In one example, reference in the foregoing paragraph(s) to CDRs within a defined sequence (i.e., SEQ ID NO) will be understood as follows:

For a $V_H$, CDR1 is between amino acids 26-35; CDR2 is between amino acids 50-66; and CDR3 is between amino acids 99-106; and For a $V_L$, CDR1 is between amino acids 24-34; CDR2 is between amino acids 44-51; and CDR3 is between amino acids 89-97.

The present disclosure also provides a CD131-binding antibody which binds to or specifically binds to CD131 and neutralizes signaling by IL-3, IL-5 and GM-CSF, and wherein the antigen binding domain comprises:

(i) a $V_H$ comprising CDRs 1, 2 and 3 of a sequence set forth in SEQ ID NO: 59 and a $V_L$ comprising CDRs 1, 2 and 3 of a sequence set forth in SEQ ID NO: 5;

(ii) a $V_H$ comprising a sequence set forth in SEQ ID NO: 59 and a $V_L$ comprising a sequence set forth in SEQ ID NO: 5;

(iii) a $V_H$ comprising CDRs 1, 2 and 3 of a sequence set forth in SEQ ID NO: 63 and a $V_L$ comprising CDRs 1, 2 and 3 of a sequence set forth in SEQ ID NO: 5;

(iv) a $V_H$ comprising a sequence set forth in SEQ ID NO: 63 and a $V_L$ comprising a sequence set forth in SEQ ID NO: 5;

(v) a $V_H$ comprising CDRs 1, 2 and 3 of a sequence set forth in SEQ ID NO: 64 and a $V_L$ comprising CDRs 1, 2 and 3 of a sequence set forth in SEQ ID NO: 5;

(vi) a $V_H$ comprising a sequence set forth in SEQ ID NO: 64 and a $V_L$ comprising a sequence set forth in SEQ ID NO: 5;
(vii) a $V_H$ comprising CDRs 1, 2 and 3 of a sequence set forth in SEQ ID NO: 65 and a $V_L$ comprising CDRs 1, 2 and 3 of a sequence set forth in SEQ ID NO: 5;
(viii) a $V_H$ comprising a sequence set forth in SEQ ID NO: 65 and a $V_L$ comprising a
(ix) a $V_H$ comprising CDRs 1, 2 and 3 of a sequence set forth in SEQ ID NO: 68 and a $V_L$ comprising CDRs 1, 2 and 3 of a sequence set forth in SEQ ID NO: 5;
(x) a $V_H$ comprising a sequence set forth in SEQ ID NO: 68 and a $V_L$ comprising a sequence set forth in SEQ ID NO: 5;
(xi) a $V_H$ comprising CDRs 1, 2 and 3 of a sequence set forth in SEQ ID NO: 69 and a $V_L$ comprising CDRs 1, 2 and 3 of a sequence set forth in SEQ ID NO: 5;
(xii) a $V_H$ comprising a sequence set forth in SEQ ID NO: 69 and a $V_L$ comprising a sequence set forth in SEQ ID NO: 5;
(xiii) a $V_H$ comprising CDRs 1, 2 and 3 of a sequence set forth in SEQ ID NO: 72 and a $V_L$ comprising CDRs 1, 2 and 3 of a sequence set forth in SEQ ID NO: 5;
(xiv) a $V_H$ comprising a sequence set forth in SEQ ID NO: 72 and a $V_L$ comprising a sequence set forth in SEQ ID NO: 5;
(xv) a $V_H$ comprising CDRs 1, 2 and 3 of a sequence set forth in SEQ ID NO: 100 and a $V_L$ comprising CDRs 1, 2 and 3 of a sequence set forth in SEQ ID NO: 5; or
(xvi) a $V_H$ comprising a sequence set forth in SEQ ID NO: 100 and a $V_L$ comprising a sequence set forth in SEQ ID NO: 5.

In one example, reference in the foregoing paragraph(s) to CDRs within a defined sequence (i.e., SEQ ID NO) will be understood as follows:

For a $V_H$, CDR1 is between amino acids 26-35; CDR2 is between amino acids 50-66; and CDR3 is between amino acids 99-106; and For a $V_L$, CDR1 is between amino acids 24-34; CDR2 is between amino acids 44-51; and CDR3 is between amino acids 89-97.

In one example, a CD131-binding protein or antibody of the disclosure comprises a $V_H$ comprising CDR2 and CDR3 of a CD131-binding protein or antibody as described herein and a $V_L$ comprising a CDR1, a CDR2 and a CDR3 of a CD131-binding protein or antibody as described herein.

In one example, a CD131-binding protein or antibody of the disclosure comprises a $V_H$ comprising CDR1 and CDR3 of a CD131-binding protein or antibody as described herein and a $V_L$ comprising a CDR1, a CDR2 and a CDR3 of a CD131-binding protein or antibody as described herein.

In one example, a CD131-binding protein or antibody of the disclosure comprises a $V_H$ comprising a CDR1, a CDR2 and a CDR3 of a CD131-binding protein or antibody as described herein and a $V_L$ comprising a CDR1 and a CDR3 of a CD131-binding protein or antibody as described herein.

In one example, a CD131-binding protein or antibody of the disclosure comprises a $V_H$ comprising a CDR1, a CDR2 and a CDR3 of a CD131-binding protein or antibody as described herein and a $V_L$ comprising a CDR2 and a CDR3 of a CD131-binding protein or antibody as described herein.

In one example, a CD131-binding protein or antibody of the disclosure binds to a polypeptide comprising a sequence set forth in SEQ ID NO: 194 with a $K_D$ of about 100 nM or less, e.g., when the polypeptide is immobilized on a solid surface and the $K_D$ is determined by surface plasmon resonance. In one example, the $K_D$ is 10 nM or less, for example, 5 nM or less or 4 nM or less, or 3 nM or less or 2 nM or less. In one example, the $K_D$ is 1 nM or less. In one example, the $K_D$ is 0.9 nM or less or 0.7 nM or less or 0.8 nM or less or 0.7 nM or less or 0.6 nM or less. In one example, the $K_D$ is 0.5 nM or less. In one example, the $K_D$ is 0.4 nM or less. In one example, the $K_D$ is 0.3 nM or less.

In one example, the CD131-binding protein or antibody of the disclosure binds to a cell expressing CD131 (e.g., a neutrophil or an eosinophil or a TF-1 cell) with a $K_D$ of about 10 nM or less, e.g., using a competition assay using labeled and unlabeled protein or antibody. In one example, the $K_D$ is 5 nM or less or 4 nM or less, or 3 nM or less or 2 nM or less. In one example, the $K_D$ is 1 nM or less. In one example, the $K_D$ is 0.9 nM or less or 0.7 nM or less or 0.8 nM or less or 0.7 nM or less or 0.6 nM or less.

In one example, the $K_D$ is about 300 nM or less for a neutrophil.

In one example, the $K_D$ is about 700 nM or less for an eosinophil.

In one example, the $K_D$ is about 400 nM or less for a TF-1 cell.

In one example, the CD131-binding protein or antibody of the disclosure reduces or prevents IL-3 and/or GM-CSF-induced STAT-5 signaling.

In one example, the CD131-binding protein or antibody of the disclosure reduces or prevents IL-3-induced STAT-5 signaling with an $IC_{50}$ of about 20 nM or less. In one example, the pStat-5 $IC_{50}$ IL-3 is about 10 nM or less, or about 9 nM or less, or about 8 nM or less. In one example, the pStat-5 $IC_{50}$ IL-3 is about 7.5 nM or less, for example 7.3 nM.

In one example, the CD131-binding protein or antibody of the disclosure reduces or prevents GM-CSF-induced STAT-5 signaling with an $IC_{50}$ of about 60 nM or less. In one example, the pStat-5 $IC_{50}$ GM-CSF is about 50 nM or less, or about 45 nM or less or about 40 nM or less. In one example, the CD131-binding protein or antibody of the disclosure reduces or prevents GM-CSF-induced STAT-5 signaling with an $IC_{50}$ of about 40 nM.

For example, the protein or antibody is contacted to a cell (e.g., a TF-1 cell) comprising a beta-lactamase reporter gene under control of the interferon regulatory factor 1 (irf1) response element in the presence of IL-3 and/or GM-CSF. Cells are also contacted with a suitable substrate (e.g., a negatively charged fluorescent beta-lactamase substrate, such as CCF2 or CCF4) and the change in signal (e.g., fluorescence) determined. A reduced change in signal in a positive control (i.e., cells contacted with IL-3 and/or GM-CSF in the absence of the protein or antibody) indicates that the protein or antibody reduces or prevents IL-3 and/or GM-CSF-induced STAT-5 signaling.

In one example, the CD131-binding protein or antibody of the disclosure competes with IL-3 and/or GM-CSF and/or IL-5 for binding to a cell expressing CD131 (e.g., TF-1 cells).

In one example, the CD131-binding protein or antibody of the disclosure competes with IL-3 for binding to a cell expressing CD131 (e.g., TF-1 cells) with an $IC_{50}$ of about 10 nM or less. In one example, the $IC_{50}$ is about 9 nM or less, or about 8 nM or less, or about 7 nM or less. In one example, the $IC_{50}$ is about 6 nM or less, for example about 5.96 nM or less.

In one example, the CD131-binding protein or antibody of the disclosure competes with GM-CSF for binding to a cell expressing CD131 (e.g., TF-1 cells) with an $IC_{50}$ of about 600 nM or less. In one example, the ICs is about 550 nM or less, or about 500 nM or less. In one example, the $IC_{50}$ is about 480 nM or less, or about 460 nM or less, for example, about 456 nM or less.

In one example, the CD131-binding protein or antibody of the disclosure competes with IL-5 for binding to a cell expressing CD131 (e.g., TF-1 cells) with an $IC_{50}$ of about 1600 nM or less. In one example, the $IC_{50}$ is about 1550 nM or less, or about 1500 nM or less. In one example, the $IC_{50}$ is about 1480 nM or less, or about 1460 nM or less, or about 1450 nM or less, for example, about 1448 nM or less.

In one example, IL-3 and/or GM-CSF and/or IL-5 compete with the CD131-binding protein or antibody of the disclosure for binding to a cell expressing CD131 (e.g., TF-1 cells).

For example, cells (e.g., about 1-2×10$^6$ TF-1 cells) are contacted with a CD131-binding protein or antibody of the disclosure for about 45 minutes. Labeled IL-3 and/or GM-CSF and/or IL-5 is then contacted to the cells (e.g., for 1-2 hours) and, following washing, and the level of label bound to the cells assessed. A reduced level of bound label compared to positive control (i.e., cells contacted with the labeled cytokine in the absence of the protein or antibody) indicates that the protein or antibody competes with IL-3 and/or GM-CSF and/or IL-5 for binding to the cell. A reciprocal assay is used to determine the ability of IL-3 and/or GM-CSF and/or IL-5 to compete with the protein or antibody to the cell.

In one example, a CD131-binding protein or antibody of the disclosure has one or more of the following activities:
(i) reduces or inhibits activation of isolated human neutrophils by GM-CSF as determined by reducing or inhibiting GM-CSF-induced increase in neutrophil cell size;
(ii) reduces or inhibits IL-3-induced IL-8 secretion by human basophils;
(iii) reduces or prevents IL-3-mediated survival or plasmacytoid dendritic cells (pDCs);
(iv) reduces or prevents activation of human peripheral blood eosinophils by IL-5 as determined by assessing change in forward scatter assessed by flow cytometry;
(v) reduces or prevents survival of human peripheral blood eosinophils in the presence of IL-5 and/or GM-CSF and/or IL-3;
(vi) reduces or prevents IL-3-induced tumor necrosis factor (TNF) a release from human mast cells;
(vii) reduces or prevents IL-3-induced IL-13 release from human mast cells;
(viii) reduces or prevents potentiation of IgE-mediated IL-8 release from human mast cells by IL-3 and/or IL-5 and/or GM-CSF;
(ix) reduces or prevents formation of colony forming units-granulocytes-macrophages (CFU-GM) by CD34+ human bone marrow cells cultured in the presence of stem cell factor (SCF), GM-CSF, IL-3 and IL-5;
(x) reduces the size or weight of polyps in a mouse xenograft model of human nasal polyposis; and/or
(xi) reduces the number of B cells in a polyp in a mouse xenograft model of human nasal polyposis.

In one example, a CD131-binding protein of the disclosure does not substantially or significantly inhibit proliferation of TF-1 cells in response to one or more of erythropoietin, IL-6, IL-4 or stem cell factor. Methods for determining the ability of a CD131-binding protein to inhibit proliferation of TF-1 cells in respect to a cytokine or growth factor are described herein and are readily adaptable to the present example of the disclosure.

In one example, a CD131-binding protein or antibody of the disclosure reduces survival of or induces death of immune cells (e.g., eosinophils) from sputum or nasal polyp tissue from a subject suffering from an inflammatory airway disease or nasal polyposis. For example, the immune cells are cultured in the presence of IL-3 and/or IL-5 and/or GM-CSF and the protein or antibody. Cell death is then assessed e.g., by detecting Annexin-V expression, e.g., using fluorescence activated cell sorting). An increased number of cells expressing Annexin-V (i.e., undergoing apoptosis) in the presence of the protein or antibody compared to in the absence of the protein or antibody indicates that the protein or antibody reduces survival of or induces death of the immune cells (e.g., eosinophils).

Reference herein to a protein or antibody that "binds to" CD131 provides literal support for a protein or antibody that "binds specifically to" or "specifically binds to" CD131.

The present disclosure also provides antigen binding domains or antigen binding fragments of the foregoing antibodies.

In one example, a protein or antibody as described herein comprises a human constant region, e.g., an IgG constant region, such as an IgG1, IgG2, IgG3 or IgG4 constant region or mixtures thereof. In the case of an antibody or protein comprising a $V_H$ and a $V_L$, the $V_H$ can be linked to a heavy chain constant region and the $V_L$ can be linked to a light chain constant region.

The C-terminal lysine of the heavy chain constant region of a whole antibody (or a CD131-binding protein comprising a constant region or a $C_H3$) of the disclosure may be removed, for example, during production or purification of the antibody or protein, or by recombinantly engineering the nucleic acid encoding a heavy chain of the antibody. Accordingly, whole antibodies (or CD131-binding proteins) may comprise populations with all C-terminal lysine residues removed, populations with no C-terminal lysine residues removed, and/or populations having a mixture of protein with and without the C-terminal lysine residue. In some examples, the populations may additionally comprise protein in which the C-terminal lysine residue is removed in one of the heavy chain constant regions. Similarly, a composition of whole antibodies may comprise the same or a similar mix of antibody populations with or without the C-terminal lysine residue.

In one example, a protein or antibody as described herein comprises a constant region of an IgG4 antibody or a stabilized constant region of an IgG4 antibody. In one example, the protein or antibody comprises an IgG4 constant region with a proline at position 241 (according to the numbering system of Kabat (Kabat et al., Sequences of Proteins of Immunological Interest Washington DC United States Department of Health and Human Services, 1987 and/or 1991)).

In one example, the heavy chain constant region comprises a sequence set forth in SEQ ID NO: 197. In one example a protein or antibody as described herein or a composition of a protein or antibody as described herein, comprises a heavy chain constant region, including a stabilized heavy chain constant region, comprising a mixture of sequences fully or partially with or without the C-terminal lysine residue.

In one example, an antibody of the disclosure comprises a $V_H$ disclosed herein linked or fused to an IgG4 constant region or stabilized IgG4 constant region (e.g., as discussed above) and the $V_L$ is linked to or fused to a kappa light chain constant region.

The functional characteristics of a CD131-binding protein of the disclosure will be taken to apply mutatis mutandis to an antibody of the disclosure.

In one example, a CD131-binding protein or antibody as described herein is isolated and/or recombinant.

In one example, a CD131-binding protein or antibody of the disclosure is conjugated to another compound, for example, a detectable label or a compound that extends the half-life of the protein or antibody, such as polyethylene glycol or an albumin binding protein. Other suitable compounds are described herein.

The present disclosure also provides a nucleic acid encoding the CD131-binding protein or antibody of the present disclosure or a polypeptide thereof.

In one example, such a nucleic acid is included in an expression construct in which the nucleic acid is operably linked to a promoter. Such an expression construct can be in a vector, e.g., a plasmid.

In examples of the disclosure directed to single polypeptide chain CD131-binding proteins, the expression construct may comprise a promoter linked to a nucleic acid encoding that polypeptide chain.

In examples directed to multiple polypeptide chains that form a CD131-binding protein, an expression construct comprises a nucleic acid encoding a polypeptide comprising, e.g., a $V_H$ operably linked to a promoter and a nucleic acid encoding a polypeptide comprising, e.g., a $V_L$ operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide,
wherein the first polypeptide comprises a $V_H$ and the second polypeptide comprises a $V_L$, or vice versa.

The present disclosure also contemplates separate expression constructs one of which encodes a first polypeptide comprising a $V_H$ and another of which encodes a second polypeptide comprising a $V_L$. For example, the present disclosure also provides a composition comprising:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter.

The present disclosure also provides an isolated or recombinant cell expressing a CD131-binding protein of the disclosure.

In one example, the cell comprises the expression construct of the disclosure or:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter,
wherein the first and second polypeptides associate to form a CD131-binding protein of the present disclosure.

Examples of cells of the present disclosure include bacterial cells, yeast cells, insect cells or mammalian cells.

The present disclosure additionally provides methods for producing a CD131-binding protein or antibody of the disclosure. For example, such a method involves maintaining the expression construct(s) of the disclosure under conditions sufficient for the CD131-binding protein or antibody to be produced.

In one example, a method for producing a CD131-binding protein or antibody of the disclosure comprises culturing the cell of the disclosure under conditions sufficient for the CD131-binding protein or antibody to be produced and, optionally, secreted.

In one example, the method for producing a CD131-binding protein or antibody of the disclosure additionally comprises isolating the protein or antibody and, optionally, formulating the Cd131-binding protein or antibody into a pharmaceutical composition.

The present disclosure additionally provides a composition comprising the CD131-binding protein or antibody of the disclosure and a pharmaceutically acceptable carrier.

In some examples, the composition comprises:
(i) an antibody of the disclosure comprising a C-terminal lysine residue from the heavy chain;
(ii) an antibody of the disclosure lacking a C-terminal lysine residue from the heavy chain; and/or
(iii) an antibody of the disclosure comprising a C-terminal lysine residue on one heavy chain and lacking a C-terminal lysine residue on another (or the other) heavy chain,
and, optionally, a pharmaceutically acceptable carrier.

The present disclosure also provides a method for treating or preventing a CD131-mediated condition in a subject, the method comprising administering the CD131-binding protein or antibody or composition of the disclosure.

The present disclosure also provides a method for inhibiting or neutralizing CD131 in a subject, the method comprising administering the CD131-binding protein, antibody or composition of the disclosure. In one example, the subject suffers from a CD131-mediated condition.

In one example, a method described herein comprises administering between about 0.05 mg/kg and 30 mg/kg of the CD131-binding protein or antibody. For example, the method comprising administering between 0.1 mg/kg and 10 mg/kg or between 0.2 mg/kg and 5 mg/kg of the CD131-binding protein or antibody. In one example, the method comprises administering about 0.5-2.0 mg/kg of the CD131-binding protein or antibody.

The present disclosure also provides for use of the CD131-binding protein or the antibody or the composition of the disclosure in medicine.

The present disclosure additionally provides for use of CD131-binding protein or the antibody of the disclosure in the manufacture of a medicament to treat a CD131-mediated condition.

The present disclosure also provides the CD131-binding protein or the antibody or the composition of the disclosure for use in the treatment of a CD131-mediated condition.

The present disclosure further provides a method for localizing and/or detecting and/or diagnosing and/or prognosing a CD131-mediated condition associated with a cell expressing CD131, the method comprising detecting in vivo the CD131-binding protein or the antibody of the disclosure bound to the CD131 expressing cell, if present, wherein the CD131-binding protein or antibody is conjugated to a detectable tag. In one example, the method additionally comprises administering the CD131-binding protein or antibody to the subject.

The present disclosure further provides a method for detecting CD131 or a cell expressing same in a sample, the method comprising contacting the sample with the CD131-binding protein or the antibody of the disclosure such that a complex forms and detecting the complex, wherein detection of the complex is indicative of CD131 or a cell expressing same in the sample. In one example, the method is performed ex vivo or in vitro. Such a method is amenable to diagnosing or prognosing a condition, wherein detection of the CD131 or cell expressing same is diagnostic or prognostic of the condition.

In one example, the CD131-mediated condition is an autoimmune condition, an inflammatory condition, an allergic condition or cancer. For example, the condition is asthma, nasal polyposis, chronic rhinosinusitis with or without nasal polyps (CRSwNP or CRSsNP) or bladder cancer. In one example, the condition is corticosteroid-resistant asthma. In another example, the condition is chronic rhinosinusitis with nasal polyps (CRSwNP). In a further example, the condition is chronic rhinosinusitis without nasal polyps (CRSsNP). In a further example, the condition is bladder cancer. In one example, the condition is acute myeloid leukemia. In a further example, the condition is chronic myeloid leukemia.

In another example, the method comprises administering an inhibitor of IL-3 and IL-5 and GM-CSF, e.g., a tri-specific antibody or a CD131-binding protein or antibody (e.g., a CD131-binding protein or antibody of the present disclosure).

The present disclosure also provides a kit (e.g., a package or article of manufacture) comprising a CD131-binding protein or antibody as described herein according to any example, optionally, packaged with instructions for use in a method as described herein.

The present disclosure additionally provides a method for selecting a compound (e.g., an antibody or protein comprising an antigen binding domain thereof) that binds to or specifically binds to CD131 and neutralizes signaling by IL-3, IL-5 and GM-CSF, the method comprising selecting a compound that competitively inhibits binding of one or more of the following antibodies to CD131 and/or a polypeptide comprising a sequence set forth in SEQ ID NO: 192:
(i) an antibody comprising a $V_L$ comprising a sequence set forth in SEQ ID NO: 5 and a $V_H$ comprising a sequence set forth in SEQ ID NO: 20;
(ii) an antibody comprising a $V_L$ comprising a sequence set forth in SEQ ID NO: 5 and a human kappa light chain constant region and a $V_H$ comprising a sequence set forth in SEQ ID NO: 20 and a human IgG4 constant region; and/or
(iii) an antibody comprising a light chain comprising a sequence set forth in SEQ ID NO: 5 and a heavy chain comprising a sequence set forth in SEQ ID NO: 20.

The present disclosure also provides a compound that binds to or specifically binds to CD131 and neutralizes signaling by IL-3, IL-5 and GM-CSF, the method comprising selecting a compound that binds to one or more (or all) of the following mutant polypeptide(s):
(i) a mutant polypeptide comprising a sequence set forth in SEQ ID NO: 119;
  (ii) a mutant polypeptide comprising a sequence set forth in SEQ ID NO: 124;
  (iii) a mutant polypeptide comprising a sequence set forth in SEQ ID NO: 131;
  (iv) a mutant polypeptide comprising a sequence set forth in SEQ ID NO: 137;
  (v) a mutant polypeptide comprising a sequence set forth in SEQ ID NO: 139;
  (vi) a mutant polypeptide comprising a sequence set forth in SEQ ID NO: 140,
at a level that is reduced compared to the level of binding of the compound to a polypeptide comprising a sequence set forth in SEQ ID NO: 192.

Key to Sequence Listing
SEQ ID NO 1: amino acid sequence of *Homo sapiens* CD131
SEQ ID NO 2: amino acid sequence of *Homo sapiens* IL3-receptor α
SEQ ID NO 3: amino acid sequence of *Homo sapiens* GCS-F receptor
SEQ ID NO 4: amino acid sequence of *Homo sapiens* IL-5 receptor
SEQ ID NO 5: amino acid sequence of $V_L$ chain of antibody 9A2
SEQ ID NO 6: amino acid sequence of $V_L$ chain of antibody 9A2-VR1
SEQ ID NO 7: amino acid sequence of $V_L$ chain of antibody 9A2-VR2
SEQ ID NO 8: amino acid sequence of $V_L$ chain of antibody 9A2-VR3
SEQ ID NO 9: amino acid sequence of $V_L$ chain of antibody 9A2-VR4
SEQ ID NO 10: amino acid sequence of $V_L$ chain of antibody 9A2-VR5
SEQ ID NO 11: amino acid sequence of $V_L$ chain of antibody 9A2-VR6
SEQ ID NO 12: amino acid sequence of $V_L$ chain of antibody 9A2-VR8
SEQ ID NO 13: amino acid sequence of $V_L$ chain of antibody 9A2-VR9
SEQ ID NO 14: amino acid sequence of $V_L$ chain of antibody 9A2-VR11
SEQ ID NO 15: amino acid sequence of $V_L$ chain of antibody 9A2-VR12
SEQ ID NO 16: amino acid sequence of $V_L$ chain of antibody 9A2-VR13
SEQ ID NO 17: amino acid sequence of $V_L$ chain of antibody 9A2-VR14
SEQ ID NO 18: amino acid sequence of $V_L$ chain of antibody 9A2-VR16
SEQ ID NO 19: amino acid sequence of $V_L$ chain of antibody 9A2-VR19
SEQ ID NO 20: amino acid sequence of $V_H$ chain of antibody 9A2
SEQ ID NO 21: amino acid sequence of $V_H$ chain of antibody 9A2-VR20
SEQ ID NO 22: amino acid sequence of $V_H$ chain of antibody 9A2-VR21
SEQ ID NO 23: amino acid sequence of $V_H$ chain of antibody 9A2-VR22
SEQ ID NO 24: amino acid sequence of $V_H$ chain of antibody 9A2-VR23
SEQ ID NO 25: amino acid sequence of $V_H$ chain of antibody 9A2-VR24
SEQ ID NO 26: amino acid sequence of $V_H$ chain of antibody 9A2-VR26
SEQ ID NO 27: amino acid sequence of $V_H$ chain of antibody 9A2-VR27
SEQ ID NO 28: amino acid sequence of $V_H$ chain of antibody 9A2-VR28
SEQ ID NO 29: amino acid sequence of $V_H$ chain of antibody 9A2-VR31
SEQ ID NO 30: amino acid sequence of $V_H$ chain of antibody 9A2-VR32
SEQ ID NO 31: amino acid sequence of $V_H$ chain of antibody 9A2-VR33
SEQ ID NO 32: amino acid sequence of $V_H$ chain of antibody 9A2-VR34
SEQ ID NO 33: amino acid sequence of $V_H$ chain of antibody 9A2-VR35

SEQ ID NO 34: amino acid sequence of $V_H$ chain of antibody 9A2-VR36
SEQ ID NO 35: amino acid sequence of $V_H$ chain of antibody 9A2-VR37
SEQ ID NO 36: amino acid sequence of $V_H$ chain of antibody 9A2-VR38
SEQ ID NO 37: amino acid sequence of $V_H$ chain of antibody 9A2-VR39
SEQ ID NO 38: amino acid sequence of $V_H$ chain of antibody 9A2-VR40
SEQ ID NO 39: amino acid sequence of $V_H$ chain of antibody 9A2-VR41
SEQ ID NO 40: amino acid sequence of $V_H$ chain of antibody 9A2-VR42
SEQ ID NO 41: amino acid sequence of $V_H$ chain of antibody 9A2-VR43
SEQ ID NO 42: amino acid sequence of $V_H$ chain of antibody 9A2-VR44
SEQ ID NO 43: amino acid sequence of $V_H$ chain of antibody 9A2-VR45
SEQ ID NO 44: amino acid sequence of $V_H$ chain of antibody 9A2-VR46
SEQ ID NO 45: amino acid sequence of $V_H$ chain of antibody 9A2-VR47
SEQ ID NO 46: amino acid sequence of $V_H$ chain of antibody 9A2-VR48
SEQ ID NO 47: amino acid sequence of $V_H$ chain of antibody 9A2-VR49
SEQ ID NO 48: amino acid sequence of $V_H$ chain of antibody 9A2-VR50
SEQ ID NO 49: amino acid sequence of $V_H$ chain of antibody 9A2-VR24.04
SEQ ID NO 50: amino acid sequence of $V_H$ chain of antibody 9A2-VR24.07
SEQ ID NO 51: amino acid sequence of $V_H$ chain of antibody 9A2-VR24.10
SEQ ID NO 52: amino acid sequence of $V_H$ chain of antibody 9A2-VR24.12
SEQ ID NO 53: amino acid sequence of $V_H$ chain of antibody 9A2-VR24.19
SEQ ID NO 54: amino acid sequence of $V_H$ chain of antibody 9A2-VR24.24
SEQ ID NO 55: amino acid sequence of $V_H$ chain of antibody 9A2-VR24.76
SEQ ID NO 56: amino acid sequence of $V_H$ chain of antibody 9A2-VR24.78
SEQ ID NO 57: amino acid sequence of $V_H$ chain of antibody 9A2-VR24.81
SEQ ID NO 58: amino acid sequence of $V_H$ chain of antibody 9A2-VR24.82
SEQ ID NO 59: amino acid sequence of $V_H$ chain of antibody 9A2-VR24.84
SEQ ID NO 60: amino acid sequence of $V_H$ chain of antibody 9A2-VR24.87
SEQ ID NO 61: amino acid sequence of $V_H$ chain of antibody 9A2-VR24.91
SEQ ID NO 62: amino acid sequence of $V_H$ chain of antibody 9A2-VR24.93
SEQ ID NO 63: amino acid sequence of $V_H$ chain of antibody 9A2-VR24.27
SEQ ID NO 64: amino acid sequence of $V_H$ chain of antibody 9A2-VR24.29
SEQ ID NO 65: amino acid sequence of $V_H$ chain of antibody 9A2-VR24.30
SEQ ID NO 66: amino acid sequence of $V_H$ chain of antibody 9A2-VR24.33
SEQ ID NO 67: amino acid sequence of $V_H$ chain of antibody 9A2-VR24.44
SEQ ID NO 68: amino acid sequence of $V_H$ chain of antibody 9A2-VR24.97
SEQ ID NO 69: amino acid sequence of $V_H$ chain of antibody 9A2-VR24.98
SEQ ID NO 70: amino acid sequence of $V_H$ chain of antibody 9A2-VR24.102
SEQ ID NO 71: amino acid sequence of $V_H$ chain of antibody 9A2-VR24.107
SEQ ID NO 72: amino acid sequence of $V_H$ chain of antibody 9A2-VR24.110
SEQ ID NO 73: amino acid sequence of $V_H$ chain of antibody 9A2-VR24.111
SEQ ID NO 74: amino acid sequence of $V_H$ chain of antibody 9A2-VR24.55
SEQ ID NO 75: amino acid sequence of $V_H$ chain of antibody 9A2-VR24.56
SEQ ID NO 76: amino acid sequence of $V_H$ chain of antibody 9A2-VR24.57
SEQ ID NO 77: amino acid sequence of $V_H$ chain of antibody 9A2-VR24.122
SEQ ID NO 78: amino acid sequence of $V_H$ chain of antibody 9A2-VR24.124
SEQ ID NO 79: amino acid sequence of $V_H$ chain of antibody 9A2-VR24.131
SEQ ID NO 80: amino acid sequence of $V_H$ chain of antibody 9A2-VR39.01
SEQ ID NO 81: amino acid sequence of $V_H$ chain of antibody 9A2-VR39.02
SEQ ID NO 82: amino acid sequence of $V_H$ chain of antibody 9A2-VR39.04
SEQ ID NO 83: amino acid sequence of $V_H$ chain of antibody 9A2-VR39.05
SEQ ID NO 84: amino acid sequence of $V_H$ chain of antibody 9A2-VR39.06
SEQ ID NO 85: amino acid sequence of $V_H$ chain of antibody 9A2-VR39.11
SEQ ID NO 86: amino acid sequence of $V_H$ chain of antibody 9A2-VR39.12
SEQ ID NO 87: amino acid sequence of $V_H$ chain of antibody 9A2-VR39.16
SEQ ID NO 88: amino acid sequence of $V_H$ chain of antibody 9A2-VR39.17
SEQ ID NO 89: amino acid sequence of $V_H$ chain of antibody 9A2-VR39.18
SEQ ID NO 90: amino acid sequence of $V_H$ chain of antibody 9A2-VR39.19
SEQ ID NO 91: amino acid sequence of $V_H$ chain of antibody 9A2-VR39.21
SEQ ID NO 92: amino acid sequence of $V_H$ chain of antibody 9A2-VR39.22
SEQ ID NO 93: amino acid sequence of $V_H$ chain of antibody 9A2-VR39.23
SEQ ID NO 94: amino acid sequence of $V_H$ chain of antibody 9A2-VR39.24
SEQ ID NO 95: amino acid sequence of $V_H$ chain of antibody 9A2-VR39.97
SEQ ID NO 96: amino acid sequence of $V_H$ chain of antibody 9A2-VR39.98
SEQ ID NO 97: amino acid sequence of $V_H$ chain of antibody 9A2-VR39.102
SEQ ID NO 98: amino acid sequence of $V_H$ chain of antibody 9A2-VR39.103
SEQ ID NO 99: amino acid sequence of $V_H$ chain of antibody 9A2-VR39.105

SEQ ID NO 100: amino acid sequence of V$_H$ chain of antibody 9A2-VR39.109
SEQ ID NO 101: amino acid sequence of V$_H$ chain of antibody 9A2-VR39.110
SEQ ID NO 102: amino acid sequence of V$_H$ chain of antibody 9A2-VR39.111
SEQ ID NO 103: amino acid sequence of V$_H$ chain of antibody 9A2-VR39.112
SEQ ID NO 104: amino acid sequence of V$_H$ chain of antibody 9A2-VR39.116
SEQ ID NO 105: amino acid sequence of V$_H$ chain of antibody 9A2-VR39.27
SEQ ID NO 106: amino acid sequence of V$_H$ chain of antibody 9A2-VR39.28
SEQ ID NO 107: amino acid sequence of V$_H$ chain of antibody 9A2-VR39.46
SEQ ID NO 108: amino acid sequence of V$_H$ chain of antibody 9A2-VR39.122
SEQ ID NO 109: amino acid sequence of V$_H$ chain of antibody 9A2-VR39.139
SEQ ID NO 110: amino acid sequence of V$_H$ chain of antibody 9A2-VR39.140
SEQ ID NO 111: amino acid sequence of V$_H$ chain of antibody 9A2-VR39.148
SEQ ID NO 112: amino acid sequence of V$_H$ chain of antibody 9A2-VR39.162
SEQ ID NO 113: amino acid sequence of V$_H$ chain of antibody 9A2-VR39.77
SEQ ID NO 114: amino acid sequence of V$_H$ chain of antibody 9A2-VR39.93
SEQ ID NO 115: amino acid sequence of V$_H$ chain of antibody 9A2-VR39.174
SEQ ID NO 116: amino acid sequence of V$_H$ chain of antibody 9A2-VR39.177
SEQ ID NO 117: amino acid sequence of soluble *Homo sapiens* CD131 comprising a C-terminal 6×His tag and comprising the substitution N37A
SEQ ID NO 118: amino acid sequence of soluble *Homo sapiens* CD131 comprising a C-terminal 6×His tag and comprising the substitution D38A
SEQ ID NO 119: amino acid sequence of soluble *Homo sapiens* CD131 comprising a C-terminal 6×His tag and comprising the substitution Y39A
SEQ ID NO 120: amino acid sequence of soluble *Homo sapiens* CD131 comprising a C-terminal 6×His tag and comprising the substitution T40A
SEQ ID NO 121: amino acid sequence of soluble *Homo sapiens* CD131 comprising a C-terminal 6×His tag and comprising the substitution S41A
SEQ ID NO 122: amino acid sequence of soluble *Homo sapiens* CD131 comprising a C-terminal 6×His tag and comprising the substitution H42A
SEQ ID NO 123: amino acid sequence of soluble *Homo sapiens* CD131 comprising a C-terminal 6×His tag and comprising the substitution S102A
SEQ ID NO 124: amino acid sequence of soluble *Homo sapiens* CD131 comprising a C-terminal 6×His tag and comprising the substitution F103A
SEQ ID NO 125: amino acid sequence of soluble *Homo sapiens* CD131 comprising a C-terminal 6×His tag and comprising the substitution V104A
SEQ ID NO 126: amino acid sequence of soluble *Homo sapiens* CD131 comprising a C-terminal 6×His tag and comprising the substitution V105A
SEQ ID NO 127: amino acid sequence of soluble *Homo sapiens* CD131 comprising a C-terminal 6×His tag and comprising the substitution T106A
SEQ ID NO 128: amino acid sequence of soluble *Homo sapiens* CD131 comprising a C-terminal 6×His tag and comprising the substitution D107A
SEQ ID NO 129: amino acid sequence of soluble *Homo sapiens* CD131 comprising a C-terminal 6×His tag and comprising the substitution V108A
SEQ ID NO 130: amino acid sequence of soluble *Homo sapiens* CD131 comprising a C-terminal 6×His tag and comprising the substitution N337A
SEQ ID NO 131: amino acid sequence of soluble *Homo sapiens* CD131 comprising a C-terminal 6×His tag and comprising the substitution I338A
SEQ ID NO 132: amino acid sequence of soluble *Homo sapiens* CD131 comprising a C-terminal 6×His tag and comprising the substitution Q339A
SEQ ID NO 133: amino acid sequence of soluble *Homo sapiens* CD131 comprising a C-terminal 6×His tag and comprising the substitution M340A
SEQ ID NO 134: amino acid sequence of soluble *Homo sapiens* CD131 comprising a C-terminal 6×His tag and comprising the substitution K362A
SEQ ID NO 135: amino acid sequence of soluble *Homo sapiens* CD131 comprising a C-terminal 6×His tag and comprising the substitution M363A
SEQ ID NO 136: amino acid sequence of soluble *Homo sapiens* CD131 comprising a C-terminal 6×His tag and comprising the substitution R364A
SEQ ID NO 137: amino acid sequence of soluble *Homo sapiens* CD131 comprising a C-terminal 6×His tag and comprising the substitution Y365A
SEQ ID NO 138: amino acid sequence of soluble *Homo sapiens* CD131 comprising a C-terminal 6×His tag and comprising the substitution E366A
SEQ ID NO 139: amino acid sequence of soluble *Homo sapiens* CD131 comprising a C-terminal 6×His tag and comprising the substitution H367A
SEQ ID NO 140: amino acid sequence of soluble *Homo sapiens* CD131 comprising a C-terminal 6×His tag and comprising the substitution I368A
SEQ ID NO 141: amino acid sequence of soluble *Homo sapiens* CD131 comprising a C-terminal 6×His tag and comprising the substitution D369A
SEQ ID NO 142: amino acid sequence of soluble *Homo sapiens* CD131 comprising a C-terminal 6×His tag and comprising the substitution R418A
SEQ ID NO 143: amino acid sequence of soluble *Homo sapiens* CD131 comprising a C-terminal 6×His tag and comprising the substitution T419A
SEQ ID NO 144: amino acid sequence of soluble *Homo sapiens* CD131 comprising a C-terminal 6×His tag and comprising the substitution n G420A
SEQ ID NO 145: amino acid sequence of soluble *Homo sapiens* CD131 comprising a C-terminal 6×His tag and comprising the substitution Y421A
SEQ ID NO 146: amino acid sequence of soluble *Homo sapiens* CD131 comprising a C-terminal 6×His tag and comprising the substitution N422A
SEQ ID NO 147: amino acid sequence of soluble *Homo sapiens* CD131 comprising a C-terminal 6×His tag and comprising the substitution G423A
SEQ ID NO 148: amino acid sequence of soluble *Homo sapiens* CD131 comprising a C-terminal 6×His tag and comprising the substitution I424A
SEQ ID NO 149: nucleotide acid sequence encoding trimer oligonucleotide 9A2 L1.1
SEQ ID NO 150: nucleotide acid sequence encoding trimer oligonucleotide 9A2 L3.1

SEQ ID NO 151: nucleotide acid sequence encoding trimer oligonucleotide 9A2 L3.2
SEQ ID NO 152: nucleotide acid sequence encoding trimer oligonucleotide 9A2 H1.1
SEQ ID NO 153: nucleotide acid sequence encoding trimer oligonucleotide 9A2 H2.1
SEQ ID NO 154: nucleotide acid sequence encoding trimer oligonucleotide 9A2 H3.1
SEQ ID NO 155: nucleotide acid sequence encoding trimer oligonucleotide 9A2 H3.2
SEQ ID NO 156: nucleotide acid sequence encoding trimer oligonucleotide 9A2-VR24-H2.1
SEQ ID NO 157: nucleotide acid sequence encoding trimer oligonucleotide 9A2-VR24-H2.2
SEQ ID NO 158: nucleotide acid sequence encoding trimer oligonucleotide 9A2-VR24-H2.3
SEQ ID NO 159: nucleotide acid sequence encoding trimer oligonucleotide 9A2-VR39-H1.1
SEQ ID NO 160: nucleotide acid sequence encoding trimer oligonucleotide 9A2-VR39-H1.2
SEQ ID NO 161: nucleotide acid sequence encoding trimer oligonucleotide 9A2-VR39-H2.2
SEQ ID NO 162: nucleotide acid sequence encoding trimer oligonucleotide 9A2-VR39-H2.3
SEQ ID NO 163: amino acid sequence of $V_H$ chain of stop template of 9A2 H1.1
SEQ ID NO 164: amino acid sequence of $V_H$ chain of stop template of 9A2 H2.1
SEQ ID NO 165: amino acid sequence of $V_H$ chain of stop template of 9A2 H3.1
SEQ ID NO 166: amino acid sequence of $V_H$ chain of stop template of 9A2 H3.2
SEQ ID NO 167: amino acid sequence of $V_L$ chain of stop template of 9A2 L1.1
SEQ ID NO 168: amino acid sequence of $V_L$ chain of stop template of 9A2 L3.1
SEQ ID NO 169: amino acid sequence of $V_L$ chain of stop template of 9A2 L3.2
SEQ ID NO 170: amino acid sequence of $V_H$ chain of stop template of 9A2 VR24-H2.1
SEQ ID NO 171: amino acid sequence of $V_H$ chain of stop template of 9A2 VR24-H2.2
SEQ ID NO 172: amino acid sequence of $V_H$ chain of stop template of 9A2 VR24-H2.3
SEQ ID NO 173: amino acid sequence of $V_H$ chain of stop template of 9A2 VR39-H1.1
SEQ ID NO 174: amino acid sequence of $V_H$ chain of stop template of 9A2 VR39-H1.2
SEQ ID NO 175: amino acid sequence of $V_H$ chain of stop template of 9A2 VR39-H2.2
SEQ ID NO 176: amino acid sequence of $V_H$ chain of stop template of 9A2 VR39-H2.3
SEQ ID NO 177: amino acid sequence of consensus of $V_L$ chain of 9A2 and derivatives
SEQ ID NO 178: amino acid sequence of consensus of CDR1 of $V_L$ chain of 9A2 and derivatives
SEQ ID NO 179: amino acid sequence of consensus of CDR3 of $V_L$ chain of 9A2 and derivatives
SEQ ID NO 180: amino acid sequence of consensus of $V_H$ chain of 9A2 and derivatives
SEQ ID NO 181: amino acid sequence of consensus of CDR1 of $V_H$ chain of 9A2 and derivatives
SEQ ID NO 182: amino acid sequence of consensus of CDR2 of $V_H$ chain of 9A2 and derivatives
SEQ ID NO 183: amino acid sequence of consensus of CDR3 of $V_H$ chain of 9A2 and derivatives
SEQ ID NO 184: amino acid sequence of consensus of $V_H$ chain of 9A2-VR24 and derivatives
SEQ ID NO 185: amino acid sequence of consensus of CDR1 of $V_H$ chain of 9A2-VR24 and derivatives
SEQ ID NO 186: amino acid sequence of consensus of CDR2 of $V_H$ chain of 9A2-VR24 and derivatives
SEQ ID NO 187: amino acid sequence of consensus of CDR3 of $V_H$ chain of 9A2-VR24 and derivatives
SEQ ID NO 188: amino acid sequence of consensus of $V_H$ chain of 9A2-VR39 and derivatives
SEQ ID NO 189: amino acid sequence of consensus of CDR1 of $V_H$ chain of 9A2-VR39 and derivatives
SEQ ID NO 190: amino acid sequence of consensus of CDR2 of $V_H$ chain of 9A2-VR39 and derivatives
SEQ ID NO 191: amino acid sequence of consensus of CDR3 of $V_H$ chain of 9A2-VR39 and derivatives
SEQ ID NO: 192: amino acid sequence of soluble *Homo sapiens* CD131 comprising a C-terminal 6×His tag
SEQ ID NO: 193: amino acid sequence of $V_H$ chain of 9A2-VR24 HCDR2 mutants
SEQ ID NO: 194: amino acid sequence of antibody 9A2 heavy chain
SEQ ID NO: 195: amino acid sequence of antibody 9A2 light chain
SEQ ID NO: 1%: amino acid sequence of stabilized IgG4 heavy chain constant region
SEQ ID NO: 197: amino acid sequence of kappa light chain constant region

BRIEF DESCRIPTION OF THE DRAWINGS

FIG. 1 is a diagrammatic representation showing sequences of variable regions of the $V_L$ of antibody 9A2 and derivatives. Boxed regions contain CDRs (as indicated) as defined by the Kabat numbering system.

Figure 2A:
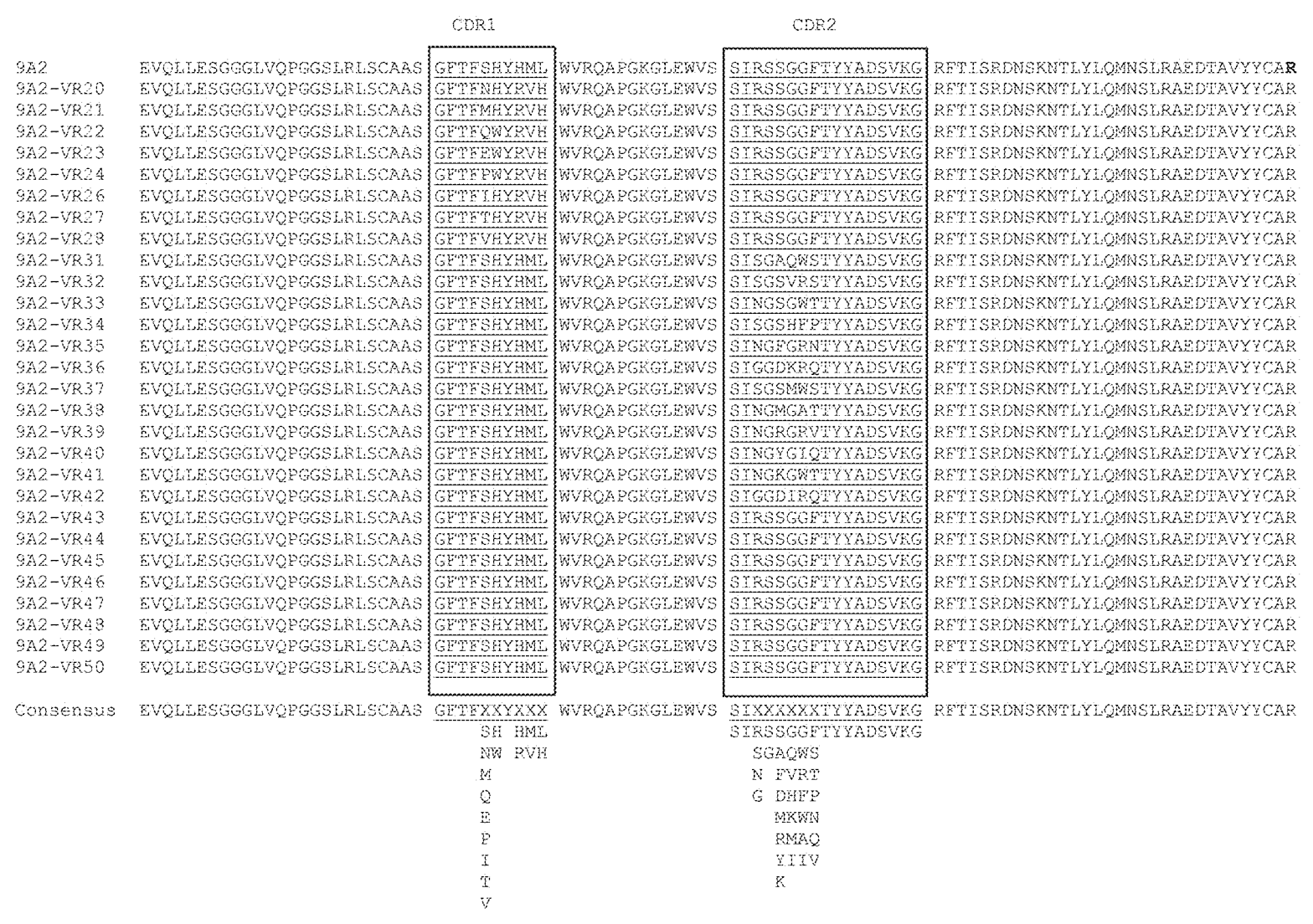

FIGS. 2A and 2B are diagrammatic representations showing sequences of variable regions of the $V_H$ of antibody 9A2 and derivatives. Boxed regions contain CDRs (as indicated) as defined by the Kabat numbering system.

FIGS. 3A and 3B are diagrammatic representations showing sequences of variable regions of the $V_H$ of antibody 9A2-VR24 and derivatives. Boxed regions contain CDRs (as indicated) as defined by the Kabat numbering system.

Figure 4A:
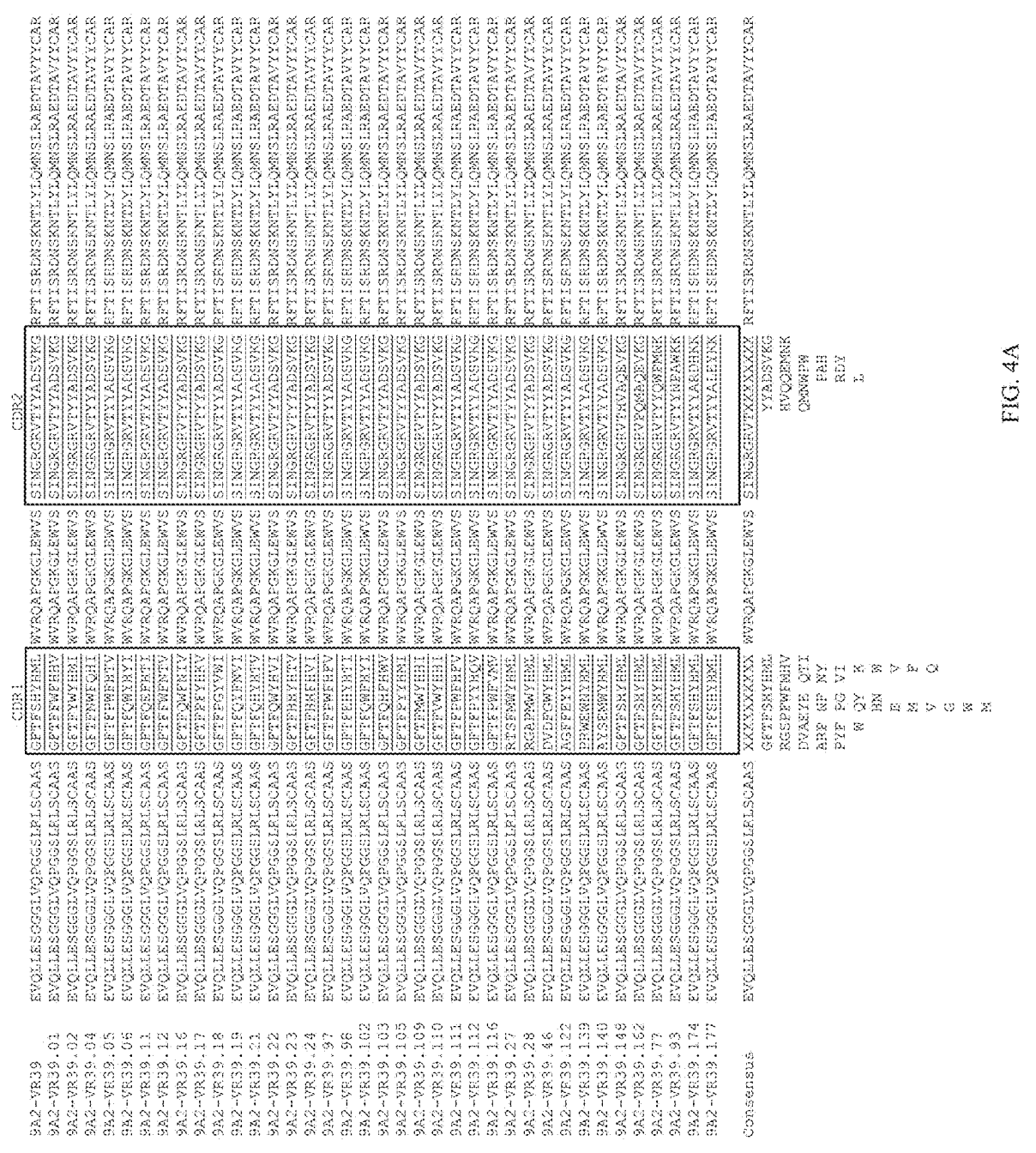

FIGS. 4A and 4B are diagrammatic representations showing sequences of variable regions of the $V_H$ of antibody 9A2-VR39 and derivatives. Boxed regions contain CDRs (as indicated) as defined by the Kabat numbering system.

FIGS. 5A and 5B show a diagrammatic representation showing amino acid sequences of variable regions of antibody 9A2 used for affinity maturation. FIG. 5 A shows sequence of the light chain and FIG. 5B shows sequence of the heavy chain variable regions of 9A2 are shown with CDRs underlined and regions selected for randomization boxed and numbered according to Kabat.

(FIG. 6A) IL-3. (FIG. 6B) GM-CSF. (FIG. 6C) IL-5. Subsequently, proliferation was assessed by $^3$[H]-thymidine incorporation and $IC_{50}$ values are plotted in FIG. 6D for BION-1 (○) and 9A2 (●). Histograms show mean and standard error of technical replicates. Experiments were repeated at least 3 times. Representative experiments are shown. FIG. 6E shows the potency of affinity matured libraries of 9A2 (as described in FIGS. 5A and 5B) on GM-CSF signaling. Individual IC$_{50}$ values plotted. FIG. 6F shows the potency of affinity matured libraries of the 9A2-VR24 and 9A2-VR39 derivatives of 9A2 on GM-CSF signaling. Individual IC$_{50}$ values plotted. Variants 9A2-VR24 (▼), 9A2-VR39 (●) and 9A2-VR-24.29 (▲) are highlighted.

FIGS. 12A-12D are graphical representations showing 9A2-VR24.29 binds with high affinity to cells expressing human CD131. Saturation binding studies were performed on (FIGS. 12A and 12B) neutrophils or (FIGS. 12C and 12D) eosinophils incubated with radioiodinated 9A2-VR24.29 IgG or radio-iodinated 9A2-VR24.29 Fab. (FIGS. 12A and 12C) Binding curves are shown for total (○, solid line), specific (●, solid line) and non-specifically (□, dashed line) bound 9A2-VR24.29 IgG. Scatchard transformation of the 9A2-VR24.29 IgG (♦, solid line) and 9A2-VR24.29 Fab (◇, dashed line) binding data is shown with lines indicating the best fit for the binding of each radio-iodinated antibody (FIGS. 12B and 12D). Each point is the mean of duplicate determinations of cell-bound radio-iodinated antibody after subtraction of non-specific binding. Data from a single neutrophil binding experiment and a representative eosinophil binding experiment, n=2 is shown.

FIG. 13 is a tabular representation showing the affinity of 9A2-VR24.29 IgG or 9A2-VR24.29 Fab for neutrophils, eosinophils or TF1 cells.

FIGS. 14A-14J are graphical representations showing 9A2-VR24.29 inhibits survival of cells isolated from human inflammatory airway disease tissue. FIG. 14A shows analysis of sputum samples from subjects with mild atopic asthma at baseline (solid symbols) and 24 hours after inhaled allergen challenge (open symbols) which were collected and cytospins were made for differential cell counts and the percentage of cell types present was determined. FIG. 14B shows analysis of the sputum samples incubated with 9A2-VR24.29 (100 µg/ml) or an isotype control (100 µg/ml) at 37° C. for 24 h and cells analyzed for the viability by flow cytometry. Data are expressed as percent cell viability compared to the isotype control for each donor. FIG. 14C shows analysis of the sputum samples incubated with 9A2-VR24.29 (100 µg/ml) or an isotype control (100 µg/ml) at 37° C. for 24 h in the presence of 1 ng/ml each IL-3, GM-CSF and IL-5 and cells analyzed for the viability by flow cytometry. Non-adherent mononuclear cells (NAMC) from (FIGS. 14D-14E) bone marrow and (FIGS. 14F-14G) blood samples collected at baseline and 24 h after inhaled allergen challenge from allergic asthmatic subjects were incubated with 9A2-VR24.29 (100 µg/ml, filled bars) or an isotype control mAb (100 µg/ml, open bars) at 37° C. for 24 h in the presence of diluent (neg) or 1 ng/ml each IL-3, GM-CSF and IL-5, or cytokines combined (All) and (FIGS. 14D, 14F) GM CFU and (FIGS. 14E, 14G) Eo/Baso CFU were enumerated. FIG. 14H shows that eosinophils were the predominant cell type in un-stimulated nasal polyp cells cultured ex vivo. FIG. 14I shows that 9A2-VR24.29 inhibited the survival of unstimulated eosinophils isolated from NP tissue after 72 hours in culture. FIG. 14J shows the effect of 9A2-VR24.29 on the survival of cultured cell infiltrates compared to prednisolone and individual anti-β chain antibodies. Data are expressed as median±range and 95% confidence intervals. ns, not significant p>0.05; *p<0.05; p<0.01;*p<0.005.

FIGS. 16A-16O are graphical representations showing 9A2-VR24.29 inhibits the activation of primary myeloid cells following stimulation with CD131 family cytokines. (FIG. 16A) Primary human neutrophils were pre-treated with 9A2-VR24.29, stimulated with GM-CSF for 18 h and their activation was determined by change in forward scatter by flow cytometry. (FIG. 16B) Primary human basophils were pre-treated with 9A2-VR24.29, stimulated with IL-3 for 18 h and IL-8 release was determined by ELISA. (FIG. 16C) pDCs were pre-treated with 9A2-VR24.29, stimulated with IL-3 for 24 h and cell survival was determined by ViaLight®Plus Cell Proliferation and Cytotoxicity BioAssay. (FIGS. 16D-16E) Primary human eosinophils were isolated from normal healthy donors then pre-treated with (FIG. 16D) 9A2-VR24.29 prior to stimulation with IL-5 and change in side scatter determined by flow cytometry or (FIG. 16E) 9A2-VR24.29 (▲), anti-IL-5Rα (□), anti-IL-3Rα (Δ), anti-GM-CSFRα (◇), or a combination of anti-IL-5Rα, anti-IL-3Rα and anti-GM-CSFRα (●) before treatment with a cocktail of IL-3, IL-5, GM-CSF for 72 h and cell survival determined. Data from representative experiments are shown, n=5. Eosinophils were treated with (FIG. 16F) IL-3, (FIG. 16G) GM-CSF and (FIG. 16H) IL-5 at EC80 concentrations, and cell survival determined. The dotted line indicates the number of cells in the absence of stimulation. Eosinophils were pre-treated with test antibodies (FIG. 16I) anti-IL-3Rα (□), (FIG. 16J) anti-GMRα (▲) and (FIG. 16K) anti-IL-5Rα (□) before treatment with (FIG. 16F) IL-3, (FIG. 16G) GM-CSF (FIG. 16H) IL-5, for 72 h and cell survival determined. (FIGS. 16L-16N) HCMCs were pre-treated with 9A2-VR24.29 for 1 h prior to the addition of IL-3 (1 ng/ml), IL-5 (10 ng/ml) or GM-CSF (1 ng/ml) for a further 48 h incubation. Human myeloma IgE (0.5 µg/ml) was added at 20 h before anti-IgE stimulation. Medium was refreshed after incubation and HCMCs were then stimulated with anti-IgE (1 µg/ml) in the presence of IL-3 (1 ng/ml) for (FIG. 16L) TNF release (18 h) and (FIG. 16M) IL-13 release (8 h), and (FIG. 16N) IL-3 (1 ng/ml), IL-5 (10 ng/ml) or GM-CSF (1 ng/ml) for IL-8 release (8 h). anti-IgE (●), anti-IgE+IL-3 (⑤), anti-IgE+GM-CSF ( ), anti-IgE+IL-5 (Δ), anti-IgE+IL-3+9A2-VR24.29 (◐), anti-IgE+GM-CSF+9A2-VR24.29 (□), anti-IgE+IL-5+9A2-VR24.29 (○). Cytokine levels in the supernatants were measured by ELISA. Significant differences between cytokine release in the absence or presence of 9A2-VR24.29 were analyzed by one-way ANOVA with Dunnett's posttest, $*p<0.05$, $p<0.01$, $*p<0.001$. All values expressed as mean+S.E.M for 4 independent experiments. (FIG. 16O) CD34$^+$ BM cells were pre-treated with 9A2-VR24.29 (▲), anti-IL-5R⟨(□), anti-IL-3R⟨(Δ), anti-GM-CSFR⟨(◇), or anti-IL-5R⟨, anti-IL-3R ⟨□□□ anti-GM-CSFR⟨ in combination (●) and grown in semi-solid media containing SCF (50 ng/ml), IL-3 (10 ng/ml), IL-5 (10 ng/ml) and GM-CSF (10 ng/ml). Cells were incubated at 37° C. for 14-16 days and colonies counted. All values expressed as mean+S.E.M. All experiments were repeated at least 4 times with representative experiments shown.

FIGS. 17A-17C are graphical representations showing the effect of 9A2-VR24.29 on nasal polyps in a human xenograft model. (FIG. 17A) shows the external size of polyps isolated from the xenograft model following treatment with 9A2-VR24.29 (□) or an iotype-control antibody (○). Mice were treated with the antibodies at the times indicated by the arrows. Data presented at mean+S.E.M. The number of eosinophils (FIG. 17B) and neutrophils (FIG. 17C) infiltrating the polyps were also assessed. $p>0.05$; $*p<0.05$; $p<0.01$; $*p<0.005$.

FIGS. 18A-18G are a series of graphical representations showing 9A2-VR24.29 inhibits survival of human nasal polyp xenograft inflammatory cells in vivo. Nasal polyp xenografts were treated weekly with a total of 4 subcutaneous intra-polyp injections of isotype control mAb or 9A2-VR24.29 (5 mg/kg/injection) and the polyps excised 5 weeks post-transplantation. (FIG. 18A) Toluidine blue stained mast cells/mm$^2$ (n=11 mice per treatment; 9 different patient samples); (FIGS. 18B-18G) number of recovered human cells from nasal polyp xenografts determined by flow cytometric analysis of (FIG. 18B) eosinophils (CD16$^-$ CD15$^+$ CD49d$^+$ Siglec8$^+$); (FIG. 18 C) Neutrophils (CD14$^-$ CD49d$^-$ CD15$^+$ CD16$^+$); (FIG. 18D) Macrophages (CD16$^-$ CD49d$^-$ CD14$^+$ CD15$^+$); (FIG. 18E) B cells (CD45$^+$ CD19$^+$ CD20$^+$); (FIG. 18F) Plasma B cells (CD45$^+$ CD19$^+$ CD138$^+$); and (FIG. 18G) T cells (CD3$^+$ CD4$^+$, CD3$^+$CD8$^+$, CD3$^+$CD4$^+$CD8$^+$). Data: median±range; (FIGS. 18B-18D) n=14 mice/treatment, nasal polyp samples from 6 different patients; (FIGS. 18E-18G) n=6 or 7 mice for isotype control mAb and 9A2-VR24.29, respectively, 3 different nasal polyp patients; (FIGS. 18A, 18D-18G) $*p<0.05$ Mann-Whitney U or (FIG. 18B) $*p<0.05$ Wilcoxon Signed Rank test for indicated comparisons; ns=not significant.

(FIG. 19A) Cells were then equilibrated with 340 pM radio-iodinated IL-3, (FIG. 19B) 40 pM radio-iodinated GM-CSF (FIG. 19C) 200 pM radio-iodinated IL-5. Each point is the mean of duplicate determinations of cell-bound radioiodinated cytokine and error bars represent the standard deviation. Data from representative experiments is shown, n=2. (FIG. 19D) TF-1 cells were pre-incubated with IL-3 (▲), GM-CSF (■) or IL-5 (●) then cells were equilibrated with 85 pM radioiodinated 9A2-VR24.29. Each point is the mean of duplicate determinations of cell-bound radio-iodinated 9A2-VR24.29 and error bars represent the standard deviation. Data from a representative experiment is shown, n=3.

(FIG. 20A) Superimposition of the CD131/9A2-VR24.29 Fab complex on the GM-CSF receptor ternary structure, showing the overlap of the interaction interface between 9A2-VR24.29 Fab (heavy chain shown in orange and light chain in yellow) and GM-CSF (grey). The CD131 dimer from the GM-CSF ternary structure is colored in green and purple. (FIG. 20B) A surface representation of the key residues on the CD131 dimer that interact with 9A2-VR24.29 is shown. Individual residues are colored to indicate the effect of specific alanine substitution mutations on 9A2-VR24.29 binding affinity: mutations that lead to no binding or negligible binding are colored in red, mutations that reduce binding to the $10^{-5}$ to $10^{-7}$ M range are shown in yellow and mutations that improve binding are shown in blue. The detailed interactions involving CDRs H1-H3 and CDR L1 and L3 are shown in the adjoining zoom-in panels. Polar interactions are shown as black broken lines and key van der Waals interactions are shown in yellow. All figures were made using PyMOL. (FIG. 20C) Key CD131 residues (Y365 and H367) involved in forming a $\pi$-$\pi$ interaction network with D101 and Y100 from CDR H3 are shown. Hydrogen bonds are shown as black broken lines and van der Waals contacts shown as yellow broken lines. (FIG. 20D) The involvement of F103 and 1338 in stabilizing the side chain of Y39 on CD131, which hydrogen bonds with D101 from CDR H3, is shown. Hydrogen bonds are shown as black broken lines and van der Waals contacts shown as yellow broken lines.

(FIG. 21A) shows the external size of polyps isolated from the xenograft model following treatment with 9A2-VR24.29, Prednisolone, saline vehicle or an iotype-control antibody. Mice were treated with the antibodies at the times indicated by the arrows. Data presented at mean+S.E.M. #$p<0.05$; $p<0.01$. (FIG. 21B) shows the weight of polyps isolated from the xenograft model following treatment with 9A2-VR24.29, Prednisolone, saline vehicle or an iotype-control antibody. (FIGS. 21C-21J) number of recovered human cells from nasal polyp xenografts determined by flow cytometric analysis of (FIG. 21C) eosinophils (CD16$^-$ CD15$^+$ CD49d$^+$ Siglec8$^+$); (FIG. 21D) Neutrophils (CD14$^-$ CD49d$^-$ CD15$^+$ CD16$^+$); (E) Macrophages (CD16$^-$ CD49d$^-$ CD14$^+$ CD15$^+$); (FIGS. 21F-21H) (T cells (CD3$^+$CD4$^+$, CD3$^+$CD8$^+$, CD3$^+$CD4$^+$CD8$^+$, respectively); (FIG. 21I) B cells (CD45$^+$ CD19$^+$ CD20$^+$; CD45$^+$ CD19$^+$ CD138$^+$). (FIG. 21J) Plasma cells. Data: median±range; (FIG. 21A) #$p<0.05$, ##$p<0.01$, $p<0.01$, $***p<0.005$ 2 way ANOVA with Bonferroni post; or (FIGS. 21B-21J) Kruskal-Wallis test $*p<0.05$.

(FIG. 22A) shows the number of Toluidine blue stained mast cells/mm$^2$; and (FIG. 22B) the mucus area (mm²) from polyps isolated from the xenograph model following treatment with 9A2-VR24.29, Prednisolone, saline vehicle or an isotype-control antibody. Data: median±range; Kruskal-Wallis test *p<0.05.

(FIG. 23A) shows the external size of polyps and (FIG. 23B) weight of polyps isolated from the xenograft model following treatment with intra-poly or systemic 9A2-VR24.29 or an iotype-control antibody.

DETAILED DESCRIPTION

General

Figures 6A, 6B, 6C:
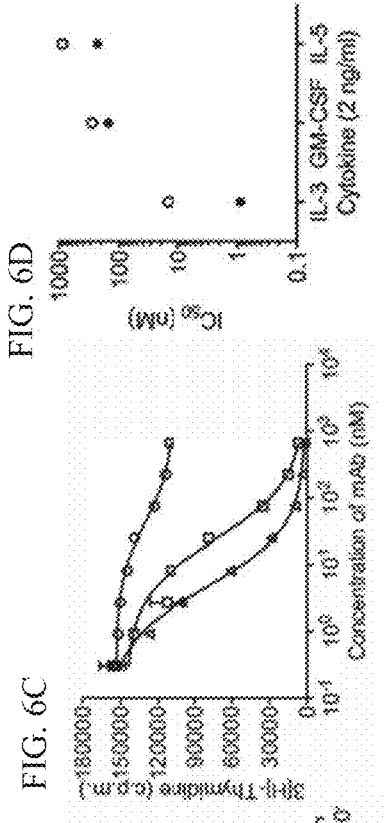
FIGS. 6A-6F are graphical representations showing the effect of antibody 9A2 and select derivatives on IL-3, GM-CSF and IL-5 signaling. TF-1 cells were treated with test antibodies (BION-1 (∇), 9A2 (○), 9A2-VR24 (□) and 9A2-VR24.29 (Δ)) for 30 minutes prior to the addition of cytokines.
Figure 6D:
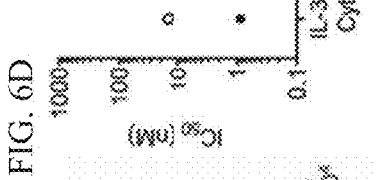

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only.

Functionally-equivalent products, compositions and methods are clearly within the scope of the present disclosure.

Any example of the present disclosure herein shall be taken to apply mutatis mutandis to any other example of the disclosure unless specifically stated otherwise.

Any example of the present disclosure related to a CD131-binding protein will be taken to apply mutatis mutandis to a CD131-binding antibody.

Any example of the present disclosure related to a CD131-binding protein will be taken to apply mutatis mutandis to a CD131-binding compound.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) *Antibodies: A Laboratory Manual*, Cold Spring Harbour Laboratory, (1988), and J. E. Coligan et al. (editors) *Current Protocols in Immunology*, John Wiley & Sons (including all updates until present).

The description and definitions of variable regions and parts thereof, immunoglobulins, antibodies and fragments thereof herein may be further clarified by the discussion in Kabat Sequences of *Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Reference herein to a range of, e.g., residues, will be understood to be inclusive. For example, reference to "a region comprising amino acids 56 to 65" will be understood in an inclusive manner, i.e., the region comprises a sequence of amino acids as numbered 56, 57, 58, 59, 60, 61, 62, 63, 64 and 65 in a specified sequence.

Selected Definitions

For the purposes of nomenclature only and not limitation an exemplary sequence of a human CD131 (pre-CD131) is set out in NCBI Reference Sequence: NP_000386.1 and NCBI Genbank Accession Number P32927 (and set out in SEQ ID NO: 1). A sequence of a mature human CD131 lacks amino acids 1 to 16 of SEQ ID NO: 1. Positions of amino acids are often referred to herein by reference to pre-CD131. The positions in mature CD131 is readily determined by accounting for the signal sequence (amino acids 1-16 in the case of SEQ ID NO: 1). The sequence of CD131 from other species can be determined using sequences provided herein and/or in publicly available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)). Reference to human CD131 may be abbreviated to hCD131.

Reference to soluble CD131 refers to polypeptides comprising the extracellular region of CD131, e.g., amino acids 17 to 438 of SEQ ID NO: 1.

Reference herein to CD131 includes native forms of CD131 and mutant forms thereof retaining an ability to bind to CD131 (e.g., hCD131) and induce signaling.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding domain" shall be taken to mean a region of an antibody that is capable of specifically binding to an antigen, i.e., a $V_H$ or a $V_L$ or an Fv comprising both a $V_H$ and a $V_L$. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., CD131) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kD) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies.

Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H1$ which is 330 to 440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain ($V_H$ or $V_L$) typically has three CDRs identified as CDR1, CDR2 and CDR3. In one example, the amino acid positions assigned to CDRs and FRs are defined according to Kabat *Sequences of Proteins of Immunological Interest*, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). According to the numbering system of Kabat, $V_H$ FRs and CDRs are positioned as follows: residues 1 to 30 (FR1), 31 to 35 (CDR1), 36 to 49 (FR2), 50 to 65 (CDR2), 66 to 94 (FR3), 95 to 102 (CDR3) and 103 to 113 (FR4). According to the numbering system of Kabat, $V_L$ FRs and CDRs are positioned as follows: residues 1 to 23 (FR1), 24 to 34 (CDR1), 35 to 49 (FR2), 50 to 56 (CDR2), 57 to 88 (FR3), 89 to 97 (CDR3) and 98 to 107 (FR4). The present disclosure is not limited to FRs and CDRs as defined by the Kabat numbering system, but includes all numbering systems, including the canonical numbering system or of Chothia and Lesk *J. Mol. Biol.* 196: 901-917, 1987; Chothia et al., *Nature* 342: 877-883, 1989; and/or Al-Lazikani et al., *J. Mol. Biol.* 273: 927-948, 1997; the numbering system of Honnegher and Plakthun *J. Mol. Biol.* 309: 657-670, 2001; or the IMGT system discussed in Giudicelli et al., *Nucleic Acids Res.* 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In this regard, Padlan et al., *FASEB J.*, 9: 133-139, 1995 established that the five C-terminal amino acids of heavy chain CDR2 are not generally involved in antigen binding.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain, i.e., capable of specifically binding to an antigen. The $V_H$ and the $V_L$ which form the antigen binding domain can be in a single polypeptide chain or in different polypeptide chains. Furthermore, an Fv of the disclosure (as well as any protein of the disclosure) may have multiple antigen binding domains which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a CD131-binding protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a CD131-binding protein of the disclosure reacts or associates more frequently, more rapidly, with greater duration and/or with greater affinity with a particular antigen or cell expressing same than it does with alternative antigens or cells. For example, a CD131-binding protein binds to CD131 (e.g., hCD131 or a polypeptide comprising a region thereof, e.g., a polypeptide comprising a sequence set forth in SEQ ID NO: 191) with materially greater affinity (e.g., 1.5 fold or 2 fold or 5 fold or 10 fold or 20 fold or 40 fold or 60 fold or 80 fold to 100 fold or 150 fold or 200 fold) than it does to other interleukin receptors or to antigens commonly recognized by polyreactive natural antibodies (i.e., by naturally occurring antibodies known to bind a variety of antigens naturally found in humans). In an example of the present disclosure, a CD131-binding protein that "specifically binds" to one form of hCD131 or a polypeptide comprising a region thereof (e.g., the extracellular region of hCD131) or a polypeptide comprising a sequence set forth in SEQ ID NO: 191 with an affinity at least 1.5 fold or 2 fold or greater (e.g., 5 fold or 10 fold or 20 fold r 50 fold or 100 fold or 200 fold) than it does to a mutant form of SEQ ID NO: 191 comprising a sequence set forth in SEQ ID NO: 119, 124, 131 or 137. Reference to "binding" provides explicit support for the term "specific binding" and vice versa.

As used herein, the term "does not detectably bind" shall be understood to mean that a CD131-binding protein, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the antigen (e.g., a polypeptide) is immobilized and contacted with a CD131-binding protein.

As used herein, the term "does not significantly bind" shall be understood to mean that the level of binding of a CD131-binding protein of the disclosure to a polypeptide is not statistically significantly higher than background, e.g., the level of binding signal detected in the absence of the CD131-binding protein and/or in the presence of a negative control protein (e.g., an isotype control antibody) and/or the level of binding detected in the presence of a negative control polypeptide. The level of binding is detected using biosensor analysis (e.g. Biacore) in which the antigen (e.g., a polypeptide) is immobilized and contacted with a CD131-binding protein.

As used herein, phrases referring to "reduced binding" or "binding being at a lower level" in relation to an antigen will be understood to mean that a CD131-binding protein, e.g., antibody, binds to an antigen (e.g., a mutant of SEQ ID NO: 191 as described herein, such as a mutant comprising the sequence set forth in SEQ ID NO: 119, 124, 131 or 137) with an affinity at least about 1.5 fold or 2 fold or 5 fold or 10 fold or 20 fold or 50 fold or 100 fold or 200 fold less than a control epitope or antigen (e.g. SEQ ID NO: 191).

A CD131-binding protein or antibody may be considered to "preferentially bind" to a polypeptide if it binds that polypeptide with a dissociation constant ($K_D$) that is less than the protein's or antibody's $K_D$ for another polypeptide. In one example, a CD131-binding protein or antibody is considered to preferentially bind to a polypeptide if it binds the polypeptide with an affinity (i.e., $K_D$) that is at least about 1.5 fold or 2 fold or 5 fold or 10 fold or 20 fold or 50 fold or 100 fold or 200 fold more than the protein's or antibody's $K_D$ for another polypeptide.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

An "$IC_{50}$ of at least about" will be understood to mean that the $IC_{50}$ is equal to the recited value or lower (i.e., the value recited as the $IC_{50}$ is lower), i.e., an $IC_{50}$ of 2 µg/ml is greater than an $IC_{50}$ of 1 µg/ml. Stated another way, this term could be "an $IC_{50}$ of X or less", wherein X is a value recited herein.

As used herein, the term "epitope" (syn. "antigenic determinant") shall be understood to mean a region of CD131 to which a CD131-binding protein comprising an antigen binding domain of an antibody binds. This term is not necessarily limited to the specific residues or structure to which the CD131-binding protein makes contact.

For example, this term includes a region spanning amino acids contacted by the CD131-binding protein and 5-10 (or more) or 2-5 or 1-3 amino acids outside of this region. In some examples, the epitope comprises a series of discontinuous amino acids that are positioned close to one another when a CD131 polypeptide is folded and, for example, associated with another C131 polypeptide, i.e., a "conformational epitope".

The term "competitively inhibits" shall be understood to mean that a CD131-binding protein of the disclosure (or an antigen binding domain thereof) reduces or prevents binding of a recited antibody or C131-binding protein to CD131, e.g., to CD131. This may be due to the CD131-binding protein (or antigen binding domain) and antibody binding to the same or an overlapping epitope. It will be apparent from the foregoing that the CD131-binding protein need not completely inhibit binding of the antibody, rather it need only reduce binding by a statistically significant amount, for example, by at least about 10% or 20% or 30% or 40% or 50% or 60% or 70% or 80% or 90% or 95%. For example, the CD131-binding protein reduces binding of the antibody by at least about 30%, for example by at least about 50%, such as, by at least about 70%, for example at least about 75%, even more preferably, by at least about 80% or 85% e.g., by at least about 90%. Methods for determining competitive inhibition of binding are known in the art and/or described herein. For example, the antibody is exposed to CD131 either in the presence or absence of the CD131-binding protein. If less antibody binds in the presence of the CD131-binding protein than in the absence of the CD131-binding protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit a CD131-binding protein (or antigen binding domain thereof) that binds to one epitope to competitively inhibit the binding of a CD131-binding protein (or antigen binding domain) that binds to the other epitope. For example, the "overlapping" epitopes share at least 1 or 2 or 3 or 4 or 5 or 6 or 7 or 8 or 9 or 20 amino acids.

As used herein, the term "neutralize" shall be taken to mean that a protein is capable of blocking, reducing or preventing CD131-mediated signaling in a cell by IL-3, IL-5 and/or GM-CSF. Methods for determining neutralization are known in the art and/or described herein.

As used herein, the term "condition" refers to a disruption of or interference with normal function, and is not to be limited to any specific condition, and will include diseases or disorders.

As used herein, a "CD131-associated condition" refers to any condition that is caused by or associated with an excess of CD131 or cells expressing CD131. The skilled artisan will be readily able to determine such conditions. Exemplary conditions are described herein.

As used herein, the terms "preventing", "prevent" or "prevention" include administering a CD131-binding protein of the disclosure to thereby stop or hinder the development of at least one symptom of a condition. This term also encompasses treatment of a subject in remission to prevent or hinder relapse.

As used herein, the terms "treating", "treat" or "treatment" include administering a CD131-binding protein described herein to thereby reduce or eliminate at least one symptom of a specified disease or condition.

As used herein, the term "subject" shall be taken to mean any animal including humans, for example a mammal. Exemplary subjects include but are not limited to humans and non-human primates. For example, the subject is a human.

Antibodies

In one example, a CD131-binding protein as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods CD131 (e.g., hCD131) or a region thereof (e.g., an extracellular region, e.g., comprising a sequence set forth in SEQ ID NO: 191) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are one exemplary form of antibody contemplated by the present disclosure. The term "monoclonal antibody" or "mAb" refers to a homogeneous antibody population capable of binding to the same antigen(s), for example, to the same epitope within the antigen. This term is not intended to be limited with regard to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies and, for example, do not express murine antibodies, can also be used to generate an antibody of the present disclosure (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison WI 53713, USA) is used to produce cell lines secreting MAbs (e.g., as described in Largaespada et al. *J. Immunol. Methods.* 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

As described herein, some CD131-binding proteins of the present disclosure that bind CD131 cross-react with some mutant forms of CD131 or polypeptides comprising regions of CD131 that have been mutated and/or not others. These characteristics can be used in the generation of an antibody or a CD131-binding protein.

For example, a phage display library is screened with a polypeptide comprising SEQ ID NO: 1 or 191 to identify proteins that bind thereto. Mutant forms of the polypeptide (e.g., comprising a sequence set forth in SEQ ID NO: 119, 124, 131 or 137) to which the CD131-binding protein is not to detectably bind or binds to at a reduced level are then used to remove cross-reactive proteins and/or mutant forms of the polypeptide (e.g., comprising a sequence set forth in SEQ ID NO: 135, 136, 138 or 142 to which the C131-binding protein is to bind are used to isolate proteins that are correctly cross-reactive. A screening process for immunization of a non-human mammal can also be devised based on the foregoing.

In a further example, CD131 or an extracellular region thereof (optionally a mutant form to which antibody 9A2 binds) or a cell expressing CD131 is contacted with 9A2. A phage display library is then brought into contact with the CD131 or region or cell and phage expressing proteins that can compete with the antibody for binding selected.

The antibody of the present disclosure may be a synthetic antibody. For example, the antibody is a chimeric antibody, a humanized antibody, a human antibody synhumanized antibody, primatized antibody or a de-immunized antibody.

Deimmunized, Chimeric, CDR Grafted, Humanized, Synhumanized, Primatized, Human and Composite CD131-Binding Proteins The CD131-binding proteins of the present disclosure may be CDR grafted proteins which include CDRs from an antibody from a non-human species (e.g., mouse or rat or non-human primate) grafted onto or inserted into FRs from a human antibody or which include CDRs from an antibody from one type of antibody (e.g., one type of human antibody) grafted onto or inserted into FRs from another type of antibody (e.g., another type of human antibody). This term also encompasses a composite CD131-binding protein comprising, for example, one or more CDR grafted variable regions and one or more, e.g., human variable regions, chimeric variable regions, synhumanized variable regions or primatized variable regions.

The CD131-binding proteins of the present disclosure may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is falls within the class of "CDR-grafted antibody"). Humanized CD131-binding proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or U.S. Pat. No. 5,585,089. The term "humanized protein" also encompasses a super-humanized protein, e.g., as described in U.S. Pat. No. 7,732,578. This term also encompasses a composite protein comprising, for example, one or more humanized variable regions and one or more, e.g., human variable regions, chimeric variable regions, synhumanized variable regions or primatized variable regions.

The CD131-binding proteins of the present disclosure may be human CD131-binding proteins. The term "human protein" as used herein refers to proteins having variable and, optionally, constant antibody regions found in humans, e.g. in the human germline or somatic cells or from libraries produced using such regions. The "human" proteins can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human proteins" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516.

Exemplary human CD131-binding proteins are antibodies comprising the following pairs of variable regions:
(i) a $V_H$ comprising a sequence set forth in SEQ ID NO: 20 and a $V_L$ Comprising a sequence set forth in SEQ ID NO: 5;
(ii) a $V_H$ comprising a sequence set forth in SEQ ID NO: 20 and a $V_L$ comprising a sequence set forth in SEQ ID NO: 6;
(iii) a $V_H$ comprising a sequence set forth in SEQ ID NO: 20 and a $V_L$ comprising a sequence set forth in SEQ ID NO: 7;
(iv) a $V_H$ comprising a sequence set forth in SEQ ID NO: 20 and a $V_L$ Comprising a sequence set forth in SEQ ID NO: 8;
(v) a $V_H$ comprising a sequence set forth in SEQ ID NO: 20 and a $V_L$ Comprising a sequence set forth in SEQ ID NO: 9;
(vi) a $V_H$ comprising a sequence set forth in SEQ ID NO: 20 and a $V_L$ Comprising a sequence set forth in SEQ ID NO: 10;
(vii) a $V_H$ comprising a sequence set forth in SEQ ID NO: 20 and a $V_L$ comprising a sequence set forth in SEQ ID NO: 11;
(viii) a $V_H$ comprising a sequence set forth in SEQ ID NO: 20 and a $V_L$ comprising a sequence set forth in SEQ ID NO: 12;
(ix) a $V_H$ comprising a sequence set forth in SEQ ID NO: 20 and a $V_L$ Comprising a sequence set forth in SEQ ID NO: 13;
(x) a $V_H$ comprising a sequence set forth in SEQ ID NO: 20 and a $V_L$ Comprising a sequence set forth in SEQ ID NO: 14;
(xi) a $V_H$ comprising a sequence set forth in SEQ ID NO: 20 and a $V_L$ Comprising a sequence set forth in SEQ ID NO: 15;
(xii) a $V_H$ comprising a sequence set forth in SEQ ID NO: 20 and a $V_L$ comprising a sequence set forth in SEQ ID NO: 16;
(xiii) a $V_H$ comprising a sequence set forth in SEQ ID NO: 20 and a $V_L$ comprising a sequence set forth in SEQ ID NO: 17;
(xiv) a $V_H$ comprising a sequence set forth in SEQ ID NO: 20 and a $V_L$ comprising a sequence set forth in SEQ ID NO: 18;
(xv) a $V_H$ comprising a sequence set forth in SEQ ID NO: 20 and a $V_L$ comprising a sequence set forth in SEQ ID NO: 19;
(xvi) a $V_H$ comprising a sequence set forth in SEQ ID NO: 21 and a $V_L$ comprising a sequence set forth in SEQ ID NO: 5;
(xvii) a $V_H$ comprising a sequence set forth in SEQ ID NO: 22 and a $V_L$ comprising a sequence set forth in SEQ ID NO: 5;
(xviii) a $V_H$ comprising a sequence set forth in SEQ ID NO: 23 and a $V_L$ comprising a sequence set forth in SEQ ID NO: 5;
(xix) a $V_H$ comprising a sequence set forth in SEQ ID NO: 24 and a $V_L$ comprising a sequence set forth in SEQ ID NO: 5;
(xx) a $V_H$ comprising a sequence set forth in SEQ ID NO: 25 and a $V_L$ comprising a sequence set forth in SEQ ID NO: 5;
(xxi) a $V_H$ comprising a sequence set forth in SEQ ID NO: 26 and a $V_L$ comprising a sequence set forth in SEQ ID NO: 5;
(xxii) a $V_H$ comprising a sequence set forth in SEQ ID NO: 27 and a $V_L$ comprising a sequence set forth in SEQ ID NO: 5;
(xxiii) a $V_H$ comprising a sequence set forth in SEQ ID NO: 28 and a $V_L$ comprising a sequence set forth in SEQ ID NO: 5;
(xxiv) a $V_H$ comprising a sequence set forth in SEQ ID NO: 29 and a $V_L$ comprising a sequence set forth in SEQ ID NO: 5;
(xxv) a $V_H$ comprising a sequence set forth in SEQ ID NO: 30 and a $V_L$ comprising a
(xxvi) a $V_H$ comprising a sequence set forth in SEQ ID NO: 31 and a $V_L$ comprising a sequence set forth in SEQ ID NO: 5;
(xxvii) a $V_H$ comprising a sequence set forth in SEQ ID NO: 32 and a $V_L$ comprising a sequence set forth in SEQ ID NO: 5;
(xxviii) a $V_H$ comprising a sequence set forth in SEQ ID NO: 33 and a $V_L$ comprising a sequence set forth in SEQ ID NO: 5;
(xxix) a $V_H$ comprising a sequence set forth in SEQ ID NO: 34 and a $V_L$ comprising a sequence set forth in SEQ ID NO: 5;
(xxx) a $V_H$ comprising a sequence set forth in SEQ ID NO: 35 and a $V_L$ comprising a sequence set forth in SEQ ID NO: 5;
(xxxi) a $V_H$ comprising a sequence set forth in SEQ ID NO: 36 and a $V_L$ comprising a sequence set forth in SEQ ID NO: 5;
(xxxii) a $V_H$ comprising a sequence set forth in SEQ ID NO: 37 and a $V_L$ comprising a sequence set forth in SEQ ID NO: 5;
(xxxiii) a $V_H$ comprising a sequence set forth in SEQ ID NO: 38 and a $V_L$ comprising a sequence set forth in SEQ ID NO: 5;
(xxxiv) a $V_H$ comprising a sequence set forth in SEQ ID NO: 39 and a $V_L$ comprising a sequence set forth in SEQ ID NO: 5;
(xxxv) a $V_H$ comprising a sequence set forth in SEQ ID NO: 40 and a $V_L$ comprising a sequence set forth in SEQ ID NO: 5;
(xxxvi) a $V_H$ comprising a sequence set forth in SEQ ID NO: 41 and a $V_L$ comprising a sequence set forth in SEQ ID NO: 5;
(xxxvii) a $V_H$ comprising a sequence set forth in SEQ ID NO: 42 and a $V_L$ comprising a sequence set forth in SEQ ID NO: 5;
(xxxviii) a $V_H$ comprising a sequence set forth in SEQ ID NO: 43 and a $V_L$ comprising a sequence set forth in SEQ ID NO: 5;
(xxxix) a $V_H$ comprising a sequence set forth in SEQ ID NO: 44 and a $V_L$ comprising a sequence set forth in SEQ ID NO: 5;
(x) a $V_H$ comprising a sequence set forth in SEQ ID NO: 45 and a $V_L$ Comprising a sequence set forth in SEQ ID NO: 5;
(xli) a $V_H$ comprising a sequence set forth in SEQ ID NO: 46 and a $V_L$ comprising a sequence set forth in SEQ ID NO: 5;
(xlii) a $V_H$ comprising a sequence set forth in SEQ ID NO: 47 and a $V_L$ comprising a sequence set forth in SEQ ID NO: 5;
(xliii) a $V_H$ comprising a sequence set forth in SEQ ID NO: 48 and a $V_L$ comprising a
(xliv) a $V_H$ comprising a sequence set forth in SEQ ID NO: 49 and a $V_L$ comprising a sequence set forth in SEQ ID NO: 5;

(xlv) a $V_H$ comprising a sequence set forth in SEQ ID NO: 50 and a $V_L$ comprising a sequence set forth in SEQ ID NO: 5;
(xlvi) a $V_H$ comprising a sequence set forth in SEQ ID NO: 51 and a $V_L$ comprising a sequence set forth in SEQ ID NO: 5;
(xlvii) a $V_H$ comprising a sequence set forth in SEQ ID NO: 52 and a $V_L$ comprising a sequence set forth in SEQ ID NO: 5;
(xlviii) a $V_H$ comprising a sequence set forth in SEQ ID NO: 53 and a $V_L$ comprising a sequence set forth in SEQ ID NO: 5;
(xlix) a $V_H$ comprising a sequence set forth in SEQ ID NO: 54 and a $V_L$ comprising a sequence set forth in SEQ ID NO: 5;
(l) a $V_H$ comprising a sequence set forth in SEQ ID NO: 55 and a $V_L$ Comprising a sequence set forth in SEQ ID NO: 5;
(li) a $V_H$ comprising a sequence set forth in SEQ ID NO: 56 and a $V_L$ comprising a sequence set forth in SEQ ID NO: 5;
(lii) a $V_H$ comprising a sequence set forth in SEQ ID NO: 57 and a $V_L$ comprising a sequence set forth in SEQ ID NO: 5;
(liii) a $V_H$ comprising a sequence set forth in SEQ ID NO: 58 and a $V_L$ comprising a sequence set forth in SEQ ID NO: 5;
(liv) a $V_H$ comprising a sequence set forth in SEQ ID NO: 59 and a $V_L$ comprising a sequence set forth in SEQ ID NO: 5;
(lv) a $V_H$ comprising a sequence set forth in SEQ ID NO: 60 and a $V_L$ Comprising a sequence set forth in SEQ ID NO: 5;
(lvi) a $V_H$ comprising a sequence set forth in SEQ ID NO: 61 and a $V_L$ comprising a sequence set forth in SEQ ID NO: 5;
(lvii) a $V_H$ comprising a sequence set forth in SEQ ID NO: 62 and a $V_L$ comprising a sequence set forth in SEQ ID NO: 5;
(lviii) a $V_H$ comprising a sequence set forth in SEQ ID NO: 63 and a $V_L$ comprising a sequence set forth in SEQ ID NO: 5;
(lix) a $V_H$ comprising a sequence set forth in SEQ ID NO: 64 and a $V_L$ comprising a sequence set forth in SEQ ID NO: 5;
(lx) a $V_H$ comprising a sequence set forth in SEQ ID NO: 65 and a $V_L$ Comprising a sequence set forth in SEQ ID NO: 5;
(lxi) a $V_H$ comprising a sequence set forth in SEQ ID NO: 66 and a $V_L$ comprising a
(lxii) a $V_H$ comprising a sequence set forth in SEQ ID NO: 67 and a $V_L$ comprising a sequence set forth in SEQ ID NO: 5;
(lxiii) a $V_H$ comprising a sequence set forth in SEQ ID NO: 68 and a $V_L$ comprising a sequence set forth in SEQ ID NO: 5;
(lxiv) a $V_H$ comprising a sequence set forth in SEQ ID NO: 69 and a $V_L$ comprising a sequence set forth in SEQ ID NO: 5;
(lxv) a $V_H$ comprising a sequence set forth in SEQ ID NO: 70 and a $V_L$ comprising a sequence set forth in SEQ ID NO: 5;
(lxvi) a $V_H$ comprising a sequence set forth in SEQ ID NO: 71 and a $V_L$ comprising a sequence set forth in SEQ ID NO: 5;
(lxvii) a $V_H$ comprising a sequence set forth in SEQ ID NO: 72 and a $V_L$ comprising a sequence set forth in SEQ ID NO: 5;
(lxviii) a $V_H$ comprising a sequence set forth in SEQ ID NO: 73 and a $V_L$ comprising a sequence set forth in SEQ ID NO: 5;
(lxix) a $V_H$ comprising a sequence set forth in SEQ ID NO: 75 and a $V_L$ comprising a sequence set forth in SEQ ID NO: 5;
(lxx) a $V_H$ comprising a sequence set forth in SEQ ID NO: 76 and a $V_L$ comprising a sequence set forth in SEQ ID NO: 5;
(lxxi) a $V_H$ comprising a sequence set forth in SEQ ID NO: 77 and a $V_L$ comprising a sequence set forth in SEQ ID NO: 5;
(lxxii) a $V_H$ comprising a sequence set forth in SEQ ID NO: 78 and a $V_L$ comprising a sequence set forth in SEQ ID NO: 5;
(lxxiii) a $V_H$ comprising a sequence set forth in SEQ ID NO: 79 and a $V_L$ Comprising a sequence set forth in SEQ ID NO: 5;
(lxxiv) a $V_H$ comprising a sequence set forth in SEQ ID NO: 80 and a $V_L$ Comprising a sequence set forth in SEQ ID NO: 5;
(lxxv) a $V_H$ comprising a sequence set forth in SEQ ID NO: 81 and a $V_L$ comprising a sequence set forth in SEQ ID NO: 5;
(lxxvi) a $V_H$ comprising a sequence set forth in SEQ ID NO: 82 and a $V_L$ comprising a sequence set forth in SEQ ID NO: 5;
(lxxvii) a $V_H$ comprising a sequence set forth in SEQ ID NO: 83 and a $V_L$ comprising a sequence set forth in SEQ ID NO: 5;
(lxxviii) a $V_H$ comprising a sequence set forth in SEQ ID NO: 84 and a $V_L$ comprising a sequence set forth in SEQ ID NO: 5;
(lxxix) a $V_H$ comprising a sequence set forth in SEQ ID NO: 85 and a $V_L$ Comprising a
(lxxx) a $V_H$ comprising a sequence set forth in SEQ ID NO: 86 and a $V_L$ comprising a sequence set forth in SEQ ID NO: 5;
(lxxxi) a $V_H$ comprising a sequence set forth in SEQ ID NO: 87 and a $V_L$ comprising a sequence set forth in SEQ ID NO: 5;
(lxxxii) a $V_H$ comprising a sequence set forth in SEQ ID NO: 88 and a $V_L$ comprising a sequence set forth in SEQ ID NO: 5;
(lxxxiii) a $V_H$ comprising a sequence set forth in SEQ ID NO: 89 and a $V_L$ comprising a sequence set forth in SEQ ID NO: 5;
(lxxxiv) a $V_H$ comprising a sequence set forth in SEQ ID NO: 90 and a $V_L$ comprising a sequence set forth in SEQ ID NO: 5;
(lxxxv) a $V_H$ comprising a sequence set forth in SEQ ID NO: 91 and a $V_L$ comprising a sequence set forth in SEQ ID NO: 5;
(lxxxvi) a $V_H$ comprising a sequence set forth in SEQ ID NO: 92 and a $V_L$ comprising a sequence set forth in SEQ ID NO: 5;
(lxxxvii) a $V_H$ comprising a sequence set forth in SEQ ID NO: 93 and a $V_L$ comprising a sequence set forth in SEQ ID NO: 5;
(lxxxviii) a $V_H$ comprising a sequence set forth in SEQ ID NO: 94 and a $V_L$ comprising a sequence set forth in SEQ ID NO: 5;

(lxxxix) a $V_H$ comprising a sequence set forth in SEQ ID NO: 95 and a $V_L$ comprising a sequence set forth in SEQ ID NO: 5;
(xc) a $V_H$ comprising a sequence set forth in SEQ ID NO: 96 and a $V_L$ Comprising a sequence set forth in SEQ ID NO: 5;
(xci) a $V_H$ comprising a sequence set forth in SEQ ID NO: 97 and a $V_L$ comprising a sequence set forth in SEQ ID NO: 5;
(xcii) a $V_H$ comprising a sequence set forth in SEQ ID NO: 98 and a $V_L$ comprising a sequence set forth in SEQ ID NO: 5;
(xciii) a $V_H$ comprising a sequence set forth in SEQ ID NO: 99 and a $V_L$ comprising a sequence set forth in SEQ ID NO: 5;
(xciv) a $V_H$ comprising a sequence set forth in SEQ ID NO: 100 and a $V_L$ comprising a sequence set forth in SEQ ID NO: 5;
(xcv) a $V_H$ comprising a sequence set forth in SEQ ID NO: 101 and a $V_L$ comprising a sequence set forth in SEQ ID NO: 5;
(xcvi) a $V_H$ comprising a sequence set forth in SEQ ID NO: 102 and a $V_L$ comprising a sequence set forth in SEQ ID NO: 5;
(xcvii) a $V_H$ comprising a sequence set forth in SEQ ID NO: 103 and a $V_L$ comprising a
(xcviii) a $V_H$ comprising a sequence set forth in SEQ ID NO: 104 and a $V_L$ comprising a sequence set forth in SEQ ID NO: 5;
(xcix) a $V_H$ comprising a sequence set forth in SEQ ID NO: 105 and a $V_L$ comprising a sequence set forth in SEQ ID NO: 5;
(c) a $V_H$ comprising a sequence set forth in SEQ ID NO: 106 and a $V_L$ comprising a sequence set forth in SEQ ID NO: 5;
(ci) a $V_H$ comprising a sequence set forth in SEQ ID NO: 107 and a $V_L$ comprising a sequence set forth in SEQ ID NO: 5;
(cii) a $V_H$ comprising a sequence set forth in SEQ ID NO: 108 and a $V_L$ comprising a sequence set forth in SEQ ID NO: 5;
(ciii) a $V_H$ comprising a sequence set forth in SEQ ID NO: 109 and a $V_L$ comprising a sequence set forth in SEQ ID NO: 5;
(civ) a $V_H$ comprising a sequence set forth in SEQ ID NO: 110 and a $V_L$ comprising a sequence set forth in SEQ ID NO: 5;
(cv) a $V_H$ comprising a sequence set forth in SEQ ID NO: 111 and a $V_L$ comprising a sequence set forth in SEQ ID NO: 5;
(cvi) a $V_H$ comprising a sequence set forth in SEQ ID NO: 112 and a $V_L$ comprising a sequence set forth in SEQ ID NO: 5;
(cvii) a $V_H$ comprising a sequence set forth in SEQ ID NO: 113 and a $V_L$ comprising a sequence set forth in SEQ ID NO: 5;
(cviii) a $V_H$ comprising a sequence set forth in SEQ ID NO: 114 and a $V_L$ comprising a sequence set forth in SEQ ID NO: 5; or
(cix) a $V_H$ comprising a sequence set forth in SEQ ID NO: 115 and a $V_L$ comprising a sequence set forth in SEQ ID NO: 5.

Optionally, the $V_H$ is linked to a heavy chain constant region, e.g., an IgG4 heavy chain constant region or a stabilized IgG4 constant region, e.g., as discussed herein, such as comprising a sequence set forth in SEQ ID NO: 197. In one example, the heavy chain constant region lacks the C-terminal lysine residue.

Optionally, the $V_L$ is linked to a light chain constant region.

The CD131-binding proteins of the present disclosure may be synhumanized proteins. The term "synhumanized protein" refers to a protein prepared by a method described in WO2007/019620. A synhumanized CD131-binding protein includes a variable region of an antibody, wherein the variable region comprises FRs from a New World primate antibody variable region and CDRs from a non-New World primate antibody variable region. For example, a synhumanized CD131-binding protein includes a variable region of an antibody, wherein the variable region comprises FRs from a New World primate antibody variable region and CDRs from a mouse or rat antibody. In one example, the synhumanized CD131-binding protein is a CD131-binding antibody in which one or both of the variable regions are synhumanized. This term also encompasses a composite protein comprising, for example, one or more synhumanized variable regions and one or more, e.g., human variable regions or humanized variable regions or chimeric variable regions.

The CD131-binding proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898. This term also encompasses a composite protein comprising, for example, one or more primatized variable regions and one or more, e.g., human variable regions or humanized variable regions or chimeric variable regions.

In one example a CD131-binding protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397). This term also encompasses a composite protein comprising, for example, one or more chimeric variable regions and one or more, e.g., human variable regions or humanized variable regions or chimeric variable regions.

The present disclosure also contemplates a deimmunized CD131-binding protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein. For example, an CD131-binding protein of the disclosure is analyzed to identify one or more B or T cell epitopes and one or more amino acid residues within the epitope is mutated to thereby reduce the immunogenicity of the CD131-binding protein.

It will be apparent to the skilled artisan from the foregoing disclosure that a "composite" protein comprises one form of $V_H$ (e.g., human) and another form of $V_L$ (e.g., humanized). The present disclosure explicitly encompasses all combinations of forms of $V_H$ and $V_L$.

Antibody Binding Domain Containing Proteins

Single-Domain Antibodies

In some examples, a CD131-binding protein of the disclosure is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, MA; see, e.g., U.S. Pat. No. 6,248,516).

Diabodies, Triabodies, Tetrabodies

In some examples, a CD131-binding protein of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding domain, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

The CD131-binding protein of the disclosure can be a scFv. The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Other Antibodies and Proteins Comprising Antigen Binding Domains Thereof

The present disclosure also contemplates other antibodies and proteins comprising antigen-binding domains thereof, such as:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

Mutations to Proteins

The present disclosure also provides a CD131-binding protein or a nucleic acid encoding same having at least 80% identity to a sequence disclosed herein. In one example, a CD131-binding protein or nucleic acid of the disclosure comprises sequence at least about 85% or 90% or 95% or 97% or 98% or 99% identical to a sequence disclosed herein, wherein the protein specifically binds to CD131 as described herein according to any example.

Alternatively, or additionally, the CD131-binding protein comprises a CDR (e.g., three CDRs) at least about 80% or 85% or 90% or 95% or 97% or 98% or 99% identical to CDR(s) of a $V_H$ or $V_L$ as described herein according to any example, wherein the protein is capable of specifically binding to CD131 as described herein according to any example. In this regard, the inventors have produced numerous antibodies having diverse sequences within their CDRs. Methods for determining binding of a protein to CD131 are described herein.

For example, the inventors have identified a group of CD131-binding proteins sharing at least 40% identity in their HCDR1.

The inventors have also identified a class of CD131-binding protein sharing at least 65% identify in their HCDR2 according to the Kabat numbering system and a subclass of CD131-binding proteins sharing at least about 77% identity in their HCDR2 according to the Kabat numbering system (e.g., derivatives of antibody 9A2-VR24 comprising mutations in HCDR2 and having an $IC_{50}$ for inhibiting GM-CSF signaling of 0.5 nM or less).

As discussed herein, it is also known in the art that the five C-terminal residues of heavy chain CDR2 can be mutated to conservative or non-conservative amino acid substitutions (31% of residues) (Padlan et al., FASEB J. 9: 133-139, 1995). Thus, a protein can comprise a CDR2 having at least about 35% identity to a heavy chain CDR2 sequence disclosed herein.

For example, the inventors have identified a group of CD131-binding proteins sharing at least about 44% identity in their HCDR3 according to the Kabat numbering system.

For example, the inventors have identified several residues in a $V_H$ comprising a sequence set forth in SEQ ID NO: 20 that can be substituted without loss of function or that result in improved function. In one example, the CD131-binding protein comprises between 1 and 12 amino acid substitutions compared to SEQ ID NO: 20. For example, the C131-binding protein comprises 1 or 2 or 3 or 4 or 5 or 6 or 7 or 8 or 9 or 10 amino acid substitutions compared to SEQ ID NO: 20. For example, the CD131-binding protein comprises 9 amino acid substitutions compared to SEQ ID NO: 37. For example, the CD131-binding protein comprises 10 amino acid substitutions compared to SEQ ID NO: 20. In one example, the substitutions are within CDR1 and/or CDR2.

In one example, the CD131-binding protein comprises between 1 and 5 amino acid substitutions in CDR2 compared to SEQ ID NO: 20. For example, the CD131-binding protein comprises 1 or 2 or 3 or 4 or 5 amino acid substitutions in the CDR2 compared to SEQ ID NO: 20.

In one example, the CD131-binding protein comprises between 1 and 6 amino acid substitutions in CDR1 compared to SEQ ID NO: 20. For example, the CD131-binding protein comprises 1 or 2 or 3 or 4 or 5 or 6 amino acid substitutions in the CDR3 compared to SEQ ID NO: 20.

In one example, a CD131-binding protein of the disclosure comprises a mutant of a sequence set forth in SEQ ID NO: 20, wherein the mutant sequence at least comprises a proline at position 58 of SEQ ID NO: 20.

In one example, a CD131-binding protein of the disclosure comprises a mutant of a sequence set forth in SEQ ID NO: 20, wherein the mutant sequence at least comprises a histidine or an asparagine or a serine at position 61 of SEQ ID NO: 20.

In one example, a CD131-binding protein of the disclosure comprises a mutant of a sequence set forth in SEQ ID NO: 20, wherein the mutant sequence at least comprises a proline at position 30, a tryptophan at position 31, an arginine at position 33, a valine at position 34 and a histidine at position 35 each relevant to SEQ ID NO: 20.

For example, the inventors have identified a group of CD131-binding proteins sharing at least 45% identity in their LCDR1 according to the Kabat numbering system.

The present disclosure also contemplates mutant forms of a CD131-binding protein of the disclosure comprising one or more conservative amino acid substitutions compared to a sequence set forth herein. In some examples, the CD131-binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle *J. Mol. Biol.,* 157: 105-132, 1982 and hydrophylic indices are described in, e.g., U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the CD131-binding protein comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of an CD131-binding protein of the disclosure. In another example, the mutation(s) occur within a CDR of an CD131-binding protein of the disclosure.

Exemplary methods for producing mutant forms of an CD131-binding protein include:
  mutagenesis of DNA (Thie et al., *Methods Mol. Biol.* 525: 309-322, 2009) or RNA (Kopsidas et al., *Immunol. Lett.* 107:163-168, 2006; Kopsidas et al. *BMC Biotechnology,* 7: 18, 2007; and WO1999/058661);
  introducing a nucleic acid encoding the polypeptide into a mutator cell, e.g., XL-1Red, XL-mutS and XL-mutS-Kanr bacterial cells (Stratagene);
  DNA shuffling, e.g., as disclosed in Stemmer, *Nature* 370: 389-91, 1994; and
  site directed mutagenesis, e.g., as described in Dieffenbach (ed) and Dveksler (ed) (In: PCR Primer: A Laboratory Manual, Cold Spring Harbor Laboratories, NY, 1995).

Exemplary methods for determining biological activity of the mutant CD131-binding proteins of the disclosure will be apparent to the skilled artisan and/or described herein, e.g., antigen binding. For example, methods for determining antigen binding, competitive inhibition of binding, affinity, association, dissociation and therapeutic efficacy are described herein.

In another example, a nucleic acid of the disclosure comprises a sequence at least about 80% or 85% or 90% or 95% or 97% or 98% or 99% identical to a sequence set forth herein and encoding a CD131-binding protein having a function as described herein according to any example. The present disclosure also encompasses nucleic acids encoding a CD131-binding protein of the disclosure, which differs from a sequence exemplified herein as a result of degeneracy of the genetic code.

The % identity of a nucleic acid or polypeptide is determined by GAP (Needleman and Wunsch. *Mol. Biol.* 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

The present disclosure also contemplates a nucleic acid that hybridizes under stringent hybridization conditions to a nucleic acid encoding a CD131-binding protein described herein. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

Constant Regions

The present disclosure encompasses CD131-binding proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies include: complement dependent cytotoxicity (CDC); antibody-dependent-cell-mediated cytotoxicity (ADCC); antibody-dependent-cell-phagocytosis (ADCP); and B-cell activation. In one example, the effector function is ADCC and/or ADCP and/or CDC. Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., Proc. Natl. Acad. USA. 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulfide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., Eur J Immunol. 29:2613-2624, 1999; Shields et al., J Biol Chem. 276(9):6591-604, 2001). Additional examples of non-immunostimulatory Fc regions are described, for example, in Dall'Acqua et al., J Immunol. 177: 1129-1138 2006; and/or Hezareh J Virol 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present disclosure also contemplates additional modifications to an antibody or CD131 binding protein comprising an Fc region or constant region.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half-life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Exemplary CD131-Binding Proteins

Exemplary variable region containing CD131-binding proteins produced by the inventors are described in Table 1.

TABLE 1

Sequences of exemplary CD131-binding proteins

| | Antibody name | $V_L$ amino acid SEQ ID NO. | $V_H$ amino acid SEQ ID NO. |
|---|---|---|---|
| 1 | 9A2 | 5 | 20 |
| 2 | 9A2-VR1 | 6 | 20 |

TABLE 1-continued

Sequences of exemplary CD131-binding proteins

| | Antibody name | $V_L$ amino acid SEQ ID NO. | $V_H$ amino acid SEQ ID NO. |
|---|---|---|---|
| 3 | 9A2-VR2 | 7 | 20 |
| 4 | 9A2-VR3 | 8 | 20 |
| 5 | 9A2-VR4 | 9 | 20 |
| 6 | 9A2-VR5 | 10 | 20 |
| 7 | 9A2-VR6 | 11 | 20 |
| 8 | 9A2-VR8 | 12 | 20 |
| 9 | 9A2-VR9 | 13 | 20 |
| 10 | 9A2-VR11 | 14 | 20 |
| 11 | 9A2-VR12 | 15 | 20 |
| 12 | 9A2-VR13 | 16 | 20 |
| 13 | 9A2-VR14 | 17 | 20 |
| 14 | 9A2-VR16 | 18 | 20 |
| 15 | 9A2-VR19 | 19 | 20 |
| 16 | 9A2-VR20 | 5 | 21 |
| 17 | 9A2-VR21 | 5 | 22 |
| 18 | 9A2-VR22 | 5 | 23 |
| 19 | 9A2-VR23 | 5 | 24 |
| 20 | 9A2-VR24 | 5 | 25 |
| 21 | 9A2-VR26 | 5 | 26 |
| 22 | 9A2-VR27 | 5 | 27 |
| 23 | 9A2-VR28 | 5 | 28 |
| 24 | 9A2-VR31 | 5 | 29 |
| 25 | 9A2-VR32 | 5 | 30 |
| 26 | 9A2-VR33 | 5 | 31 |
| 27 | 9A2-VR34 | 5 | 32 |
| 28 | 9A2-VR35 | 5 | 33 |
| 29 | 9A2-VR36 | 5 | 34 |
| 30 | 9A2-VR37 | 5 | 35 |
| 31 | 9A2-VR38 | 5 | 36 |
| 32 | 9A2-VR39 | 5 | 37 |
| 33 | 9A2-VR40 | 5 | 38 |
| 34 | 9A2-VR41 | 5 | 39 |
| 35 | 9A2-VR42 | 5 | 40 |
| 36 | 9A2-VR43 | 5 | 41 |
| 37 | 9A2-VR44 | 5 | 42 |
| 38 | 9A2-VR45 | 5 | 43 |
| 39 | 9A2-VR46 | 5 | 44 |
| 40 | 9A2-VR47 | 5 | 45 |
| 41 | 9A2-VR48 | 5 | 46 |
| 42 | 9A2-VR49 | 5 | 47 |
| 43 | 9A2-VR50 | 5 | 48 |
| 44 | 9A2-VR24.04 | 5 | 49 |
| 45 | 9A2-VR24.07 | 5 | 50 |
| 46 | 9A2-VR24.10 | 5 | 51 |
| 47 | 9A2-VR24.12 | 5 | 52 |
| 48 | 9A2-VR24.19 | 5 | 53 |
| 49 | 9A2-VR24.24 | 5 | 54 |
| 50 | 9A2-VR24.76 | 5 | 55 |
| 51 | 9A2-VR24.78 | 5 | 56 |
| 52 | 9A2-VR24.81 | 5 | 57 |
| 53 | 9A2-VR24.82 | 5 | 58 |
| 54 | 9A2-VR24.84 | 5 | 59 |
| 55 | 9A2-VR24.87 | 5 | 60 |
| 56 | 9A2-VR24.91 | 5 | 61 |
| 57 | 9A2-VR24.93 | 5 | 62 |
| 58 | 9A2-VR24.27 | 5 | 63 |
| 59 | 9A2-VR24.29 | 5 | 64 |
| 60 | 9A2-VR24.30 | 5 | 65 |
| 61 | 9A2-VR24.33 | 5 | 66 |
| 62 | 9A2-VR24.44 | 5 | 67 |
| 63 | 9A2-VR24.97 | 5 | 68 |
| 64 | 9A2-VR24.98 | 5 | 69 |
| 65 | 9A2-VR24.102 | 5 | 70 |
| 66 | 9A2-VR24.107 | 5 | 71 |
| 67 | 9A2-VR24.110 | 5 | 72 |
| 68 | 9A2-VR24.111 | 5 | 73 |
| 69 | 9A2-VR24.55 | 5 | 74 |
| 70 | 9A2-VR24.56 | 5 | 75 |
| 71 | 9A2-VR24.57 | 5 | 76 |
| 72 | 9A2-VR24.122 | 5 | 77 |
| 73 | 9A2-VR24.124 | 5 | 78 |
| 74 | 9A2-VR24.131 | 5 | 79 |
| 75 | 9A2-VR39.01 | 5 | 80 |
| 76 | 9A2-VR39.02 | 5 | 81 |
| 77 | 9A2-VR39.04 | 5 | 82 |
| 78 | 9A2-VR39.05 | 5 | 83 |
| 79 | 9A2-VR39.06 | 5 | 84 |
| 80 | 9A2-VR39.11 | 5 | 85 |
| 81 | 9A2-VR39.12 | 5 | 86 |
| 82 | 9A2-VR39.16 | 5 | 87 |
| 83 | 9A2-VR39.17 | 5 | 88 |
| 84 | 9A2-VR39.18 | 5 | 89 |
| 85 | 9A2-VR39.19 | 5 | 90 |
| 86 | 9A2-VR39.21 | 5 | 91 |
| 87 | 9A2-VR39.22 | 5 | 92 |
| 88 | 9A2-VR39.23 | 5 | 93 |
| 89 | 9A2-VR39.24 | 5 | 94 |
| 90 | 9A2-VR39.97 | 5 | 95 |
| 91 | 9A2-VR39.98 | 5 | 96 |
| 92 | 9A2-VR39.102 | 5 | 97 |
| 93 | 9A2-VR39.103 | 5 | 98 |
| 94 | 9A2-VR39.105 | 5 | 99 |
| 95 | 9A2-VR39.109 | 5 | 100 |
| 96 | 9A2-VR39.110 | 5 | 101 |
| 97 | 9A2-VR39.111 | 5 | 102 |
| 98 | 9A2-VR39.112 | 5 | 103 |
| 99 | 9A2-VR39.116 | 5 | 104 |
| 100 | 9A2-VR39.27 | 5 | 105 |
| 101 | 9A2-VR39.28 | 5 | 106 |
| 102 | 9A2-VR39.46 | 5 | 107 |
| 103 | 9A2-VR39.122 | 5 | 108 |
| 104 | 9A2-VR39.139 | 5 | 109 |
| 105 | 9A2-VR39.140 | 5 | 110 |
| 106 | 9A2-VR39.148 | 5 | 111 |
| 107 | 9A2-VR39.162 | 5 | 112 |
| 108 | 9A2-VR39.77 | 5 | 113 |
| 109 | 9A2-VR39.93 | 5 | 114 |
| 110 | 9A2-VR39.174 | 5 | 115 |
| 111 | 9A2-VR39.177 | 5 | 116 |

Protein Production

In one example, a CD131-binding protein described herein according to any example is produced by culturing a hybridoma under conditions sufficient to produce the protein, e.g., as described herein and/or as is known in the art.

Recombinant Expression

In another example, a CD131-binding protein described herein according to any example is recombinant.

In the case of a recombinant protein, nucleic acid encoding same can be cloned into expression constructs or vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub.

Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. Nos. 4,816,567 or 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein.

Exemplary signal sequences include prokaryotic secretion signals (e.g., peiB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, 0-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris. Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where a CD131-binding protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The CD131-binding protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or an influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Non-Antibody-Derived Compounds
Immunoglobulins and Immunoglobulin Fragments

An example of a compound of the present disclosure is a protein comprising a variable region of an immunoglobulin, such as a T cell receptor or a heavy chain immunoglobulin (e.g., an IgNAR, a camelid antibody).

Heavy Chain Immunoglobulins

Heavy chain immunoglobulins differ structurally from many other forms of immunoglobulin (e.g., antibodies), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a compound of the disclosure is a T-cell receptor. T cell receptors have two V-domains that combine into a structure similar to the Fv module of an antibody. Novotny et al., *Proc Natl Acad Sci USA* 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid O-sheet secondary structure with a plurality of loops at the open end of the conical structure which can be engineered to bind to an antigen. Such engineered lipocalins are known as anticalins. For further description of anticalins see U.S. Pat. No. 7,250, 297B1 or US20070224633.

Affibodies

In a further example, a compound of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Other Non-Antibody Polypeptides

Other non-antibody proteins comprising binding domains include those based on human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins).

Peptides

In one example, a binding molecule is a peptide, e.g., isolated from a random peptide library. To identify a suitable peptide, a random peptide library is generated and screened as described in U.S. Pat. Nos. 5,733,731, 5,591,646 and 5,834,318. Generally, such libraries are generated from short random oligonucleotides that are expressed either in vitro or in vivo and displayed in such a way to facilitate screening of the library to identify a peptide that. is capable of specifically binding to an antigen described herein. Methods of display include, phage display, retroviral display, bacterial surface display, bacterial flagellar display, bacterial spore display, yeast surface display, mammalian surface display, and methods of in vitro display including, mRNA display, ribosome display and covalent display.

A peptide that is capable of binding an antigen described herein is identified by any of a number of methods known in the art, such as, for example, standard affinity purification methods as described, for example in Scopes, 1994) purification using FACS analysis as described in US645563.

Small Molecules

In another example, a binding molecule is a small molecule. Such a small molecule may be isolated from a library. Chemical small molecule libraries are available commercially or alternatively may be generated using methods known in the art, such as, for example, those described in U.S. Pat. No. 5,463,564.

Techniques for synthesizing small organic compounds will vary considerably depending upon the compound, however such methods will be known to those skilled in the art.

In one example, informatics is used to select suitable chemical building blocks from known compounds, for producing a combinatorial library. For example, QSAR (Quantitative Structure Activity Relationship) modeling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and log P (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens, can be used to expand the list of compounds being screened to thereby identify highly active compounds.

Nucleic Acid Aptamers

In another example, a compound is a nucleic acid aptamer (adaptable oligomer). Aptamers are single stranded oligonucleotides or oligonucleotide analogs that are capable of forming a secondary and/or tertiary structure that provides the ability to bind to a particular target molecule, such as a protein or a small molecule, e.g., CD131. Thus, aptamers are the oligonucleotide analogy to antibodies. In general, aptamers comprise about 15 to about 100 nucleotides, such as about 15 to about 40 nucleotides, for example about 20 to about 40 nucleotides, since oligonucleotides of a length that falls within these ranges can be prepared by conventional techniques.

An aptamer can be isolated from or identified from a library of aptamers. An aptamer library is produced, for example, by cloning random oligonucleotides into a vector (or an expression vector in the case of an RNA aptamer), wherein the random sequence is flanked by known sequences that provide the site of binding for PCR primers. An aptamer that provides the desired biological activity (e.g., binds specifically to an epitope of CD131) is selected. An aptamer with increased activity is selected, for example, using SELEX (Sytematic Evolution of Ligands by EXponential enrichment). Suitable methods for producing and/or screening an aptamer library are described, for example, in Elloington and Szostak, Nature 346:818-22, 1990; U.S. Pat. No. 5,270,163; and/or U.S. Pat. No. 5,475,096.

Conjugates

In one example, a CD131-binding protein of the present disclosure is conjugated to a compound. For example, the compound is selected from the group consisting of a radioisotope, a detectable label, a therapeutic compound, a colloid, a toxin, a nucleic acid, a peptide, a protein, a compound that increases the half-life of the CD131-binding protein in a subject and mixtures thereof.

The other compound can be directly or indirectly bound to the CD131-binding protein (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal or quantum dot), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), a compound that increases the half-life of the CD131-binding protein in a subject (e.g., polyethylene glycol or other water soluble polymer having this activity) and mixtures thereof. Exemplary compounds that can be conjugated to a CD131-binding protein of the disclosure and methods for such conjugation are known in the art and described, for example, in WO2010/059821.

The CD131-binding protein may be conjugated to nanoparticles (for example as reviewed in Kogan et al., Nanomedicine (Lond). 2: 287-306, 2007). The nanoparticles may be metallic nanoparticles.

The CD131-binding protein may be comprised in antibody-targeted bacterial minicells (for example as described in PCT/IB2005/000204).

Some exemplary compounds that can be conjugated to a CD131-binding protein of the present disclosure are listed in Table 2.

TABLE 2

Compounds useful in conjugation.

| Group | Detail |
|---|---|
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Rc, $^{203}$Pb, $^{64}$Cu, $^{105}$Rh, $^{198}$Au, $^{199}$Ag or $^{177}$Lu |
| Half-life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | fluorescent proteins such as Renilla luciferase, GFP<br>immune modulators or proteins, such as cytokines, e.g., an interferon<br>toxins<br>an immunoglobulin or antibody or antibody variable region<br>half-life extenders such as albumin or antibody variable regions or peptides that bind to albumin |
| Chemotherapeutics | Taxol<br>5-FU<br>Doxorubicin<br>Idarubicin |

Assaying Activity of a CD131-Binding Protein Binding to CD131 and Mutants Thereof It will be apparent to the skilled artisan from the disclosure herein that some CD131-binding proteins of the present disclosure bind to the extracellular region (e.g., a region as described herein) of hCD131 and to specific mutant forms of extracellular region of hCD131 (e.g., SEQ ID NO: 3 or SEQ ID NO: 192 without or with certain point mutations). Methods for assessing binding to a protein are known in the art, e.g., as described in Scopes (In: Protein purification: principles and practice, Third Edition, Springer Verlag, 1994). Such a method generally involves immobilizing the CD131-binding protein and contacting it with labeled antigen. Following washing to remove non-specific bound protein, the amount of label and, as a consequence, bound antigen is detected. Of course, the CD131-binding protein can be labeled and the antigen immobilized. Panning-type assays can also be used. Alternatively, or additionally, surface plasmon resonance assays can be used.

The assays described above can also be used to detect the level of binding of a protein to CD131 or an extracellular region thereof (e.g., as contained within SEQ ID NO: 192).

In one example, a CD131-binding protein of the present disclosure binds to a polypeptide comprising a sequence set forth in SEQ ID NO: 119 at a level at least about 1.5 fold or 2 fold or 5 fold or 10 fold or 50 fold or 100 fold or 150 fold or 160 fold or 200 fold lower than it binds to a polypeptide of SEQ ID NO: 192. In one example, a CD131-binding protein of the present disclosure does not detectably bind to a polypeptide comprising a sequence set forth in SEQ ID NO: 119.

In one example, a CD131-binding protein of the present disclosure binds to a polypeptide of SEQ ID NO: 124 at a level at least about 1.5 fold or 2 fold or 5 fold or 10 fold or 50 fold or 100 fold or 150 fold or 160 fold or 200 fold lower than it binds to a polypeptide of SEQ ID NO: 192. In one example, a CD131-binding protein of the present disclosure does not detectably bind to a polypeptide comprising a sequence set forth in SEQ ID NO: 124.

In one example, a CD131-binding protein of the present disclosure binds to a polypeptide of SEQ ID NO: 131 at a level at least about 1.5 fold or 2 fold or 5 fold or 10 fold or 50 fold or 100 fold or 150 fold or 160 fold or 200 fold lower than it binds to a polypeptide of SEQ ID NO: 192. In one example, a CD131-binding protein of the present disclosure does not detectably bind to a polypeptide comprising a sequence set forth in SEQ ID NO: 131.

In one example, a CD131-binding protein of the present disclosure binds to a polypeptide of SEQ ID NO: 137 at a level at least about 1.5 fold or 2 fold or 5 fold or 10 fold or 50 fold or 100 fold or 150 fold or 160 fold or 200 fold lower than it binds to a polypeptide of SEQ ID NO: 192. In one example, a CD131-binding protein of the present disclosure does not detectably bind to a polypeptide comprising a sequence set forth in SEQ ID NO: 137.

In one example, a CD131-binding protein of the present disclosure binds to a polypeptide of SEQ ID NO: 139 at a level at least about 1.5 fold or 2 fold or 5 fold or 10 fold or 50 fold or 100 fold or 150 fold or 160 fold or 200 or 1000 or 2000 fold lower than it binds to a polypeptide of SEQ ID NO: 192.

In one example, a CD131-binding protein of the present disclosure binds to a polypeptide of SEQ ID NO: 138 at a level at least about 1.5 fold or 2 fold or 5 fold or 10 fold or 50 fold or 100 fold lower than it binds to a polypeptide of SEQ ID NO: 192.

The level of binding is conveniently determined using a biosensor, e.g., by surface plasmon resonance.

The present disclosure contemplates any combination of the foregoing characteristics. In one example, a CD131-binding protein described herein has all of the binding characteristics set forth in the preceding seven paragraphs.

Epitope Mapping

In another example, the epitope bound by a protein described herein is mapped. Epitope mapping methods will be apparent to the skilled artisan. For example, a series of overlapping peptides spanning the CD132 sequence or a region thereof comprising an epitope of interest, e.g., peptides comprising 10-15 amino acids are produced. The CD131-binding protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, amino acid residues within CD131 are mutated, e.g., by alanine scanning mutagenesis or substitution of evolutionarily conserved amino acids, and mutations that reduce or prevent binding of the CD131-binding protein are determined. Any mutation that reduces or prevents binding of the CD131-binding protein is likely to be within the epitope bound by the CD131-binding protein.

A further method for determining a region comprising an epitope involves binding CD131 or a region thereof to an immobilized CD131-binding protein of the present disclosure and digesting the resulting complex with proteases. Peptide(s) that remains bound to the immobilized CD131-binding protein are then isolated and analyzed, e.g., using mass spectrometry, to determine their sequence.

A further method involves converting hydrogens in CD131 or a region thereof to deutrons and binding the resulting protein to an immobilized CD131-binding protein of the present disclosure. The deutrons are then converted back to hydrogen, the CD131 or region thereof isolated, digested with enzymes and analyzed, e.g., using mass spectrometry to identify those regions comprising deutrons, which would have been protected from conversion to hydrogen by the binding of a CD131-binding protein described herein.

Optionally, the dissociation constant (Kd), association constant (Ka) and/or affinity constant ($K_D$) of an immobilized CD131-binding protein for CD131 or an epitope thereof is determined. The "Kd" or "Ka" or "$K_D$" for a CD131-binding protein is in one example measured by a radiolabeled or fluorescently-labeled CD131 binding assay. In the case of a "Kd", this assay equilibrates the CD131-binding protein with a minimal concentration of labeled CD131 in the presence of a titration series of unlabeled CD131. Following washing to remove unbound CD131, the amount of label is determined, which is indicative of the Kd of the protein.

According to another example the Kd, Ka or $K_D$ is measured by using surface plasmon resonance assays, e.g., using BIAcore surface plasmon resonance (BIAcore, Inc., Piscataway, NJ) with immobilized CD131 or a region thereof or immobilized IL-CD131-binding protein.

In some examples, the CD131-binding protein has a similar $K_D$ or an improved $K_D$ (i.e., a $K_D$ value lower than) than antibody 9A2 or 9A2-VR24 or 9A2-VR39, because they are likely to compete for binding to CD131.

Determining Competitive Binding

Assays for determining a protein that competitively inhibits binding of antibody 9A2 or an antibody comprising the V regions thereof another antibody described herein will be apparent to the skilled artisan. One such method is exemplified herein.

For example, the antibody is conjugated to a detectable label, e.g., a fluorescent label or a radioactive label. The labeled antibody and the test CD131-binding protein are then mixed and contacted with CD131 or a region thereof (e.g., as contained within a polypeptide comprising SEQ ID NO: 192) or a cell expressing same. The level of labeled antibody is then determined and compared to the level determined when the labeled antibody is contacted with the CD131, region or cells in the absence of the CD131-binding protein. If the level of labeled antibody is reduced in the presence of the test CD131-binding protein compared to the absence of the CD131-binding protein, the CD131-binding protein is considered to competitively inhibit binding of the antibody to CD131.

Optionally, the test CD131-binding protein is conjugated to different label to the antibody. This alternate labeling permits detection of the level of binding of the test CD131-binding protein to CD131 or the region thereof or the cell.

In another example, the CD131-binding protein is permitted to bind to CD131 or a region thereof (e.g., as contained within a polypeptide comprising SEQ ID NO: 192) or a cell expressing same prior to contacting the CD131, region or cell with the antibody. A reduction in the amount of bound antibody in the presence of the CD131-binding protein compared to in the absence of the CD131-binding protein indicates that the protein competitively inhibits binding of the antibody to CD131. A reciprocal assay can also be performed using labeled CD131-binding protein and first allowing the antibody to bind to CD131. In this case, a reduced amount of labeled CD131-binding protein bound to CD131 in the presence of the antibody compared to in the absence of the antibody indicates that the CD131-binding protein competitively inhibits binding of the antibody to CD131.

Any of the foregoing assays can be performed with a mutant form of CD131 and/or SEQ ID NO: 192 and/or an extracellular region of CD131 to which antibody 9A2 binds, e.g., as described herein.

Determining Neutralization

In one example, the CD131-binding protein reduces or prevents binding of IL-3, IL-5 and/or GM-CSF to a receptor comprising CD131 (e.g., an IL-3R, an IL-5R and/or a GM-CSF-R, respectively). These assays can be performed as a competitive binding assay using labeled IL-3/Il-5/GM-CSF and/or labeled CD131-binding protein. For example, cells expressing the relevant receptor is contacted with IL-3/Il-5/GM-CSF in the presence or absence of a CD131-binding protein and the amount of bound label detected. A reduction in the amount of bound label in the presence of the CD131-binding protein compared to in the absence of the compound indicates that the compound reduces or prevents binding of IL-3/Il-5/GM-CSF to a receptor comprising CD131. By testing multiple concentrations of the compound an $IC_{50}$ is determined, i.e., a concentration of the protein that reduces the amount of IL-3/Il-5/GM-CSF that binds to a receptor comprising CD131, or an $EC_{50}$ can be determined, i.e., a concentration of the protein that achieves 50% of the maximum inhibition of binding of IL-3/Il-5/GM-CSF to CD131 achieved by the compound.

In a further example, the CD131-binding protein reduces or prevents IL-3/Il-5/GM-CSF-mediated proliferation of leukemic cell line TF-1. For example, TF-1 cells are cultured without IL-3/Il-5/GM-CSF for a time sufficient for them to stop proliferating (e.g., 24-48 hours). Cells are then cultured in the presence of IL-3/Il-5/GM-CSF and various concentrations of the CD131-binding protein. Control cells are not contacted with the compound (positive control) or IL-3/Il-5/GM-CSF (negative control). Cell proliferation is then assessed using a standard technique, e.g., $^3$H-thymidine incorporation. A CD131-binding protein that reduces or prevents cell proliferation in the presence of IL-3 to a level less than the positive control is considered to neutralize IL-3 signaling. By testing multiple concentrations of the CD131-binding protein, an $IC_{50}$ is determined.

In another example, a CD131-binding protein inhibits or prevents STAT-5 activation. For example, cells (e.g., TF-1 cells) comprising a beta-lactamase reporter gene under control of the interferon regulatory factor 1 (irf1) response element in the presence of IL-3 and/or GM-CSF. Suitable cells are available from Life Technologies Corporation. Cells are also contacted with a suitable substrate (e.g., a negatively charged fluorescent beta-lactamase substrate, such as CCF2 or CCF4) and the change in signal (e.g., fluorescence) determined. A reduced change in signal in a positive control (i.e., cells contacted with IL-3 and/or GM-CSF in the absence of the protein or antibody) indicates that the protein or antibody reduces or prevents IL-3 and/or GM-CSF-induced STAT-5 signaling.

In a further example, a CD131-binding protein of the disclosure affects an immune cell.

For example, the CD131-binding protein reduces or inhibits activation of isolated human neutrophils by GM-CSF as determined by reducing or inhibiting GM-CSF-induced increase in neutrophil cell size. For example, neutrophils (e.g., about $1\times10^5$ cells) are cultured in the presence of the CD-131-binding protein and GM-CSF for a suitable time (e.g., about 24 hours). Cells are then fixed (e.g., with formaldehyde) and analyzed for forward scatter using flow cytometry.

In one example, the CD131-binding protein reduces or inhibits IL-3-induced IL-8 secretion by human basophils. For example, basophils (e.g., about $1\times10^5$ cells) are cultured in the presence of a CD131-binding protein and IL-3 for a suitable time (e.g., 24 hours). IL-8 secretion is then assessed, e.g., using an ELISA, e.g., as is available from R&D Systems.

In a further example, the CD131-binding protein reduces or prevents IL-3-mediated survival or pDCs. For example, pDCs are cultured in the presence of a CD131-binding protein and IL-3 for a suitable time (e.g., 24 hours). Cell survival is then assessed, e.g., using a standard method, such as a ViaLight Plus Kit from Lonza.

In a further example, the CD131-binding protein reduces or prevents activation of human peripheral blood eosinophils by IL-5 as determined by assessing change in forward scatter assessed by flow cytometry. For example, eosinophils (e.g., about $1\times10^5$ cells) are cultured in the presence of a CD131-binding protein and IL-5 for a suitable time (e.g., about 24 hours). Cells are then fixed (e.g., in formaldehyde) and assessed for change in forward scatter, e.g., using flow cytometry.

In a further example, a CD131-binding protein of the disclosure reduces or prevents survival of human peripheral blood eosinophils in the presence of IL-5 and/or GM-CSF and/or IL-3. For example, eosinophils (e.g., about $1\times10^4$ cells) are cultured in the presence of a CD131-binding protein and IL-5 and/or GM-CSF and/or IL-3 for a suitable time (e.g., about 5 days) and cell numbers assessed using a standard method (e.g., a ViaLight Plus Kit from Lonza).

In a still further example, a CD131-binding protein of the disclosure reduces or prevents IL-3-induced TNFα release from human mast cells. For example, human cultured mast cells (e.g., ten-week old peripheral blood-derived cells) are cultured in the presence of a CD131-binding protein and IL-3. Levels of TNFα secretion are then assessed by, e.g., ELISA.

In a further example, a CD131-binding protein of the disclosure reduces or prevents IL-3-induced IL-13 release from human mast cells. For example, human cultured mast cells (e.g., ten-week old peripheral blood-derived cells) are cultured in the presence of a CD131-binding protein and IL-3. Levels of IL-13 secretion are then assessed by, e.g., ELISA.

In a further example, a CD131-binding protein of the disclosure reduces or prevents potentiation of IgE-mediated IL-8 release from human mast cells by IL-3 and/or IL-5 and/or GM-CSF. For example, human cultured mast cells (e.g., ten-week old peripheral blood-derived cells) are cultured in the presence of a CD131-binding protein and IL-3/IL-5/GM-CSF (e.g., for about 48 hours). Cells are then cultured with IgE (e.g., human myeloma IgE) for a suitable time (e.g., about 24 hours) and IL-8 secretion assessed, e.g., by ELISA.

In a further example, a CD131-binding protein reduces or prevents formation of CFU-GM by CD34+ human bone marrow cells (or cord blood cells) cultured in the presence of SCF, GM-CSF, IL-3 and IL-5. For example, CD34+ cells (e.g., about $1\times10^3$ cells) are cultured (e.g., on methylcellulose (such as 1% methylcellulose) supplemented with fetal calf serum, bovine serum albumin, SCF, GM-CSF, IL-3 and IL-5) and in the presence of a CD131-binding protein. Cells are cultured for a suitable time (e.g., about 16 days) and the number of colonies formed subsequently enumerated.

In a further example, a CD131-binding protein a CD131-binding protein or antibody of the disclosure reduces survival of or induces death of immune cells (e.g., eosinophils) from sputum or nasal polyp tissue from a subject suffering from an inflammatory airway disease or nasal polyposis. For example, the immune cells are cultured in the presence of IL-3 and/or IL-5 and/or GM-CSF and the protein or antibody. Cell death is then assessed using standard methods, e.g., by detecting Annexin-V expression, e.g., using fluorescence activated cell sorting).

In another example, the CD131-binding protein reduces or prevents IL-3-mediated histamine release from basophils. For example, low density leukocytes comprising basophils are incubated with IgE, IL-3 and various concentrations of the antibody or antigen binding fragment. Control cells do not comprise immunoglobulin (positive control) or IL-3 (negative control). The level of released histamine is then assessed using a standard technique, e.g., RIA. A CD131-binding protein that reduces the level of histamine release to a level less than the positive control is considered to neutralize IL-3 signaling. In one example, the level of reduction is correlated with protein concentration. An exemplary method for assessing IL-3-mediated histamine release is described, for example, in Lopez et al., *J. Cell. Physiol.*, 145: 69, 1990.

Another assay for assessing IL-3 signaling neutralization comprises determining whether or not the CD131-binding protein reduces or prevents IL-3-mediated effects on endothelial cells. For example, human umbilical vein endothelial cells (HUVECs) are cultured in the presence of IL-3 (optionally, with IFN-γ) and various concentrations of the CD131-binding protein. The amount of secreted IL-6 is then assessed, e.g., using an enzyme linked immunosorbent assay (ELISA). Control cultures do not comprise the CD131-binding protein (positive control) or IL-3 (negative control). A CD131-binding protein that reduces or prevents IL-6 production in the presence of IL-3 to a level less than the positive control is considered to neutralize IL-3 signaling.

Other methods for assessing neutralization signaling are contemplated by the present disclosure.

Determining Effector Function

As discussed herein, some CD131-binding proteins of the present disclosure have reduced effector function or have effector function (or enhanced effector function). Methods for assessing ADCC activity are known in the art.

In one example, the level of ADCC activity is assessed using a $^{51}$Cr release assay, an europium release assay or a $^{35}$S release assay. In each of these assays, cells expressing CD131 are cultured with one or more of the recited compounds for a time and under conditions sufficient for the compound to be taken up by the cell. In the case of a $^{35}$S release assay, cells expressing CD131 can be cultured with $^{35}$S-labeled methionine and/or cysteine for a time sufficient for the labeled amino acids to be incorporated into newly synthesized proteins. Cells are then cultured in the presence or absence of the CD131-binding protein and in the presence of immune effector cells, e.g., peripheral blood mononuclear cells (PBMC) and/or NK cells. The amount of $^{51}$Cr, europium and/or $^{35}$S in cell culture medium is then detected, and little or no change in the presence of the CD131-binding protein compared to in the absence of the CD131-binding protein indicates that the protein has reduced effector function and an increased amount compared to in the absence of the CD131-binding protein (or increased compared to in the presence of the CD131-binding protein comprising an IgG1 Fc region) indicating effector function or enhanced effector function. Exemplary publications disclosing assays for assessing the level of ADCC induced by a protein include Hellstrom, et al. *Proc. Natl Acad. Sci. USA* 83:7059-7063, 1986 and Bruggemann, et al., *J. Exp. Med.* 166:1351-1361, 1987.

Other assays for assessing the level of ADCC induced by a protein include ACTI® nonradioactive cytotoxicity assay for flow cytometry (CellTechnology, Inc. CA, USA) or CytoTox 96® non-radioactive cytotoxicity assay (Promega, WI, USA).

C1q binding assays may also be carried out to confirm that the CD131-binding protein is able to bind C1q and may induce CDC. To assess complement activation, a CDC assay may be performed (see, for example, Gazzano-Santoro et al. *J. Immunol. Methods* 202: 163, 1996).

Determining Half Life

Some CD131-binding proteins encompassed by the present disclosure have an improved half-life, e.g., are modified to extend their half-life compared to CD131-binding proteins that are unmodified. Methods for determining a CD131-binding protein with an improved half-life will be apparent to the skilled person. For example, the ability of a CD131-binding protein to bind to a neonatal Fc receptor (FcRn) is assessed. In this regard, increased binding affinity for FcRn increases the serum half-life of the CD131-binding protein (see for example, Kim et al., *Eur J Immunol.*, 24:2429, 1994).

The half-life of a CD131-binding protein of the disclosure can also be measured by pharmacokinetic studies, e.g., according to the method described by Kim et al, *Eur J of Immunol* 24:542, 1994. According to this method radiolabeled CD131-binding protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Assessing Therapeutic Efficacy

Assays for assessing therapeutic efficacy are described hereinabove in relation to determining neutralization by a CD131-binding protein.

In another example, the efficacy of a protein to treat a condition is assessed using an in vivo assay.

For example, the CD131-binding protein can be tested in a Th2-inflammatory condition, such as asthma or airway hyperreactivity. An exemplary model of allergic asthma is the mouse OVA-model, e.g., as described in Wang et al. *J. Immunol.* 165: 2222, 2000. Following induction of inflammation, a CD131-binding protein is administered to the mice and symptoms of asthma, such as numbers of eosinophils in bronchoalveolar lavage fluid (BAL), mucus secretion and/or goblet cell hyperplasia are assessed. Other models of asthma are known in the art and include an ovine model of inflammatory asthma as described in WO2002/098216, a mouse model of allergic asthma, e.g., induced by host dust mite protein (Fattouh et al., *Am J Respir Crit Care Med* 172: 314-321, 2005), a mouse model of severe asthma in which IL-5 and eotaxin are overexpressed, or mice receiving intratracheal instillation of poly-l-lysine which are hypersensitive to methacholine when delivered as an aerosol (Homma et al., *Am J Physiol Lung Cell Mol Physiol* 289: L413-L418, 2005).

In another example, the CD131-binding protein is tested in an animal model of arthritis. Exemplary models include a SKG strain of mouse (Sakaguchi et al., Nature, 426: 454-460), rat type II collagen arthritis model, mouse type II collagen arthritis model or antigen induced arthritis models in several species (Bendele *J Musculoskel Neuron Interact;* 1(4):377-385, 2001). In these assays, arthritis is induced and the ability of the CD131-binding protein to reduce one or more symptoms of arthritis, e.g., joint inflammation and/or markers of inflammation in synovial fluid is assessed. A CD131-binding protein that reduces a symptom of arthritis is considered useful for treating this condition or a CD131-mediated condition (e.g., a CD131-mediated inflammatory condition).

The CD131-binding protein can also or alternatively be tested in a model of COPD, e.g., in which a non-human mammal (e.g., a rodent, such as, a mouse) is exposed to cigarette smoke. Following exposure, the mammal is administered a CD131-binding protein and the level of lung inflammation and/or the number of neutrophils in the lung is assessed or estimated using standard techniques. A CD131-binding protein that reduces lung inflammation and/or the number of neutrophils is considered useful for treating lung inflammation or COPD or a CD131-mediated condition (e.g., a CD131-mediated inflammatory condition, such as a CD131-mediated inflammatory lung condition).

In a further example, a CD131-binding protein is tested in a model of colitis, e.g., in oxazolone-treated mice, which develop colonic eosinophilia or a model as described in Albert et al., *Am. J. Pathol.,* 178: 150-160, 2011).

In another example, the CD131-binding protein is administered to a non-human animal (e.g., a non-human primate) and the number/level of immune cells, e.g., eosinophils, in circulation or in a tissue or other sample (e.g., BAL fluid) is assessed. A CD131-binding protein that reduces the number/level of immune cells compared to prior to administration and/or in a control mammal to which the protein has not been administered is considered suitable for treating the disease or condition.

In another example, a CD131-binding protein is tested in a model of passive cutaneous anaphylaxis, e.g., in which a non-human mammal (e.g., a rodent, such as a mouse) sensitized with anti-dinitrophenyl (DNP)-IgE and subsequently stimulated by DNP-human serum albumin (HSA) is administered a CD131-binding protein and the change in ear thickness from baseline (i.e., prior to administration) and/or the level of a cytokine, such as TNF or IL-13, is assessed or estimated using standard techniques. A CD131-binding protein that reduces the change in ear thickness and/or reduces the level of the cytokine compared to a control mammal to which the compound has not been administered is considered suitable for treating the disease or condition.

In another example, the level of a cytokine, such as IFNα or TNFα is detected in the circulation of a mammal, e.g., using an ELISA. A CD131-binding protein that reduces the level of the cytokine compared to the level prior to administration and/or in a control mammal to which the compound has not been administered is considered suitable for treating the disease or condition.

Conditions to be Treated

The present disclosure contemplates treatment or prevention of any condition that is caused by or exacerbated by signaling through CD131 (e.g., by IL-3 and/or IL-5 and/or GM-CSF) in a subject.

In one example, the condition is an autoimmune or inflammatory condition or allergic condition.

In one example, the condition is an autoimmune-mediated inflammatory condition. For example, the autoimmune-mediated inflammatory condition is rheumatoid arthritis, multiple sclerosis, interstitial lung disease, colitis or systemic lupus erythematosus. In one example, the autoimmune condition is multiple sclerosis. In one example, the autoimmune condition is interstitial lung disease. In a further example, the autoimmune condition is systemic lupus erythematosus.

In one example, the inflammatory condition is a chronic inflammatory condition. For example, the chronic inflammatory condition is bullous pemphigoid or Churg-Strauss syndrome. In one example, the condition is bullous pemphigoid. In a further example, the condition is Churg-Strauss syndrome.

In one example, the condition is an allergic condition. For example, the condition is urticaria, asthma, airway hyperreactivity, allergic rhinitis, allergic bronchopulmonary aspergillosis, coeliac disease, nasal polyposis, chronic rhinosinusitis with nasal polyps (CRSwNP), chronic rhinosinusitis without nasal polyps (CRSsNP) or atopic dermatitis. In one example, the condition is chronic rhinosinusitis with nasal polyps (CRSwNP). In one example, the condition is chronic rhinosinusitis without nasal polyps (CRSsNP). In another example, the condition is atopic dermatitis. In a further example, the condition is chronic urticaria.

In one example, the allergic condition is an allergic lung condition. For example, the condition is asthma or airway hyperreactivity. For example, the condition is asthma.

In a related example, the condition is a respiratory condition. For example, the condition is asthma or COPD or cystic fibrosis or pulmonary fibrosis or bronchiolitis or alveolitis or vasculitis or sarcoidosis. In one example, the condition is COPD. In a further example, the condition is pulmonary fibrosis.

As used herein the term "asthma" will be understood to mean a disease characterized by paroxysmal or persistent symptoms of dyspnea, chest tightness, wheezing, sputum production and cough, associated with variable airflow limitation and airway hyperresponsiveness to endogenous or exogenous stimuli (Canadian Asthma Consensus Guidelines) and/or a condition characterized by airway hyperresponsiveness that leads to recurrent episodes of wheezing, breathlessness, chest tightness, and coughing, particularly at night or in the early morning along with variable airflow obstruction which is often reversible either spontaneously or with treatment (The Global Initiative for Asthma).

In one example, the condition is severe asthma. As used herein, the term "severe asthma" will be understood to mean well controlled asthma symptoms on high to very high doses of inhaled corticosteroids, with or without the use of oral corticosteroids; and "very severe asthma" will be understood to mean well or not well controlled asthma symptoms despite very high dose of inhaled and ingested corticosteroids and with or without requiring additional therapies. For these definitions, the daily high and very high doses of inhaled corticosteroid (approximate equivalent doses) are defined as follows: High dose is beclomethasone dipropionate, 1000 to 2000 μg; fluticasone, 500 to 1000 μg; and budesonide, 800 to 1600 μg and very high dose is fluticasone, 1000 to 2000 μg and budesonide, 1600-3200 μg.

In one example, the condition is refractory asthma. As used herein, the term "refractory asthma" includes patients with "fatal" or "near fatal" asthma as well as the asthma subgroups previously described as "severe asthma" and "steroid-dependent and/or resistant asthma," "difficult to control asthma," "poorly controlled asthma," "brittle asthma," or "irreversible asthma." Refractory asthma can be defined as per the American Thoracic Society guidelines when one or both major criteria and two minor criteria, described as follows, are fulfilled. The major criteria are: In order to achieve control to a level of mild-moderate persistent asthma: (1) Treatment with continuous or near continuous (≥50% of year) oral corticosteroids 2) Requirement for treatment with high-dose inhaled corticosteroids. The minor criteria are: (1) Requirement for daily treatment with a controller medication in addition to inhaled corticosteroids e.g., LABA, theophylline or leukotriene antagonist (2) Asthma symptoms requiring short-acting β-agonist use on a daily or near daily basis (3) Persistent airway obstruction ($FEV_1$<80% predicted; diurnal peak expiratory flow (PEF) variability >20%) (4) One or more urgent care visits for asthma per year (5) Three or more oral steroid "bursts" per year (6) Prompt deterioration with ≤25% reduction in oral or inhaled corticosteroid dose (7) Near fatal asthma event in the past. For the purposes of definition of refractory asthma, the drug (μg/d) and the dose (puffs/d) are as follows: (a) Beclomethasone dipropionate >1,260>40 puffs (42 μg/inhalation) >20 puffs (84 μg/inhalation); (b) Budesonide >1,200>6 puffs; (c) Flunisolide >2,000>8 puffs; (d) Fluticasone propionate >880>8 puffs (110 μg), >4 puffs (220 μg); (e) Triamcinolone acetonide >2,000>20 puffs.

In one example, the condition is acute asthma or non-allergic asthma. As used herein, the term "acute asthma" or "allergic asthma" refers to asthma triggered by allergens (e.g., dust mite feces or pollen) activating mast cells located beneath the mucosa of the lower airways of respiratory tract. Activation of mast cells triggers release of granules that stimulate the nasal epithelium to produce mucus and subsequent contraction of smooth muscle within the airway. This contraction of smooth muscle constricts the airway, causing the characteristic asthmatic wheezing.

In one example, the condition is chronic asthma. "Chronic asthma" is not caused by allergens, but rather a result of the inflammation obtained from acute asthma. The overall effects of acute asthma causes chronic inflammation, which causes the mucosal epithelium to become hypersensitive to environmental responses. So simple environmental agents, such as smoke, can stimulate the hypersensitive epithelium to produce large amounts of mucous and constrict.

In one example, the condition is nasal polyposis.

In one example, the condition is or is characterized by eosinophilia. Exemplary conditions include lung conditions (such as asthma and Loeffler's syndrome), vasculitis (e.g., Churg-Strauss syndrome), chronic eosinophilic pneumonia, inflammatory bowel disease (e.g., colitis (such as, ulcerative colitis) or Crohn's disease), drug-induced eosinophilia, parasitic infections of the intestines, collagen vascular disease (e.g., rheumatoid arthritis), liver cirrhosis, reflux esophagitis, skin conditions (e.g., exfoliative dermatitis or atopic dermatitis), eosinophilic gastrointestinal disorders (e.g., gastroenteritis, esophagitis, gastritis), nasal polyps, hypereosinophilic bronchitis or allergic conjunctivitis.

In one example, the condition is an eosinophilic gastrointestinal disorder. In one example, the condition is esophagitis. In another example, the condition is gastritis. In a further example, the condition is gastroenteritis.

In one example, the autoimmune condition is an autoimmune joint condition, such as, inflammatory arthritis, rheumatoid arthritis or idiopathic arthritis, e.g., juvenile idiopathic arthritis. In one example, the condition is rheumatoid arthritis.

In one example, the autoimmune condition is an autoimmune bowel condition, such as inflammatory bowel disease, such as ulcerative colitis or Crohn's disease.

In one example, the autoimmune condition is an autoimmune skin condition, such as psoriasis.

In one example, the condition is bullous pemphigoid.

In one example, the condition is mastocytosis.

In one example, the condition is mast cell activation syndrome.

In one example, the condition is cancer. Exemplary cancers include bladder cancer and hematologic cancers, such as lymphoma or leukemia. In one example, the cancer is bladder cancer.

In one example, the hematologic cancer is acute myeloid leukemia. In another example, the hematologic cancer is chronic myeloid leukemia.

In one example, the subject is resistant to, does not adequately respond to, or is unsuitable for treatment with another compound used to treat the condition. For example, the subject suffering from an autoimmune or inflammatory or allergic condition is resistant to, does not adequately respond to, or is unsuitable for treatment with a corticosteroid and/or an immunosuppressant and/or cyclophosphamide and and/or methotrexate and/or an anti-TNF antibody or soluble TNF receptor and/or an anti-CD20 antibody and/or an anti-IL6 antibody and/or an anti-CD22 antibody.

The present disclosure also provides a method for inhibiting proliferation of IL-3/IL-5/GM-CSF-responsive cells in vivo, the method comprising administering to a subject a CD131-binding protein or antibody of the disclosure.

The present disclosure also provides a method for inhibiting eosinophil accumulation in vivo, the method comprising administering to a subject a CD131-binding protein or antibody of the disclosure.

Compositions

In some examples, a CD131-binding protein as described herein can be administered orally, parenterally, by inhalation spray, adsorption, absorption, topically, rectally, nasally, bucally, vaginally, intraventricularly, via an implanted reservoir in dosage formulations containing conventional nontoxic pharmaceutically-acceptable carriers, or by any other convenient dosage form. The term "parenteral" as used herein includes subcutaneous, intravenous, intramuscular, intraperitoneal, intrathecal, intraventricular, intrasternal, intrapolyp and intracranial injection or infusion techniques.

Methods for preparing a CD131-binding protein into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or administration into a body cavity or lumen of an organ or joint. The compositions for administration will commonly comprise a solution of a CD131-binding protein dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of a CD131-binding protein of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, a CD131-binding protein of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver a CD131-binding protein of the present disclosure.

WO2002/080967 describes compositions and methods for administering aerosolized compositions comprising antibodies for the treatment of, e.g., asthma, which are also suitable for administration of a CD131-binding protein of the present disclosure.

Combination Therapies

In one example, a CD131-binding protein of the present disclosure is administered in combination with another compound useful for treating a condition described herein, either as combined or additional treatment steps or as additional components of a therapeutic formulation.

For example, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is methotrexate. Alternatively, or additionally, the other compound is cyclophosphamide. Alternatively, or additionally, the other compound is mycophenolate mofetil. Alternatively, or additionally, the other compound is an anti-CD20 antibody (e.g., rituximab or ofatumumab). Alternatively, or additionally, the other compound is an anti-CD22 antibody (e.g., epratuzumab). Alternatively, or additionally, the other compound is an anti-TNF antibody (e.g., infliximab or adalimumab or golimumab) or soluble TNF receptor (e.g., etanercept). Alternatively, or additionally, the other compound is a CTLA-4 antagonist (e.g., abatacept, CTLA4-Ig). Alternatively, or additionally, the other compound is an anti-IL-6 antibody. Alternatively, or additionally, the other compound is a BLys antagonist, such as an anti-BLys antibody (e.g., belimumab).

In another example, the other compound is a chemotherapy drug or other drug used for treating cancer.

In another example, the protein described herein is administered before or after radiotherapy for the treatment of cancer.

The present disclosure also provides a method for reducing the dosage of corticosteroid required to treat a patent suffering from an allergic condition (e.g., asthma or nasal polyposis), the method comprising co-administering a CD131-binding protein of the disclosure and a corticosteroid, wherein the corticosteroid is administered at a lower dose than if it were administered alone or in the absence of the CD131-binding protein. The CD131-binding protein and the corticosteroid need not be administered at the same time, only in such a manner that that have an overlapping effect on the subject (e.g., are both active within the subject at the same time).

Dosages and Timing of Administration

Suitable dosages of a CD131-binding protein of the present disclosure will vary depending on the specific CD131-binding protein, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration or amount of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present disclosure comprises administering a prophylactically or therapeutically effective amount of a protein described herein.

The term "therapeutically effective amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present disclosure to a specific quantity, e.g., weight or amount of protein(s), rather the present disclosure encompasses any amount of the CD131-binding protein(s) sufficient to achieve the stated result in a subject.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific C131-binding protein(s) administered and/or the particular subject and/or the type or severity or level of condition and/or predisposition (genetic or otherwise) to the condition. Accordingly, this term is not to be construed to limit the present disclosure to a specific quantity, e.g., weight or amount of CD131-binding protein(s), rather the present disclosure encompasses any amount of the C131-binding protein(s) sufficient to achieve the stated result in a subject.

For in vivo administration of the CD131-binding protein described herein, normal dosage amounts may vary from about 10 ng/kg up to about 100 mg/kg of an individual's body weight or more per day. For repeated administrations over several days or longer, depending on the severity of the disease or disorder to be treated, the treatment can be sustained until a desired suppression of symptoms is achieved.

In some examples, the CD131-binding protein is administered at an initial (or loading) dose of between about 1 mg/kg to about 30 mg/kg, such as from about 1 mg/kg to about 10 mg/kg, or about 1 mg/kg or about 2 mg/kg or 5 mg/kg. The CD131-binding protein can then be administered at a lower maintenance dose of between about 0.01 mg/kg to about 2 mg/kg, such as from about 0.05 mg/kg to about 1 mg/kg, for example, from about 0.1 mg/kg to about 1 mg/kg, such as about 0.1 mg/kg or 0.5 mg/kg or 1 mg/kg. The maintenance doses may be administered every 7-30 days, such as, every 10-15 days, for example, every 10 or 11 or 12 or 13 or 14 or 15 days.

In some examples, the C131-binding protein is administered at a dose of between about 0.01 mg/kg to about 50 mg/kg, such as between about 0.05 mg/kg to about 30 mg/kg, for example, between about 0.1 mg/kg to about 20 mg/kg, for example, between about 0.1 mg/kg to about 10 mg/kg, such as between about 0.1 mg/kg to about 2 mg/kg. For example, the CD131-binding protein is administered at a dose of between about 0.01 mg/kg to about 5 mg/kg, such as from about 0.1 mg/kg to about 2 mg/kg, such as about 0.2 mg/kg or 0.3 mg/kg or 0.5 mg/kg or 1 mg/kg or 1.5 mg/kg (e.g., without a higher loading dose or a lower maintenance dose). In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the CD131-binding protein is administered every 7 days or every 14 days or every 21 days.

In some examples, at the time of commencing therapy, the mammal is administered the CD131-binding protein on no more than 7 consecutive days or 6 consecutive days or 5 consecutive days or 4 consecutive days.

In the case of a mammal that is not adequately responding to treatment, multiple doses in a week may be administered. Alternatively, or in addition, increasing doses may be administered.

In another example, for mammals experiencing an adverse reaction, the initial (or loading) dose may be split over numerous days in one week or over numerous consecutive days.

Administration of a CD131-binding protein according to the methods of the present disclosure can be continuous or intermittent, depending, for example, on the recipient's physiological condition, whether the purpose of the administration is therapeutic or prophylactic, and other factors known to skilled practitioners. The administration of a CD131-binding protein may be essentially continuous over a preselected period of time or may be in a series of spaced doses, e.g., either during or after development of a condition.

CD131 Detection Assays

The following assays can be performed with a CD131-binding protein of the disclosure, e.g., a CD131-binding protein conjugated to a detectable label as discussed herein. Detection of CD131 or cells expressing same with an assay described herein is useful for diagnosing or prognosing a condition.

An immunoassay is an exemplary assay format for diagnosing a condition in a subject or detecting CD131 and cells expressing same in a sample. The present disclosure contemplates any form of immunoassay, including Western blotting, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, and fluorescence activated cell sorting (FACS)-based assays.

One form of a suitable immunoassay is, for example, an ELISA or FLISA.

In one form such an assay involves immobilizing a CD131-binding protein of the disclosure onto a solid matrix, such as, for example a polystyrene or polycarbonate microwell or dipstick, a membrane, or a glass support (e.g. a glass slide). A test sample is then brought into direct contact with the CD131-binding protein and CD131 or cells expressing same in the sample is bound or captured. Following washing to remove any unbound protein in the sample, a CD131-binding protein that binds to CD131 at a distinct epitope or binds to a different antigen on a cell is brought into direct contact with the captured CD131 or cell. This detector protein is generally labeled with a detectable reporter molecule, such as for example, an enzyme (e.g. horseradish peroxidase (HRP), alkaline phosphatase (AP) or β-galactosidase) in the case of an ELISA or a fluorophore in the case of a FLISA. Alternatively, a second labeled protein can be used that binds to the detector protein. Following washing to remove any unbound protein the detectable reporter molecule is detected by the addition of a substrate in the case of an ELISA, such as for example hydrogen peroxide, TMB, or toluidine, or 5-bromo-4-chloro-3-indol-beta-D-galaotopyranoside (x-gal). Of course, the immobilized (capture) protein and the detector protein may be used in the opposite manner.

The level of the antigen in the sample is then determined using a standard curve that has been produced using known quantities of the marker or by comparison to a control sample.

The assays described above are readily modified to use chemiluminescence or electrochemiluminescence as the basis for detection.

As will be apparent to the skilled artisan, other detection methods based on an immunosorbent assay are useful in the performance of the present disclosure. For example, an immunosorbent method based on the description supra using a radiolabel for detection, or a gold label (e.g. colloidal gold) for detection, or a liposome, for example, encapsulating NAD+ for detection or an acridinium linked immunosorbent assay.

In some examples of the disclosure, the level of CD131 or cell expressing same is determined using a surface plasmon resonance detector (e.g., BIAcore™, GE Healthcare, Piscataway, N.J.), a flow through device, for example, as described in U.S. Pat. No. 7,205,159; a micro- or nano-immunoassay device (e.g., as described in US20030124619); a lateral flow devices (e.g., as described in US20040228761 or US20040265926); a fluorescence polarization immunoassay (FPIA e.g., as described in U.S. Pat. Nos. 4,593,089 or 4,751,190); or an immunoturbidimetric assay (e.g., as described in U.S. Pat. Nos. 5,571,728 or 6,248,597).

Samples and Control Samples

As will be apparent to the skilled artisan, some of the examples described herein require some degree of quantification to determine the level of CD131 or cell expressing same. Such quantification may be determined by the inclusion of a suitable control sample in an assay of the disclosure.

In one example, a suitable control sample is a sample that is derived from a healthy subject or a normal subject.

In the present context, the term "healthy subject" shall be taken to mean an individual who is known not to suffer from a condition associated with CD131, e.g., an inflammatory condition.

The term "normal subject" shall be taken to mean an individual having a normal level of CD131 or cell expressing same in a sample compared to a population of individuals.

The present disclosure also contemplates the control sample as being a data set obtained from a normal and/or healthy subject or a population of normal and/or healthy subjects.

In one example, a method of the disclosure additionally comprises determining the level of CD131 in a control sample, e.g., using a method described herein.

In one example, a sample from the subject and a control sample are assayed at approximately or substantially the same time.

In one example, the sample from the subject and the control sample are assayed using the same method of the disclosure as described herein in any one or more examples to allow for comparison of results.

Kits

The present disclosure additionally comprises a kit comprising one or more of the following:
(i) a CD131-binding protein of the disclosure or expression construct(s) encoding same;
(ii) a cell of the disclosure; or
(iii) a pharmaceutical composition of the disclosure.

In another example, the present disclosure provides a kit comprising a plurality of compounds, wherein together the compounds neutralizing signaling by IL-3, IL-5 and GM-CSF.

In the case of a kit for detecting CD131, the kit can additionally comprise a detection means, e.g., linked to a CD131-binding protein of the disclosure.

In the case of a kit for therapeutic/prophylactic use, the kit can additionally comprise a pharmaceutically acceptable carrier.

Optionally a kit of the disclosure is packaged with instructions for use in a method described herein according to any example.

The present disclosure includes the following non-limiting Examples.

NON-LIMITING EXAMPLES

Example 1: Methods

Cell Culture

FreeStyle™ 293-F (FS293F) cells and the mammalian expression vector pcDNA3.1 were obtained from Invitrogen. Cells were cultured in GIBCO®FreeStyle™ 293 Expression Medium (Life Technologies). All tissue culture media were supplemented with penicillin/streptomycin/fungizone reagent (GIBCO®, Life Technologies) and cells were maintained at 37° C. in incubators with an atmosphere of 8% $CO_2$.

Cytokines and Antibodies

Recombinant human GM-CSF encoding the P6YY substitution to facilitate radio-iodination was prepared from *E. coli* as previously described (Hercus et al., *Proc Natl Acad Sci USA* 91:5838-5842, 1994) Recombinant human IL-3 comprising residues 13-121 and the W13Y substitution to facilitate radio-iodination (Murphy et al., *Growth Factors* 28:104-110, 2010) was expressed and purified from *E. coli*. Carrier-free recombinant human IL-5 was purchased from R&D Systems (Minneapolis, MN). Cytokines (IL-3, GM-CSF) for cellular assays were purchased from R&D Systems (Minneapolis, MN). Anti-human IgE antibody (ε-chain specific) was purchased from Sigma (St. Louis, MO, USA) and human myeloma IgE was purchased from Calbiochem Darmstadt, Germany.

Generation of Hybridomas

Fifty μg of Hexa-His tagged shCD131 protein was injected intraperitoneally into BALB/c mice deficient in both se and $β_c$ and $β_{IL-3}$ Scott et al. *Blood* 96:1588-1590, 2000). The mice received a further 2×4 weekly injections of the same dose at the same site. Hybridomas were generated essentially as previously described (Nicola et al., *Blood* 82:1724-1731, 1993) except that spleen cells were fused with Sp2/0 myeloma cells. Individual hybridomas (3H3 which was directed against a C-terminal Hexa-His tag, and anti-hβc mAbs 7H12 and 3F1) were re-cloned by limiting-dilution. Hybridomas were cultured in Hybridoma SFM medium supplemented with 0.5-1.0% low IgG FCS (GIBCO®, Life Technologies) in roller bottles at 37° C.

Generation of cDNA Expression Plasmids

Human beta common receptor cDNA (CD131; GenBank Accession no. P32927) and amino acid mutants of the CD131 were codon-optimised for human expression and synthesized by Geneart® (Life Technologies) each with a Kozak consensus sequence (106) (GCCACC) immediately upstream of the initiating methionine (+1). Full-length transmembrane CD131 mutants and soluble CD131 (sCD131) variants (truncated after Ser438 with C-terminal 6× Histidine-tags fused in-frame) were generated using standard PCR-based mutagenesis techniques. Once each cDNA was completed, it was digested with NheI and XhoI and ligated into pcDNA3.1 (Invitrogen, Life Technologies)

The human Interleukin-3 receptor alpha chain cDNA (Hu-IL3R α chain; GenBank Accession no. NP_002174), Human Granulocyte-Macrophage Colony Stimulating Factor Receptor alpha chain cDNA (GM-CSFR α chain, GenBank Accession no. NP_006131) and Human Interleukin-5 receptor alpha chain isoform 1 (Hu-IL5R α chain, GenBank Accession no NP_000555) were obtained either from Dr H. Ramshaw (Centre for Cancer Biology, Adelaide, Australia) or Geneart® (Life Technologies) and cloned as described above. Anti-Hu-IL5R α chain antibody cDNA (U.S. Pat. No. 6,018,032) was synthesized by (Geneart®, Life Technologies) on an IgG4pK backbone.

Recombinant Fab fragments of 9A2 and affinity matured variants were generated by cloning the entire light chain and a truncated heavy chain, where a stop codon was introduced after amino acid 241, separately into pcDNA3.1 as described above.

Large-scale preparations of plasmid DNA were carried out using QIAGEN Plasmid Maxi or Giga Kits according to the manufacturer's instructions. The nucleotide sequences of all plasmid constructs were verified by sequencing both strands using BigDye™ Terminator Version 3.1 Ready Reaction Cycle Sequencing and an Applied Biosystems 3130xl Genetic Analyzer.

Transient Transfections for Generation of Recombinant Proteins

Transient transfections of expression plasmids using FS293F cells were performed using 293 fectin transfection reagent (Invitrogen, Life Technologies) according to the manufacturer's instructions either in a Cellbag 2L (GE Healthcare Life Sciences) on a 2/10 Wave Bioreactor system 2/10 (GE Healthcare) or in 50 ml Bioreactor tubes (Sartorius) for 6 days 37° C. in incubators with an atmosphere of 8% $CO_2$. Cultures were supplemented at 4 hours post-transfection with Pluronic F68 (Gibco, Life Technologies), to a final concentration of 0.1% v/v and 24 hours post-transfection with LucraTone Lupin (Millipore) to a final concentration of 0.5% v/v.

The cell culture supernatants were harvested by centrifugation at 2500 rpm and were passed through a 0.45 µm filter (Nalgene) prior to purification.

Antibody Purification

All mAbs and recombinant Fab fragments were affinity-purified using HiTrap MabSelect SuRe or KappaSelect (1 ml, GE Healthcare Life Sciences) chromatography resins respectively and then desalted with a HiPrep™ 26/10 Desalting column (GE Healthcare Life Sciences) on an ÄKTAxpress high throughput chromatography system (GE Healthcare Life Sciences). Fab fragments were generated by digestion of the purified antibodies using immobilized papain-agarose (Sigma, St. Louis, Missouri) and purified using Protein A and size exclusion chromatography. The filtered cell culture media (500 ml) was applied to the column that had been equilibrated 1×MTPBS buffer, at a rate of 1 ml/min and washed sequentially with 1×MTPBS pH 7.3 (10 ml) and 10 mM Tris, 150 mM NaCl pH 7.2 (80 ml) in the presence of 0.5 M Arginine to facilitate endotoxin removal. The bound antibody was then eluted with 8 ml 0.1 M NaAcetate pH 3.0 (or 0.1 M Glycine pH 2.5) and immediately applied to the desalting column. Protein fractions were pooled and concentrated using an Amicon Ultra-Cel 50K centrifugal device (Millipore) prior to sterile filtration using 0.22 µm filters. Antibody purity was assessed by SDS-PAGE and protein visualized using PlusOne™ Coomassie™ Blue PhastGel™ R-350 Stain, as per the manufacturer's instructions and antibody concentration was determined chromatographically by comparison to control antibody standards.

His-Tagged Protein Purification

Soluble CD131 (sCD131) and sCD131 mutants were purified by tandem Nickel and size exclusion chromatography on an AKTA™ express (GE Healthcare Life Sciences) purification system. Column chromatography was generated as per manufacturer's instructions. Post-elution samples were applied directly to a Superdex 200 pg 26/60 column (GE Healthcare Life Sciences) at 4 ml/min in PBS and fractions collected. Peak fractions containing sCD131 fractions were pooled after additional size exclusion analysis and sterile-filtered for subsequent testing.

Antibody Generation

A phagemid FAB library was screened for phagemids that bound the recombinant extracellular domain of the human βc receptor (CD131) fused to the Fc region of human IgG1 (CD131-Fc, Apollo Cytokine Research) immobilized on Dynabeads® M-280 Streptavidin (Invitrogen Life Technologies) by biotin-anti-human Fc antibody capture (Jackson ImmunoResearch Laboratories). The selection was done following methods described previously (Hoet et al., Nat Biotechnol 23:344-348, 2005). Prior to selection phage input was depleted for non-specific binders to either streptavidin or Fc by 5 consecutive incubations with a 1:1 mixture of streptavidin beads per se, or coated with an irrelevant human IgG antibody via biotin anti-human Fc capture. Three rounds of selection were performed by incubating the depleted phage input with decreasing concentrations of immobilized CD131-Fc (15 µg, 10 µg and 5 µg) in 2% milk/PBST (MTPBS, 0.1% Tween-20) for 20 minutes at room temperature and then washed 12 times. Selected phage clones were amplified in log phase E. coli TG1 cells and the Fab-phagemid rescued by superinfection with M13K07 helper phage prior to purification using standard protocols (Barbas et al., Proc Natl Acad Sci USA 88:7978-7982, 1991). Individual clones were picked after the second and third round of selection and the Fab cassettes and light chains were PCR-amplified and sequenced essentially as described (Hoet et al., supra). Competitive phage ELISA was used to screen for high affinity clones. A selection of unique antibody clones were reformatted to express full-length IgG4 antibodies with the serine 241 to proline hinge region mutation (Angal et al. Mol Immunol 30:105-108, 1993) and a kappa light chain (referred to as IgG4pK) by cloning the entire light chain (variable and constant domains) and the variable domain of the heavy chain from the selected phage-derived Fab constructs into the pRhG4 vector (Jostock et al., Immunol Methods 289:65-80, 2004).

Affinity Maturation of 9A2

Clone 9A2 was affinity matured by randomization of CDRs with primers that included a 19 amino acid combination (without cysteine) (SEQ ID NOs: 149-162). Seven different libraries were constructed using methods previously described Sidhu et al., Methods Enzymol 328:333-363, 2000) using "stop template" versions of pTac-geneIII-9A2 Fab where for each phagemid, a germline stop template (GeneArt®, Life Technologies) was created by replacing 18 codons (6 amino acid residues) in all CDRs with TAA stop codons (SEQ ID NOs: 163-176). Amino acids in the CDRS were numbered according to Kabat (1991, as discussed herein). Each stop template was used as a template for the Kunkel mutagenesis method (Kunkel et al., Methods Enzymol 154:367-382, 1997) with mutagenic oligonucleotides outlined in Supplemental Table 5. The mutagenesis reactions were electroporated into E. coli SS320 then phage production initiated with addition of M13-KO7 helper phage prior to incubation at 30° C. for 18 h. Phage were purified using standard protocols (Barbas et al., supra). Mutagenesis efficiencies ranged from 27% to 100% as assessed by sequencing of 12 clones picked randomly from each library. Primer 3254 (5' GGTTCTGGCAAATATTCTG 3', SEQ ID NO: 199) was used to sequence clones from libraries L1, L3.1 and L3.2 and primer SeqCL (5' ATGCGTGC-GAAGTGACCCATCAGG 3', SEQ ID NO: 200) was used to sequence clones from libraries H1.1, H2.1, H3.1 and H3.2. Each library contained $4\times10^9$-$1.05\times10^{10}$ individual clones.

Libraries were subjected to five rounds of selection in solution with immobilized CD131-Fc where the concentration was reduced 10-fold with each round, from 100 nM to 10 pM in Round 5 for all libraries, except H3.1 which was reduced 10-fold from 100 nM to 10 nM in Round 2, and kept constant at 10 nM in all consecutive selection rounds. Affinity matured phage were isolated from the libraries essentially as described above for antibody generation. Unique phage clones were identified by sequencing 20 randomly selected clones from each library using the primers 3254 (for light chain clones) and SeqCL (for heavy chain clones) and consensus sequence was determined. Unique variants were reformatted into full-length human IgG4/Kappa antibodies as described above.

Variants 9A2-VR24 and 9A2-VR39 were selected for further affinity maturation. Libraries were based on the amino acid sequences of 9A2-VR24 and 9A2-VR39. Stop templates generated by GeneArt® (Life Technologies) are listed in above and libraries constructed using the methods described above with mutagenic oligonucleotides above. The mutagenesis efficiencies ranged from 50% to 90% as assessed by sequencing 12 clones selected randomly from each library. Each library contained $0.25\times10^9$-$2.5\times10^9$ individual clones. Libraries were subjected to four rounds of selection in solution with decreasing concentration of immobilised CD131-Fc, using methods essentially as described above. The target concentration was reduced 10-fold with each round, from 100 pM down to 1 pM in Round 4.

Following Round 4 of selection, beads with 1 pM output phage and the corresponding blank sample were washed as described above and resuspended in PBS. This was either subsequently eluted with 50 mM (Dithiothreitol) DTT then neutralized or incubated at room temperature for 1 h in the presence of excess immobilized CD131-Fc (1 nM) to select for variants with improved off-rates, followed by washing, elution and neutralization as described above. Unique variants from each library were identified by sequencing using the SeqCL primer and reformatted into fully human IgG4/kappa antibodies as described above.

ELISA

Phagemid-Fab clones were tested for target binding by ELISA. Purified CD131-Fc protein or irrelevant human IgG antibody were coated at 2 µg/ml in MTPBS; pH 7.3 onto 96-well Maxisorp ELISA plates overnight at 4° C. Plates were blocked for 2 hours at 37° C. with 200 µl/well of 5% skim milk/PBST, washed twice with PBST before incubation with phage supernatant (100 µl/well) for 90 minutes at room temperature. Plates were washed ×5 with PBST prior to incubation with anti-M13-HRP antibody (GE Healthcare) diluted 1:10,000 in PBST. Plates were washed ×6 with PBST and signal developed with 100 µl TMB/E substrate (Chemicon International, Inc). The reaction was stopped with 2 M Phosphoric acid (50 µl/well) and measured at 450 nm. To determine approximate binding affinities of phagemid clones to CD131-Fc protein, competition ELISAs were performed. The phage supernatant was diluted with 2% skim milk/PBST to give an absorbance 450 nm value of 1.5 from extrapolating phage titration ELISA results. Prior to addition of 50 µl/well of appropriately diluted phage supernatant, an equal vol of competitor CD131-Fc protein was added per well at a starting concentration of 2.5 µM and subsequently diluted 4-fold in 2% skim milk/PBST.

Binding Affinity Determination

Binding kinetics were measured using SPR with a BIAcore™ A-100 instrument (GE Healthcare Life Sciences). An anti-C-terminal Hexa-His antibody (3H3) was immobilized on spots 1, 2, 4 and 5 of each flow cell of a CM-5 sensor chip (GE Healthcare Life Sciences) using amine-coupling chemistry (116). The 3H3 mAb was injected for 7 minutes at a concentration of 30 µg/ml in 10 mM $CH_3COONa$, pH 5.0 and typically resulted in an immobilization level of between 13000 and 15000 response units (RU). As sh$\beta_c$ is a dimer, kinetics assays were performed with sh$\beta_c$ captured on the sensor surface, and purified Fab injected as the analyte. Avidity effects were avoided by the use of Fab rather than whole IgG.

shCD131 was captured on spots 1 and 5 of each flow cell for 2 minutes at a concentration of 0.4 µg/ml. For 9A2 analysis purified Fab was injected over each flow cell for 2 minutes and dissociation was monitored for a further 5 minutes. For some analysis purified Fab was injected over each flow cell for 3 minutes and dissociation was monitored for a further 10 minutes. Regeneration of the surface was performed after each cycle with a 40 second injection of 25 mM glycine, pH 2.0. The analysis was performed with Fabs at several concentrations between 100 and 0.31 nM, with each concentration analyzed twice and in random order. The analysis was performed at a flow rate of 30 µl/min in HBS-EP buffer (10 mM Hepes, 150 mM NaCl, 3 mM EDTA, 0.005% Tween 20, pH 7.4) at 37° C. Responses from spots 2 and 4 of each flow cell, (in which sh$\beta_c$ was not captured, but otherwise treated identically), were subtracted from those of spots 1 and 5 respectively to produce reference subtracted data. Reference subtracted responses from a blank injection comprising buffer alone were subtracted from the resultant sensorgrams to produce double referenced data suitable for kinetic analysis. Double-referenced sensorgrams were fitted using non-linear regression to a model describing 1:1 kinetics, including a term for mass transport limitation. The $R_{max}$ value was fitted locally to account for slight deviations in the level of sCD131 captured, with association rate ($k_a$), dissociation rate ($k_d$) and equilibrium dissociation constant ($K_D$) fitted globally.

Epitope Mapping

Mapping of the shCD131 epitope was performed by measurement of the affinity of Fabs for various alanine point mutants of shCD131 essentially as described above, with the following exceptions. Each shCD131 mutant was captured for 120 seconds at concentrations between 1 and 5 µg/ml. For kinetic analysis, purified recombinant Fabs were injected for 2 minutes, and dissociation was monitored for a further 2 minutes. For steady-state affinity analysis, Fab was injected for 2 or 3 minutes and dissociation monitored for 60 seconds. Fab concentrations ranged from 16 µM to 3.9 nM in two-fold dilutions. The assays were conducted at 25° C. All sensorgrams were reference subtracted as described above. For determination of steady-state affinity ($K_D$ only), the response at the end of the binding phase was used to fit the data to a single-site binding model. Kinetic parameters were determined as described above. The kinetics of two control Fabs (7H12 and 3F1) with epitopes distinct from 9A2 were also determined for each point mutant to establish whether the mutation had caused structural perturbations to shCD131. 7H12 and 3F1 bind epitopes within domain 4 and 3 of h$\beta_c$, respectively (data not shown).

Crystallization of the Fab Complex

The Fab complex was purified from a mixture of monomeric components by size exclusion chromatography. All crystallization trials of the complex were carried out at 18° C. using commercially available protein crystallization screens with the protein at a concentration of 6 mg/ml. Crystallization trials were set up using an Art Robbins liquid handler (Gryphon) in 96-well sitting drop format. Rectangular plate shaped crystals appeared between 2-3 days in 40% PEG 200 and 100 mM Tris pH 8.5 from the PEGs Suite (Qiagen 130904). Crystals were optimized by the hanging-drop vapour-diffusion method.

Several pre-crystallization and post crystallization methods were used to optimize crystal diffraction. Treatment of crystals with 0.3% to 1% of gluteraldehyde (Sigma-Aldrich 111-30-8) for 15 minutes to 1 hr improved diffraction from 8 Å to 4 Å. After screening several crystals, three partial datasets were combined to obtain complete dataset at 3.9 Å resolution.

Structural Determination of the Fab Complex

Data collection was carried out with a 20% attenuated beam. The crystals belonged to the C2 space group with unit cell dimensions of a=99.95, b=71.28, c=221.23. Data were scaled and processed using XDS (Kabsch W. Xds. Acta crystallographica Section D, Biological crystallography 2010; 66:125-32) and Aimless (Evans P R, Murshudov G N. How good are my data and what is the resolution? Acta crystallographica Section D, Biological crystallography 2013; 69:1204-14) and molecular replacement was carried out using Phaser (CCP4 suite) (McCoy A J, Grosse-Kunstleve R W, Adams P D, Winn M D, Storoni L C, Read R J. Phaser crystallographic software. Journal of applied crystallography 2007; 40:658-74). The CD131 ectodomain structure (PDB 2GYS) was modified to a partial CD131 dimer consisting of domains D4 and D1 only and was used as a search model to locate the CD131 molecule. The Fab molecule was located using PDB 3HI5 as the search model (sequence similarity of ~84% for heavy chain of 9A2-VR24.29) after deleting the CDR loops. A single solution comprising a partial CD131 dimer (comprising domains D1 and D2 from monomer A and domains D3 and D4 from monomer B) and one molecule of the Fab comprising heavy (H) and light (L) chains was obtained with an $R_{work}/R_{free}$, of 0.38/0.45 after first round of rigid body refinement. Initial electron density was clearest for the Fab molecule and domains D4 and D1 of CD131, while density for CD131 domains D2 and D3 was the weakest. The initial Fab model was further improved by iterative cycles of model building in Coot and model refinement using Phenix.

Although the electron density maps for domains D4 and D1 of CD131 and the variable domains of Fab H and L chains was continuous, no electron density was observed for parts of D2 and D3 of CD131 and parts of the constant domains of the Fab H and L chains even at the end of refinement. The structure was refined to a final $R_{work}/R_{free}$ of 0.30/0.34. The structure was validated using Molprobity.

Cell Surface Receptor Binding Assays

Cytokines and antibodies were radio-iodinated using Pierce Pre-Coated Iodination tubes (Thermo Scientific) according to the manufacturer's instructions. MAb binding to cells expressing hβc was determined by incubating 1-2× $10^6$ cells with radio-iodinated mAb at a range of concentrations at 23° C. for 1-2 hours with gentle mixing. Cell suspensions were then centrifuged through fetal calf serum (FCS) and radioactivity associated with the cells pellets was assessed by counting in a Wizard² 2470 Automatic Gamma Counter (Perkin Elmer, Rowville, VIC, Australia). Non-specific binding was assessed for each radio-iodinated mAb in the presence of at least a 500-fold excess of unlabeled mAb. Dissociation constants and receptor numbers were calculated using the EBDA and LIGAND programs (117) (KELL Radlig, Biosoft, Cambridge, UK). Competition binding assays were performed essentially as previously described (41). Briefly 1-2×$10^6$ cells were incubated with mAb or cytokine competitor at a range of concentrations at 4° C. for 45 minutes with gentle mixing. Radio-iodinated cytokine or mAb was then added and the mixture incubated at 23° C. for a further 1-2 hours with gentle mixing. Cell suspensions were then centrifuged through FCS and radioactivity associated with the cells pellets assessed by counting.

TF-1 Proliferation Assays

TF-1 cells were maintained in RPMI media with 10% FCS, 1× glutamine, 1× penicillin/streptomycin and 2 ng/ml hGM-CSF (R&D Systems) at 37° C. and 5% $CO_2$. Cells were starved of growth factor for 18 hours, plated in 96 well flat bottom plates at 1×$10^4$ cells/well then treated with test antibodies for 30 minutes prior to the addition of IL-3 (R&D Systems), IL-5 (R&D Systems) or GM-CSF. Cells were incubated at 37° C. and 5% $CO_2$ for 72 hours and pulsed with $^3$[H]-thymidine for the final 6 hours before harvesting to glass filters. $^3$[H]-thymidine incorporation was determined by liquid-scintillation counting with a Beckman β-counter.

Cell Signaling Assays

GeneBLAzer® TF-1 bla pStat5 Assay

TF-1 bla cells (Invitrogen) were cultured in RPMI with 10% FCS, 0.1 mM Non-Essential Amino Acids (NEAA), 1 mM sodium pyruvate, pen/strep, Blasticidin (Invitrogen, Life Technologies) (5 μg/ml) and hGM-CSF (2 ng/ml). Prior to assay, cells were washed 3× with PBS with 0.1% FCS to remove growth factor then resuspended in assay media (Opti-MEM with 0.5% FCS, 0.1 mM NEAA, 1 mM sodium pyruvate, pen/strep) and incubated at 37° C. and 5% $CO_2$ for 18 hours. Cells were plated in assay media at 1.2×$10^5$ cells per well in 96 well flat, clear bottom, black-walled plates then treated with test antibodies for 30 minutes prior to the addition of IL-3 (R&D Systems) or GM-CSF (R&D Systems). Cells were incubated at 37° C. and 5% $CO_2$ for 5 hours then FRET B/G substrate (Invitrogen, Life Technologies) added for 2.5 hours before reading (Invision, Perkin Elmer).

Intracellular pSTAT5 Staining

Transfected or non-transfected FS293F cells were plated in 96 well round bottom plates at 5×$10^5$ cells/well then treated with IL-3 (R&D Systems), IL-5 (R&D Systems) or GM-CSF (R&D Systems). Cells were incubated at 37° C. and 5% $CO_2$ for 20 min then supernatant removed and cells fixed in 2% formaldehyde at 37° C. and 5% $CO_2$ for 10 min. Cells were washed ×2 with cold PBS, 0.1% BSA then permeabilized with 90% ice-cold methanol for 20 min. Cells were washed as above the incubated with anti-phospho-STAT5-PE antibodies (BD Biosciences) for 1 hour at room temperature. Cells were washed again, resuspended in 200 μl PBS, 0.1% BSA and analyzed by flow cytometry.

Primary Human Cell Activation Assays

Isolation of Neutrophils, Eosinophils, Basophils, pDCs and Mast Cells.

Neutrophils, eosinophils, basophils were isolated from the buffy coats from healthy donors (Australian Red Cross Blood Service (ARCBS), Melbourne, Victoria and Adelaide, South Australia). Peripheral blood mononuclear cells (PBMCs) were separated from granulocytes and red blood cells by centrifugation over Ficoll-Paque™ PLUS (GE Healthcare Life Sciences) density gradients. Neutrophils were separated from the red blood cell pellet by dextran sedimentation. Neutrophils were washed with cold PBS and red-blood cells were lysed by hypotonic shock. The red blood cell pellet containing granulocytes was lysed with Ammonium Chloride Solution (Stem Cell Technologies) and eosinophils were isolated using a MACS® Eosinophil Isolation Kit (Miltenyi Biotec). Basophils and pDCs were isolated from the PBMC fraction using a MACS® Basophil or pDC Isolation Kits (Miltenyi Biotec). HCMCs were derived from the $CD34^+$ progenitor cell fraction isolated from the PBMC fraction using MACS® CD34 Microbeads (Miltenyi Biotec). Isolated $CD34^+$ cells were transferred into 6-well plates at a density of 5×$10^6$ cells/ml in IMDM supplemented with 1% insulin-transferrin-selenium, 5×$10^{-5}$M 2-mercaptoethanol, 1% penicillin-streptomycin, 0.1% BSA, 100 ng/ml rhSCF, 50 ng/ml rhIL-6 and 5 ng/ml rhIL-3 and placed in a $CO_2$ incubator at 37° C. The cytokine-supplemented medium was replaced weekly for a total of 10 weeks after which >95% mast cell purity was achieved. rhIL-3 was omitted from the culture medium after the first 2 weeks of culture and from week 6 onwards 10% FCS was added to the culture medium.

Basophil Assays.

For detection of IL-8 release from basophils, isolated basophils were plated at 1×$10^5$/well in round bottom 96-well plates then test antibodies were added for 30 minutes prior to the addition of IL-3 (R&D Systems). Cells were incubated at 37° C. and 5% $CO_2$ for 18 h and cell-free supernatants were collected and assayed for IL-8 by ELISA (R&D systems).

Eosinophil Assay.

Purified eosinophils were plated at $1\times10^5$ cells/well in round bottom 96-well plates then test antibodies were added for 30 minutes prior to the addition of IL-5 (R&D Systems). Cells were incubated at 37° C. and 5% $CO_2$ for 2 hours, fixed with 2% formaldehyde for 20 minutes and analyzed for change in forward scatter by flow cytometry.

Purified eosinophils were plated at $1\times10^4$/well in flat bottom 96-well plates then test antibodies were added for 30 minutes prior to the addition of IL-5 (R&D Systems), IL-3 (R&D Systems) and GM-CSF (R&D Systems). Cells were incubated at 37° C. and 5% $CO_2$ for 5 days and cell number determined with the ViaLight®Plus Cell Proliferation and Cytotoxicity BioAssay Kit (Lonza).

Neutrophil Assays

Purified neutrophils were plated at $1\times10^5$/well in round bottom 96-well plates then test antibodies were added for 30 minutes prior to the addition of GM-CSF (R&D Systems). Cells were incubated at 37° C. and 5% $CO_2$ for 24 hours, fixed with 2% formaldehyde for 20 minutes and analyzed for change in forward scatter by flow cytometry.

Mast Cell Assays

Ten-week old cultured peripheral blood-derived HCMCs were pre-incubated with test antibodies for 1 h prior to the addition of IL-3 (1 ng/ml), IL-5 (10 ng/ml) or GM-CSF (1 ng/ml) for a further 48 h incubation. Human myeloma IgE (0.5 µg/ml) was added at 24 h before anti-IgE Ab stimulation with anti-IgE (1 µg/ml) in the presence of IL-3 (1 ng/ml), IL-5 (10 ng/ml) or GM-CSF (1 ng/ml) for 18 h for TNF or 8 h for IL8 and IL-13 release. Cytokine levels in the supernatant were measured by ELISA. Levels of human TNF-α in cell culture supernatants were determined using a human TNF-α ELISA Ready-SET-Go! Kit (eBioscience, San Diego, CA, USA).

Human Bone Marrow Colony Forming Assays

For colony forming unit (CFU) assays, CD34+ BM cells (Stem Cell Technologies) were seeded at $1\times10^3$ cells per 35 mm dish in IMDM containing 1% methylcellulose supplemented with 30% fetal calf serum, 1% BSA, 50 ng/ml hSCF, 10 ng/mL hGM-CSF, 10 ng/ml hIL-3 (MethoCult H4534 Classic; Stem Cell Technologies) and 10 ng/ml hIL-5 (Peprotech). Cultures were incubated at 37° C. in a humidified atmosphere of 5% $CO_2$ for 14-16 days after which colonies were enumerated.

Nasal Polyp (NP) Cellular Assays

Fresh NP specimens were obtained from Victoria Parade Surgical Centre (VPSC) with Institutional Ethics Approval and under informed written consent. NPs were cut into small pieces and placed into 3 ml media (RPMI with 10% FCS, 1× glutamine, 1× penicillin/streptomycin) per well in 6 well plates. The tissue was incubated for 18 hours at 37° C. and 5% $CO_2$ then a single cell suspension was collected by passing media containing tissue and cellular exudate through a 70 µm nylon filter (BD Biosciences). Red-blood cells were lysed then cells were plated at $1\times10^6$/well in 3 ml media in 6 well plates. Cells were incubated for 6 hours at 37° C. and 5% $CO_2$ to remove adherent cells, then non-adherent cells were plated at $1-5\times10^4$ cells/well in 96 well flat bottom plates in the presence of test antibodies or Prednisolone (50 µM, Sigma). Cell cultures were incubated for 5 days at 37° C. and 5% C02 then supernatants collected for cytokine and chemokine analysis. Cytokine levels were determined using human cytokine/chemokine Luminex kits (Millipore) as per the manufacturer's instructions. Data acquisition and analysis was carried out on a Luminex-100 machine (Luminex, Texas USA) with MasterPlex software. The number of viable cells remaining was determined using the ViaLight®Plus Cell Proliferation and Cytotoxicity BioAssay Kit (Lonza).

Inhaled Allergen Challenge Assays

Subjects with stable, mild atopic asthma who were also non-smokers, free of other lung diseases and not pregnant with baseline FEV1≥70% of predicted were chosen for allergen challenge. The study was approved by the McMaster Faculty of Health Sciences/Hamilton Health Sciences Research Ethics Board and signed informed consent was obtained from subjects. Allergen challenge was performed as previously described (O'Byrne et al., *Am Rev Respir Dis* 136:740-751, 2987). Sputum samples were mixed in PBS (without DTT) to disperse the cells, and the mixture filtered to remove mucous before centrifugation. The cell pellet was resuspended at a concentration of $1\times10^6$ cells/ml in RPMI with 100 U/ml pen/strep and 10% FCS. A cytospin was made for differential cell counting, including percentage eosinophils, neutrophils, macrophages, lymphocytes, and bronchial epithelial cells. The mixed cell population was incubated for 24 hours with 9A2-VR24.29 at a final concentration of 100 µg/ml. Outcomes were compared to incubation with an irrelevant isotype control antibody at a final concentration of 100 µg/ml. No growth factors were added. Cells were incubated at 37° C. for 24 hours in a humidified incubator with 5% carbon dioxide. After 24 hours, the cells were removed from the wells, washed, and re-suspended in Binding Buffer (BD Pharmingen, Cat no. 556454). The cells were co-stained with specific cell lineage markers using the following antibodies and isotype controls: anti-CD16 FITC anti-IgG1 FITC, anti-CD3 PeCy7, anti-IgG1 PeCy7, anti-CD68 APC, anti-IgG2b APC, Siglec 8-PE and anti-IgG1 PE, and the viability of specific populations evaluated at baseline and 24 h post allergen-challenge.

Nasal Polyp Xenograft Assays

A human nasal polyp xenograft model was produced essentially as described in Bernstein et al., *Ann Otol Rhinol Laryngol* 115:65-73, 2006; Bernstein et al., *Ann Otol Rhinol Laryngol* 118:866-875, 2009; and Bernstein et al., *Ann Otol Rhinol Laryngol* 121:307-316, 2012 using Rag2$^{-/-}$ Il2rg$^{-/-}$ hIL-3/GM-CSF knock-in mice. A prophylactic approach was used in which Rag2$^{-/-}$ Il2rg$^{-/-}$hIL-3/GM-CSF knock-in mice were implanted, in subcutaneous pockets, with 4 mm$^3$ pieces of non-disrupted human nasal polyps (obtained from 9 different patients undergoing surgery for nasal polyposis) that had been pre-treated for 1 hour with 100 µg/ml either 9A2-VR24.29 or isotype control antibody. After 1 week the mice were injected (intra-polyp) with 9A2-VR24.29 (5 mg/kg) or isotype control antibody (5 mg/kg) weekly for 4 weeks and the size of the polyps monitored externally.

Preparation of Bone Marrow and Peripheral Blood Cells for Quantification of Eo/Baso-CFU and GM-CFU from CD34+ Cells Populations.

Blood samples (80 ml) and bone marrow aspirates (5 ml) were collected from mild atopic asthmatic subjects pre- and 24 h post-allergen challenge. Low-density mononuclear cells (MNCs) were isolated by sedimentation on Accuprep™ density gradients (Cedarlane, AN551). Non-adherent mononuclear cells (NAMNCs) were resuspended in Iscove's 2+(Iscove's modified Dulbecco's medium with 1% pen/strep (Gibco, 15140-122) and 1% 2-mercaptoethanol (Sigma, M3148) and placed in Methocult® cultures (Stemcell Technologies, 04236) in the presence of 16% fetal bovine serum (Sigma, 13G210) and IL-5 (10 ng/ml) (R&D Systems, 205-IL-005), IL-3 (25 ng/mL) (R&D Systems, 203-IL-010), GM-CSF (10 ng/ml) (R&D Systems, 215-GM-010), or a combination of all 3 growth factors. The NAMNC cells were cultured at a concentration of $0.5 \times 10^6$ cells/ml for 2 weeks at 5% $CO_2$, with high humidity at 37° C. The number of Eo/B CFU was quantified in duplicate plates using an inverted light microscope at 40× magnification and the average number of colony-forming units per plate was calculated. A colony was defined as a cluster of eosinophils/basophils with a minimum density of 40 cells.

Example 2: Results

Generation of a Neutralizing, Fully Human mAb with Specificity for the Human CD131 Receptor.

A naïve human Fab library was screened using the entire recombinant extracellular region of CD131 to facilitate the identification of Fabs allowing simultaneous antagonism of IL-3, GM-CSF and IL-5 with high potency. Competitive phage ELISA was then used to screen for the highest affinity clones and unique clones were chosen and reformatted as whole IgG4pK antibodies.

Figure 9:
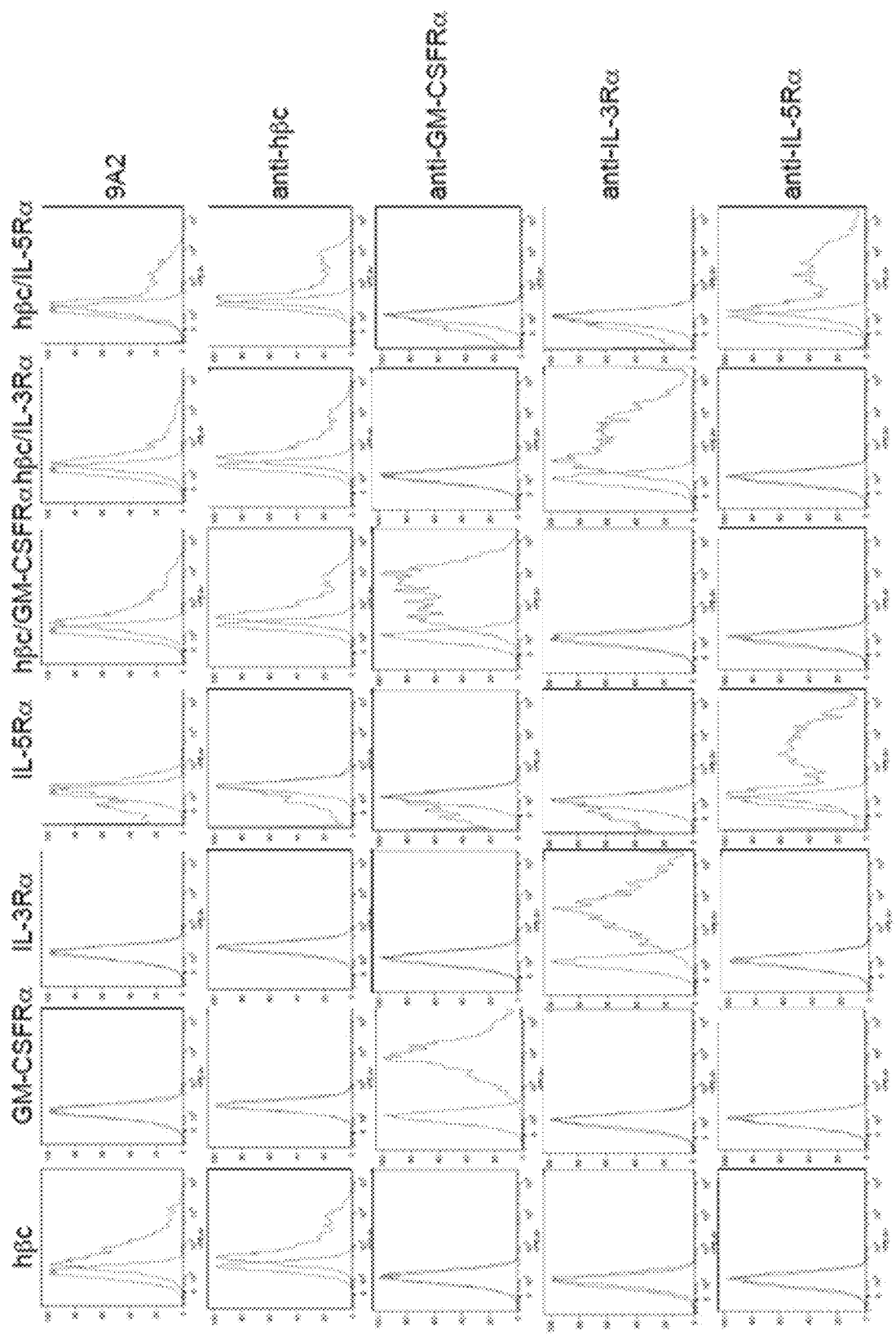
FIG. 9 is a series of graphical representations showing antibody 9A2 binds to cells transiently transfected with human CD131 and not to cells expressing human GM-CSFR α-chain, the IL-3R α-chain or IL-5R α-chain alone as determined by flow cytometry. Control antibodies to the human GM-CSFR α-chain, the IL-3R α-chain or the IL-5R α-chain confirmed expression of these proteins in the transfected cells.

Potency assessment was screened in GM-CSF-dependent TF-1 proliferation assays. Antibody 9A2 was identified that could dose-dependently inhibit IL-3, GM-CSF- and IL-5-induced proliferation of TF-1 erythroleukemic cells (FIGS. 6A-6D). The amino acid sequence of the heavy and light chain variable regions of 9A2 is outlined in FIGS. 5A and 5B. 9A2 also blocked the activity of IL-3 and GM-CSF using a STAT-5 reporter assay in TF-1 cells (FIGS. 7A and 7B). TF-1 cells also proliferate in response to IL-6, IL-4, Epo and SCF. 9A2 did not inhibit the proliferation of TF-1 erythroleukemic cells stimulated with Epo, IL-6, IL-4 and SCF (FIGS. 8A-8D) demonstrating the specificity of this antibody. 9A2 bound specifically to cells expressing human CD131 but not to cells expressing only the human IL-3R α-chain, human GM-CSFR α-chain or human IL-5R α-chain (FIG. 9).

Affinity Maturation of the 9A2 Antibody Results in a 1500-Fold Improvement in Potency.

Figures 7A, 7B:
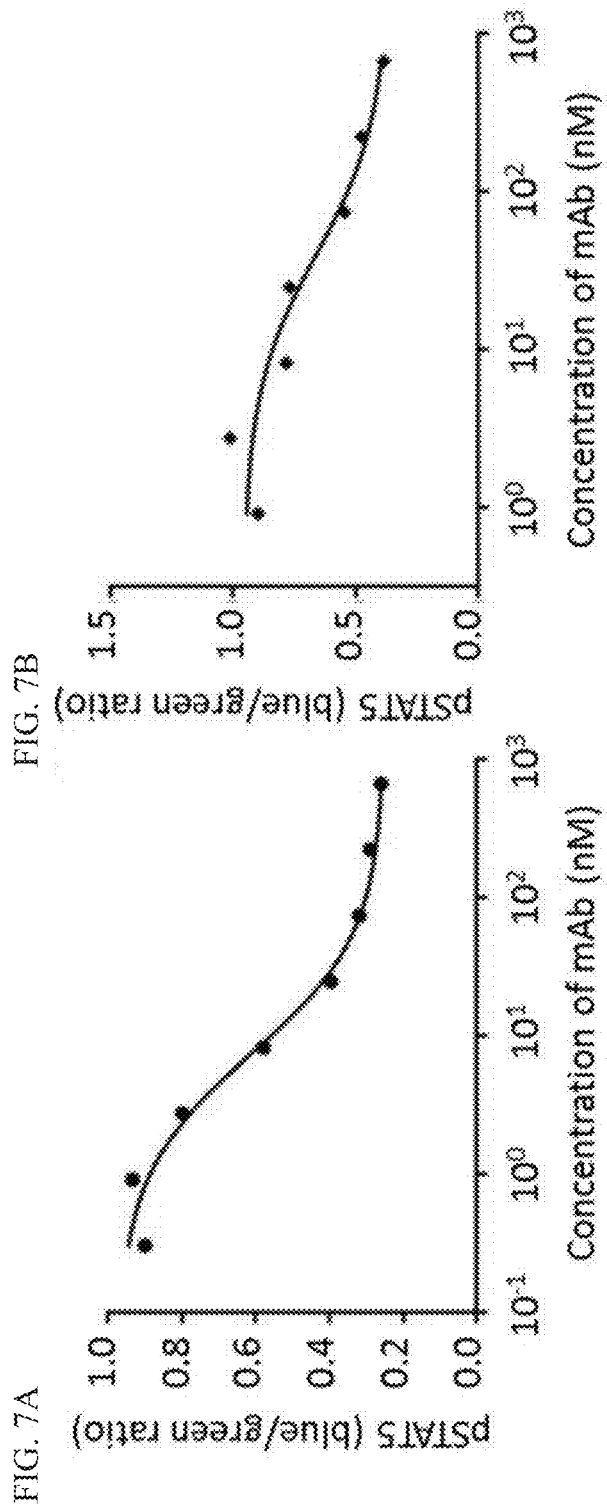
FIGS. 7A and 7B are graphical representations showing results of an assay using TF-1-bla to assess IL-3 (FIG. 7A) or GM-CSF (FIG. 7B) signaling in the presence of antibody 9A2 Histograms show mean and standard error of technical replicates. Representative experiments are shown.
Figure 8A:
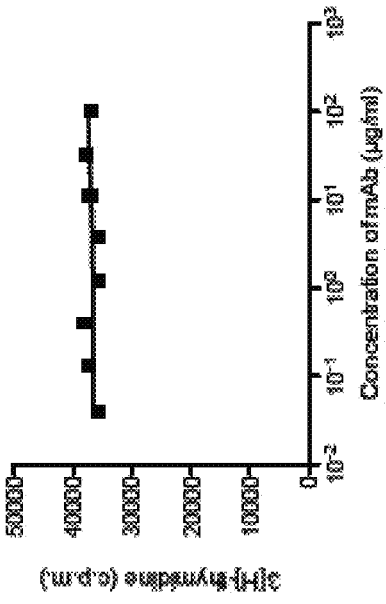
FIGS. 8A-8D are graphical representations showing antibody 9A2 does not neutralize IL-6- (FIG. 8A), IL-4- (FIG. 8B), SCF- (FIG. 8C) or Erythropoietin- (FIG. 8D) stimulated proliferation of TF-1 erythroleukemic cells. Proliferation was assessed by $^3$[H]-thymidine incorporation. Histograms show mean and standard error of technical replicates. All experiments were repeated at least 4 times with the exception of Epo stimulation of TF-1 cells, which was repeated twice.
Figure 8B:
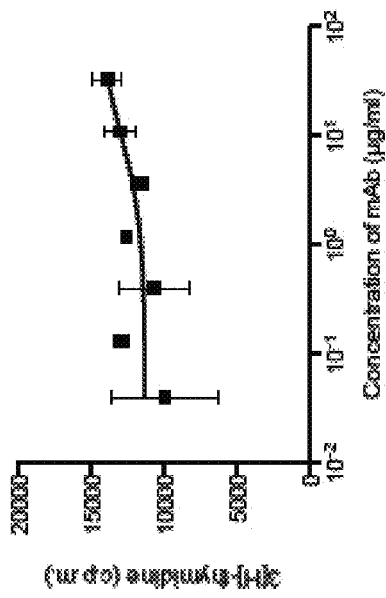
Figure 8C:
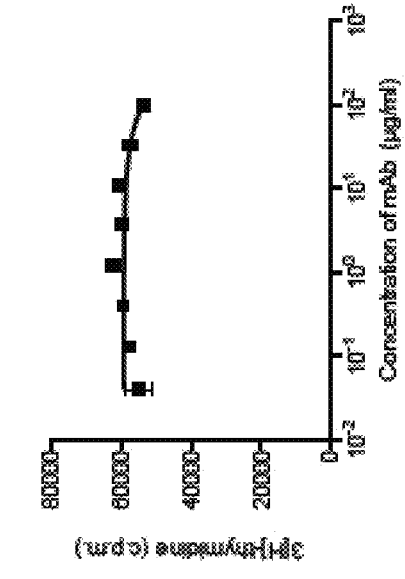
Figure 8D:
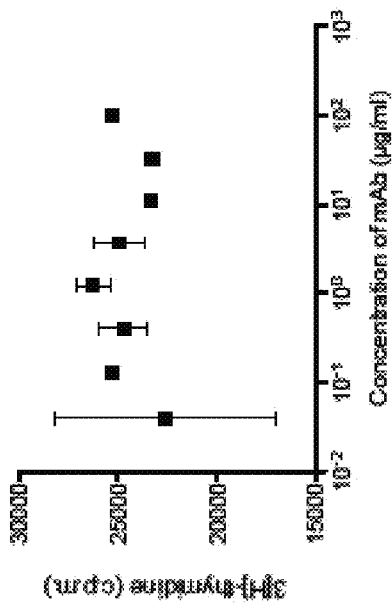

9A2 is an antagonist of GM-CSF and IL-5 activity with an $IC_{50}$ of 456 nM (GM-CSF) in the TF-1 cell proliferation assay (FIG. 6B).

Affinity maturation of this antibody was undertaken to identify variants with higher affinities for CD131 than parental 9A2 and that are able to substantially inhibit IL-3-, GM-CSF- and IL-5-mediated receptor activation at clinically relevant therapeutic doses.

Seven phage libraries each covering 6 amino acid residues and randomized for all 19 possible amino acids (excluding cysteine) were generated to systematically analyze the contribution of each 9A2 CDR (excluding CDR2 of the light chain) to the binding of the antibody to CD131. The location of each library is outlined in FIGS. 5A and 5B. After several rounds of selection unique variants from each library were converted to human IgG4pK molecules, expressed, purified and screened in TF-1 proliferation assays. Representative variants from all libraries were either similar to or showed an improvement in potency compared to parental 9A2 (Table 3) with the exception of those targeting CDR3 from the light chain of parental 9A2.

TABLE 3

List of variants from round 1 of 9A2 affinity maturation.

| Antibody | $k_a$ (1/Ms) | $k_d$ (1/s) (Fab) | $K_D$ (nM) | $IC_{50}$ GM-CSF (nM) | $IC_{50}$ IL-3 (nM) | $IC_{50}$ IL-5 (nM) | pStat5 $IC_{50}$ IL-3 (nM) | pStat5 $IC_{50}$ GM-CSF (nM) |
|---|---|---|---|---|---|---|---|---|
| 9A2 | 2.0E+06 ± 1.7E+05 | 9.6E−02 ± 8.6E−03 | 49 ± 1.3 (N = 6) | 456.0 | 5.96 | 1448 | 7.3 | 40 |
| 9A2-VR1 | | | | 294.0 | | | | |
| 9A2-VR2 | | | | 443.9 | | | | |
| 9A2-VR3 | | | | 101.0 | | | | |
| 9A2-VR4 | | | | 121.9 | | | | |
| 9A2-VR5 | | | | 87.0 | | | | |
| 9A2-VR6 | | | | 249.8 | | | | |
| 9A2-VR8 | | | | 57.7 | | | | |
| 9A2-VR9 | | | | 72.7 | | | | |
| 9A2-VR11 | | | | 353.0 | | | | |
| 9A2-VR12 | | | | 198.3 | | | | |
| 9A2-VR13 | | | | >1000 | | | | |
| 9A2-VR14 | | | | >1000 | | | | |
| 9A2-VR16 | | | | >1000 | | | | |
| 9A2-VR19 | | | 30.0 (N = 2) | >1000 | | | | |
| 9A2-VR20 | | | 0.58 (N = 2) | 79.3 | | | | |
| 9A2-VR21 | | | 0.39 (N = 2) | 99.8 | | | | |
| 9A2-VR22 | | | | 39.9 | | | | |
| 9A2-VR23 | | | | 60.0 | | | | 24 |
| 9A2-VR24 | 2.3E+06 ± 7.4E+04 | 1.1E−03 ± 1.8E−05 | 0.46 ± 0.03 (N = 5) | 2.5 | 0.726 | 23.52 | | 8.6 |
| 9A2-VR26 | 2.4E+06 ± 1.1E+05 | 5.5E−04 ± 1.9E−05 | 0.23 ± 0.005 (N = 3) | 4.6 | | | | 23.6 |
| 9A2-VR27 | 2.3E+06 ± 1.6E+05 | 1.1E−03 ± 2.8E−05 | 0.47 ± 0.07 (N = 5) | 4.9 | | | | 8.5 |
| 9A2-VR28 | | | | 47.9 | | | | |
| 9A2-VR31 | | | | 232.9 | | | | |
| 9A2-VR32 | | | 0.34 (N = 1) | 31.2 | | | | |
| 9A2-VR33 | | | | 602.1 | | | | |
| 9A2-VR34 | | | | 184.5 | | | | |
| 9A2-VR35 | | | 0.34 (N = 2) | 76.0 | | | | |
| 9A2-VR36 | | | 0.30 (N = 1) | 38.1 | | | | |
| 9A2-VR37 | | | | 48.1 | | | | |
| 9A2-VR38 | | | | 5.0 | | | | |
| 9A2-VR39 | 3.0E+06 ± 5.76E+05 | 5.9E−04 ± 1.0E−05 | 0.27 ± 0.17 (N = 5) | 0.88 | | | | 4.1 |
| 9A2-VR40 | 1.3E+06 ± 4.7E+04 | 6.6E−04 ± 1.9E−05 | 0.52 ± 0.05 (N = 5) | 5.7 | | | | |
| 9A2-VR41 | 1.7E+06 ± 6.0E+04 | 7.6E−04 ± 1.7E−05 | 0.46 ± 0.05 (N = 5) | 7.0 | | | | |
| 9A2-VR42 | | | 0.38 (N = 2) | 54.7 | | | | |
| hu9A2-G4pK | | | | | | | | |

TABLE 3-continued

List of variants from round 1 of 9A2 affinity maturation.

| Antibody | $k_a$ (1/Ms) | $k_d$ (1/s) (Fab) | $K_D$ (nM) | IC$_{50}$ GM-CSF (nM) | IC$_{50}$ IL-3 (nM) | IC$_{50}$ IL-5 (nM) | pStat5 IC$_{50}$ IL-3 (nM) | pStat5 IC$_{50}$ GM-CSF (nM) |
|---|---|---|---|---|---|---|---|---|
| 9A2-VR43 | | | | 53.7 | | | | |
| 9A2-VR44 | | | 5 (N = 1) | 36.4 | | | | |
| 9A2-VR45 | | | | 88.7 | | | | |
| 9A2-VR46 | | | | 23.4 | | | | |
| 9A2-VR47 | | | | 27.2 | | | | |
| 9A2-VR48 | | | | 21.7 | | | | |
| 9A2-VR49 | | | | 23.4 | | | | |
| 9A2-VR50 | | | | 46.5 | | | | |

Figure 6E:
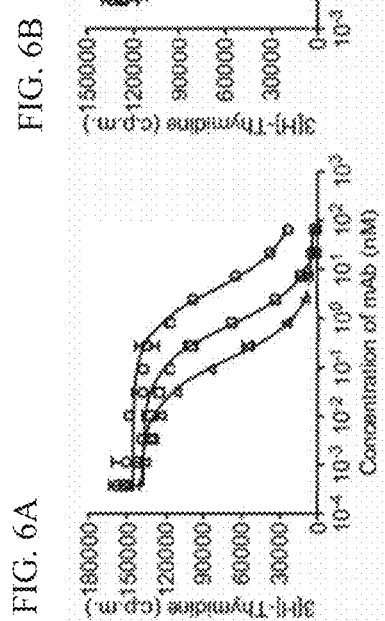
Figure 10A:
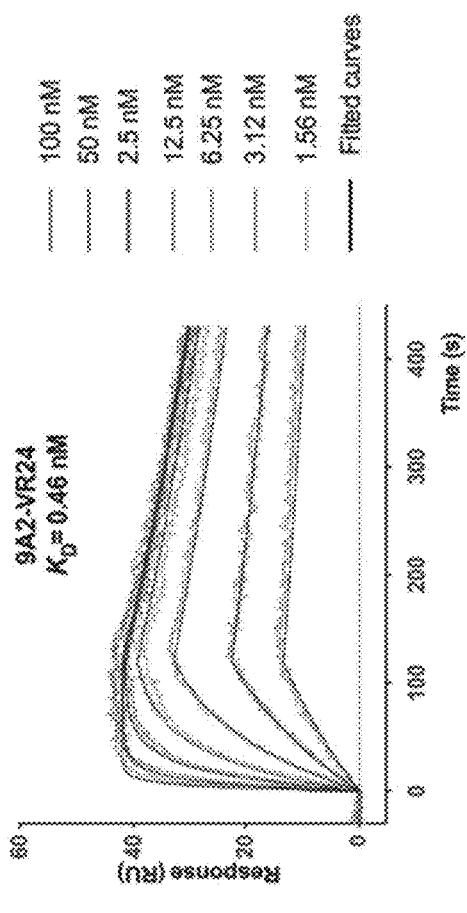
FIGS. 10A-10C are a series of graphical representations showing kinetic binding analysis of recombinant Fabs of 9A2 (FIG. 10A), 9A2-VR24 (FIG. 10B) and 9A2-VR24.29 (FIG. 10C) binding to shCD131 using surface plasmon resonance.
Figure 10B:
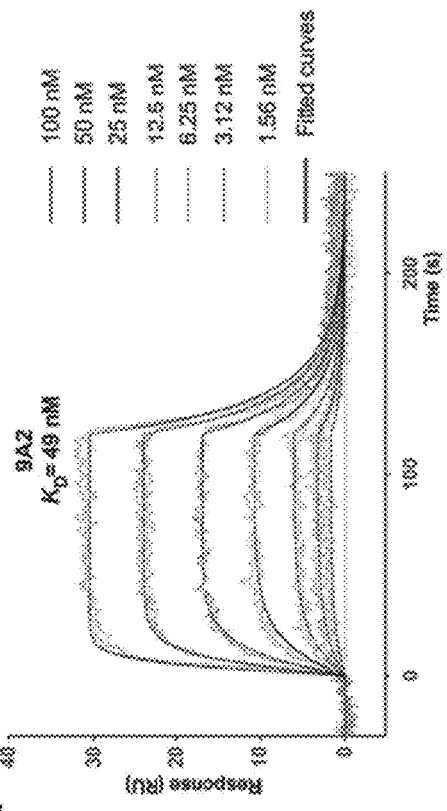
Figure 10C:
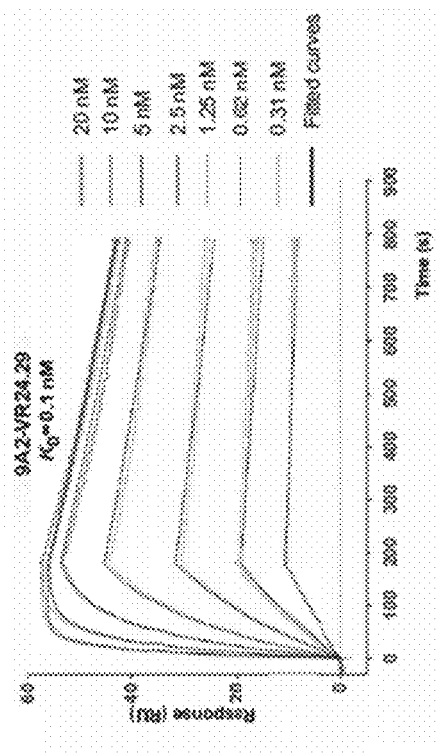

Improved dissociation rates were observed for all variants that showed increased affinities (Table 3). Potency improvements were greatest for clones derived from heavy chain CDR1 (H1.1) and CDR2 (H2.1) libraries (FIG. 6E). Variant 9A2-VR24 originated from the heavy chain CDR1 library (H1.1) and had a 182-fold potency improvement over parental 9A2 (Table 3). Variant 9A2-VR24 bound to shCD131 with 106-fold higher affinity ($K_D$=0.46 nM) compared to parental 9A2 ($K_D$=49 nM) due to an 87-fold decrease in the dissociation rate ($k_d$) (Table 3). SPR analysis of recombinant Fabs of 9A2 (FIG. 10A) and 9A2-VR24 (FIG. 10B) binding to shCD131 showed that while dissociation of 9A2 occurred within 2 minutes, 9A2-VR24 was still associated after 5 minutes. The most potent CDR2 (H2.1) variant (9A2-VR39) showed an approximately 180-fold improvement in binding affinity ($K_D$=0.27 nM) and 518-fold improvement in GM-CSF potency over parental 9A2 (see Table 3 for all variants tested).

Figure 6F:
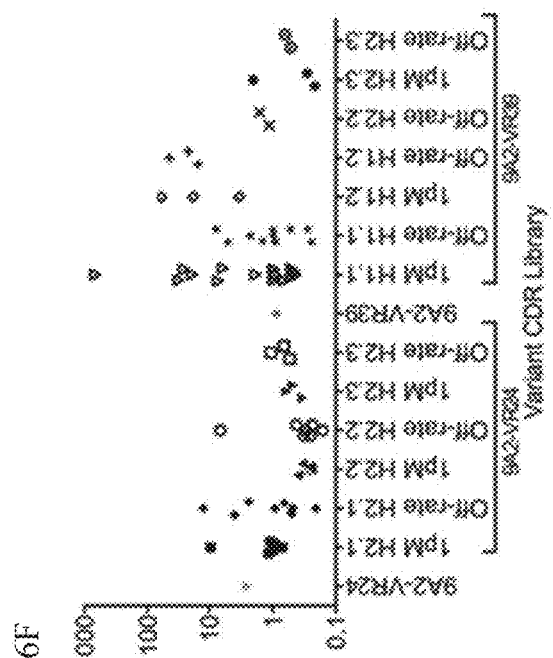
Figure 11A:
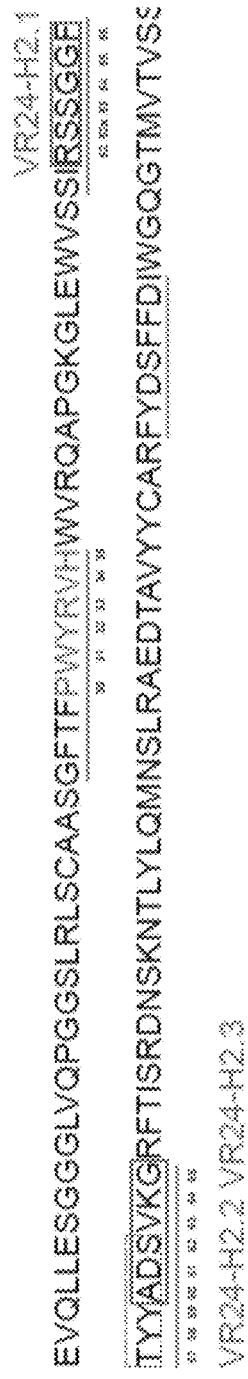
FIGS. 11A and 11B are diagrammatic representations showing amino acid sequences of heavy chain variable regions of antibodies used for affinity maturation. Sequences of (FIG. 11A) the heavy chain variable region of 9A2-VR24 and (FIG. 11B) heavy chain variable region of 9A2-VR39 are shown with CDRs underlined and regions selected for randomization boxed and numbered according to Kabat.
Figure 11B:
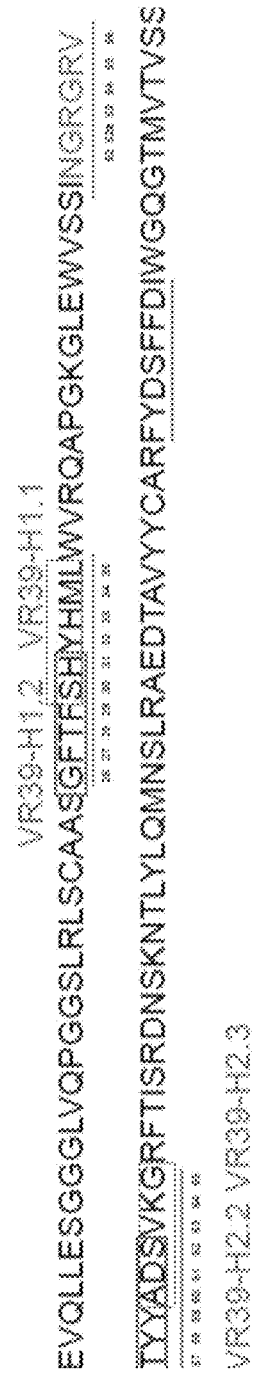

Variants 9A2-VR24 and 9A2-VR39 were chosen for additional affinity optimization. Under a combinatorial approach the sequence for either 9A2-VR24 or 9A2-VR39 (FIGS. 11A and 11B) was fixed and libraries were generated targeting all residues for CDRH2 with the 9A2-VR24 amino acid sequence (VR24-H2.1-2.3) and all residues in CDRH1 and residues 57-65 in CDRH2 with the 9A2-VR39 amino acid sequence (VR39-H1.1, H2.1, H2.1, H2.3). An additional "off rate" selection step was included as all previous potency improvements correlated with improvements in antibody off-rates. Unique variants from all selection strategies were converted to IgG4pK molecules for further analysis in TF-1 proliferation assays. FIG. 6F shows that variants with improved potency against GM-CSF were generated from each of the 7 libraries. The combination of the VR24 CDR1 sequence and the VR39 CDR2 sequence was not identified as a high potency inhibitor from this second round of affinity maturation. The affinity and potency (IC$_{50}$ GM-CSF) measurements from all variants tested are summarized in Table 4.

TABLE 4

List of the variants from round 2 of affinity maturation (sequences as described in Table 1). Recombinant Fabs were generated for selected variants and kinetics performed.

| Variant | $k_a$(1/Ms) (Fab) | $k_d$ (1/s) (Fab) | $K_D$ (M) (Fab) | IC$_{50}$ GM-CSF (nM) |
|---|---|---|---|---|
| 9A2-VR24 | 2.3E+06 | 1.1E−03 | 0.46 ± 0.03 (N = 5) | 2.5 |
| 9A2-VR24.04 | | | | 0.7 |
| 9A2-VR24.07 | | | | 1.17 |
| 9A2-VR24.10 | 1.481E+6 | 5.502E−4 | 3.716E−10 (N = 1) | 9.52 |
| 9A2-VR24.12 | | | | 0.93 |
| 9A2-VR24.19 | | | | 0.98 |
| 9A2-VR24.24 | | | | 1.09 |
| 9A2-VR24.76 | | | | 12.4 |
| 9A2-VR24.78 | | | | 0.65 |
| 9A2-VR24.81 | 2.851E+6 | 4.921E−4 | 1.726E−10 (N = 1) | 0.48 |
| 9A2-VR24.82 | | | | 3.99 |
| 9A2-VR24.84 | 3.949E+6 | 4.177E−4 | 1.058E−10 (N = 1) | 0.21 |
| 9A2-VR24.87 | | | | 2.37 |
| 9A2-VR24.91 | 2.776E+6 | 4.478E−4 | 1.613E−10 (N = 1) | 0.50 |
| 9A2-VR24.93 | | | | 0.92 |
| 9A2-VR24.27 | 3.097E+6 | 5.270E−4 | 1.702E−10 (N = 1) | 0.25 |
| 9A2-VR24.29 | 4E+6 ± 5.5E4 | 4.18E−4 ± 8.1E−6 | 1.0E−10 ± 3.1E−12 (N = 4) | 0.29 |
| 9A2-VR24.30 | 3.802E+6 | 4.642E−4 | 1.221E−10 (N = 1) | 0.25 |
| 9A2-VR24.33 | 3.156E+6 | 4.720E−4 | 1.495E−10 (N = 1) | 0.34 |
| 9A2-VR24.44 | 3.003E+6 | 4.882E−4 | 1.626E−10 (N = 1) | 0.40 |
| 9A2-VR24.97 | 3.2E+6 ± 1.0E5 | 5.24E−4 ± 7.0E−6 | 1.6E−10 ± 6.1E−12 (N = 4) | 0.16 |
| 9A2-VR24.98 | 3.211E+6 | 5.586E−4 | 1.739E−10 (N = 1) | 0.25 |
| 9A2-VR24.102 | 2.952E+6 | 5.559E−4 | 1.883E−10 (N = 1) | 0.32 |
| 9A2-VR24.107 | 2.892E+6 | 5.304E−4 | 1.834E−10 (N = 1) | 0.30 |
| 9A2-VR24.110 | 3.146E+6 | 4.747E−4 | 1.509E−10 (N = 1) | 0.24 |
| 9A2-VR24.111 | 2.700E+6 | 6.370E−4 | 2.359E−10 (N = 1) | 0.42 |
| 9A2-VR24.55 | 2.552E+6 | 9.425E−4 | 3.693E−10 (N = 1) | 0.60 |
| 9A2-VR24.56 | 2.823E+6 | 9.968E−4 | 3.531E−10 (N = 1) | 0.48 |
| 9A2-VR24.57 | 4.0E+6 ± 1.0E5 | 8.41E−4 ± 7.3E−6 | 2.11E−10 ± 5.2E−12 (N = 4) | 0.33 |
| 9A2-VR24.122 | 2.539E+6 | 8.973E−4 | 3.535E−10 (N = 1) | 0.66 |

TABLE 4-continued

List of the variants from round 2 of affinity maturation (sequences as described in Table 1). Recombinant Fabs were generated for selected variants and kinetics performed.

| Variant | $k_a$ (1/Ms) (Fab) | $k_d$ (1/s) (Fab) | $K_D$ (M) (Fab) | $IC_{50}$ GM-CSF (nM) |
|---|---|---|---|---|
| 9A2-VR24.124 | 2.9E+6 ± 7.8E4 | 7.6E−4 ± 1.5E−5 | 2.5E−10 ± 1.7E−12 (N = 4) | 0.54 |
| 9A2-VR24.131 | | | | 1.06 |
| 9A2-VR39 | 3.0E+6 | 5.9E−4 | 2.7E−10 | 0.88 |
| 9A2-VR39.01 | 3.042E+6 | 3.099E−4 | 1.019E−10 (N = 1) | 0.51 |
| 9A2-VR39.02 | 3.888E+6 | 3.411E−4 | 8.772E−11 (N = 1) | 0.46 |
| 9A2-VR39.04 | 3.548E+6 | 0.001167 | 3.289E−10 (N = 1) | 30.39 |
| 9A2-VR39.05 | | | | 0.96 |
| 9A2-VR39.06 | | | | 1.85 |
| 9A2-VR39.11 | | | | 18.61 |
| 9A2-VR39.12 | | | | 25.10 |
| 9A2-VR39.16 | | | | 6.07 |
| 9A2-VR39.17 | 2.811E+6 | 5.661E−4 | 2.014E−10 (N = 1) | 0.67 |
| 9A2-VR39.18 | | | | >1000 |
| 9A2-VR39.19 | | | | 7.26 |
| 9A2-VR39.21 | | | | 0.96 |
| 9A2-VR39.22 | 3.130E+6 | 4.411E−4 | 1.410E−10 (N = 1) | 0.50 |
| 9A2-VR39.23 | | | | 0.90 |
| 9A2-VR39.24 | 2.965E+6 | 5.001E−4 | 1.687E−10 (N = 1) | 0.42 |
| 9A2-VR39.97 | | | | 0.92 |
| 9A2-VR39.98 | | | | 1.44 |
| 9A2-VR39.102 | | | | 2.29 |
| 9A2-VR39.103 | | | | 5.14 |
| 9A2-VR39.105 | | | | 0.53 |
| 9A2-VR39.109 | 3.4E+6 ± 8.6E4 | 3.3E−4 ± 2.2E−6 | 9.8E−11 ± 2.7E−12 (N = 4) | 0.24 |
| 9A2-VR39.110 | 3.8E+6 ± 4.8E4 | 3.9E−4 ± 3.2E−6 | 1.1E−10 ± 2.2E−12 (N = 4) | 0.28 |
| 9A2-VR39.111 | | | | 0.99 |
| 9A2-VR39.112 | | | | 1.00 |
| 9A2-VR39.116 | | | | 7.93 |
| 9A2-VR39.27 | | | | 17.90 |
| 9A2-VR39.28 | | | | 57.16 |
| 9A2-VR39.46 | | | | 3.34 |
| 9A2-VR39.122 | | | | 15.04 |
| 9A2-VR39.139 | | | | 21.50 |
| 9A2-VR39.140 | | | | 42.48 |
| 9A2-VR39.148 | | | | 1.12 |
| 9A2-VR39.162 | | | | 1.60 |
| 9A2-VR39.77 | | | | 2.03 |
| 9A2-VR39.93 | 4.154E+6 | 7.098E−4 | 1.709E−10 (N = 1) | 0.28 |
| 9A2-VR39.174 | | | | 0.64 |
| 9A2-VR39.177 | 3.691E+6 | 5.536E−4 | 1.500E−10 (N = 1) | 0.52 |

Variant 9A2-VR24.29 was selected for further analysis. The ability of 9A2-VR24.29 to inhibit the proliferation of TF-1 cells in response to IL-3, GM-CSF and IL-5 was compared with parental antibodies 9A2 and 9A2-VR24, and BION-1 (Sun et al., *Blood* 94:1943-1951, 1999). 9A2-VR24.29 was significantly more potent than both parental antibodies and BION-1 at inhibiting the proliferation of TF-1 cells in response to all three CD131-family cytokines with an $IC_{50}$ of 0.29 nM against GM-CSF (FIGS. 6A-6C). This is an 8.6-fold improvement compared to 9A2-VR24 (2.5 nM) and a 1572-fold improvement over the parental antibody, 9A2. Improvements in potency of 9A2-VR24.29 compared to parental 9A2 were also observed for IL-3 (41-fold, $IC_{50}$=0.144 nM) and IL-5 (310-fold, $IC_{50}$=4.67 nM). 9A2-VR24.29 bound to shCD131 ($K_D$=100 pM) with a 4.6-fold greater affinity than 9A2-VR24 due to a further 2.6-fold improvement in dissociation rate ($k_d$), (Table 3).

The radiolabelled antibody $^{125}$I-9A2-VR24.29 bound the CD131 receptor on neutrophils with a $K_D$=246 pM and a recombinant Fab fragment of 9A2-VR24.29 bound with similar affinity, $K_D$=384 pM (FIGS. 12A and 12B, FIG. 13). 9A2-VR24.29 IgG bound to human eosinophils with an average $K_D$=629 pM (FIG. 12 C, FIG. 13).

9A2-VR24.29 Reduces Survival of Primary Cells Isolated and Cultured Ex Vivo from Human Airway Disease Tissue.

Figure 14D:
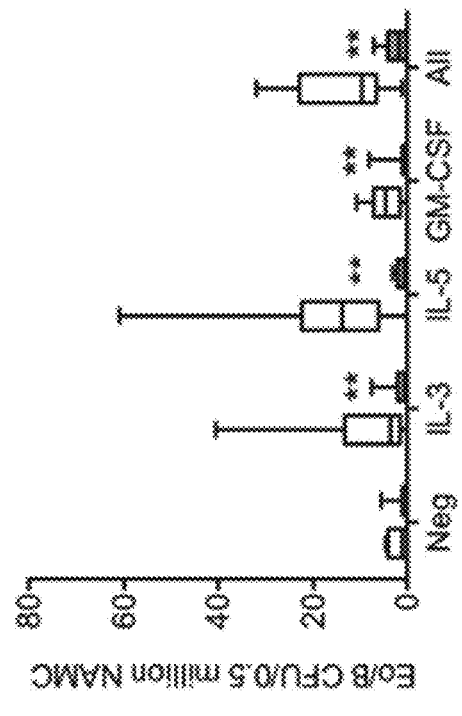
Figure 14E:
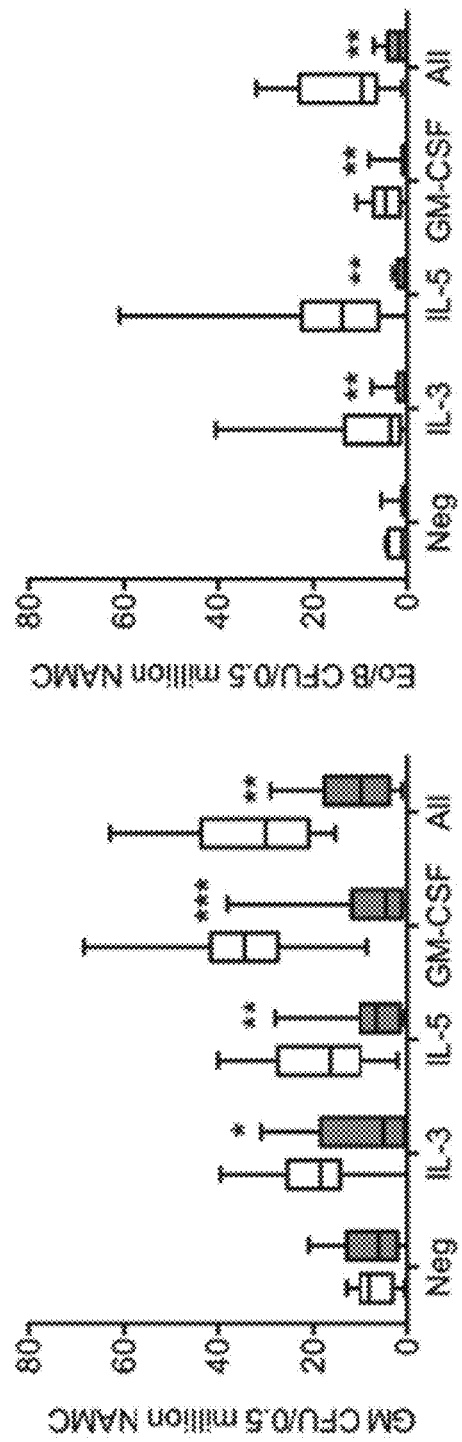
Figure 14F:
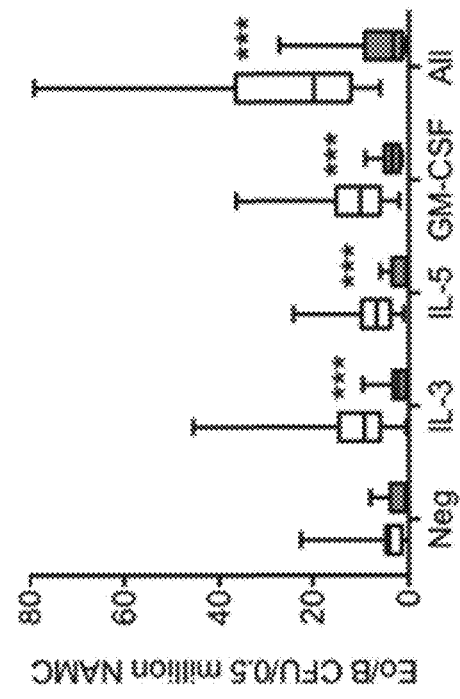
Figure 14G:
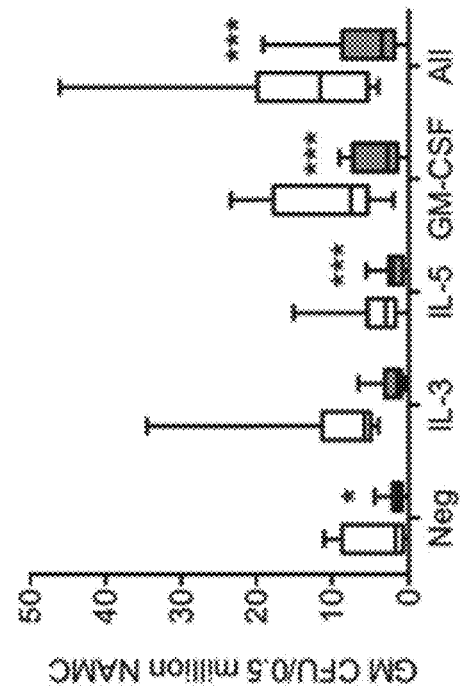

The effect of 9A2-VR24.29 on the survival of myeloid and lymphoid cells isolated from induced sputum at baseline and 24 hours after inhaled allergen challenge was investigated by flow cytometry. Induced sputum was collected from donors before and 24 h after inhaled allergen challenge. Differential cell counting of the mixed cell population indicated that the predominant cell types were neutrophils and macrophages with a smaller proportion of eosinophils, lymphocytes, and bronchial epithelial cells (FIG. 14A). Sputum-derived cells were incubated ex vivo, in the absence of exogenous growth factors, for 24 hours and the effect of 9A2-VR24.29 on these cultures was compared to duplicate cultures treated with an isotype control antibody. Cells where the baseline viability was less than 10% were excluded from the analysis. 9A2-VR24.29 caused a significant decrease in cell survival in sputum eosinophils (P value=0.0391) as detected by annexin V staining (FIG. 14B). No significant effect of 9A2-VR24.29 compared to isotype control antibody on the survival of neutrophil, lymphocyte or macrophage populations was observed.

In a similar study sputum cells were isolated and incubated as previously described but in the presence of 1 ng/ml each of IL-3, IL-5 and GM-CSF. In this situation 9A2-VR24.29 caused a significant decrease in the survival of both sputum eosinophils (6 of 8 subjects, P value=0.0078) and neutrophils (6 of 8 subjects, P value=0.0391) collected at baseline and 24 hours after allergen challenge as detected by annexin V staining (FIG. 14C) when compared to isotype control antibody. A non-significant decrease in the survival of basophils was also observed (5 of 8 subjects, P value=0.3828).

Peripheral blood and bone marrow samples were obtained from asymptomatic allergic asthmatics pre- and post-allergen challenge and cultured in the presence of either IL-3, GM-CSF or IL-5 or a combination of all three cytokines. The effect of 9A2-VR24.29 or an isotype control antibody treatment on GM- or Eo/B-CFU arising from CD34+ progenitors from bone marrow and blood samples was determined. Treatment with 9A2-VR24.29, compared to isotype control, significantly reduced the numbers of peripheral blood and bone marrow GM-CFU cultured under all conditions (FIGS. 14D-14G). Treatment with 9A2-VR24.29, compared to isotype control, also significantly reduced the numbers of peripheral blood and bone marrow Eo/B-CFU cultured under all conditions.

Figure 15:
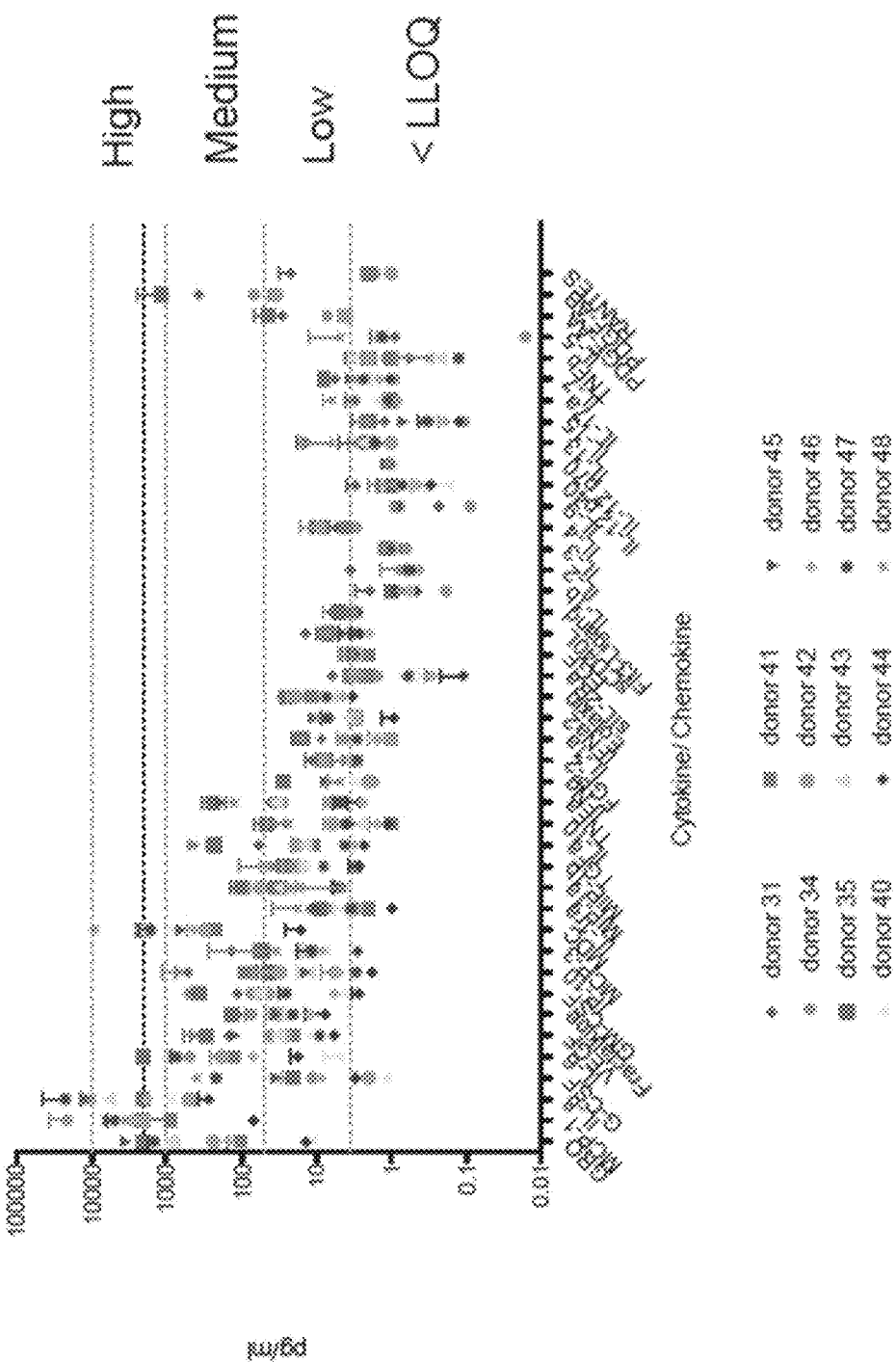
FIG. 15 is a graphical representation showing results of Luminex analysis of the supernatants of nasal polyp tissue cellular infiltrates from 12 different donors cultured for 5 days. Single cell suspensions were assayed for various chemokine and cytokine concentrations by Luminex human 42-plex bead assays. Concentrations for each analyte for each individual donor are shown, n=12 donors.

A culture of NP inflammatory cell infiltrates was used to determine the expression levels of inflammatory cytokines and chemokines. The levels of inflammatory cytokines and chemokines produced by unstimulated NP cells were evaluated by Luminex analysis (FIG. 15). High to very high levels (100 pg/ml->1000 pg/ml) of neutrophil, monocyte and T-cell recruiting chemokines were observed including GRO, IL-8, MCP-1, Fractalkine, IP-10, MCP-3 and MDC as well as growth factors that mediate activation of these cells, such as G-CSF, GM-CSF and IL-6. In addition, the chemokines MIP-1α and MIP-1β, which activate neutrophils, eosinophils and basophils were present in the range of 10-100 pg/ml and both pro-inflammatory (TNFα, IFNγ, IL-1α, IFNβ) and anti-inflammatory (IL-10, IL-IRA) factors were detected at similar concentrations. Cytokines present at low but detectable levels included Th2 cytokines such as IL-5, Th-1/Th17 cytokines and others that are involved in T-cell and B-cell survival and NK cell survival and activation. These data confirm that NPs provide a relevant pathogenic inflammatory environment from which to study immune cells that contribute to airway disease.

To determine whether 9A2-VR24.29 can directly inhibit the survival of unstimulated cells from human disease tissue, cells were cultured for 5 days ex vivo from freshly isolated human NP tissue obtained from 16 patients who had undergone elective polypectomy and then contacted with 9A2-VR24.29. Consistent with previous studies, eosinophils were the predominant cell type in the majority of donors (FIG. 14H). Moreover, as determined by flow cytometry, 9A2-VR24.29 inhibited the survival of unstimulated eosinophils isolated from NP tissue after 72 hours in culture (FIG. 14I). 9A2-VR24.29 had no significant effect on the survival of neutrophils, lymphocytes or macrophages.

Figure 14J:
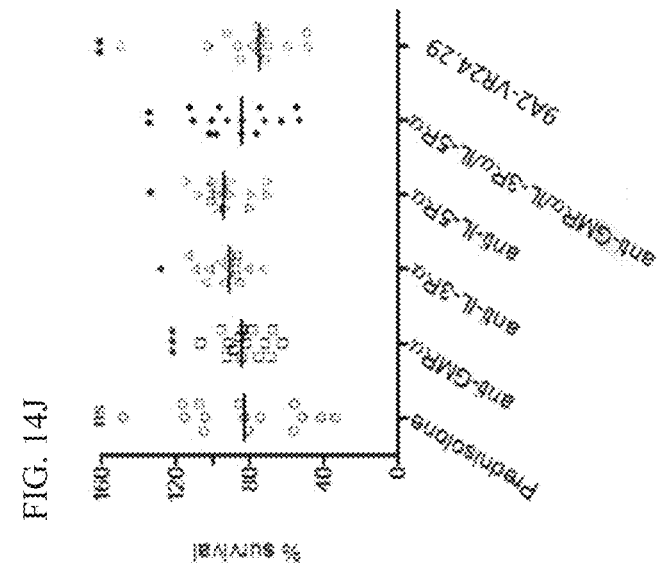
Figure 14I:
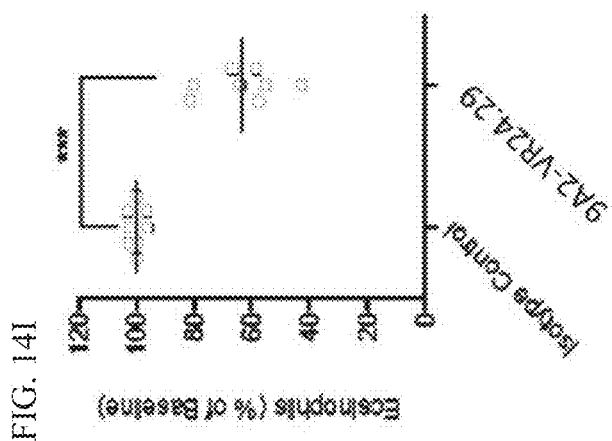
Figure 14H:
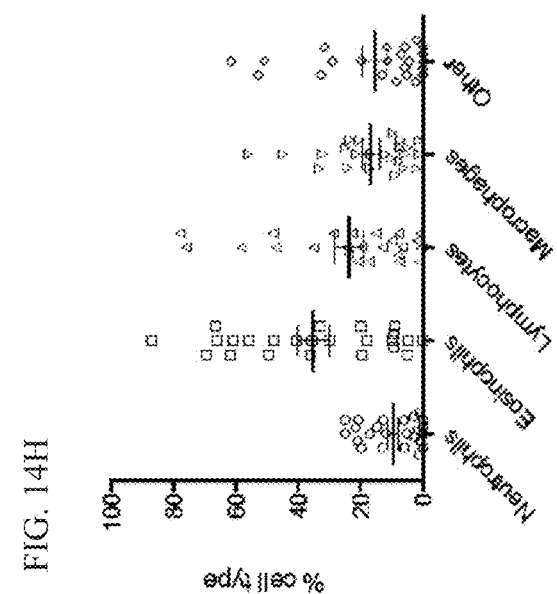

The effect of 9A2-VR24.29 on the survival of cultured NP inflammatory total cell infiltrates was compared to that of prednisolone, the current standard of care, as well as individual anti-β chain antibodies (FIG. 14J). Each test condition was expressed as percent survival compared to the untreated control for each donor where the untreated control is maximum survival (100%). Treatment with prednisolone reduced overall cell survival, with a mean and median of 83.9% and 83.02% respectively. Each individual anti-β chain mAb reduced survival ranging from 82.3% (anti-GM-CSFR β-chain) to 92.3% (anti-IL-5R β-chain) of untreated control. The combination of all three anti-β-chain mAbs reduced survival to a level similar to that observed with prednisolone treatment. In these assays 9A2-VR24.29 was able to inhibit the survival of the total cellular infiltrate to a similar extent compared to that observed following treatment with prednisolone with a mean survival of 79.4% and a median of 74.8% but also in a wider range of patients.

9A2-VR24.29 Inhibits Activation and Survival of Primary Human Myeloid Cells Stimulated with IL-3, GM-CSF and IL-5.

Human myeloid cells including neutrophils, basophils, plasmacytoid dendritic cells (pDCs), mast cells and human CD34+ BM cells from normal donors were isolated to test the inhibitory activity of 9A2-VR24.29 in other primary human myeloid cells that contribute to airway disease. 9A2-VR24.29 inhibited GM-CSF-induced activation of human neutrophils as determined by an increase in cell size measured by flow cytometry in a dose-dependent manner (FIG. 16A). IL-8, a chemotactic factor that attracts predominantly neutrophils, basophils, eosinophils and T-cells is secreted by human basophils in response to stimulation with IL-3. 9A2-VR24.29 was able to block IL-3 induced IL-8 secretion from purified human basophils in a dose-dependent manner (FIG. 16B). DCs play a crucial role in the development of asthma and allergy and their levels are elevated in subjects with asthma. CD11c$^-$ pDCs depend on IL-3 for survival. 9A2-VR24.29 inhibited the IL-3-mediated survival of CD11c$^-$ pDCs in a dose-dependent manner as measured by VialightPlus assay (FIG. 16C).

Figures 16G, 16H, 16I, 16J, 16K, 16L, 16M, 16N, 16O:
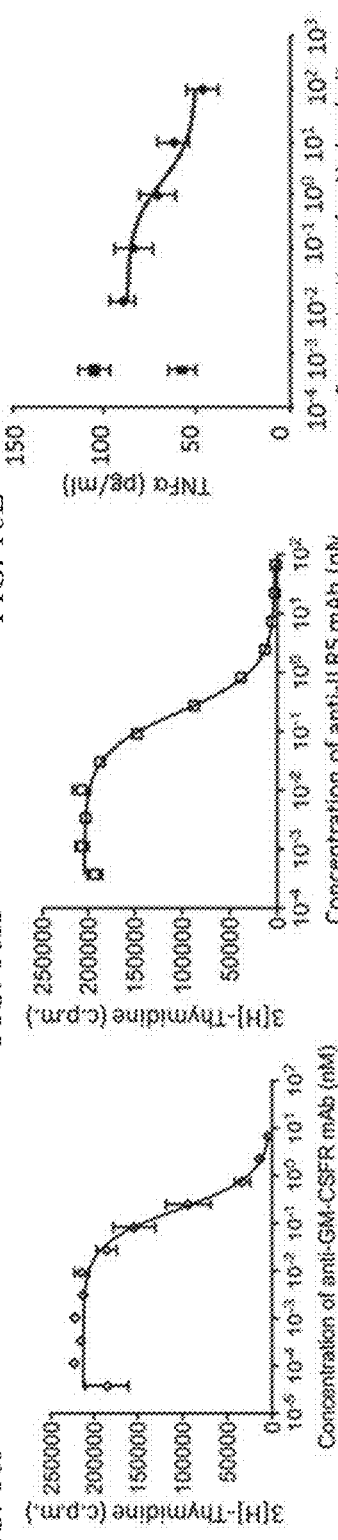

Eosinophils are the dominating immune effector cells in asthma and through their activation and degranulation contribute to airway inflammation. The importance of eosinophils in the pathogenesis of asthma has been confirmed with the reduction of symptoms seen in patients treated with antibodies to IL-5 or the IL-5 receptor. IL-5 is a key differentiation and survival factor of eosinophils from hemopoietic progenitors and contributes to the activation of mature eosinophils. 9A2-VR24.29 was able to inhibit IL-5-induced activation of purified peripheral blood human eosinophils, as determined by an increase in forward scatter, in a dose-dependent manner (FIG. 16D). In addition to IL-5 human eosinophils also respond to stimulation with GM-CSF and IL-3 (FIGS. 16 F-16H). In particular, administration of recombinant IL-3 or GM-CSF in humans causes a rise in levels of circulating eosinophils. Therefore, in diseases where eosinophilia is a pathogenic feature, all three cytokines in combination may contribute to enhanced eosinophil numbers by mediating their recruitment from the BM and their increased survival at the site of pathology. An eosinophil survival assay was used to assess the ability of 9A2-VR24.29 to block eosinophil survival in response to a cocktail of all three cytokines (at $EC_{80}$ doses). Individual antagonists to the IL-3R α-chain, the GM-CSFRα-chain, or the IL-5R α-chain were also assessed in the same assay. The potency of each individual receptor antagonist in response to stimulation with their corresponding cytokine was determined and complete inhibition was observed at ~10 nM for each antagonist (FIGS. 16I-16K). However, in contrast, treatment of eosinophils with 9A2-VR24.29 at concentrations as low as 200 nM or 30 μg/ml was able to completely block their survival in the presence of IL-5, GM-CSF and IL-3. A similar decrease in cell survival could only be achieved by the individual α-chain antagonists when they were combined (at $EC_{80}$ for each cytokine) (FIG. 16E). These data suggest that 9A2-VR24.29 may be more effective than single target antibodies in controlling eosinophil-mediated diseases such as asthma.

Human mast cells are abundantly present in mucosal tissues that interface with the environment where they can exacerbate, partly through TNF-α release, allergic inflammatory responses. IL-3 has been previously shown to regulate mast cell generation and some mast cell functions in vitro and is a strong activator of TNF-α release in mast cells stimulated with IgE+anti-IgE. 9A2-VR24.29 inhibited this effect of IL-3 in human cultured mast cells (HCMC) in a dose-dependent manner (FIG. 16L). Mast cells also play a role in the late phase of the allergic reaction through their IgE-dependent release of multifunctional cytokines such as IL-13 and so influence the development, strength and/or persistence of Th2-cell-associated immune responses. IL-3 (but not GM-CSF and IL-5) was also able to potentiate IL-13 release from IgE-stimulated mast cells. 9A2-VR24.29 was able to block IL-3 potentiated IL-13 release in a dose dependent manner (FIG. 16M). IL-3, IL-5 and GM-CSF were all able to potentiate IgE-mediated IL-8 release from HCMCs and these responses were also blocked by 9A2-VR24.29 (FIG. 16N).

9A2-VR24.29 was able to reduce CD34$^+$ human BM CFU-GM colony formation in response to a cytokine cocktail comprising SCF, GM-CSF, IL-3 and IL-5. 9A2-VR24.29 was able to dose-dependently inhibit the formation of CFU-GM colonies to a level observed when cells are cultured in the presence of SCF alone. The ability of individual antagonists directed against the IL-3R α-chain, the GM-CSFRα-chain, or the IL-5R α-chain were also tested for their ability to reduce colony formation. The reduction in CFU-GM colony formation by treatment with 9A2-VR24.29 was similar to that observed when CD34$^+$ human BM cells were treated with a combination of all three alpha chain inhibitors (FIG. 16O). These data concur with those obtained in eosinophil survival assays, demonstrating that 9A2-VR24.29 can simultaneously inhibit the actions of IL-3, IL-5 and GM-CSF when these cytokines are added in combination.

Prophylactic Administration of 9A2-VR24.29 Reduces Nasal Polyp Xenograft Growth in Rag2$^{-/-}$ Il2rg$^{-/-}$hIL-3/GM-CSF KI Mice Since 9A2-VR24.29 is neither active on the mouse CD131/$β_{IL-3}$ receptor nor are mouse IL-3 or GM-CSF cross-reactive on human IL-3Rα or GMRα, the capacity of 9A2-VR24.29 to work in an in vivo setting was determined using a previously described human nasal polyp xenograft model (see methods). A prophylactic approach was used in which Rag2$^{-/-}$ Il2rg$^{-/-}$hIL-3/GM-CSF KI mice were implanted, in subcutaneous pockets, with 4 mm$^3$ pieces of non-disrupted human nasal polyps (obtained from 9 different patients undergoing surgery for nasal polyposis) that had been pre-treated for 1 hour with 100 μg/ml either 9A2-VR24.29 or isotype control antibody. After 1 week the mice were injected (intra-polyp) with 9A2-VR24.29 (5 mg/kg) or isotype control antibody (5 mg/kg) weekly for 4 weeks and the size of the polyps monitored externally. After 5 weeks the mice were sacrificed and the polyps weighed and analyzed histologically and by flow cytometry. There was a statistically significant decrease in size for the 9A2-VR24.29 treated polyps (FIG. 17A). 9A2-VR24.29 also caused a statistically significant decrease in the weight of the nasal polyps at the end of the treatment period whereas this was not observed with isotype control treated polyps. 9A2-VR24.29 also reduced mucous gland size, mucus accumulation and cellular infiltrate into polyps (FIGS. 17B and 17C). After 5 weeks the polyps were examined by flow cytometry for human T and B lymphocytes, eosinophils, neutrophils and macrophages. A statistically significant reduction in the numbers of toluidine blue-stained mast cells, eosinophils (CD16-CD15$^+$CD49d$^+$Siglec8$^+$), neutrophils (CD14$^-$CD49d$^-$CD15$^+$CD16$^+$), B cells populations (CD45$^+$CD19$^+$) but not macrophages (CD16$^-$CD49d$^-$CD14$^+$CD15$^+$) and T cell populations (i.e. CD3$^+$CD4$^+$ and CD3$^+$CD8+) was observed in the 9A2-VR24.29 treated nasal polyps compared to the isotype control treated nasal polyps (FIGS. 18A-18G).

9A2-VR24.29 Inhibits IL-3, GM-CSF and IL-5 Function by Binding to Residues in Site 2 of CD131.

Figure 19A:
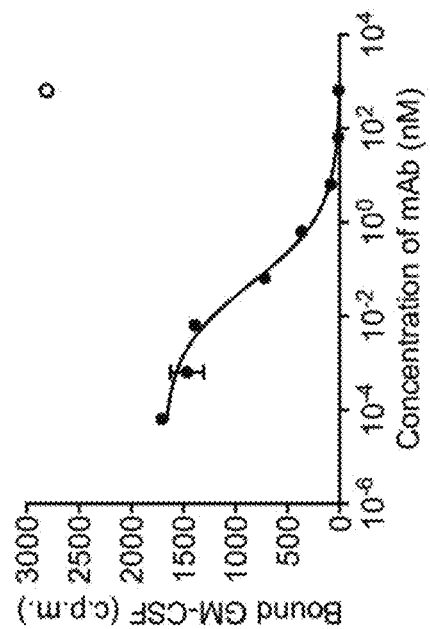
FIGS. 19A-19D are graphical representations showing 9A2-VR24.29 competes with IL-3, GM-CSF, and IL-5 for binding to primary human myeloid cells and human TF-1 cells. Purified human eosinophils were pre-incubated with 9A2-VR24.29 (●) or a human IgG4 control antibody (0).
Figure 19B:
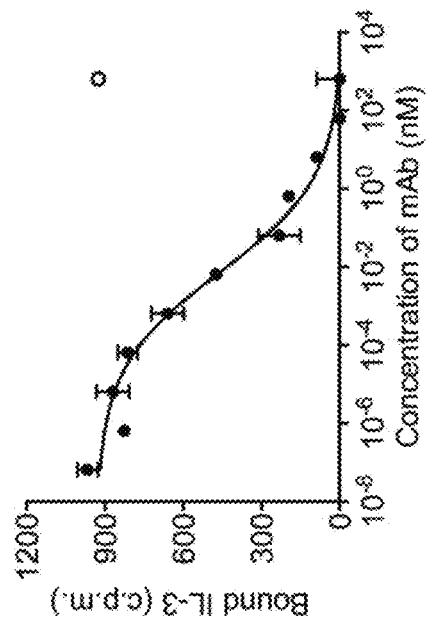
Figure 19C:
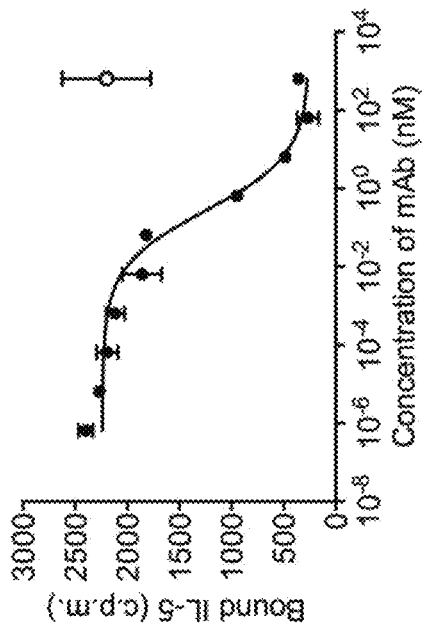

Reciprocal inhibition experiments were performed to assess the ability of 9A2-VR24.29 to compete for the binding of IL-3, GM-CSF, and IL-5 to cells expressing receptors for these cytokines. Pre-incubation of human eosinophils with 9A2-VR24.29 but not an irrelevant isotype control IgG abolished the binding of $^{125}$I-labelled IL-3 and reduced $^{125}$I-labelled IL-5 binding by 85% (FIGS. 19A and 19C). Pre-incubation of human neutrophils with 9A2-VR24.29, but not an irrelevant isotype control IgG, completely abolished $^{125}$I-labelled GM-CSF binding (FIG. 19B).

Figure 19D:
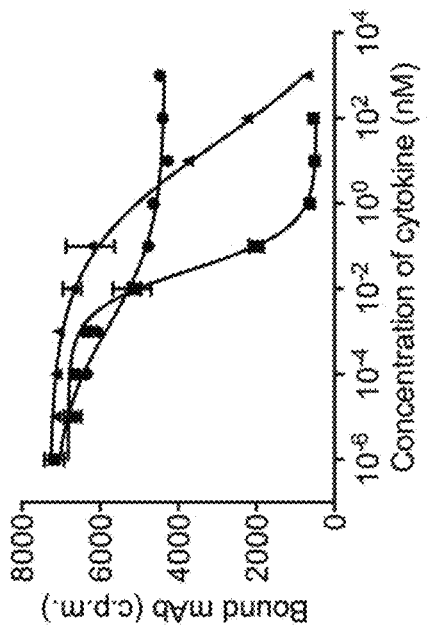

Pre-incubation of TF-1 cells with IL-3 and GM-CSF reduced the binding of $^{125}$I-labelled 9A2-VR24.29 by 90% at the highest concentration tested (FIG. 19D). IL-5 pre-incubation also reduced 9A2-VR24.29 binding but only by 40% (FIG. 19D) which is most likely a consequence of the relatively low affinity of the IL-5/IL-5R complex for the CD131 chain. These studies indicate that Site 2 on CD131 (which is the site of cytokine binding) is likely to overlap with the 9A2 epitope.

Structural Analysis of the 9A2-VR24.29 Binding Epitope on CD131

Figure 20A:
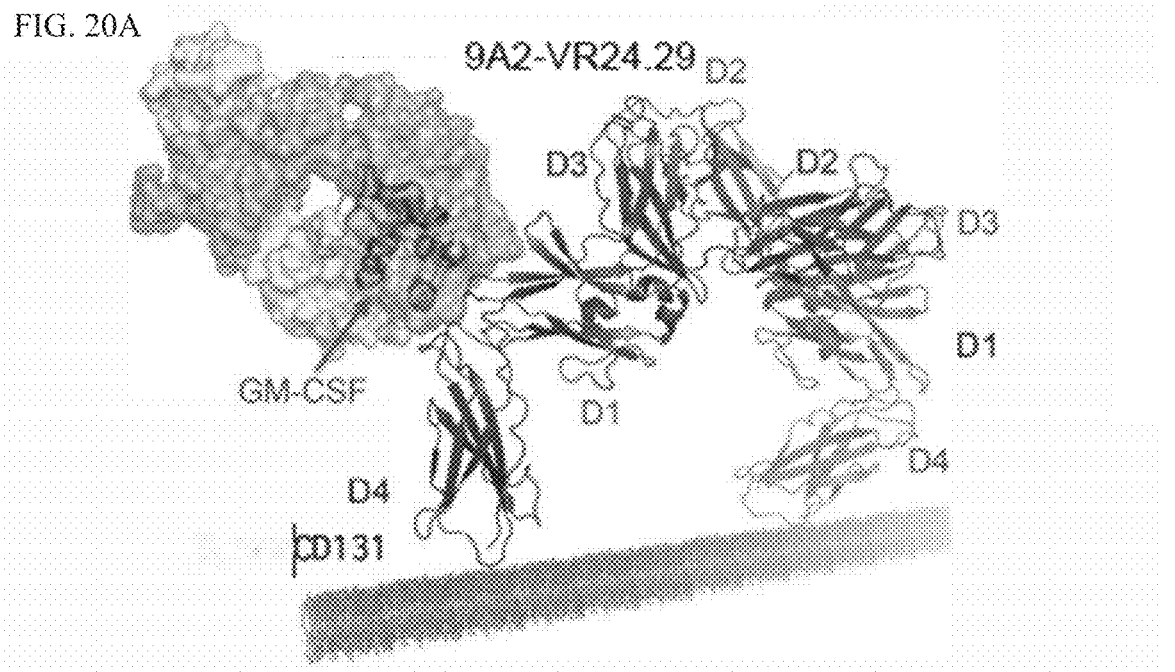
FIGS. 20A-20D are graphical representation of Site 2 interaction interface between 9A2-VR24.29 and CD131.
Figure 20B:
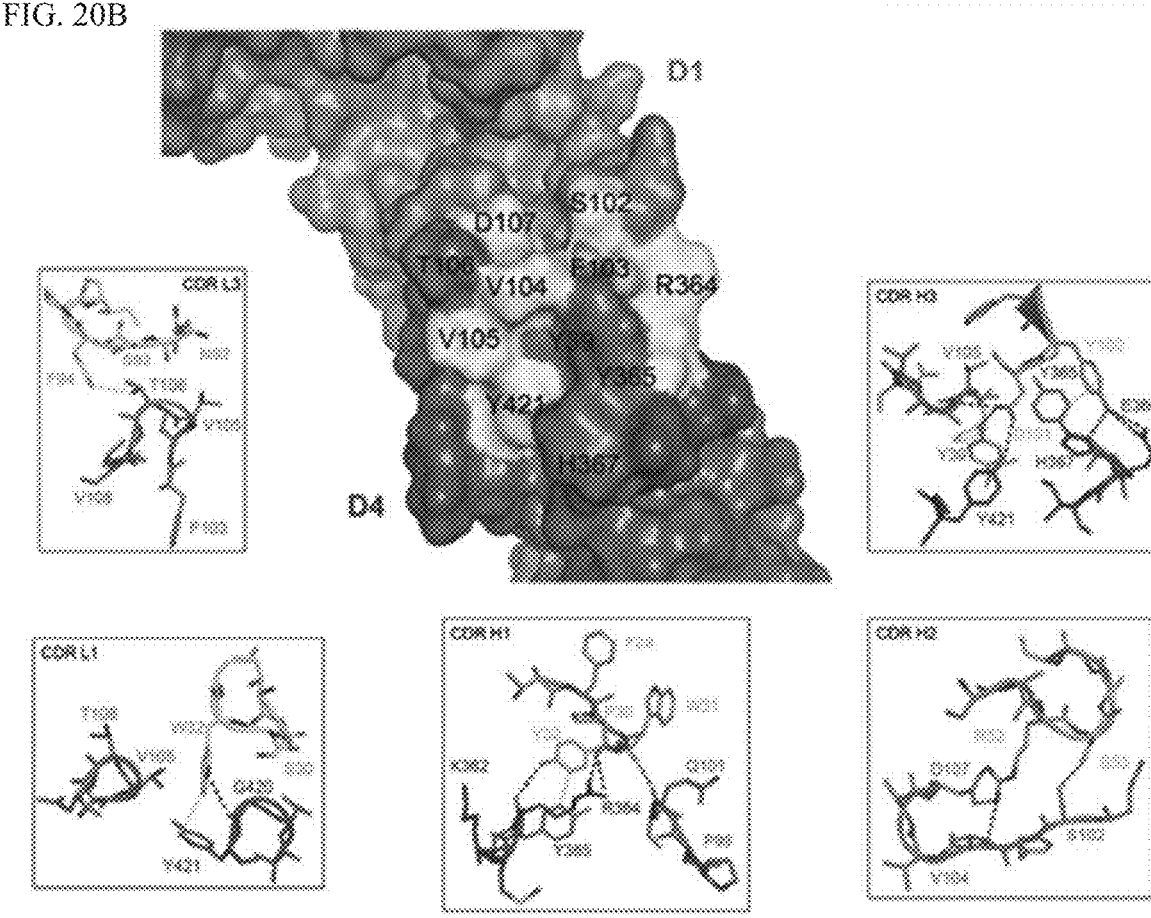

The amino acid residues of human CD131 that bind 9A2 and its affinity-matured derivative 9A2-VR24.29 were determined by using site-directed alanine mutagenesis. Mutagenesis and crystallization studies of human CD131 have defined Site 2 as a non-contiguous interface composed of the A-B and E-F loops of domain 1 from one CD131 chain and the B-C and F-G loops of domain 4 from another CD131 chain. Superimposition of the GM-CSF receptor ternary structure (PDB 4NKQ) on the CD131/9A2-VR24.29 complex reveals that 9A2-VR24.29 exerts its inhibitory function on CD131 by direct blockade of the cytokine binding site (FIG. 20A). A surface area of 933 Å$^2$ is buried in the complex and the surface complementary of the interface ($S_c$=0.59) is consistent with the tight binding affinity of the complex with a $K_D$ of 100 pM as measured by SPR. The structure reveals that majority of 9A2-VR24.29 contacts are mediated through heavy chain CDR loops (CDR H1 to H3) (FIG. 20B), consistent with changes in these CDRs providing the greatest improvements in affinity.

Figure 20C:
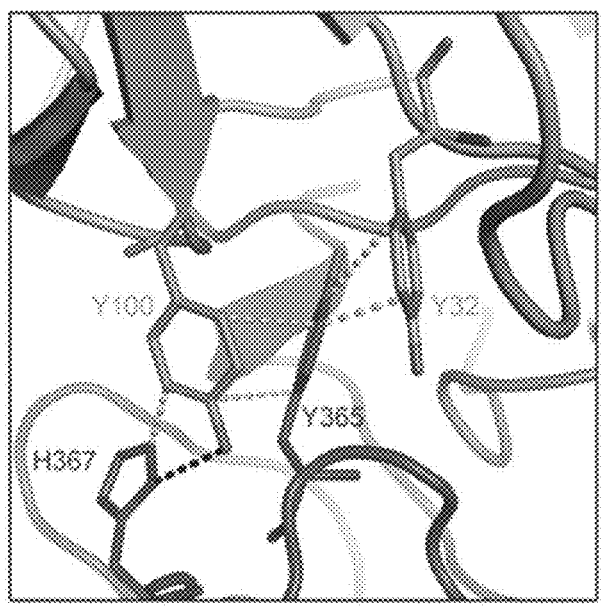

Hydrophobic and polar contacts contribute to the binding of 9A2-VR24.29 to CD131. CDR H1 main-chain carbonyls of P30 and W31 make polar contacts with the guanidine side chain of R364 and main-chain carbonyl of Q101 on CD131 respectively. The side-chain of Y32 from CDR H1 can hydrogen bond with the main-chain carbonyl of R364 and can potentially form n-n interactions with Y365 from CD131. S53 from CDR H2 makes polar contacts with S102 from D1 of CD131. The side-chain of R52 forms a salt bridge with D107 and it is also within hydrogen bond distance from the main-chain amine of V104 on CD131. The side-chain of Y100 from the CDR H3 of 9A2-VR24.29 hydrogen bonds with CD131 residues E366 and H367 and forms n-n interactions with Y365 on CD131. The side-chain of D101 from the CDR H3 makes polar contacts with the side-chains of Y39, Y421 and the main-chain amine of V105 on CD131. By comparison the 9A2-VR24.29 light chain appears to play a more limited role in the interaction with CD131. The side-chain of W32 on CDR L1 makes a polar contact with the main-chain carbonyl of G420 and van der Waals contact with the side-chain of Y421. No residues from CDR L2 make contact CD131. F94 on CDR L3 is within van der Waals contact of the side-chain T106 from D1 of CD131. In addition to these contacts, the aromatic side-chains of Y32 from CDR H1 and Y100 from CDR H3, are buried in a cleft in the Site 2 interface of CD131 and form π-π interactions with the side-chains of Y365 and H367 from CD131, further stabilizing the CD131/9A2-VR24.29 complex (FIG. 20C).

Figure 20D:
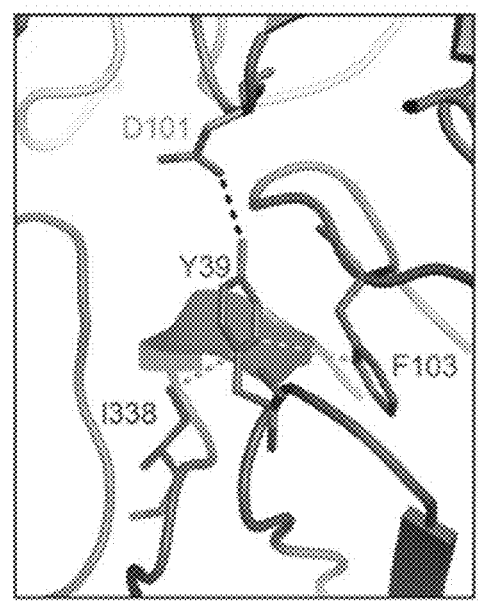

Several alanine point mutants were generated on and around the known ligand-binding sites on hCD131. Several shCD131 alanine point mutants were generated on and around the known ligand-binding sites on CD131. Using SPR the affinities of a purified recombinant Fab fragment of 9A2 was measured for binding to these mutants relative to WT shCD131 (Table 5). The most prominent effects were noted for F103A, Q339A and I424A mutants, which resulted in negligible binding and the I388A mutation, which resulted in no binding of 9A2/9A2-VR24.29. Structurally, F103 and I338 are involved in stabilizing the side chain of Y39, which makes an important hydrogen bond with the side-chain of D101 on CDR H3 (FIG. 20D). Mutation of these residues may affect the orientation of Y39, which in turn affects binding of 9A2-VR24.29. Q399 and 1424 do not make any interactions with 9A2-VR24.29, in contrast they are buried deep in the D1-D4 interface of the dimer, therefore the loss of binding of 9A2-VR24.29 may be due to the structural effect on the dimer.

The Y39A mutation from D1 of CD131 resulted in weak binding of 9A2 and 9A2-VR24.29 further emphasizing the importance of Y39 for high affinity binding. Mutation of residues Tyr365, His367 and I368 from D4 resulted in weak binding. Of these, Y365 and H367 are involved in making important hydrogen bonds with D101 and Y100 on CDR H3 respectively. These residues also form a part of the π-π interaction network comprising Y32 and Y100 from CDRs H1 and H3, further emphasizing their role in 9A2-VR24.29 engagement. Although I368 does not interact with 9A2-VR24.29 directly, it is part of the hydrophobic groove at the Site 2 interface and may be structurally important for maintaining proper orientation of the surrounding aromatic side chains of Y39, Y421, Y365 and H367. Interestingly, mutation of Thr106 increased affinity by approximately 10-fold. Together this suggests that the 9A2 epitope is centered around these residues. The surface residues Ser102, Val104 and Arg364 also form part of the 9A2 epitope as mutations of these amino acids reduced binding of 9A2 to WT shCD131 by 3-7 fold. These experiments were repeated using 9A2-VR24.29 with essentially identical results (Table 5) indicating that the original epitope specificity was retained after two rounds of affinity maturation.

This site to which 9A2 and 9A2-VR24.29 bind is also distant to the site of binding of antibody BION-1 for which residues 363, 364 and 366 are important for binding (Sun et al., supra).

TABLE 5

Effect of single amino acid substitutions of human CD131 on binding to 9A2 Fab.

| shCD131 mutant | Location | Method | $K_D$ (nM) 9A2 | $K_D$ (nM) 9A2-VR24.29 |
|---|---|---|---|---|
| Wild-type | N/A | Kinetics | 49 ± 2.1 (N = 3) | 0.100 ± 0.003 (N = 4) |
| N37A | Domain 1 A-B Loop | Steady state | 620 (N = 1) | |
| D38A | Domain 1 A-B Loop | No Expression | No Expression | |
| Y39A | Domain 1 A-B Loop | | No Binding (N = 1) | Weak binding (N = 1) |
| T40A | Domain 1 A-B Loop | Steady state | 236 (N = 1) | |
| S41A | Domain 1 A-B Loop | Kinetics | 56 (N = 1) | |
| H42A | Domain 1 A-B Loop | Kinetics | 41 (N = 1) | |
| S102A | Domain 1 E-F Loop | Steady state | 324 (N = 1) | |
| F103A | Domain 1 E-F Loop | | No Binding (N = 1) | Negligible binding (N = 6) |
| V104A | Domain 1 E-F Loop | Kinetics | 117 (N = 1) | |
| V105A | Domain 1 E-F Loop | Kinetics | 78 (N = 1) | |
| T106A | Domain 1 E-F Loop | Kinetics | 5.8 (N = 1) | |
| D107A | Domain 1 E-F Loop | Kinetics | 191 (N = 1) | |
| V108A | Domain 1 E-F Loop | Kinetics | 83 (N = 1) | |
| N337A | Domain 4 A-Loop | Kinetics | 91 (N = 1) | |
| I338A | Domain 4 A-Loop | | No Binding (N = 1) | No Binding (N = 1) |
| Q339A | Domain 4 A-Loop | Kinetics | 144 (N = 1) | Negligible binding (N = 6) |
| M340A | Domain 4 A-Loop | Steady state | 235 (N = 1) | |
| K362A | Domain 4 B-C Loop | Kinetics | 64.8; 65 (N = 2) | |
| M363A | Domain 4 B-C Loop | Kinetics | 171 (N = 1) | |
| R364A | Domain 4 B-C Loop | Kinetics | 119 (N = 1) | |
| Y365A | Domain 4 B-C Loop | | No Binding (N = 1) | Weak binding (N = 6) |
| E366A | Domain 4 B-C Loop | Kinetics | 32 (N = 1) | |
| H367A | Domain 4 B-C Loop | Steady state* | 10300; 10800 (N = 2) | Weak binding (N = 6) |
| I368A | Domain 4 B-C Loop | Steady state* | 4770 (N = 1) | Weak binding (N = 6) |
| D369A | Domain 4 B-C Loop | Kinetics | 28 (N = 1) | |
| R418A | Domain 4 F-G Loop | Kinetics | 70 (N = 1) | |
| T419A | Domain 4 F-G Loop | Kinetics | 53 (N = 1) | |
| G420A | Domain 4 F-G Loop | Kinetics | 63 (N = 1) | |
| Y421A | Domain 4 F-G Loop | Kinetics | 167 (N = 1) | |
| N422A | Domain 4 F-G Loop | Kinetics | 54 (N = 1) | |
| G423A | Domain 4 F-G Loop | Steady state | 197 (N = 1) | |
| I424A | Domain 4 F-G Loop | Kinetics | 126 (N = 1) | Negligible binding (N = 6) |

Figure 21C:
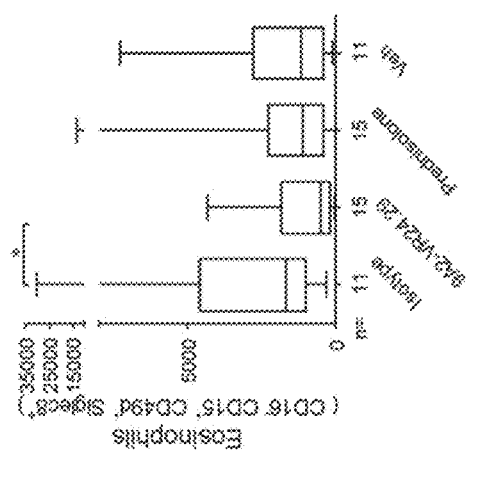
FIGS. 21A-21J are graphical representations showing the effect of 9A2-VR24.29 and Prednisolone on nasal polyps in a human xenograft model.
Figure 21B:
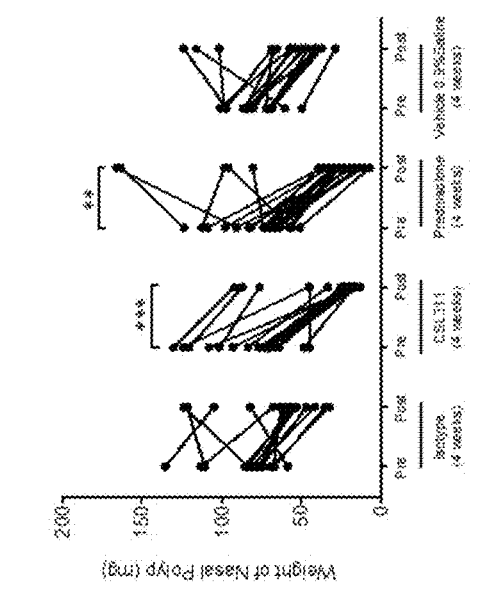
Figure 21E:
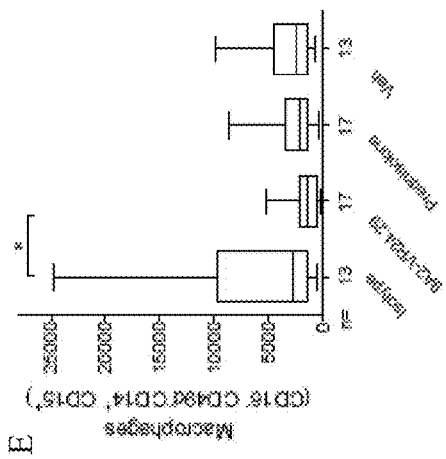
Figure 21A:
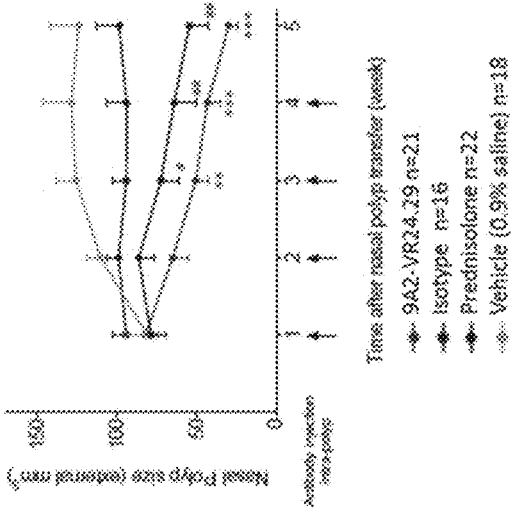
Figure 21D:
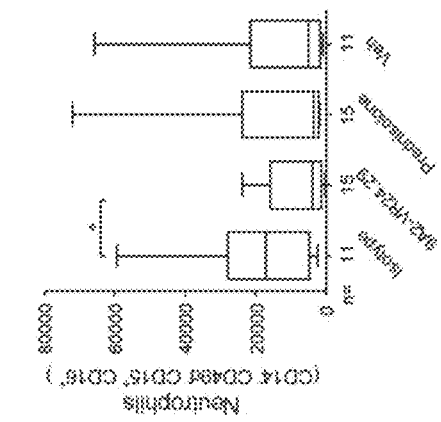
Figure 21F:
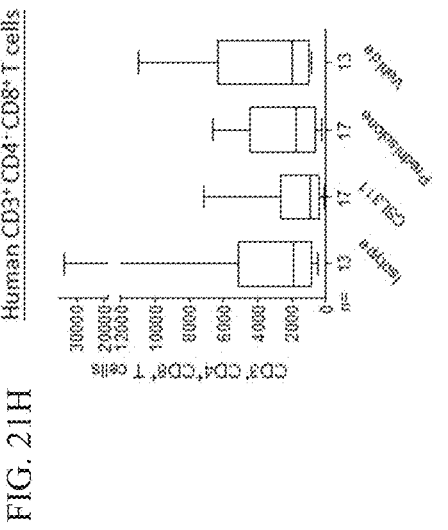
Figure 21G:
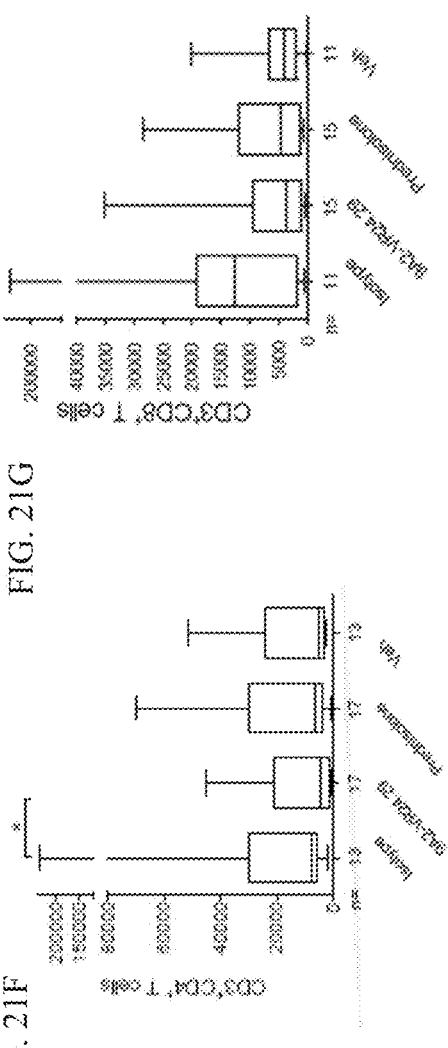
Figure 21H:
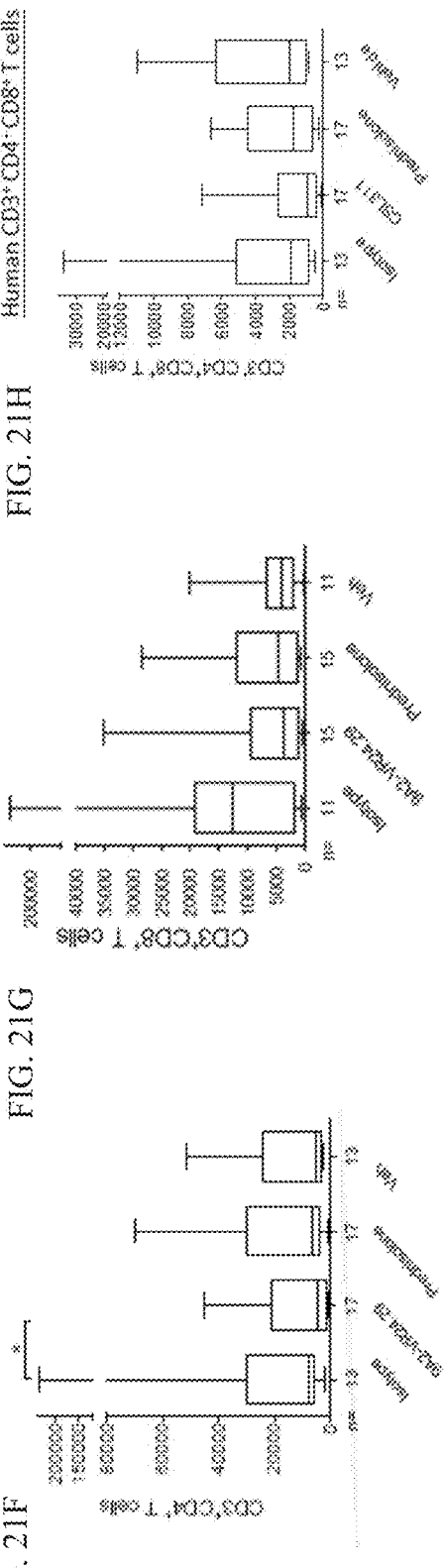

Therapeutic Administration of 9A2-VR24.29 Reduces Nasal Polyp Xenograft Growth in Rag2$^{-/-}$ R2rg$^{-/-}$hIL-3/GM-CSF KI Mice Rag2$^{-/-}$ Il2rg$^{-/-}$hIL-3/GM-CSF KI mice were implanted, in subcutaneous pockets, with 4 mm$^3$ pieces of non-disrupted human nasal polyps as described above. After 1 week the mice were injected (intra-polyp) with 9A2-VR24.29 (5 mg/kg), isotype control antibody (5 mg/kg), Prednisolone (1 mg/kg) or saline vehicle (0.9%) weekly for 4 weeks and the size of the polyps monitored externally. After 5 weeks the mice were sacrificed and the polyps weighed and analyzed histologically and by flow cytometry. There was a significant decrease in size for the 9A2-VR24.29 treated polyps compared to isotype control treated polyps. There was a significant decrease in the weight of the polyps after treatment with 9A2-VR24.29 whereas there was no significant difference in weight after treatment with isotype control antibody. There was a significant decrease in the size of polyps treated with Prednisolone compared to those treated with vehicle (0.9% saline) (FIG. 21A). There was a significant decrease in the weight of the polyps after treatment with Prednisolone whereas there was no significant difference in weight after treatment with vehicle (FIG. 21B).

Figure 21I:
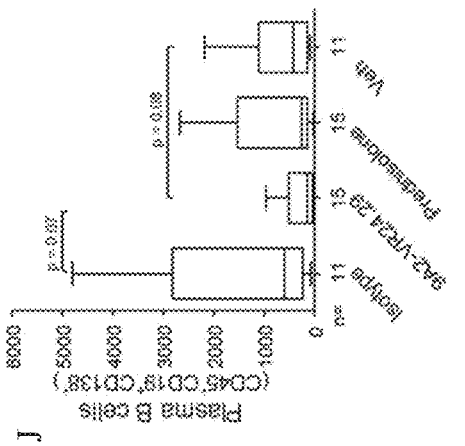
Figure 21J:
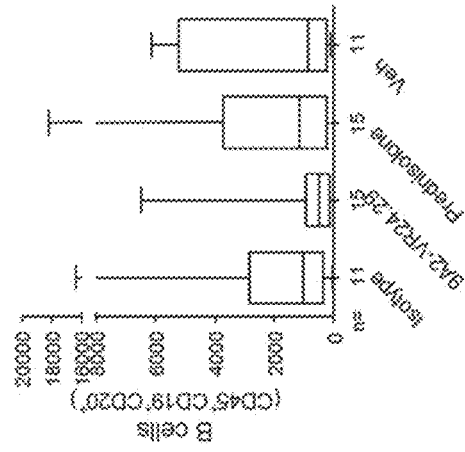

After 5 weeks the polyps were examined by flow cytometry for human T and B lymphocytes, eosinophils, neutrophils and macrophages. A statistically significant reduction in the numbers of eosinophils (CD16$^-$CD15$^+$CD49d$^+$Siglec8$^+$), neutrophils (CD14$^-$CD49d$^-$CD15$^+$CD16$^+$) macrophage (CD16$^-$CD49d$^-$CD14$^+$CD15$^+$) and CD3$^+$ CD4$^+$ (but not CD3$^+$CD8$^+$ and CD3$^+$CD4$^+$CD8$^+$) T cells populations was observed in the 9A2-VR24.29 treated polyps compared to isotype treated polyps. No reduction in any of these populations was observed for polyps treated with Prednisolone compared to those treated with vehicle (FIGS. 21C-21H). Both 9A2-VR24.29 and Prednisolone do not alter plasma B cells (CD45$^+$CD19$^+$CD20$^+$ and CD45$^+$CD19$^+$CD138$^+$) (FIGS. 21I-21J).

Figure 22A:
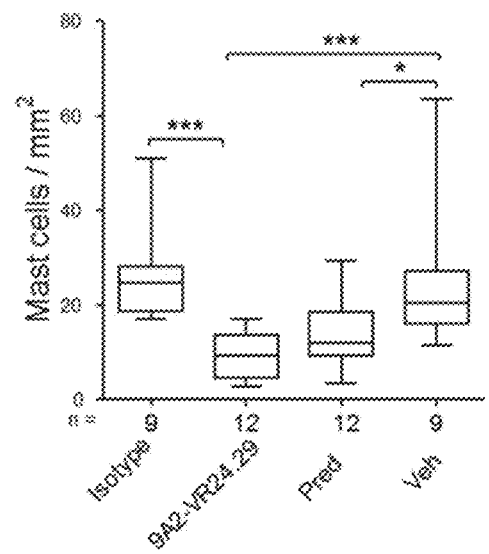
FIGS. 22A and 22B are graphical representations showing the effect of 9A2-VR24.29 and Prednisolone on nasal polyp mast cell number and mucus production in a human xenograft model.
Figure 22B:
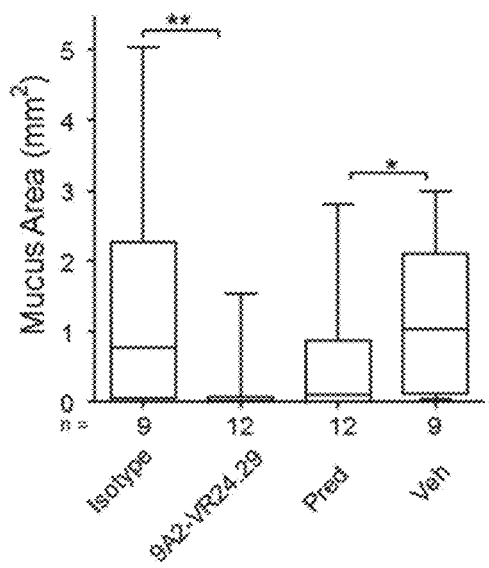

Both 9A2-VR24.29 and Prednisolone reduced the numbers of toluidine blue-stained mast cells and mucus production in human nasal polyps although the effect was more pronounced for 9A2-VR24.29 (FIGS. 22A and 22B).

Systemic Administration of 9A2-VR24.29 is as Effective as Intra-Polyp Administration of 9A2-VR24.29 in Reducing Nasal Polyp Size and Weight Rag2$^{-/-}$ Il2rg$^{-/-}$hIL-3/GM-CSF KI mice were implanted, in subcutaneous pockets, with 4 mm$^3$ pieces of non-disrupted human nasal polyps as described above. After 1 week the mice were injected (intra-polyp) with 9A2-VR24.29 (5 mg/kg) or isotype control antibody (5 mg/kg) or mice were injected systemically (intra-venous) with 9A2-VR24.29 (10 mg/kg) or isotype control antibody (10 mg/kg) weekly for 4 weeks and the size of the polyps monitored externally.

Figure 23A:
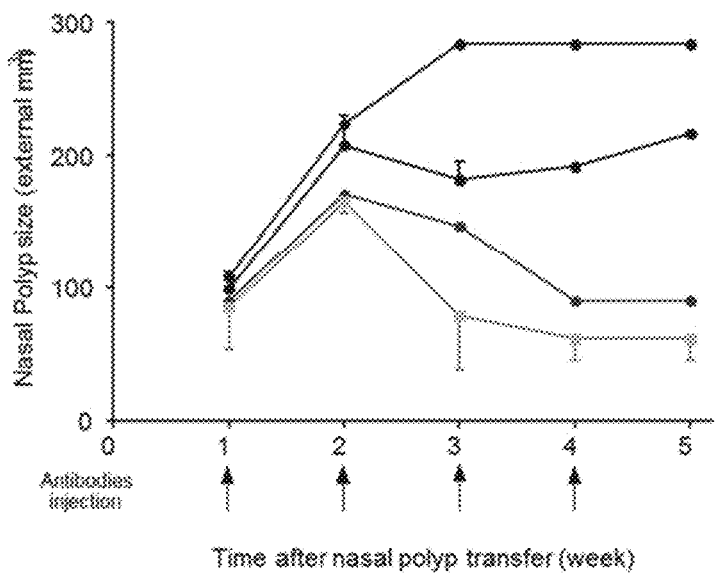
FIGS. 23A and 23B are a graphical representation showing the effect of 9A2-VR24.29 administered intra-polyp and systemically on nasal polyps in a human xenograft model.
Figure 23B:
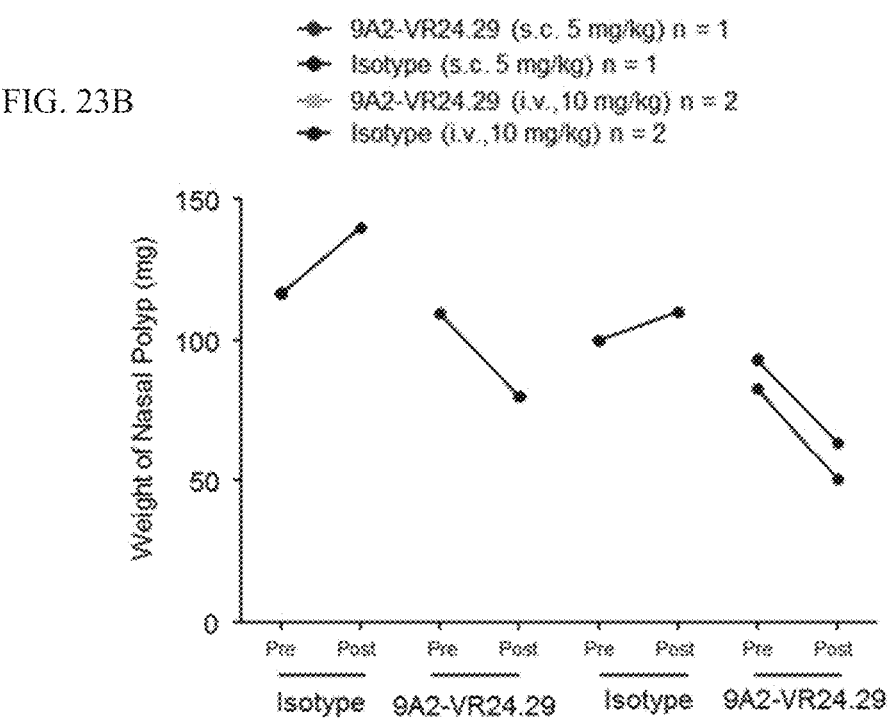

After 5 weeks the mice were sacrificed and the polyps weighed. Both intra-polyp and systemic injection of 9A2-VR24.29 reduced nasal polyp size (FIG. 23A) and weight (FIG. 23B).

9A2-VR24.29 does not Bind or Neutralize IL-3, GM-CSF and IL-5 Function from Other Primate Species The ability of 9A2-VR24.29 to bind or neutralize IL-3, GM-CSF and IL-5 function was investigated in rhesus monkeys, baboons, squirrel monkeys and cynomolgus monkeys. Despite similarities in amino acid sequences between the species 9A2-VR24.29 was unable to bind or neutralize IL-3, GM-CSF and IL-5 function.

The invention claimed is:

1. A CD131-binding protein comprising an antigen binding domain of an antibody, wherein the antigen binding domain binds to or specifically binds to CD131 and neutralizes signaling by interleukin (IL) 3, IL-5 and granulocyte-macrophage colony stimulating factor (GM-CSF) and wherein the antigen binding domain comprises a heavy chain variable region ($V_H$) comprising the sequence set forth in SEQ ID NO: 193 and a light chain variable region ($V_L$) comprising the sequence set forth in SEQ ID NO: 5.

2. The CD131-binding protein of claim 1, wherein the $K_D$ of the CD131-binding protein comprises a polypeptide comprising the sequence set forth in SEQ ID NO: 194 is about 100 nM or less, when the polypeptide is immobilized on a solid surface and the $K_D$ is determined by surface plasmon resonance.

3. The CD131-binding protein of claim 1, which has one or more of the following activities:
   (i) reduces or inhibits activation of isolated human neutrophils by GM-CSF as determined by reducing or inhibiting GM-CSF-induced increase in neutrophil cell size;
   (ii) reduces or inhibits IL-3-induced IL-8 secretion by human basophils;
   (iii) reduces or prevents IL-3-mediated survival or plasmacytoid dendritic cells (pDCs);
   (iv) reduces or prevents activation of human peripheral blood eosinophils by IL-5 as determined by assessing change in forward scatter assessed by flow cytometry;
   (v) reduces or prevents survival of human peripheral blood eosinophils in the presence of IL-5 and/or GM-CSF and/or IL-3;
   (vi) reduces or prevents IL-3-induced tumor necrosis factor (TNF) a release from human mast cells;
   (vii) reduces or prevents IL-3-induced IL-13 release from human mast cells;
   (viii) reduces or prevents potentiation of IgE-mediated IL-8 release from human mast cells by IL-3 and/or IL-5 and/or GM-CSF; or
   (ix) reduces or prevents formation of colony forming units-granulocytes-macrophages (CFU-GM) by CD34+ human bone marrow cells cultured in the presence of stem cell factor (SCF), GM-CSF, IL-3 and IL-5.

4. The CD131-binding protein of claim 1, wherein if the $V_H$ and $V_L$ are in a single polypeptide chain, the protein is:
   (i) a single chain Fv fragment (scFv);
   (ii) a dimeric scFv (di-scFv);
   (iii) one of (i) or (ii) linked to a constant region of an antibody, Fc or a heavy chain constant domain ($C_H$) 2 and/or $C_H$3; or
   (iv) one of (i) or (ii) linked to a protein that binds to an immune effector cell, or if the $V_H$ and $V_L$ are in separate polypeptide chains the protein is:
   (i) a diabody;
   (ii) a triabody;
   (iii) a tetrabody;
   (iv) a Fab;
   (v) a F(ab')$_2$;
   (vi) a Fv;
   (vii) one of (i) to (vi) linked to a constant region of an antibody, Fc or a heavy chain constant domain ($C_H$) 2 and/or $C_H$3;
   (viii) one of (i) to (vi) linked to a protein that binds to an immune effector cell; or
   (ix) an antibody.

5. The CD131-binding protein of claim 1, which is conjugated to another compound.

6. A nucleic acid encoding the CD131-binding protein of claim 1.

7. An expression construct comprising the nucleic acid of claim 6.

8. An isolated or recombinant cell comprising the expression construct of claim 7.

9. An isolated or recombinant cell expressing the CD131-binding protein of claim 1.

10. A composition comprising the CD131-binding protein of claim 1 and a pharmaceutically acceptable carrier.

11. A CD131-binding protein comprising an antigen binding domain of an antibody, wherein the antigen binding domain binds to or specifically binds to CD131 and neutralizes signaling by interleukin (IL) 3, IL-5 and granulocyte-macrophage colony stimulating factor (GM-CSF), and wherein the antigen binding domain comprises:
   (i) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 5;
   (ii) a $V_H$ comprising the sequence set forth in SEQ ID NO: 20 and a $V_L$ comprising the sequence set forth in SEQ ID NO: 5;
   (iii) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 6;
   (iv) a $V_H$ comprising the sequence set forth in SEQ ID NO: 20 and a $V_L$ comprising the sequence set forth in SEQ ID NO: 6;
   (v) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 7;
   (vi) a $V_H$ comprising the sequence set forth in SEQ ID NO: 20 and a $V_L$ comprising the sequence set forth in SEQ ID NO: 7;

(vii) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 8;

(viii) a $V_H$ comprising the sequence set forth in SEQ ID NO: 20 and a $V_L$ comprising the sequence set forth in SEQ ID NO: 8;

(ix) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 9;

(x) a $V_H$ comprising the sequence set forth in SEQ ID NO: 20 and a $V_L$ comprising the sequence set forth in SEQ ID NO: 9;

(xi) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 10;

(xii) a $V_H$ comprising the sequence set forth in SEQ ID NO: 20 and a $V_L$ comprising the sequence set forth in SEQ ID NO: 10;

(xiii) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 11;

(xiv) a $V_H$ comprising the sequence set forth in SEQ ID NO: 20 and a $V_L$ comprising the sequence set forth in SEQ ID NO: 11;

(xv) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 12;

(xvi) a $V_H$ comprising the sequence set forth in SEQ ID NO: 20 and the $V_L$ comprising a sequence set forth in SEQ ID NO: 12;

(xvii) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 13;

(xviii) a $V_H$ comprising the sequence set forth in SEQ ID NO: 20 and a $V_L$ comprising the sequence set forth in SEQ ID NO: 13;

(xix) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 14;

(xx) a $V_H$ comprising the sequence set forth in SEQ ID NO: 20 and a $V_L$ comprising the sequence set forth in SEQ ID NO: 14;

(xxi) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 15;

(xxii) a $V_H$ comprising the sequence set forth in SEQ ID NO: 20 and a $V_L$ comprising the sequence set forth in SEQ ID NO: 15;

(xxiii) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 16;

(xxiv) a $V_H$ comprising the sequence set forth in SEQ ID NO: 20 and a $V_L$ comprising the sequence set forth in SEQ ID NO: 16;

(xxv) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 17;

(xxvi) a $V_H$ comprising the sequence set forth in SEQ ID NO: 20 and a $V_L$ comprising the sequence set forth in SEQ ID NO: 17;

(xxvii) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 18;

(xxviii) a $V_H$ comprising the sequence set forth in SEQ ID NO: 20 and a $V_L$ comprising the sequence set forth in SEQ ID NO: 18;

(xxix) a $V_H$ comprising CDRs 1, 2 and 3 of the sequence set forth in SEQ ID NO: 20 and a $V_L$ comprising CDRs 1, 2 and 3 of the sequence set forth in SEQ ID NO: 19;

(xxx) a $V_H$ comprising the sequence set forth in SEQ ID NO: 20 and a $V_L$ comprising the sequence set forth in SEQ ID NO: 19;

(xxxi) a $V_H$ comprising CDRs 1, 2 and 3 of the sequence set forth in SEQ ID NO: 21 and a $V_L$ comprising CDRs 1, 2 and 3 of the sequence set forth in SEQ ID NO: 5;

(xxxii) a $V_H$ comprising the sequence set forth in SEQ ID NO: 21 and a $V_L$ comprising the sequence set forth in SEQ ID NO: 5;

(xxxiii) a $V_H$ comprising CDRs 1, 2 and 3 of the sequence set forth in SEQ ID NO: 22 and a $V_L$ comprising CDRs 1, 2 and 3 of the sequence set forth in SEQ ID NO: 5;

(xxxiv) a $V_H$ comprising the sequence set forth in SEQ ID NO: 22 and a $V_L$ comprising the sequence set forth in SEQ ID NO: 5;

(xxxv) a $V_H$ comprising CDRs 1, 2 and 3 of the sequence set forth in SEQ ID NO: 23 and a $V_L$ comprising CDRs 1, 2 and 3 of the sequence set forth in SEQ ID NO: 5;

(xxxvi) a $V_H$ comprising the sequence set forth in SEQ ID NO: 23 and a $V_L$ comprising the sequence set forth in SEQ ID NO: 5;

(xxxvii) a $V_H$ comprising CDRs 1, 2 and 3 of the sequence set forth in SEQ ID NO: 24 and a $V_L$ comprising CDRs 1, 2 and 3 of the sequence set forth in SEQ ID NO: 5;

(xxxviii) a $V_H$ comprising a sequence set forth in SEQ ID NO: 24 and a $V_L$ comprising a sequence set forth in SEQ ID NO: 5;

(xxxix) a $V_H$ comprising CDRs 1, 2 and 3 of the sequence set forth in SEQ ID NO: 25 and a $V_L$ comprising CDRs 1, 2 and 3 of the sequence set forth in SEQ ID NO: 5;

(xl) a $V_H$ comprising the sequence set forth in SEQ ID NO: 25 and a $V_L$ comprising the sequence set forth in SEQ ID NO: 5;

(xli) a $V_H$ comprising CDRs 1, 2 and 3 of the sequence set forth in SEQ ID NO: 26 and a $V_L$ comprising CDRs 1, 2 and 3 of the sequence set forth in SEQ ID NO: 5;

(xlii) a $V_H$ comprising the sequence set forth in SEQ ID NO: 26 and a $V_L$ comprising the sequence set forth in SEQ ID NO: 5;

(xliii) a $V_H$ comprising CDRs 1, 2 and 3 of the sequence set forth in SEQ ID NO: 27 and a $V_L$ comprising CDRs 1, 2 and 3 of the sequence set forth in SEQ ID NO: 5;

(xliv) a $V_H$ comprising the sequence set forth in SEQ ID NO: 27 and a $V_L$ comprising the sequence set forth in SEQ ID NO: 5;

(xlv) a $V_H$ comprising CDRs 1, 2 and 3 of the sequence set forth in SEQ ID NO: 28 and a $V_L$ comprising CDRs 1, 2 and 3 of the sequence set forth in SEQ ID NO: 5;

(xlvi) a $V_H$ comprising the sequence set forth in SEQ ID NO: 28 and a $V_L$ comprising the sequence set forth in SEQ ID NO: 5;

(xlvii) a $V_H$ comprising CDRs 1, 2 and 3 of the sequence set forth in SEQ ID NO: 29 and a $V_L$ comprising CDRs 1, 2 and 3 of the sequence set forth in SEQ ID NO: 5;

(xlviii) a $V_H$ comprising the sequence set forth in SEQ ID NO: 29 and a $V_L$ comprising the sequence set forth in SEQ ID NO: 5;

(xlix) a $V_H$ comprising CDRs 1, 2 and 3 of the sequence set forth in SEQ ID NO: 30 and a $V_L$ comprising CDRs 1, 2 and 3 of the sequence set forth in SEQ ID NO: 5;

(l) a $V_H$ comprising the sequence set forth in SEQ ID NO: 30 and a $V_L$ comprising the sequence set forth in SEQ ID NO: 5;

(li) a $V_H$ comprising CDRs 1, 2 and 3 of the sequence set forth in SEQ ID NO: 31 and a $V_L$ comprising CDRs 1, 2 and 3 of the sequence set forth in SEQ ID NO: 5;

(lii) a $V_H$ comprising the sequence set forth in SEQ ID NO: 31 and a $V_L$ comprising the sequence set forth in SEQ ID NO: 5;

(liii) a $V_H$ comprising CDRs 1, 2 and 3 of the sequence set forth in SEQ ID NO: 32 and a $V_L$ comprising CDRs 1, 2 and 3 of the sequence set forth in SEQ ID NO: 5;

(liv) a $V_H$ comprising the sequence set forth in SEQ ID NO: 32 and a $V_L$ comprising the sequence set forth in SEQ ID NO: 5;

(lv) a $V_H$ comprising CDRs 1, 2 and 3 of the sequence set forth in SEQ ID NO: 33 and a $V_L$ comprising CDRs 1, 2 and 3 of the sequence set forth in SEQ ID NO: 5;

(lvi) a $V_H$ comprising the sequence set forth in SEQ ID NO: 33 and a $V_L$ comprising the sequence set forth in SEQ ID NO: 5;

(lvii) a $V_H$ comprising CDRs 1, 2 and 3 of the sequence set forth in SEQ ID NO: 34 and a $V_L$ comprising CDRs 1, 2 and 3 of the sequence set forth in SEQ ID NO: 5;

(lviii) a $V_H$ comprising the sequence set forth in SEQ ID NO: 34 and a $V_L$ comprising the sequence set forth in SEQ ID NO: 5;

(lix) a $V_H$ comprising CDRs 1, 2 and 3 of the sequence set forth in SEQ ID NO: 35 and a $V_L$ comprising CDRs 1, 2 and 3 of the sequence set forth in SEQ ID NO: 5;

(lx) a $V_H$ comprising the sequence set forth in SEQ ID NO: 35 and a $V_L$ comprising the sequence set forth in SEQ ID NO: 5;

(lxi) a $V_H$ comprising CDRs 1, 2 and 3 of the sequence set forth in SEQ ID NO: 36 and a $V_L$ comprising CDRs 1, 2 and 3 of the sequence set forth in SEQ ID NO: 5;

(lxii) a $V_H$ comprising the sequence set forth in SEQ ID NO: 36 and a $V_L$ comprising the sequence set forth in SEQ ID NO: 5;

(lxiii) a $V_H$ comprising CDRs 1, 2 and 3 of the sequence set forth in SEQ ID NO: 37 and a $V_L$ comprising CDRs 1, 2 and 3 of the sequence set forth in SEQ ID NO: 5;

(lxiv) a $V_H$ comprising the sequence set forth in SEQ ID NO: 37 and a $V_L$ comprising the sequence set forth in SEQ ID NO: 5;

(lxv) a $V_H$ comprising CDRs 1, 2 and 3 of the sequence set forth in SEQ ID NO: 38 and a $V_L$ comprising CDRs 1, 2 and 3 of the sequence set forth in SEQ ID NO: 5;

(lxvi) a $V_H$ comprising the sequence set forth in SEQ ID NO: 38 and a $V_L$ comprising the sequence set forth in SEQ ID NO: 5;

(lxvii) a $V_H$ comprising CDRs 1, 2 and 3 of the sequence set forth in SEQ ID NO: 39 and a $V_L$ comprising CDRs 1, 2 and 3 of the sequence set forth in SEQ ID NO: 5;

(lxviii) a $V_H$ comprising the sequence set forth in SEQ ID NO: 39 and a $V_L$ comprising the sequence set forth in SEQ ID NO: 5;

(lxix) a $V_H$ comprising CDRs 1, 2 and 3 of the sequence set forth in SEQ ID NO: 40 and a $V_L$ comprising CDRs 1, 2 and 3 of the sequence set forth in SEQ ID NO: 5;

(lxx) a $V_H$ comprising the sequence set forth in SEQ ID NO: 40 and a $V_L$ comprising the sequence set forth in SEQ ID NO: 5;

(lxxi) a $V_H$ comprising CDRs 1, 2 and 3 of the sequence set forth in SEQ ID NO: 41 and a $V_L$ comprising CDRs 1, 2 and 3 of the sequence set forth in SEQ ID NO: 5;

(lxxii) a $V_H$ comprising the sequence set forth in SEQ ID NO: 41 and a $V_L$ comprising the sequence set forth in SEQ ID NO: 5;

(lxxiii) a $V_H$ comprising CDRs 1, 2 and 3 of the sequence set forth in SEQ ID NO: 42 and a $V_L$ comprising CDRs 1, 2 and 3 of the sequence set forth in SEQ ID NO: 5;

(lxxiv) a $V_H$ comprising the sequence set forth in SEQ ID NO: 42 and a $V_L$ comprising the sequence set forth in SEQ ID NO: 5;

(lxxv) a $V_H$ comprising CDRs 1, 2 and 3 of the sequence set forth in SEQ ID NO: 43 and a $V_L$ comprising CDRs 1, 2 and 3 of the sequence set forth in SEQ ID NO: 5;

(lxxvi) a $V_H$ comprising the sequence set forth in SEQ ID NO: 43 and a $V_L$ comprising the sequence set forth in SEQ ID NO: 5;

(lxxvii) a $V_H$ comprising CDRs 1, 2 and 3 of the sequence set forth in SEQ ID NO: 44 and a $V_L$ comprising CDRs 1, 2 and 3 of the sequence set forth in SEQ ID NO: 5;

(lxxviii) a $V_H$ comprising the sequence set forth in SEQ ID NO: 44 and a $V_L$ comprising the sequence set forth in SEQ ID NO: 5;

(lxxix) a $V_H$ comprising CDRs 1, 2 and 3 of the sequence set forth in SEQ ID NO: 45 and a $V_L$ comprising CDRs 1, 2 and 3 of the sequence set forth in SEQ ID NO: 5;

(lxxx) a $V_H$ comprising the sequence set forth in SEQ ID NO: 45 and a $V_L$ comprising the sequence set forth in SEQ ID NO: 5;

(lxxxi) a $V_H$ comprising CDRs 1, 2 and 3 of the sequence set forth in SEQ ID NO: 46 and a $V_L$ comprising CDRs 1, 2 and 3 of the sequence set forth in SEQ ID NO: 5;

(lxxxii) a $V_H$ comprising the sequence set forth in SEQ ID NO: 46 and a $V_L$ comprising the sequence set forth in SEQ ID NO: 5;

(lxxxiii) a $V_H$ comprising CDRs 1, 2 and 3 of the sequence set forth in SEQ ID NO: 47 and a $V_L$ comprising CDRs 1, 2 and 3 of the sequence set forth in SEQ ID NO: 5;

(lxxxiv) a $V_H$ comprising the sequence set forth in SEQ ID NO: 47 and a $V_L$ comprising the sequence set forth in SEQ ID NO: 5;

(lxxxv) a $V_H$ comprising CDRs 1, 2 and 3 of the sequence set forth in SEQ ID NO: 48 and a $V_L$ comprising CDRs 1, 2 and 3 of the sequence set forth in SEQ ID NO: 5;

(lxxxvi) a $V_H$ comprising the sequence set forth in SEQ ID NO: 48 and a $V_L$ comprising the sequence set forth in SEQ ID NO: 5;

(lxxxvii) a $V_H$ comprising CDRs 1, 2 and 3 of the sequence set forth in SEQ ID NO: 49 and a $V_L$ comprising CDRs 1, 2 and 3 of the sequence set forth in SEQ ID NO: 5;

(lxxxviii) a $V_H$ comprising the sequence set forth in SEQ ID NO: 49 and a $V_L$ comprising the sequence set forth in SEQ ID NO: 5;

(lxxxix) a $V_H$ comprising CDRs 1, 2 and 3 of the sequence set forth in SEQ ID NO: 50 and a $V_L$ comprising CDRs 1, 2 and 3 of the sequence set forth in SEQ ID NO: 5;

(xc) a $V_H$ comprising the sequence set forth in SEQ ID NO: 50 and a $V_L$ comprising the sequence set forth in SEQ ID NO: 5;

(xci) a $V_H$ comprising CDRs 1, 2 and 3 of the sequence set forth in SEQ ID NO: 51 and a $V_L$ comprising CDRs 1, 2 and 3 of the sequence set forth in SEQ ID NO: 5;

(xcii) a $V_H$ comprising the sequence set forth in SEQ ID NO: 51 and a $V_L$ comprising the sequence set forth in SEQ ID NO: 5;

(xciii) a $V_H$ comprising CDRs 1, 2 and 3 of the sequence set forth in SEQ ID NO: 52 and a $V_L$ comprising CDRs 1, 2 and 3 of the sequence set forth in SEQ ID NO: 5;

(xciv) a $V_H$ comprising the sequence set forth in SEQ ID NO: 52 and a $V_L$ comprising the sequence set forth in SEQ ID NO: 5;

(xcv) a $V_H$ comprising CDRs 1, 2 and 3 of the sequence set forth in SEQ ID NO: 53 and a $V_L$ comprising CDRs 1, 2 and 3 of the sequence set forth in SEQ ID NO: 5;
(xcvi) a $V_H$ comprising the sequence set forth in SEQ ID NO: 53 and a $V_L$ comprising the sequence set forth in SEQ ID NO: 5;
(xcvii) a $V_H$ comprising CDRs 1, 2 and 3 of the sequence set forth in SEQ ID NO: 54 and a $V_L$ comprising CDRs 1, 2 and 3 of the sequence set forth in SEQ ID NO: 5;
(xcviii) a $V_H$ comprising the sequence set forth in SEQ ID NO: 54 and a $V_L$ comprising the sequence set forth in SEQ ID NO: 5;
(xcix) a $V_H$ comprising CDRs 1, 2 and 3 of the sequence set forth in SEQ ID NO: 55 and a $V_L$ comprising CDRs 1, 2 and 3 of the sequence set forth in SEQ ID NO: 5;
(c) a $V_H$ comprising the sequence set forth in SEQ ID NO: 55 and a $V_L$ comprising the sequence set forth in SEQ ID NO: 5;
(ci) a $V_H$ comprising CDRs 1, 2 and 3 of the sequence set forth in SEQ ID NO: 56 and a $V_L$ comprising CDRs 1, 2 and 3 of the sequence set forth in SEQ ID NO: 5;
(cii) a $V_H$ comprising the sequence set forth in SEQ ID NO: 56 and a $V_L$ comprising the sequence set forth in SEQ ID NO: 5;
(ciii) a $V_H$ comprising CDRs 1, 2 and 3 of the sequence set forth in SEQ ID NO: 57 and a $V_L$ comprising CDRs 1, 2 and 3 of the sequence set forth in SEQ ID NO: 5;
(civ) a $V_H$ comprising the sequence set forth in SEQ ID NO: 57 and a $V_L$ comprising the sequence set forth in SEQ ID NO: 5;
(cv) a $V_H$ comprising CDRs 1, 2 and 3 of the sequence set forth in SEQ ID NO: 58 and a $V_L$ comprising CDRs 1, 2 and 3 of the sequence set forth in SEQ ID NO: 5;
(cvi) a $V_H$ comprising the sequence set forth in SEQ ID NO: 58 and a $V_L$ comprising the sequence set forth in SEQ ID NO: 5;
(cvii) a $V_H$ comprising CDRs 1, 2 and 3 of the sequence set forth in SEQ ID NO: 59 and a $V_L$ comprising CDRs 1, 2 and 3 of the sequence set forth in SEQ ID NO: 5;
(cviii) a $V_H$ comprising the sequence set forth in SEQ ID NO: 59 and a $V_L$ comprising the sequence set forth in SEQ ID NO: 5;
(cix) a $V_H$ comprising CDRs 1, 2 and 3 of the sequence set forth in SEQ ID NO: 60 and a $V_L$ comprising CDRs 1, 2 and 3 of the sequence set forth in SEQ ID NO: 5;
(cx) a $V_H$ comprising the sequence set forth in SEQ ID NO: 60 and a $V_L$ comprising the sequence set forth in SEQ ID NO: 5;
(cxi) a $V_H$ comprising CDRs 1, 2 and 3 of the sequence set forth in SEQ ID NO: 61 and a $V_L$ comprising CDRs 1, 2 and 3 of the sequence set forth in SEQ ID NO: 5;
(cxii) a $V_H$ comprising the sequence set forth in SEQ ID NO: 61 and a $V_L$ comprising the sequence set forth in SEQ ID NO: 5;
(cxiii) a $V_H$ comprising CDRs 1, 2 and 3 of the sequence set forth in SEQ ID NO: 62 and a $V_L$ comprising CDRs 1, 2 and 3 of the sequence set forth in SEQ ID NO: 5;
(cxiv) a $V_H$ comprising the sequence set forth in SEQ ID NO: 62 and a $V_L$ comprising the sequence set forth in SEQ ID NO: 5;
(cxv) a $V_H$ comprising CDRs 1, 2 and 3 of the sequence set forth in SEQ ID NO: 63 and a $V_L$ comprising CDRs 1, 2 and 3 of the sequence set forth in SEQ ID NO: 5;
(cxvi) a $V_H$ comprising the sequence set forth in SEQ ID NO: 63 and a $V_L$ comprising the sequence set forth in SEQ ID NO: 5;
(cxvii) a $V_H$ comprising CDRs 1, 2 and 3 of the sequence set forth in SEQ ID NO: 64 and a $V_L$ comprising CDRs 1, 2 and 3 of the sequence set forth in SEQ ID NO: 5;
(cxviii) a $V_H$ comprising the sequence set forth in SEQ ID NO: 64 and a $V_L$ comprising the sequence set forth in SEQ ID NO: 5;
(cxix) a $V_H$ comprising CDRs 1, 2 and 3 of the sequence set forth in SEQ ID NO: 65 and a $V_L$ comprising CDRs 1, 2 and 3 of the sequence set forth in SEQ ID NO: 5;
(cxx) a $V_H$ comprising the sequence set forth in SEQ ID NO: 65 and a $V_L$ comprising the sequence set forth in SEQ ID NO: 5;
(cxxi) a $V_H$ comprising CDRs 1, 2 and 3 of the sequence set forth in SEQ ID NO: 66 and a $V_L$ comprising CDRs 1, 2 and 3 of the sequence set forth in SEQ ID NO: 5;
(cxxii) a $V_H$ comprising the sequence set forth in SEQ ID NO: 66 and a $V_L$ comprising the sequence set forth in SEQ ID NO: 5;
(cxxiii) a $V_H$ comprising CDRs 1, 2 and 3 of the sequence set forth in SEQ ID NO: 67 and a $V_L$ comprising CDRs 1, 2 and 3 of the sequence set forth in SEQ ID NO: 5;
(cxxiv) a $V_H$ comprising the sequence set forth in SEQ ID NO: 67 and a $V_L$ comprising the sequence set forth in SEQ ID NO: 5;
(cxxv) a $V_H$ comprising CDRs 1, 2 and 3 of the sequence set forth in SEQ ID NO: 68 and a $V_L$ comprising CDRs 1, 2 and 3 of the sequence set forth in SEQ ID NO: 5;
(cxxvi) a $V_H$ comprising the sequence set forth in SEQ ID NO: 68 and a $V_L$ comprising the sequence set forth in SEQ ID NO: 5;
(cxxvii) a $V_H$ comprising CDRs 1, 2 and 3 of the sequence set forth in SEQ ID NO: 69 and a $V_L$ comprising CDRs 1, 2 and 3 of the sequence set forth in SEQ ID NO: 5;
(cxxviii) a $V_H$ comprising the sequence set forth in SEQ ID NO: 69 and a $V_L$ comprising the sequence set forth in SEQ ID NO: 5;
(cxxix) a $V_H$ comprising CDRs 1, 2 and 3 of the sequence set forth in SEQ ID NO: 70 and a $V_L$ comprising CDRs 1, 2 and 3 of the sequence set forth in SEQ ID NO: 5;
(cxxx) a $V_H$ comprising the sequence set forth in SEQ ID NO: 70 and a $V_L$ comprising the sequence set forth in SEQ ID NO: 5;
(cxxxi) a $V_H$ comprising CDRs 1, 2 and 3 of the sequence set forth in SEQ ID NO: 71 and a $V_L$ comprising CDRs 1, 2 and 3 of the sequence set forth in SEQ ID NO: 5;
(cxxxii) a $V_H$ comprising the sequence set forth in SEQ ID NO: 71 and a $V_L$ comprising the sequence set forth in SEQ ID NO: 5;
(cxxxiii) a $V_H$ comprising CDRs 1, 2 and 3 of the sequence set forth in SEQ ID NO: 72 and a $V_L$ comprising CDRs 1, 2 and 3 of the sequence set forth in SEQ ID NO: 5;
(cxxxiv) a $V_H$ comprising the sequence set forth in SEQ ID NO: 72 and a $V_L$ comprising the sequence set forth in SEQ ID NO: 5;
(cxxxv) a $V_H$ comprising CDRs 1, 2 and 3 of the sequence set forth in SEQ ID NO: 73 and a $V_L$ comprising CDRs 1, 2 and 3 of the sequence set forth in SEQ ID NO: 5;
(cxxxvi) a $V_H$ comprising the sequence set forth in SEQ ID NO: 73 and a $V_L$ comprising the sequence set forth in SEQ ID NO: 5;
(cxxxvii) a $V_H$ comprising CDRs 1, 2 and 3 of the sequence set forth in SEQ ID NO: 75 and a $V_L$ comprising CDRs 1, 2 and 3 of the sequence set forth in SEQ ID NO: 5;

(cxxxviii) a $V_H$ comprising the sequence set forth in SEQ ID NO: 75 and a $V_L$ comprising the sequence set forth in SEQ ID NO: 5;
(cxxxix) a $V_H$ comprising CDRs 1, 2 and 3 of the sequence set forth in SEQ ID NO: 76 and a $V_L$ comprising CDRs 1, 2 and 3 of the sequence set forth in SEQ ID NO: 5;
(cxl) a $V_H$ comprising the sequence set forth in SEQ ID NO: 76 and a $V_L$ comprising the sequence set forth in SEQ ID NO: 5;
(cxli) a $V_H$ comprising CDRs 1, 2 and 3 of the sequence set forth in SEQ ID NO: 77 and a $V_L$ comprising CDRs 1, 2 and 3 of the sequence set forth in SEQ ID NO: 5;
(cxlii) a $V_H$ comprising the sequence set forth in SEQ ID NO: 77 and a $V_L$ comprising the sequence set forth in SEQ ID NO: 5;
(cxliii) a $V_H$ comprising CDRs 1, 2 and 3 of the sequence set forth in SEQ ID NO: 78 and a $V_L$ comprising CDRs 1, 2 and 3 of the sequence set forth in SEQ ID NO: 5;
(cxliv) a $V_H$ comprising the sequence set forth in SEQ ID NO: 78 and a $V_L$ comprising the sequence set forth in SEQ ID NO: 5;
(cxlv) a $V_H$ comprising CDRs 1, 2 and 3 of the sequence set forth in SEQ ID NO: 79 and a $V_L$ comprising CDRs 1, 2 and 3 of the sequence set forth in SEQ ID NO: 5;
(cxlvi) a $V_H$ comprising the sequence set forth in SEQ ID NO: 79 and a $V_L$ comprising the sequence set forth in SEQ ID NO: 5;
(cxlvii) a $V_H$ comprising CDRs 1, 2 and 3 of the sequence set forth in SEQ ID NO: 80 and a $V_L$ comprising CDRs 1, 2 and 3 of the sequence set forth in SEQ ID NO: 5;
(cxlviii) a $V_H$ comprising the sequence set forth in SEQ ID NO: 80 and a $V_L$ comprising the sequence set forth in SEQ ID NO: 5;
(cxlix) a $V_H$ comprising CDRs 1, 2 and 3 of the sequence set forth in SEQ ID NO: 81 and a $V_L$ comprising CDRs 1, 2 and 3 of the sequence set forth in SEQ ID NO: 5;
(cl) a $V_H$ comprising the sequence set forth in SEQ ID NO: 81 and a $V_L$ comprising the sequence set forth in SEQ ID NO: 5;
(cli) a $V_H$ comprising CDRs 1, 2 and 3 of the sequence set forth in SEQ ID NO: 82 and a $V_L$ comprising CDRs 1, 2 and 3 of the sequence set forth in SEQ ID NO: 5;
(clii) a $V_H$ comprising the sequence set forth in SEQ ID NO: 82 and a $V_L$ comprising the sequence set forth in SEQ ID NO: 5;
(cliii) a $V_H$ comprising CDRs 1, 2 and 3 of the sequence set forth in SEQ ID NO: 83 and a $V_L$ comprising CDRs 1, 2 and 3 of the sequence set forth in SEQ ID NO: 5;
(cliv) a $V_H$ comprising the sequence set forth in SEQ ID NO: 83 and a $V_L$ comprising the sequence set forth in SEQ ID NO: 5;
(clv) a $V_H$ comprising CDRs 1, 2 and 3 of the sequence set forth in SEQ ID NO: 84 and a $V_L$ comprising CDRs 1, 2 and 3 of the sequence set forth in SEQ ID NO: 5;
(clvi) a $V_H$ comprising the sequence set forth in SEQ ID NO: 84 and a $V_L$ comprising the sequence set forth in SEQ ID NO: 5;
(clvii) a $V_H$ comprising the sequence set forth in SEQ ID NO: 85 and a $V_L$ comprising CDRs 1, 2 and 3 of the sequence set forth in SEQ ID NO: 5;
(clviii) a $V_H$ comprising the sequence set forth in SEQ ID NO: 85 and a $V_L$ comprising the sequence set forth in SEQ ID NO: 5;
(clix) a $V_H$ comprising CDRs 1, 2 and 3 of the sequence set forth in SEQ ID NO: 86 and a $V_L$ comprising CDRs 1, 2 and 3 of the sequence set forth in SEQ ID NO: 5;
(clx) a $V_H$ comprising the sequence set forth in SEQ ID NO: 86 and a $V_L$ comprising the sequence set forth in SEQ ID NO: 5;
(clxi) a $V_H$ comprising CDRs 1, 2 and 3 of the sequence set forth in SEQ ID NO: 87 and a $V_L$ comprising CDRs 1, 2 and 3 of the sequence set forth in SEQ ID NO: 5;
(clxii) a $V_H$ comprising the sequence set forth in SEQ ID NO: 87 and a $V_L$ comprising the sequence set forth in SEQ ID NO: 5;
(clxiii) a $V_H$ comprising CDRs 1, 2 and 3 of the sequence set forth in SEQ ID NO: 88 and a $V_L$ comprising CDRs 1, 2 and 3 of the sequence set forth in SEQ ID NO: 5;
(clxiv) a $V_H$ comprising the sequence set forth in SEQ ID NO: 88 and a $V_L$ comprising the sequence set forth in SEQ ID NO: 5;
(clxv) a $V_H$ comprising CDRs 1, 2 and 3 of the sequence set forth in SEQ ID NO: 89 and a $V_L$ comprising CDRs 1, 2 and 3 of the sequence set forth in SEQ ID NO: 5;
(clxvi) a $V_H$ comprising the sequence set forth in SEQ ID NO: 89 and a $V_L$ comprising the sequence set forth in SEQ ID NO: 5;
(clxvii) a $V_H$ comprising CDRs 1, 2 and 3 of the sequence set forth in SEQ ID NO: 90 and a $V_L$ comprising CDRs 1, 2 and 3 of the sequence set forth in SEQ ID NO: 5;
(clxviii) a $V_H$ comprising the sequence set forth in SEQ ID NO: 90 and a $V_L$ comprising the sequence set forth in SEQ ID NO: 5;
(clxix) a $V_H$ comprising CDRs 1, 2 and 3 of the sequence set forth in SEQ ID NO: 91 and a $V_L$ comprising CDRs 1, 2 and 3 of the sequence set forth in SEQ ID NO: 5;
(clxx) a $V_H$ comprising the sequence set forth in SEQ ID NO: 91 and a $V_L$ comprising the sequence set forth in SEQ ID NO: 5;
(clxxi) a $V_H$ comprising CDRs 1, 2 and 3 of the sequence set forth in SEQ ID NO: 92 and a $V_L$ comprising CDRs 1, 2 and 3 of the sequence set forth in SEQ ID NO: 5;
(clxxii) a $V_H$ comprising the sequence set forth in SEQ ID NO: 92 and a $V_L$ comprising the sequence set forth in SEQ ID NO: 5;
(clxxiii) a $V_H$ comprising CDRs 1, 2 and 3 of the sequence set forth in SEQ ID NO: 93 and a $V_L$ comprising CDRs 1, 2 and 3 of the sequence set forth in SEQ ID NO: 5;
(clxxiv) a $V_H$ comprising the sequence set forth in SEQ ID NO: 93 and a $V_L$ comprising the sequence set forth in SEQ ID NO: 5;
(clxxv) a $V_H$ comprising CDRs 1, 2 and 3 of the sequence set forth in SEQ ID NO: 94 and a $V_L$ comprising CDRs 1, 2 and 3 of the sequence set forth in SEQ ID NO: 5;
(clxxvi) a $V_H$ comprising the sequence set forth in SEQ ID NO: 94 and a $V_L$ comprising the sequence set forth in SEQ ID NO: 5;
(clxxvii) a $V_H$ comprising CDRs 1, 2 and 3 of the sequence set forth in SEQ ID NO: 95 and a $V_L$ comprising CDRs 1, 2 and 3 of the sequence set forth in SEQ ID NO: 5;
(clxxviii) a $V_H$ comprising the sequence set forth in SEQ ID NO: 95 and a $V_L$ comprising the sequence set forth in SEQ ID NO: 5;
(clxxix) a $V_H$ comprising CDRs 1, 2 and 3 of the sequence set forth in SEQ ID NO: 96 and a $V_L$ comprising CDRs 1, 2 and 3 of the sequence set forth in SEQ ID NO: 5;
(clxxx) a $V_H$ comprising the sequence set forth in SEQ ID NO: 96 and a $V_L$ comprising the sequence set forth in SEQ ID NO: 5;
(clxxxi) a $V_H$ comprising CDRs 1, 2 and 3 of the sequence set forth in SEQ ID NO: 97 and a $V_L$ comprising CDRs 1, 2 and 3 of the sequence set forth in SEQ ID NO: 5;

(clxxxii) a $V_H$ comprising the sequence set forth in SEQ ID NO: 97 and a $V_L$ comprising the sequence set forth in SEQ ID NO: 5;

(clxxxiii) a $V_H$ comprising CDRs 1, 2 and 3 of the sequence set forth in SEQ ID NO: 98 and a $V_L$ comprising CDRs 1, 2 and 3 of the sequence set forth in SEQ ID NO: 5;

(clxxxiv) a $V_H$ comprising the sequence set forth in SEQ ID NO: 98 and a $V_L$ comprising the sequence set forth in SEQ ID NO: 5;

(clxxxv) a $V_H$ comprising CDRs 1, 2 and 3 of the sequence set forth in SEQ ID NO: 99 and a $V_L$ comprising CDRs 1, 2 and 3 of the sequence set forth in SEQ ID NO: 5;

(clxxxvi) a $V_H$ comprising the sequence set forth in SEQ ID NO: 99 and a $V_L$ comprising the sequence set forth in SEQ ID NO: 5;

(clxxxvii) a $V_H$ comprising CDRs 1, 2 and 3 of the sequence set forth in SEQ ID NO: 100 and a $V_L$ comprising CDRs 1, 2 and 3 of the sequence set forth in SEQ ID NO: 5;

(clxxxviii) a $V_H$ comprising the sequence set forth in SEQ ID NO: 100 and a $V_L$ comprising the sequence set forth in SEQ ID NO: 5;

(clxxxix) a $V_H$ comprising CDRs 1, 2 and 3 of the sequence set forth in SEQ ID NO: 101 and a $V_L$ comprising CDRs 1, 2 and 3 of the sequence set forth in SEQ ID NO: 5;

(cxc) a $V_H$ comprising the sequence set forth in SEQ ID NO: 101 and a $V_L$ comprising the sequence set forth in SEQ ID NO: 5;

(cxci) a $V_H$ comprising CDRs 1, 2 and 3 of the sequence set forth in SEQ ID NO: 102 and a $V_L$ comprising CDRs 1, 2 and 3 of the sequence set forth in SEQ ID NO: 5;

(cxcii) a $V_H$ comprising the sequence set forth in SEQ ID NO: 102 and a $V_L$ comprising the sequence set forth in SEQ ID NO: 5;

(cxciii) a $V_H$ comprising CDRs 1, 2 and 3 of the sequence set forth in SEQ ID NO: 103 and a $V_L$ comprising CDRs 1, 2 and 3 of the sequence set forth in SEQ ID NO: 5;

(cxciv) a $V_H$ comprising the sequence set forth in SEQ ID NO: 103 and a $V_L$ comprising the sequence set forth in SEQ ID NO: 5;

(cxcv) a $V_H$ comprising CDRs 1, 2 and 3 of the sequence set forth in SEQ ID NO: 104 and a $V_L$ comprising CDRs 1, 2 and 3 of the sequence set forth in SEQ ID NO: 5;

(cxcvi) a $V_H$ comprising the sequence set forth in SEQ ID NO: 104 and a $V_L$ comprising the sequence set forth in SEQ ID NO: 5;

(cxcvii) a $V_H$ comprising CDRs 1, 2 and 3 of the sequence set forth in SEQ ID NO: 105 and a $V_L$ comprising CDRs 1, 2 and 3 of the sequence set forth in SEQ ID NO: 5;

(cxcviii) a $V_H$ comprising the sequence set forth in SEQ ID NO: 105 and a $V_L$ comprising the sequence set forth in SEQ ID NO: 5;

(cxcix) a $V_H$ comprising CDRs 1, 2 and 3 of the sequence set forth in SEQ ID NO: 106 and a $V_L$ comprising CDRs 1, 2 and 3 of the sequence set forth in SEQ ID NO: 5;

(cc) a $V_H$ comprising the sequence set forth in SEQ ID NO: 106 and a $V_L$ comprising the sequence set forth in SEQ ID NO: 5;

(cci) a $V_H$ comprising CDRs 1, 2 and 3 of the sequence set forth in SEQ ID NO: 107 and a $V_L$ comprising CDRs 1, 2 and 3 of the sequence set forth in SEQ ID NO: 5;

(ccii) a $V_H$ comprising the sequence set forth in SEQ ID NO: 107 and a $V_L$ comprising the sequence set forth in SEQ ID NO: 5;

(cciii) a $V_H$ comprising CDRs 1, 2 and 3 of the sequence set forth in SEQ ID NO: 108 and a $V_L$ comprising CDRs 1, 2 and 3 of the sequence set forth in SEQ ID NO: 5;

(cciv) a $V_H$ comprising the sequence set forth in SEQ ID NO: 108 and a $V_L$ comprising the sequence set forth in SEQ ID NO: 5;

(ccv) a $V_H$ comprising CDRs 1, 2 and 3 of the sequence set forth in SEQ ID NO: 109 and a $V_L$ comprising CDRs 1, 2 and 3 of the sequence set forth in SEQ ID NO: 5;

(ccvi) a $V_H$ comprising the sequence set forth in SEQ ID NO: 109 and a $V_L$ comprising the sequence set forth in SEQ ID NO: 5;

(ccvii) a $V_H$ comprising CDRs 1, 2 and 3 of the sequence set forth in SEQ ID NO: 110 and a $V_L$ comprising CDRs 1, 2 and 3 of the sequence set forth in SEQ ID NO: 5;

(ccviii) a $V_H$ comprising the sequence set forth in SEQ ID NO: 110 and a $V_L$ comprising the sequence set forth in SEQ ID NO: 5;

(ccix) a $V_H$ comprising CDRs 1, 2 and 3 of the sequence set forth in SEQ ID NO: 111 and a $V_L$ comprising CDRs 1, 2 and 3 of the sequence set forth in SEQ ID NO: 5;

(ccx) a $V_H$ comprising the sequence set forth in SEQ ID NO: 111 and a $V_L$ comprising the sequence set forth in SEQ ID NO: 5;

(ccxi) a $V_H$ comprising CDRs 1, 2 and 3 of the sequence set forth in SEQ ID NO: 112 and a $V_L$ comprising CDRs 1, 2 and 3 of the sequence set forth in SEQ ID NO: 5;

(ccxii) a $V_H$ comprising the sequence set forth in SEQ ID NO: 112 and a $V_L$ comprising the sequence set forth in SEQ ID NO: 5;

(ccxiii) a $V_H$ comprising CDRs 1, 2 and 3 of the sequence set forth in SEQ ID NO: 113 and a $V_L$ comprising CDRs 1, 2 and 3 of the sequence set forth in SEQ ID NO: 5;

(ccxiv) a $V_H$ comprising the sequence set forth in SEQ ID NO: 113 and a $V_L$ comprising the sequence set forth in SEQ ID NO: 5;

(ccxv) a $V_H$ comprising CDRs 1, 2 and 3 of the sequence set forth in SEQ ID NO: 114 and a $V_L$ comprising CDRs 1, 2 and 3 of the sequence set forth in SEQ ID NO: 5;

(ccxvi) a $V_H$ comprising the sequence set forth in SEQ ID NO: 114 and a $V_L$ comprising the sequence set forth in SEQ ID NO: 5;

(ccxvii) a $V_H$ comprising CDRs 1, 2 and 3 of the sequence set forth in SEQ ID NO: 115 and a $V_L$ comprising CDRs 1, 2 and 3 of the sequence set forth in SEQ ID NO: 5;

(ccxviii) a $V_H$ comprising the sequence set forth in SEQ ID NO: 115 and a $V_L$ comprising the sequence set forth in SEQ ID NO: 5;

(ccxix) a $V_H$ comprising CDRs 1, 2 and 3 of the sequence set forth in SEQ ID NO: 116 and a $V_L$ comprising CDRs 1, 2 and 3 of the sequence set forth in SEQ ID NO: 5; or (ccxx) a $V_H$ comprising the sequence set forth in SEQ ID NO: 116 and a $V_L$ comprising the sequence set forth in SEQ ID NO: 5.

12. The CD131-binding protein of claim 11, wherein the Ko of the CD131-binding protein comprises a polypeptide comprising the sequence set forth in SEQ ID NO: 194 is about 100 nM or less, when the polypeptide is immobilized on a solid surface and the Ko is determined by surface plasmon resonance.

13. The CD131-binding protein of claim 11, which has one or more of the following activities:
(i) reduces or inhibits activation of isolated human neutrophils by GM-CSF as determined by reducing or inhibiting GM-CSF-induced increase in neutrophil cell size;
(ii) reduces or inhibits IL-3-induced IL-8 secretion by human basophils;
(iii) reduces or prevents IL-3-mediated survival or plasmacytoid dendritic cells (pDCs);
(iv) reduces or prevents activation of human peripheral blood eosinophils by IL-5 as determined by assessing change in forward scatter assessed by flow cytometry;
(v) reduces or prevents survival of human peripheral blood eosinophils in the presence of IL-5 and/or GM-CSF and/or IL-3;
(vi) reduces or prevents IL-3-induced tumor necrosis factor (TNF) a release from human mast cells;
(vii) reduces or prevents IL-3-induced IL-13 release from human mast cells;
(viii) reduces or prevents potentiation of IgE-mediated IL-8 release from human mast cells by IL-3 and/or IL-5 and/or GM-CSF; or
(ix) reduces or prevents formation of colony forming units-granulocytes-macrophages (CFU-GM) by CD34+ human bone marrow cells cultured in the presence of stem cell factor (SCF), GM-CSF, IL-3 and IL-5.

14. The CD131-binding protein of claim 11, wherein if the $V_H$ and $V_L$ are in a single polypeptide chain, the protein is:
a single chain Fv fragment (scFv);
(ii) a dimeric scFv (di-scFv);
(iii) one of (i) or (ii) linked to a constant region of an antibody, Fc or a heavy chain constant domain $(C_H)$ 2 and/or $C_H3$; or
(iv) one of (i) or (ii) linked to a protein that binds to an immune effector cell, or if the $V_H$ and $V_L$ are in separate polypeptide chains the protein is:
(i) a diabody;
(ii) a triabody;
(iii) a tetrabody;
(iv) a Fab;
(v) a $F(ab')_2$;
(vi) a Fv;
(vii) one of (i) to (vi) linked to a constant region of an antibody, Fc or a heavy chain constant domain $(C_H)$ 2 and/or $C_H3$;
(viii) one of (i) to (vi) linked to a protein that binds to an immune effector cell; or
(ix) an antibody.

15. The CD131-binding protein of claim 11, which is conjugated to another compound.

16. A nucleic acid encoding the CD131-binding protein of claim 11.

17. An expression construct comprising the nucleic acid of claim 16.

18. An isolated or recombinant cell comprising the expression construct of claim 17.

19. An isolated or recombinant cell expressing the CD131-binding protein of claim 11.

20. A composition comprising the CD131-binding protein of claim 11 and a pharmaceutically acceptable carrier.

* * * * *

UNITED STATES PATENT AND TRADEMARK OFFICE
CERTIFICATE OF CORRECTION

PATENT NO. : 11,840,573 B2
APPLICATION NO. : 16/953499
DATED : December 12, 2023
INVENTOR(S) : Catherine Owczarek et al.

It is certified that error appears in the above-identified patent and that said Letters Patent is hereby corrected as shown below:

In the Claims

Claim 3, Column 353, Line 50, "(TNF) a" should read --(TNF) α--.

Claim 12, Column 365, Line 5, "Ko" should read --$K_D$--.

Claim 12, Column 365, Line 8, "Ko" should read --$K_D$--.

Claim 13, Column 365, Line 26, "(TNF) a" should read --(TNF) α--.

Claim 14, Column 366, Line 3, "a single chain Fv fragment (scFv);" should read --(i) a single chain Fv fragment (scFv);--.

Signed and Sealed this
Twenty-second Day of October, 2024

Katherine Kelly Vidal
*Director of the United States Patent and Trademark Office*